US009543530B2

(12) United States Patent
Kim et al.

(10) Patent No.: US 9,543,530 B2
(45) Date of Patent: Jan. 10, 2017

(54) COMPOUND FOR ORGANIC OPTOELECTRONIC DEVICE, ORGANIC LIGHT EMITTING DIODE INCLUDING THE SAME AND DISPLAY INCLUDING THE ORGANIC LIGHT EMITTING DIODE

(71) Applicants: Hyung-Sun Kim, Uiwang-si (KR);
Eun-Sun Yu, Uiwang-si (KR);
Mi-Young Chae, Uiwang-si (KR);
Ho-Jae Lee, Uiwang-si (KR);
Soo-Hyun Min, Uiwang-si (KR)

(72) Inventors: Hyung-Sun Kim, Uiwang-si (KR);
Eun-Sun Yu, Uiwang-si (KR);
Mi-Young Chae, Uiwang-si (KR);
Ho-Jae Lee, Uiwang-si (KR);
Soo-Hyun Min, Uiwang-si (KR)

(73) Assignee: CHEIL INDUSTRIES, INC., Gumi-Si, Kyeongsangbuk-Do (KR)

( * ) Notice: Subject to any disclaimer, the term of this patent is extended or adjusted under 35 U.S.C. 154(b) by 795 days.

(21) Appl. No.: 13/668,550

(22) Filed: Nov. 5, 2012

(65) Prior Publication Data
US 2013/0056720 A1 Mar. 7, 2013

Related U.S. Application Data

(63) Continuation-in-part of application No. PCT/KR2011/003235, filed on Apr. 29, 2011.

(30) Foreign Application Priority Data

May 3, 2010 (KR) .................. 10-2010-0041466
Oct. 28, 2010 (KR) .................. 10-2010-0106077

(51) Int. Cl.
*H01L 51/54* (2006.01)
*C09K 11/06* (2006.01)
*H01L 51/00* (2006.01)
*C07D 401/14* (2006.01)
*C07D 405/14* (2006.01)
(Continued)

(52) U.S. Cl.
CPC ......... *H01L 51/0072* (2013.01); *C07D 401/14* (2013.01); *C07D 403/14* (2013.01); *C07D 405/14* (2013.01); *C07D 409/14* (2013.01); *C07D 413/14* (2013.01); *C07D 421/14* (2013.01); *C09B 57/00* (2013.01); *C09K 11/06* (2013.01); *H01L 51/0067* (2013.01); *H05B 33/14* (2013.01); *C09K 2211/1022* (2013.01); *C09K 2211/1029* (2013.01); *C09K 2211/1044* (2013.01); *C09K 2211/1059* (2013.01); *H01L 51/5012* (2013.01); *Y02E 10/549* (2013.01)

(58) Field of Classification Search
CPC ... C07D 401/00; C07D 401/02; C07D 401/04; C07D 401/14; C07D 403/00; C07D 403/02; C07D 403/04; C07D 403/14; C07D 405/00; C07D 405/02; C07D 405/04; C07D 405/14; C07D 409/00; C07D 409/02; C07D 409/04; C07D 409/14; C07D 411/00; C07D 411/02; C07D 411/04; C07D 411/14; C07D 413/00; C07D 413/02; C07D 413/04; C07D 413/14; C07D 417/00; C07D 417/02; C07D 417/04; C07D 417/14; C07D 421/00; C07D 421/02; C07D 421/04; C07D 421/14; C07D 209/00; C07D 209/80; C07D 209/82; C07D 307/00; C07D 307/77; C07D 307/91; C07D 333/00; C07D 333/50; C07D 333/76; C09K 11/06; C09K 2211/00; C09K 2211/10; C09K 2211/1018; C09K 2211/1022; C09K 2211/1029; C09K 2211/1044; C09K 2211/1033; C09K 2211/1037; C09K 2211/1048; C09K 2211/1051; C09K 2211/1059; C09K 2211/1062; C09K 2211/1074; C09K 2211/1077; C09K 2211/1081; C09K 2211/1088; C09K 2211/1092; C09K 57/00; C09K 2211/1066; Y02E 10/549; H01L 51/0032; H01L 51/005; H01L 51/0051; H01L 51/0062; H01L 51/0071; H01L 51/0072; H01L 51/0073; H01L 51/0074; H01L 51/0067; H01L 51/50; H01L 51/5012; H01L 51/5016; H05B 33/14
USPC ....... 428/690, 691, 917, 411.4, 336; 427/58, 427/66; 313/500–512; 257/40, 88–104, 257/E51.001–E51.052; 252/301.16–301.35; 544/212, 331; 546/276.7

See application file for complete search history.

(56) References Cited

U.S. PATENT DOCUMENTS 5,759,444 A * 6/1998 Enokida ................ C07C 211/61
252/301.16
6,458,475 B1 10/2002 Adachi et al.
(Continued)

FOREIGN PATENT DOCUMENTS

CN 102421772 A 4/2012
CN 102439004 A 5/2012
(Continued)

OTHER PUBLICATIONS

Machine translation of JP2010-215759. Date of publication: Sep. 30, 2010.*
(Continued)

*Primary Examiner* — Andrew K Bohaty
(74) *Attorney, Agent, or Firm* — Lee & Morse, P.C.

(57) ABSTRACT

A compound for an organic optoelectronic device and an organic photoelectric device including the same are provided. A compound for an organic optoelectronic device represented by Chemical Formula 1 is provided to fabricate an organic photoelectric device having excellent electrochemical and thermal stability and life-span characteristics, and high luminous efficiency at a low driving voltage.

14 Claims, 3 Drawing Sheets

(51) Int. Cl.
*C07D 413/14* (2006.01)
*C07D 403/14* (2006.01)
*C07D 409/14* (2006.01)
*C07D 421/14* (2006.01)
*H05B 33/14* (2006.01)
*C09B 57/00* (2006.01)
*H01L 51/50* (2006.01)

(56) References Cited

U.S. PATENT DOCUMENTS

| | | |
|---|---|---|
| 2002/0045061 A1 | 4/2002 | Hosokawa |
| 2004/0086745 A1 | 5/2004 | Iwakuma et al. |
| 2004/0110031 A1 | 6/2004 | Fukuda et al. |
| 2005/0222429 A1 | 10/2005 | Hosokawa |
| 2006/0046172 A1 | 3/2006 | Vaitkeviciene et al. |
| 2008/0135498 A1 | 6/2008 | Bright et al. |
| 2008/0269461 A1 | 10/2008 | Van Dijken et al. |
| 2009/0134784 A1 | 5/2009 | Lin et al. |
| 2009/0153034 A1 | 6/2009 | Lin et al. |
| 2009/0302745 A1 | 12/2009 | Otsu et al. |
| 2010/0044695 A1* | 2/2010 | Kai .................... C07D 251/18 257/40 |
| 2010/0187977 A1* | 7/2010 | Kai .................... C07D 487/04 313/504 |
| 2010/0187984 A1* | 7/2010 | Lin .................... C07D 491/04 313/504 |
| 2010/0237339 A1* | 9/2010 | Nomura et al. ............... 257/40 |
| 2011/0248217 A1 | 10/2011 | Tanabe et al. |
| 2011/0272687 A1* | 11/2011 | Katakura ............ C07D 405/14 257/40 |
| 2011/0278552 A1 | 11/2011 | Numata et al. |
| 2011/0278555 A1 | 11/2011 | Inoue et al. |
| 2011/0279020 A1 | 11/2011 | Inoue et al. |
| 2011/0291081 A1 | 12/2011 | Inoue et al. |
| 2012/0119197 A1 | 5/2012 | Nishimura et al. |
| 2012/0138911 A1 | 6/2012 | Inoue et al. |
| 2012/0138912 A1 | 6/2012 | Inoue et al. |
| 2012/0138915 A1 | 6/2012 | Nishimura et al. |
| 2012/0211736 A1 | 8/2012 | Kim et al. |
| 2012/0235123 A1 | 9/2012 | Lee et al. |
| 2012/0235129 A1 | 9/2012 | Iwakuma et al. |
| 2012/0267620 A1 | 10/2012 | Min et al. |

FOREIGN PATENT DOCUMENTS

| | | | |
|---|---|---|---|
| CN | 102597158 A | 7/2012 | |
| CN | 102918134 A | 2/2013 | |
| EP | 1 486 550 A1 | 12/2004 | |
| EP | 1 489 155 A1 | 12/2004 | |
| EP | 1 589 789 A1 | 10/2005 | |
| EP | 1 808 433 A1 | 7/2007 | |
| EP | 1962354 A1 | 8/2008 | |
| EP | 2270895 A2 | 1/2011 | |
| EP | 2415769 A1 | 2/2012 | |
| EP | 2423209 A1 | 2/2012 | |
| JP | 03-205479 A | 9/1991 | |
| JP | 08-003547 A | 1/1996 | |
| JP | 08-143861 A | 6/1996 | |
| JP | 08-143862 A | 6/1996 | |
| JP | 09-249876 A | 9/1997 | |
| JP | 63-040160 A | 2/1998 | |
| JP | 11-144866 A | 5/1999 | |
| JP | 11-144867 A | 5/1999 | |
| JP | 11-329737 A | 11/1999 | |
| JP | 2000-286056 A | 10/2000 | |
| JP | 2002-308837 A | 10/2002 | |
| JP | 2003-133075 A | 5/2003 | |
| JP | 2004-178895 A | 6/2004 | |
| JP | 2007-288035 A | 11/2007 | |
| JP | WO 2008056746 A1 * | 5/2008 | ............ C07D 487/04 |
| JP | 2008-135498 A | 6/2008 | |
| JP | 2010-114180 A | 5/2010 | |
| JP | WO 2010090077 A1 * | 8/2010 | ............ C07D 405/14 |
| JP | 2010215759 A * | 9/2010 | |
| JP | 2010-241801 A | 10/2010 | |
| KR | 10 2010-0079458 A | 7/2010 | |
| KR | 10-2010-0094415 A | 8/2010 | |
| KR | 10 2010-0099460 A | 9/2010 | |
| KR | 10-2010-0105501 A | 9/2010 | |
| KR | 10 2011-0015836 A | 2/2011 | |
| KR | 10 2011-0048840 A | 5/2011 | |
| KR | 10-2012-0034648 A | 4/2012 | |
| KR | 10-2012-0057561 A | 6/2012 | |
| WO | WO 01/39234 A2 | 5/2001 | |
| WO | WO 01/41512 A1 | 6/2001 | |
| WO | WO 01/72927 A1 | 10/2001 | |
| WO | WO 03/078541 A1 | 9/2003 | |
| WO | WO 03/080760 A1 | 10/2003 | |
| WO | WO 2006/025186 A1 | 3/2006 | |
| WO | WO 2006/049013 A1 | 5/2006 | |
| WO | WO 2006/128800 A1 | 12/2006 | |
| WO | WO 2007/069569 A1 | 6/2007 | |
| WO | WO-2007/119816 A1 | 10/2007 | |
| WO | WO 2008-090912 A1 | 7/2008 | |
| WO | WO 2008-090912 A1 | 7/2008 | |
| WO | WO 2008/127057 A1 | 10/2008 | |
| WO | WO-2008/156105 A1 | 12/2008 | |
| WO | WO 2009/031855 A1 | 3/2009 | |
| WO | WO 2009/085344 A1 | 7/2009 | |
| WO | WO 2010/044342 A1 | 4/2010 | |
| WO | WO 2010/074439 A1 | 7/2010 | |
| WO | WO 2011-019156 A1 | 2/2011 | |
| WO | WO 2011-055934 A2 | 5/2011 | |
| WO | WO 2011/081061 A1 | 7/2011 | |
| WO | WO 2011/081286 A2 | 7/2011 | |
| WO | WO 2011/108707 A1 | 9/2011 | |
| WO | WO 2011/125680 A1 | 10/2011 | |
| WO | WO 2011/132683 A1 | 10/2011 | |
| WO | WO 2011/132684 A1 | 10/2011 | |
| WO | WO 2011/139055 A1 | 11/2011 | |
| WO | WO 2011/148909 A1 | 12/2011 | |
| WO | WO 2011/155508 A1 | 12/2011 | |
| WO | WO 2012/014841 A1 | 2/2012 | |

OTHER PUBLICATIONS

Tang, et al.; Organic electroluminescent diodes; Applied Physics Letters; Sep. 21, 1987; pp. 913-915; vol. 51, No. 12; American Institute of Physics; USA.
O'Brien, et al.; Improved energy transfer in electrophosphorescent devices; Applied Physics Letters; Jan. 18, 1999; pp. 442-444; vol. 74, No. 3; American Institute of Physics; USA.
Baldo, et al.; Very high-efficiency green organic light-emitting devices based on electrophosphorescence; Applied Physics Letters; Jul. 5, 1999; pp. 4-6; vol. 75, No. 1; American Institute of Physics; USA.
International Search Report in PCT/KR2011/003235, dated Feb. 6, 2012 (Kim, et al.).
M. Carrad, et al., "Improved stability of interfaces in organic light emitting diodes with high $T_g$ materials and self-assembled monolayers", Thin Solid Films 352 (1999) pp. 189-194.
Search Report mailed Oct. 24, 2014 in corresponding European Patent Application No. 11777536.1.
Office Action mailed Mar. 26, 2013 in corresponding Chinese Patent Application No. 201180022469X.

(56) References Cited

OTHER PUBLICATIONS

Search Report dated Oct. 10, 2015 in corresponding Chinese Patent Application No. 201180022469.

* cited by examiner

COMPOUND FOR ORGANIC OPTOELECTRONIC DEVICE, ORGANIC LIGHT EMITTING DIODE INCLUDING THE SAME AND DISPLAY INCLUDING THE ORGANIC LIGHT EMITTING DIODE

CROSS-REFERENCE TO RELATED APPLICATIONS

This application is a continuation-in-part of pending International Application No. PCT/KR2011/003235, entitled "COMPOUND FOR ORGANIC OPTOELECTRONIC DEVICE, ORGANIC LIGHT EMITTING DIODE INCLUDING THE SAME, AND DISPLAY INCLUDING THE ORGANIC LIGHT EMITTING DIODE," which was filed on Apr. 29, 2011, the entire contents of which are hereby incorporated by reference.

This application claims priority to and the benefit of Korean Patent Application No. 10-2010-0106077, filed in the Korean Intellectual Property Office on Oct. 28, 2010, and Korean Patent Application No. 10-2010-0041466, filed in the Korean Intellectual Property Office on May 3, 2010, the entire contents of each of which are incorporated herein by reference.

BACKGROUND OF THE INVENTION

1. Field

Embodiments relate to a compound for an organic optoelectronic device, an organic light emitting diode including the same, and a display including the organic light emitting diode.

2. Description of the Related Art

An organic optoelectronic device may be used for transforming photo-energy to electrical energy or, conversely, electrical energy to photo-energy.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

SUMMARY

Embodiments are directed to a compound for an organic optoelectronic device, the compound being represented by the following Chemical Formula 1:

[Chemical Formula 1]

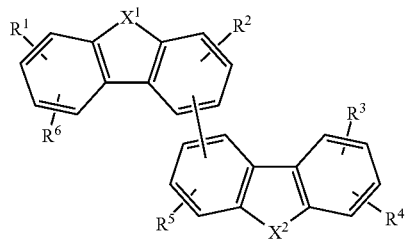

In Chemical Formula 1,
$X^1$ and $X^2$ may each independently be selected from the group of —$NR'$—, —O—, —Se—, —P—, and —S—, wherein R' may be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties, and at least one of $R^1$ to $R^6$ or R' may be a substituted or unsubstituted C2 to C30 heteroaryl group, the C2 to C30 heteroaryl group having electronic properties.

The substituted or unsubstituted C2 to C30 heteroaryl group that has electronic properties may be selected from the group of a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted phthalazinyl group, a substituted or unsubstituted benzoquinolinyl group, a substituted or unsubstituted benzoisoquinolinyl group, a substituted or unsubstituted quinoxalinyl group, a substituted or unsubstituted quinazolinyl group, a substituted or unsubstituted acridinyl group, a substituted or unsubstituted phenanthrolinyl group, and a substituted or unsubstituted phenazinyl group.

The compound may be represented by the following Chemical Formula 2:

[Chemical Formula 2]

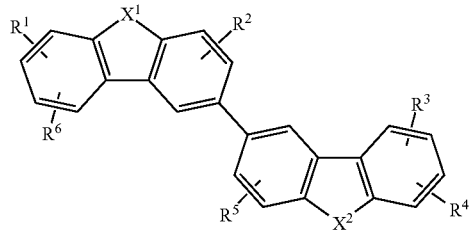

In Chemical Formula 2,
$X^1$ and $X^2$ may each independently be selected from the group of —$NR'$—, —O—, —Se—, —P—, and —S—, wherein R' may be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties, and at least one of $R^1$ to $R^6$ or R' may be a substituted or unsubstituted C2 to C30 heteroaryl group, the C2 to C30 heteroaryl group having electronic properties.

The compound may be represented by the following Chemical Formula A or A-1:

[Chemical Formula A]

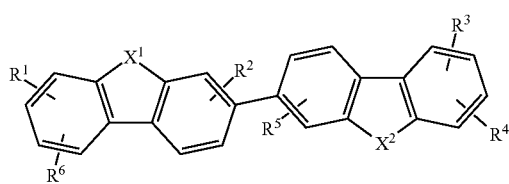

[Chemical Formula A-1]

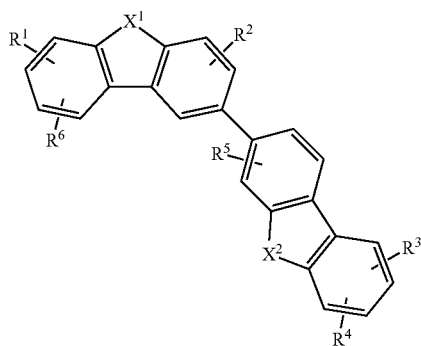

In Chemical Formulae A and A-1, $X^1$ and $X^2$ may each independently be selected from the group of —NR'—, —O—, —Se—, —P—, and —S—, wherein R' may be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties, and at least one of $R^1$ to $R^6$ or R' may be a substituted or unsubstituted C2 to C30 heteroaryl group, the C2 to C30 heteroaryl group having electronic properties.

The compound may be represented by the following Chemical Formula B:

[Chemical Formula B]

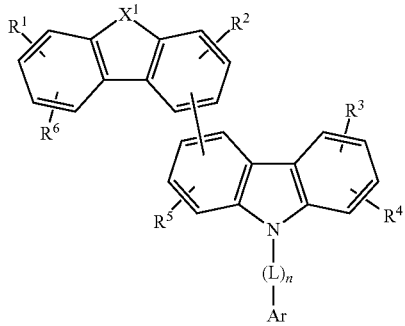

In Chemical Formula B, $X^1$ may be selected from the group of —O—, —Se—, —P—, and —S—, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, Ar may be a substituted or unsubstituted C2 to C30 heteroaryl group, the C2 to C30 heteroaryl group having electronic properties, L may be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, and n may be an integer ranging from 1 to 2.

The compound may be represented by the following Chemical Formula B-1 or B-2:

[Chemical Formula B-1]

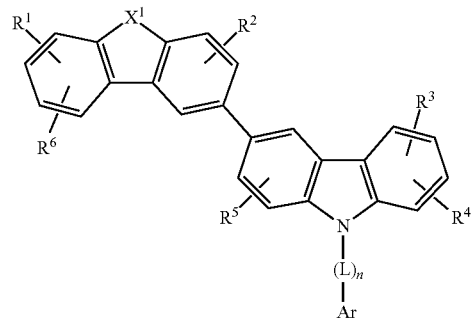

[Chemical Formula B-2]

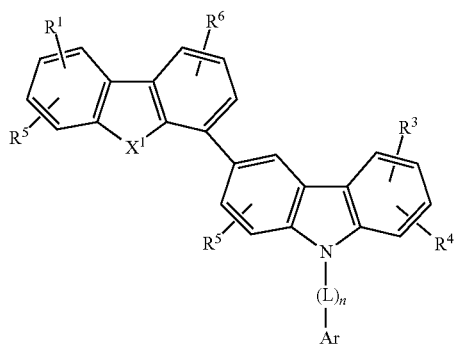

In Chemical Formulae B-1 and B-2, $X^1$ may be selected from the group of —O—, —Se—, —P—, and —S—, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, Ar may be a substituted or unsubstituted C2 to C30 heteroaryl group, the C2 to C30 heteroaryl group having electronic properties, L may be selected from the group of a single bond, a substituted or unsubstituted C2 to C10 alkenylene group, a substituted or unsubstituted C2 to C10 alkynylene group, a substituted or unsubstituted C6 to C30 arylene group, and a substituted or unsubstituted C2 to C30 heteroarylene group, and n may be an integer ranging from 1 to 2.

Embodiments are also directed to a compound for an organic optoelectronic device, the compound being represented by the following Chemical Formula S-1:

[Chemical Formula S-1]

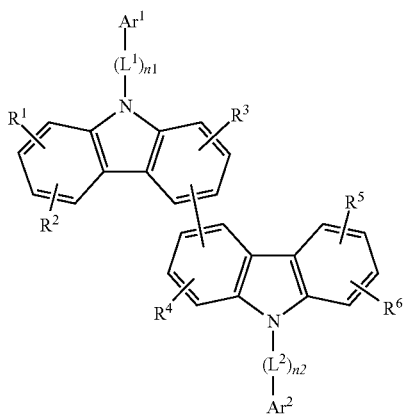

In Chemical Formula S-1, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ and $L^2$ may each independently be selected from the group of a single bond, a substituted or unsubstituted C2 to C10 alkenylene group, a substituted or unsubstituted C2 to C10 alkynylene group, a substituted or unsubstituted C6 to C30 arylene group, and a substituted or unsubstituted C2 to C30 heteroarylene group, n1 and n2 may each independently be an integer ranging from 1 to 2, $Ar^1$ and $Ar^2$ may each independently be selected from the group of a substituted or unsubstituted C6 to C30 aryl group and a substituted or unsubstituted C2 to C30 heteroaryl group, the C2 to C30 heteroaryl group having electronic properties, and one of $Ar^1$ and $Ar^2$ may be a substituted or unsubstituted C2 to C30 heteroaryl group, the C2 to C30 heteroaryl group having electronic properties.

The compound may be represented by the following Chemical Formula S-2:

[Chemical Formula S-2]

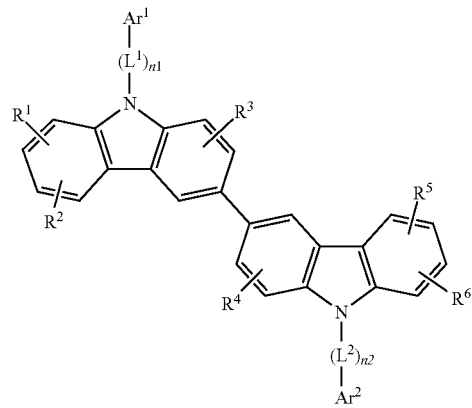

In Chemical Formula S-2, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ and $L^2$ may each independently be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 and n2 may each independently be an integer ranging from 1 to 2, $Ar^1$ and $Ar^2$ may each independently be selected from the group of a substituted or unsubstituted C6 to C30 aryl group and a substituted or unsubstituted C2 to C30 heteroaryl group, the C2 to C30 heteroaryl group having electronic properties, and one of $Ar^1$ and $Ar^2$ may be a substituted or unsubstituted C2 to C30 heteroaryl group, the C2 to C30 heteroaryl group having electronic properties.

The compound may be represented by the following Chemical Formula S-3:

[Chemical Formula S-3]

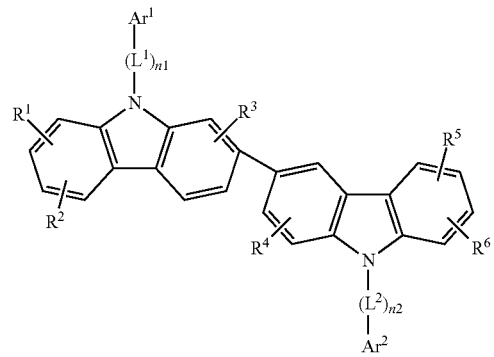

In Chemical Formula S-3, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ and $L^2$ may each independently be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 and n2 may each independently be an integer ranging from 1 to 2, $Ar^1$ and $Ar^2$ may each independently be selected from the group of a substituted or unsubstituted C6 to C30 aryl group and a substituted or unsubstituted C2 to C30 heteroaryl group, the C2 to C30 heteroaryl group having electronic properties, and one of $Ar^1$ and $Ar^2$ may be a substituted or unsubstituted C2 to C30 heteroaryl group, the C2 to C30 heteroaryl group having electronic properties.

The compound may be represented by the following Chemical Formula S-4:

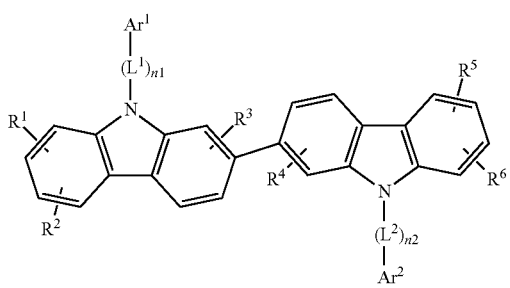

[Chemical Formula S-4]

In Chemical Formula S-4, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ and $L^2$ may each independently be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 and n2 may each independently be an integer ranging from 1 to 2, $Ar^1$ and $Ar^2$ may each independently be selected from the group of a substituted or unsubstituted C6 to C30 aryl group and a substituted or unsubstituted C2 to C30 heteroaryl group, the C2 to C30 heteroaryl group having electronic properties, and one of $Ar^1$ and $Ar^2$ may be a substituted or unsubstituted C2 to C30 heteroaryl group, the C2 to C30 heteroaryl group having electronic properties.

The compound may be represented by the following Chemical Formula S-5:

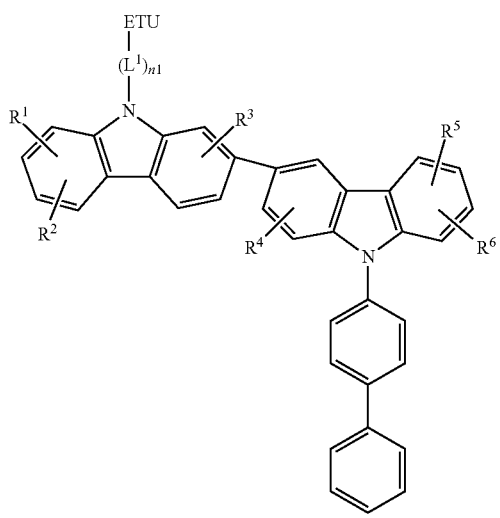

[Chemical Formula S-5]

In Chemical Formula S-5, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ may be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 may be an integer ranging from 1 to 2, and ETU may be a substituted or unsubstituted C2 to C30 heteroaryl group, the C2 to C30 heteroaryl group having electronic properties.

The compound may be represented by the following Chemical Formula S-6:

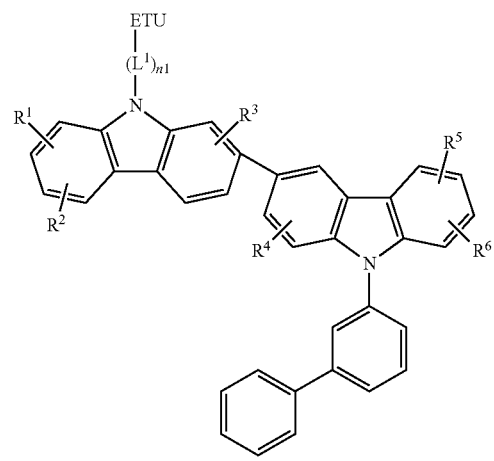

[Chemical Formula S-6]

In Chemical Formula S-6, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ may be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 may be an integer ranging from 1 to 2, and ETU may be a substituted or unsubstituted C2 to C30 heteroaryl group, the C2 to C30 heteroaryl group having electronic properties.

The compound may be represented by the following Chemical Formula S-7:

[Chemical Formula S-7]

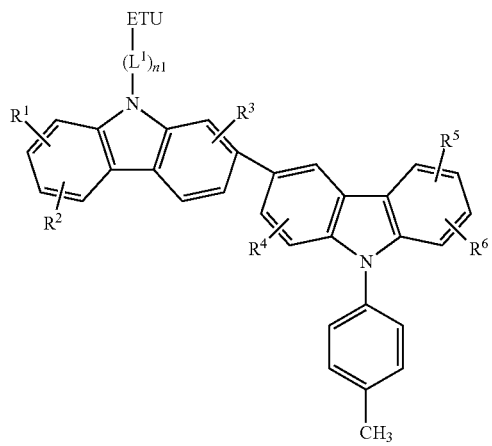

In Chemical Formula S-7, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ may be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 may be an integer ranging from 1 to 2, and ETU may be a substituted or unsubstituted C2 to C30 heteroaryl group, the C2 to C30 heteroaryl group having electronic properties.

The substituted or unsubstituted C2 to C30 heteroaryl group that has electronic properties may be represented by one of the following Chemical Formulae E-1 to E-5:

[Chemical Formula E-1]

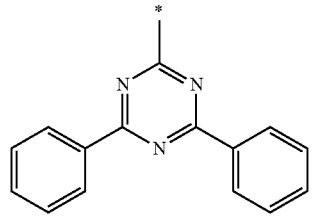

[Chemical Formula E-2]

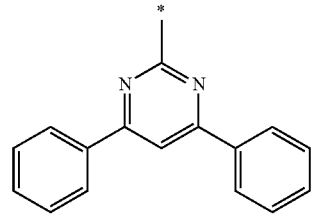

[Chemical Formula E-3]

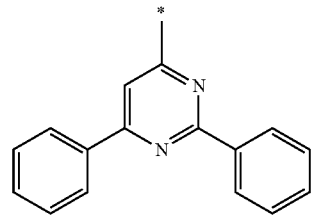

[Chemical Formula E-4]

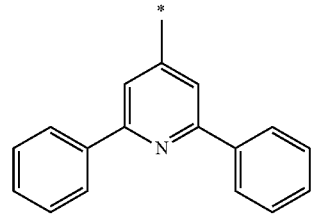

[Chemical Formula E-5]

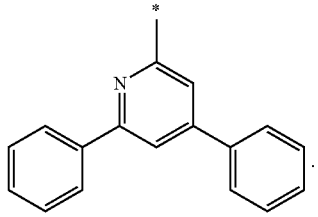

Embodiments are also directed to a compound for an organic optoelectronic device represented by one of the following Chemical Formulae A-19, A-20, A-22, A-23, D-11, D-14, D-15, D-19, D-24, D-25, D-35, D-36, D-40, D-41, D-45, D-46, D-65, or D-66:

[Chemical Formula A-19]

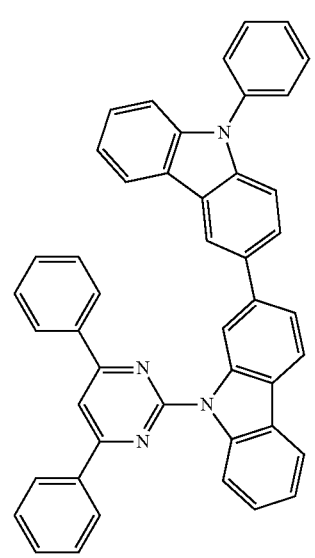
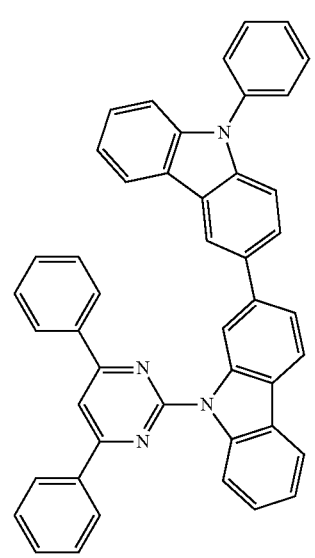

[Chemical Formula A-20]
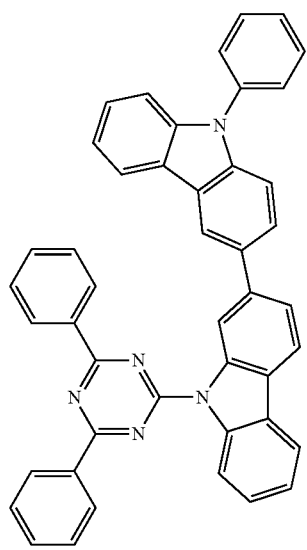
[Chemical Formula A-22]
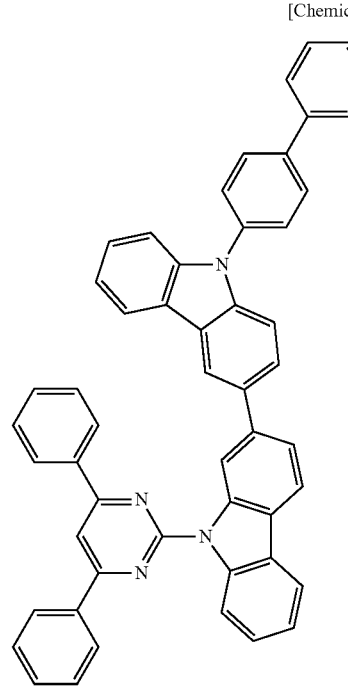
[Chemical Formula A-23]
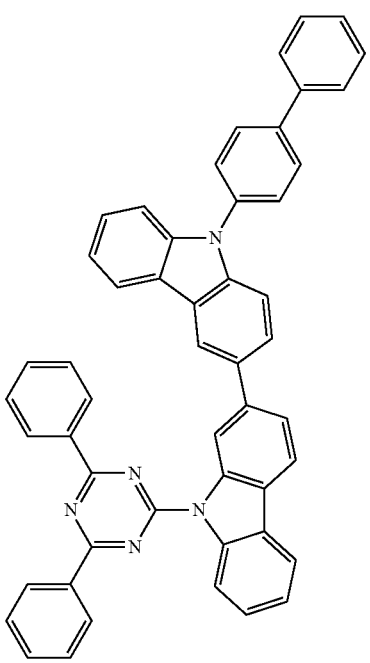
[D-11]
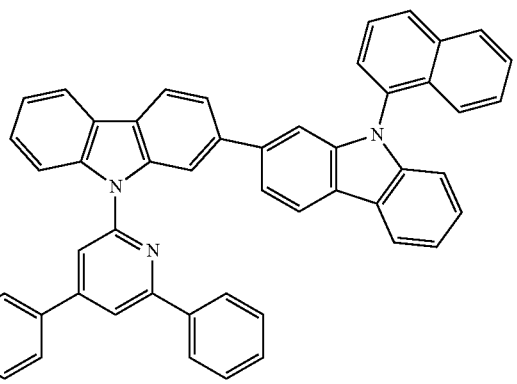
[D-14]
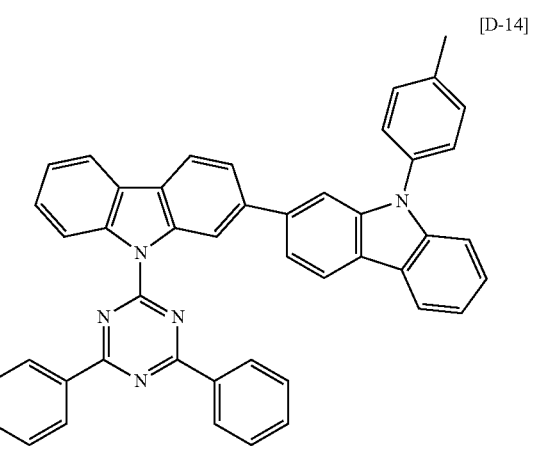

[D-15]
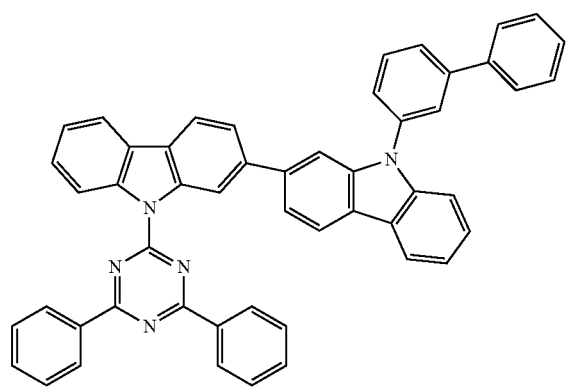
[D-19]
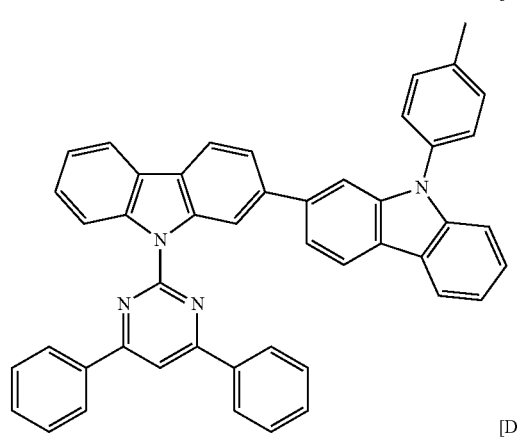
[D-24]
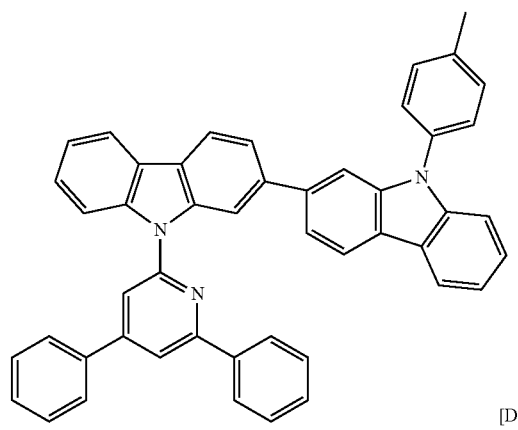
[D-25]
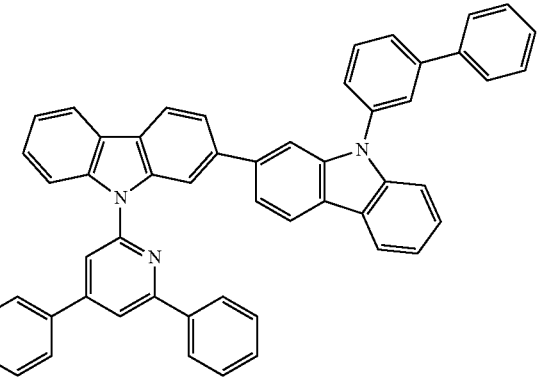
[D-35]
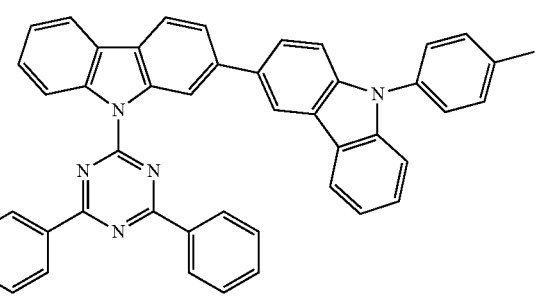
[D-36]
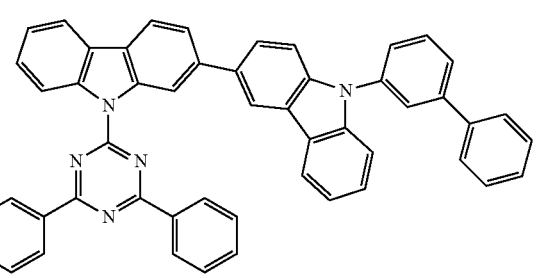
[D-40]
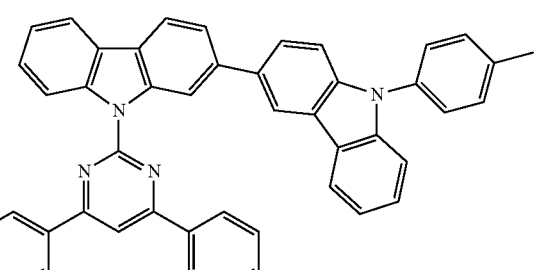
[D-41]
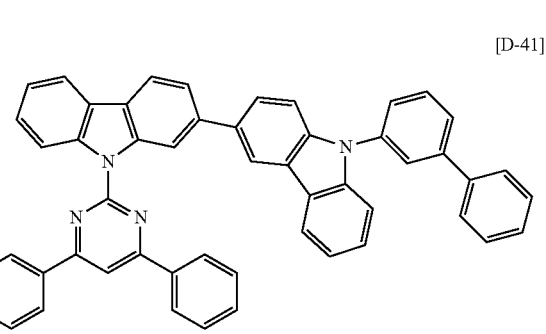
[D-45]
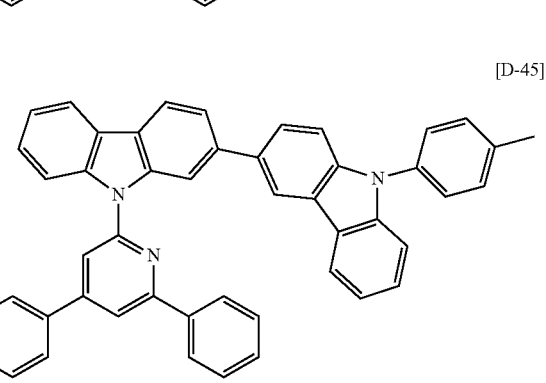

[D-46]

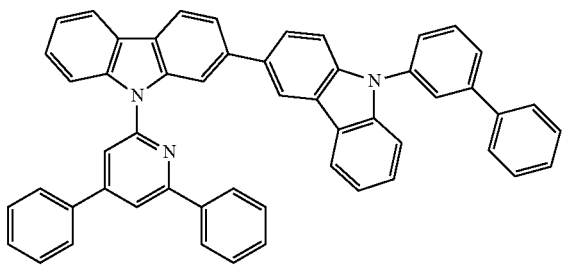

[D-65]

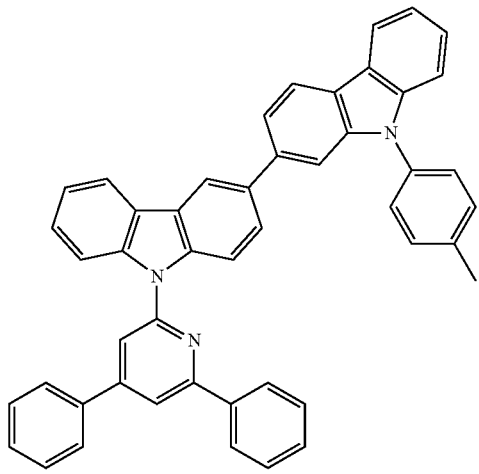

[D-66]

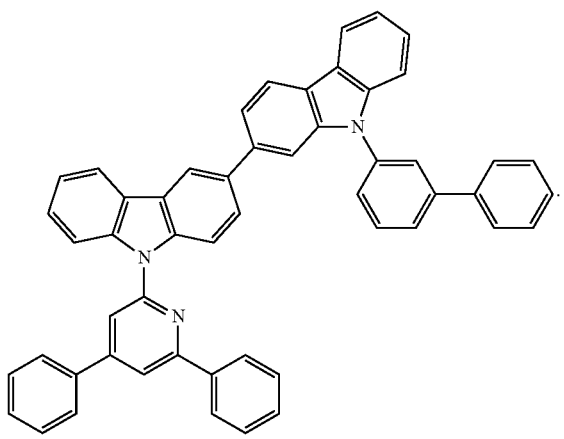

Embodiments are also directed to an organic light emitting diode, including: an anode; a cathode; and at least one organic thin layer between the anode and the cathode, the at least one organic thin layer including a compound for an organic optoelectronic device according to an embodiment.

The compound may be included in an emission layer.

The compound may be used as a phosphorescent or fluorescent host material in the emission layer.

The compound may be used as a fluorescent blue dopant material in the emission layer.

Embodiments are also directed to a display device including an organic light emitting diode according to an embodiment.

BRIEF DESCRIPTION OF THE DRAWINGS

Features will become apparent to those of skill in the art by describing in detail example embodiments with reference to the attached drawings in which.

DETAILED DESCRIPTION

Figure 1:
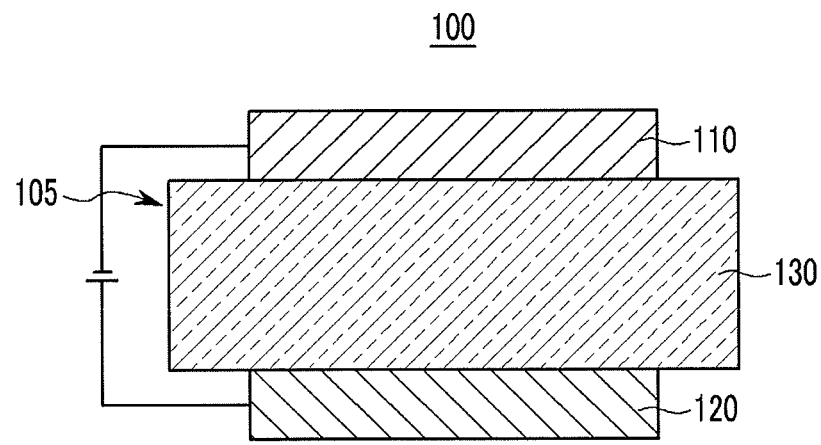
FIGS. 1 to 5 illustrate cross-sectional views showing organic light emitting diodes according to various embodiments of the present invention including compound for an organic optoelectronic device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, when specific definition is not otherwise provided, the term "substituted" refers to one substituted with deuterium, a halogen, a hydroxyl group, an amino group, a substituted or unsubstituted C1 to C20 amine group, a nitro group, a substituted or unsubstituted C3 to C40 silyl group, a C1 to C30 alkyl group, a C1 to C10 an alkylsilyl group, a C3 to C30 cycloalkyl group, a C6 to C30 aryl group, a C1 to C20 alkoxy group, a fluoro group, a C1 to C10 trifluoro alkyl group such as trifluoromethyl group, or a cyano group, instead of hydrogen of a compound.

As used herein, when specific definition is not otherwise provided, the term "hetero" refers to one including 1 to 3 hetero atoms selected from the group of N, O, S, and P, and remaining carbons in one functional group.

As used herein, when a definition is not otherwise provided, the term "combination thereof" refers to at least two substituents bound to each other by a linker, or at least two substituents condensed to each other.

As used herein, when a definition is not otherwise provided, the term "alkyl group" refers to an aliphatic hydrocarbon group. The alkyl group may be a "saturated alkyl group" that does not include a double bond or triple bond. In addition, the alkyl group may be branched, linear, or cyclic.

As used herein, when a definition is not otherwise provided, the term "alkenyl group" may be an "unsaturated aliphatic hydrocarbon group" having at least of a double bond. For example, the alkenyl group may be an ethenyl group, a propenyl group, a butenyl group, and the like.

The alkyl group may be a C1 to C20 alkyl group. The alkyl group may be a C1 to C10 medium-sized alkyl group. The alkyl group may be a C1 to C6 lower alkyl group.

For example, a C1 to C4 alkyl group may have 1 to 4 carbon atoms and may be selected from the group of methyl, ethyl, propyl, iso-propyl, n-butyl, iso-butyl, sec-butyl, and tert-butyl.

For example, the alkyl group may be a methyl group, an ethyl group, a propyl group, an isopropyl group, a butyl group, an isobutyl group, a tert-butyl group, a pentyl group, a hexyl group, a cyclopropyl group, a cyclobutyl group, a cyclopentyl group, a cyclohexyl group, and the like.

"Aromatic group" is a cyclic functional group where all ring atoms have p-orbitals, and these p-orbitals form conjugation. Specific examples are an aryl group and a heteroaryl group.

"Aryl group" includes monocyclic or fused ring polycyclic (i.e., rings sharing adjacent pairs of carbon atoms) aryl groups.

"Heteroaryl group" may refer to an aryl group including 1 to 3 hetero atoms selected from the group of N, O, S, and P, and remaining carbons. The aryl group may be a fused ring cyclic group where each cycle may include the 1 to 3 heteroatoms.

"Spiro structure" may refer to a plurality of cyclic structures having a contact point of one carbon. The spiro structure may include a compound having a spiro structure or a substituent having a spiro structure.

In this specification, hole properties refer to a characteristic that holes from the positive electrode are injected into the emission layer and transported in the emission layer due to conductive characteristic according to HOMO level.

In this specification, electronic properties refer to a characteristic that electrons from the negative electrode are injected into the emission layer and transported in the emission layer due to conductive characteristics according to LUMO level.

A compound for an organic optoelectronic device according to an embodiment includes a core part including two carbazole or carbazole-based derivatives bonded to each other and a substituent selectively bonded to the core part.

At least one of the substituents bonded to the core part may be a substituent having excellent electronic properties.

The compound may be used for an emission layer, and may have hole properties of its carbazole structure complemented with electronic properties. In an embodiment, the compound may be used as a host material for an emission layer.

In an embodiment, the compound for an organic optoelectronic device includes a core part and various substituents at the core part, and thus may have various energy band gaps. The compound may be used in, e.g., an electron injection layer (EIL) and transport layer or a hole injection layer (HIL) and transport layer.

The compound may have an appropriate energy level depending on the substituents and thus may fortify electron transport capability of an organic photoelectric device and bring about excellent effects on efficiency and driving voltage. Also, the compound may have excellent electrochemical and thermal stability and thus improve a life-span characteristic during the operation of the organic photoelectric device.

According to an embodiment, a compound for an organic optoelectronic device is represented by the following Chemical Formula 1.

[Chemical Formula 1]

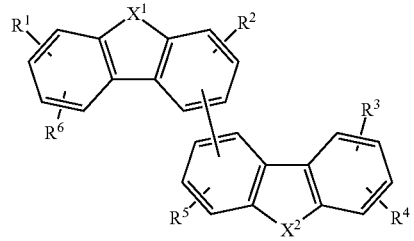

In Chemical Formula 1, $X^1$ and $X^2$ may each independently be selected from the group of —NR'—, —O—, —Se—, —P—, and —S—.

The R' may be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties.

The compound represented by the above Chemical Formula 1 may have a carbazole or carbazole-based derivative having an excellent bi-polar characteristic as a core.

$R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties. In an embodiment, at least one of $R^1$ to $R^6$ or R' is a substituted or unsubstituted C2 to C30 heteroaryl group, the C2 to C30 heteroaryl group having electronic properties.

A substituent having a π-bond (pi-bond) of the $R^1$ to $R^6$ and R' may increase a triplet energy band gap by controlling the total π-conjugation length of compound, and may be applied to the emission layer of organic photoelectric device, e.g., as a phosphorescent host.

In addition, an appropriate combination of the substituents may provide a compound having excellent thermal stability and/or resistance against oxidation.

An appropriate combination of the substituents may provide a compound having an asymmetric bipolar characteristic. The asymmetric bipolar characteristic may improve hole and electron transport capability and thus luminous efficiency and performance of a device. In addition, the substituents may be adjusted to make the structure of a compound bulky and thus decrease crystallinity of the compound. Accordingly, the compound having low crystallinity may improve life-span of a device.

In an embodiment, a substituent of the compound is a substituted or unsubstituted C2 to C30 heteroaryl group, the C2 to C30 heteroaryl group having electronic properties. The substituted or unsubstituted C2 to C30 heteroaryl group that has electronic properties may include one or more of a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted phthalazinyl group, a substituted or unsubstituted benzoquinolinyl group, a substituted or unsubstituted benzoisoquinolinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or the like.

In an embodiment, the compound represented by the above Chemical Formula 1 for an organic optoelectronic device may be represented by the following Chemical Formula 2.

[Chemical Formula 2]

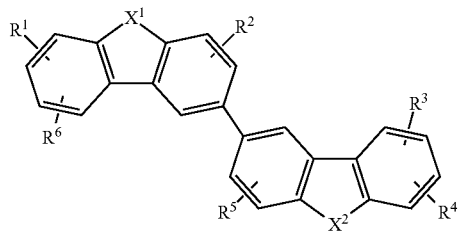

A carbazole or carbazole-based derivative as a core may be bonded as shown in the above Chemical Formula 2. The carbazole or carbazole-based derivative may be bonded where a precursor compound provides good reactivity, which may be advantageous for synthesis of the compound.

In the above Chemical Formula 1 or 2, $X^1$ and $X^2$ may be the aforementioned hetero atoms, and may be the same or different. In an implementation, $X^1$ and $X^2$ may be —NR'—.

In the above Chemical Formula 1 or 2, the substituted or unsubstituted C2 to C30 heteroaryl group that has electronic properties may be bonded at R' when $X^1$ is —NR'—.

The substituted or unsubstituted C2 to C30 heteroaryl group may be bonded at the R' and thus may minimize change of the conjugation length of the compound. Also, the substituted or unsubstituted C2 to C30 heteroaryl group may change an energy band and provide a substituent having electronic properties, i.e., electron transfer/transport characteristic, into the compound.

The compound for an organic optoelectronic device may be represented by the following Chemical Formula A or A-1.

[Chemical Formula A]

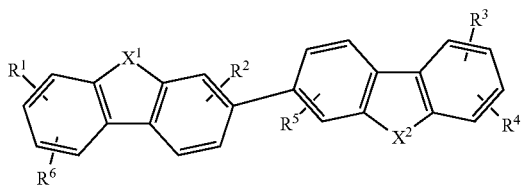

[Chemical Formula A-1]

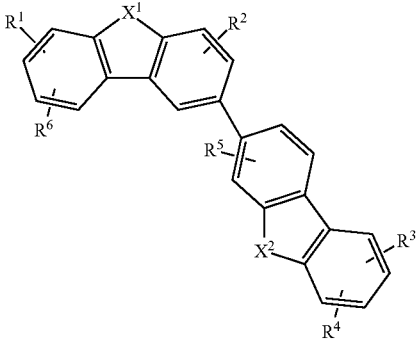

In the above Chemical Formulae A and A-1, $X^1$ and $X^2$ may each independently be selected from the group of —NR'—, —O—, —Se—, —P—, and —S— (wherein R' may be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties), $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties, and at least one of $R^1$ to $R^6$ or R' may be a substituted or unsubstituted C2 to C30 heteroaryl group, the C2 to C30 heteroaryl group having electronic properties.

The compound may have a different structure from the aforementioned compound represented by Chemical Formula 1 for an organic optoelectronic device when both of carbazolyl groups are bonded at different positions. The structure of the compound may result in non-planarization of molecular structure and limit the conjugation length of the compound. Thus, the structure may improved band gaps and triplet energy band gaps of the compound.

At least one of $X^1$ or $X^2$ may be —NR'—, wherein R' is selected from the group of a substituted or unsubstituted C2 to C30 heteroaryl group, the C2 to C30 heteroaryl group having electronic properties. $R^1$ to $R^6$ may each independently be selected from the group of hydrogen, deuterium, a substituted or unsubstituted C1 to C20 alkyl group, and a substituted or unsubstituted C6 to C30 aryl group.

At least one of $X^1$ or $X^2$ may be —NR'—, wherein R' is a substituted or unsubstituted triphenylenyl group.

In the compound, the triphenylenyl group has a bulky structure and may cause a resonance effect and thus may suppress a side reaction possibly occurring in a solid state and improve performance of an organic light emitting diode.

In addition, the triphenylenyl group may makes the compound bulky and thus may have an effect on lowering crystallinity and increasing life-span.

The triphenylenyl group may provide a wider band gap and high triplet excitation energy relative to other substituents and thus may be bonded with carbazole without undue decrease in the band gap or triplet excitation energy of the compound.

Specific substituents of the above Chemical Formula A and A-1 may be similar to those already discussed in connection with Chemical Formula 1 and will not be repeated.

The compound for an organic optoelectronic device may be represented by the following Chemical Formula B.

[Chemical Formula B]

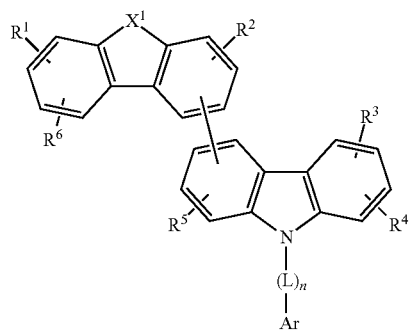

In Chemical Formula B, $X^1$ may be selected from the group of —O—, —Se—, —P—, and —S—, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, Ar may be a substituted or unsubstituted C2 to C30 heteroaryl group, the C2 to C30 heteroaryl group having electronic properties, L may be selected from the group of a single bond, a substituted or unsubstituted C2 to C10 alkenylene group, a substituted or unsubstituted C2 to C10 alkynylene group, a substituted or unsubstituted C6 to C30 arylene group, and a substituted or unsubstituted C2 to C30 heteroarylene group, and n may be an integer ranging from 1 to 2.

The compound represented by the above Chemical Formula B includes carbazole as one of the carbazole-based derivatives in the compound represented by the aforementioned Chemical Formula 1 and includes a carbazolyl-based derivative as the other carbazole-based derivative except for the carbazole. In an embodiment, a substituent having electronic properties is bonded to N of the carbazole. This structure has may not influence conjugation length of the compound while providing a substituent having electronic properties.

The compound for an organic optoelectronic device may be represented by the following Chemical Formula B-1 or B-2.

[Chemical Formula B-1]

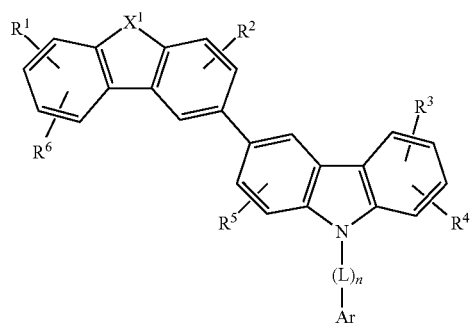

[Chemical Formula B-2]

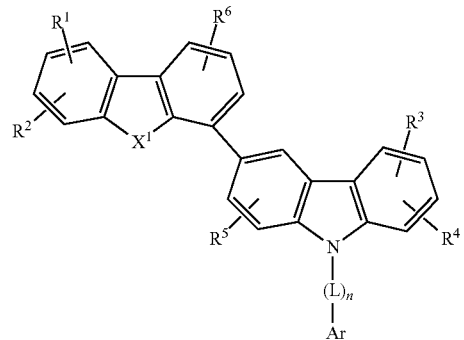

The Chemical Formulas B-1 and B-2 may be obtained by limiting positions of both carbazolyl-based derivatives in the above Chemical Formula B. This core structure may appropriately adjust HOMO energy of a compound and bring about easy synthesis of the compound.

Other substituents in the above Chemical Formulas B, B-1, and B-2 may be similar to those discussed above in connection with Chemical Formula 1 and thus will not be repeated.

The compound for an organic optoelectronic device may be represented by the following Chemical Formula C.

[Chemical Formula C]

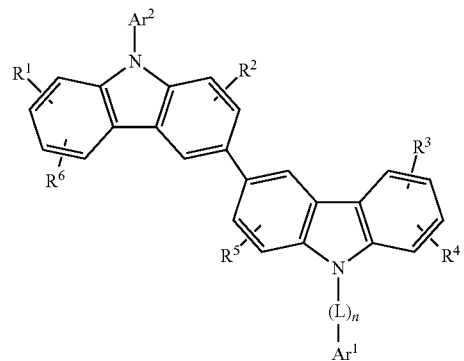

In Chemical Formula C, $R^1$ to $R^6$ and $Ar^2$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $Ar^1$ may be a substituted or unsubstituted C2 to C30 heteroaryl group, the C2 to C30 heteroaryl group having electronic properties, L may be selected from the group of a single bond, a substituted or unsubstituted C2 to C10 alkenylene group, a substituted or unsubstituted C2 to C10 alkynylene group, a substituted or unsubstituted C6 to C30 arylene group, and a substituted or unsubstituted C2 to C30 heteroarylene group, and n may be 1 or 2.

The above Chemical Formula C has a structure with carbazole for both of the carbazole-based derivatives, with the illustrated bonding positions of the carbazoles. In addition, a substituent having electronic properties may be bonded with the nitrogen of carbazole, e.g., through a linking group. This structure may provide an advantage of more widely and uniformly distributing LUMO energy, which may improve stability of the substituent having electronic properties and lowering LUMO energy band.

$Ar^2$ may be a substituted or unsubstituted triphenylenyl group. The triphenylenyl group is discussed above and will not be repeated. In addition, other substituents may be the same as aforementioned in Chemical Formula 1 and will not be repeated.

A compound for an organic optoelectronic device according to an embodiment is represented by the following Chemical Formula S-1.

[Chemical Formula S-1]

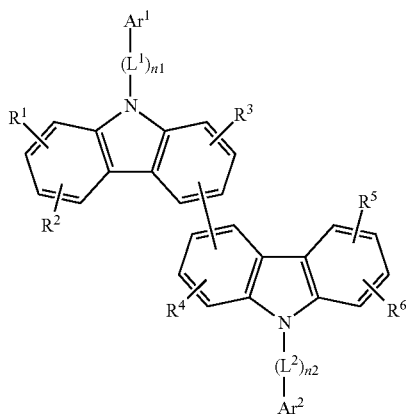

In Chemical Formula S-1, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ and $L^2$ may each independently be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 and n2 may each independently be an integer ranging from 1 to 2, $Ar^1$ and $Ar^2$ may each independently be selected from the group of a substituted or unsubstituted C6 to C30 aryl group and a substituted or unsubstituted C2 to C30 heteroaryl group, the C2 to C30 heteroaryl group having electronic properties, and one of $Ar^1$ and $Ar^2$ may be a substituted or unsubstituted C2 to C30 heteroaryl group, the C2 to C30 heteroaryl group having electronic properties.

The compound for an organic optoelectronic device may be represented by the following Chemical Formula S-2.

[Chemical Formula S-2]

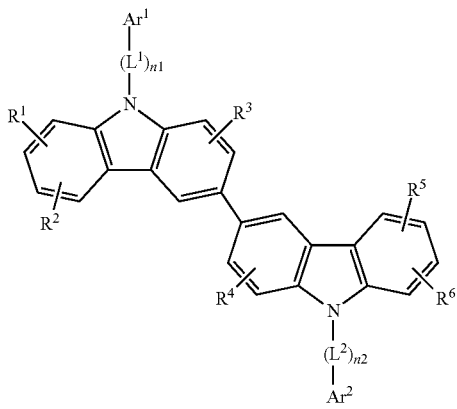

In Chemical Formula S-2, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ and $L^2$ may each independently be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 and n2 may each independently be an integer ranging from 1 to 2, $Ar^1$ and $Ar^2$ may each independently be selected from the group of a substituted or unsubstituted C6 to C30 aryl group and a substituted or unsubstituted C2 to C30 heteroaryl group, the C2 to C30 heteroaryl group having electronic properties, and one of $Ar^1$ and $Ar^2$ may be a substituted or unsubstituted C2 to C30 heteroaryl group, the C2 to C30 heteroaryl group having electronic properties.

The compound for an organic optoelectronic device may be represented by the following Chemical Formula S-3.

[Chemical Formula S-3]

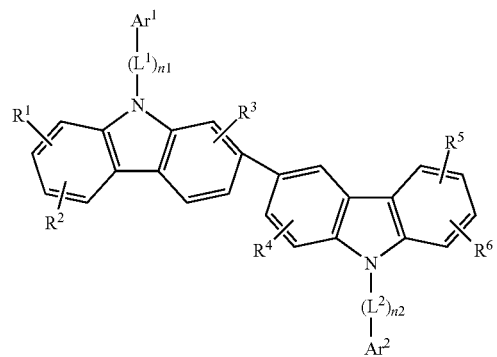

In Chemical Formula S-3, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ and $L^2$ may each independently be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 and n2 may each independently be an integer ranging from 1 to 2, $Ar^1$ and $Ar^2$ may each independently be selected from the group of a substituted or unsubstituted C6 to C30 aryl group and a substituted or unsubstituted C2 to C30 heteroaryl group, the C2 to C30 heteroaryl group having electronic properties, and one of $Ar^1$ and $Ar^2$ may be a substituted or unsubstituted C2 to C30 heteroaryl group, the C2 to C30 heteroaryl group having electronic properties.

The compound for an organic optoelectronic device may be represented by the following Chemical Formula S-4.

[Chemical Formula S-4]

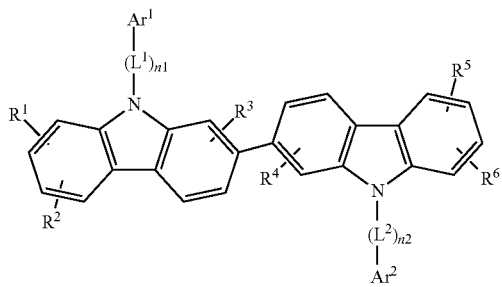

In Chemical Formula S-4, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ and $L^2$ may each independently be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 and n2 may each independently be an integer ranging from 1 to 2, $Ar^1$ and $Ar^2$ may each independently be selected from the group of a substituted or unsubstituted C6 to C30 aryl group and a substituted or unsubstituted C2 to C30 heteroaryl group, the C2 to C30 heteroaryl group having electronic properties, and one of $Ar^1$ and $Ar^2$ may be a substituted or unsubstituted C2 to C30 heteroaryl group, the C2 to C30 heteroaryl group having electronic properties.

The compound for an organic optoelectronic device may be represented by the following Chemical Formula S-5.

[Chemical Formula S-5]

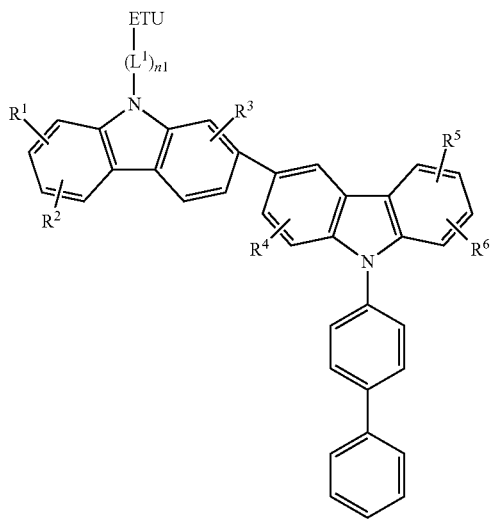

In Chemical Formula S-5, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ may be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 may be an integer ranging from 1 to 2, and ETU may be a substituted or unsubstituted C2 to C30 heteroaryl group, the C2 to C30 heteroaryl group having electronic properties.

The compound for an organic optoelectronic device may be represented by the following Chemical Formula S-6.

[Chemical Formula S-6]

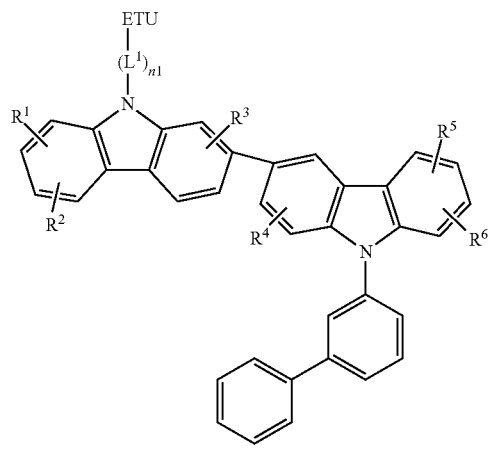

In Chemical Formula S-6, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ may be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 may be an integer ranging from 1 to 2, and ETU may be a substituted or unsubstituted C2 to C30 heteroaryl group, the C2 to C30 heteroaryl group having electronic properties.

The compound for an organic optoelectronic device may be represented by the following Chemical Formula S-7.

[Chemical Formula S-7]

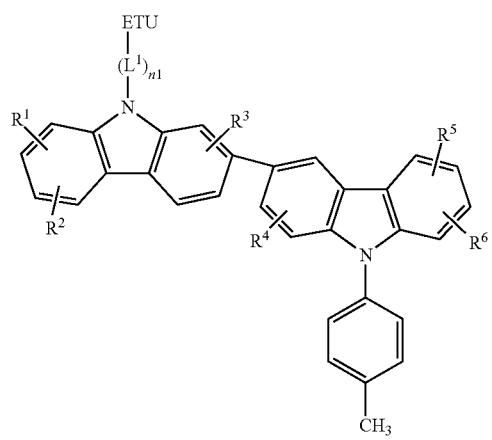

In Chemical Formula S-7, $R^1$ to $R^6$ may each independently be selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ may be selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 may be an integer ranging from 1 to 2, and ETU may be a substituted or unsubstituted C2 to C30 heteroaryl group, the C2 to C30 heteroaryl group having electronic properties.

The compound for an organic optoelectronic device may be represented by, e.g., the following Chemical Formulae D-1 to D-474.

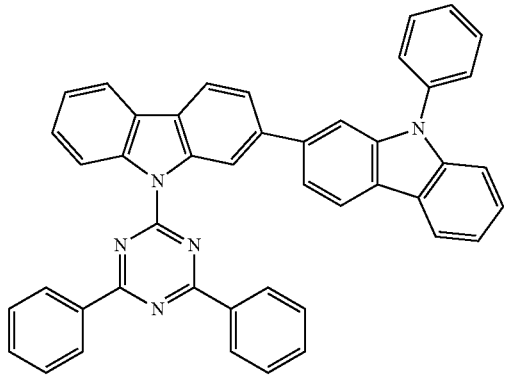

[D-1]

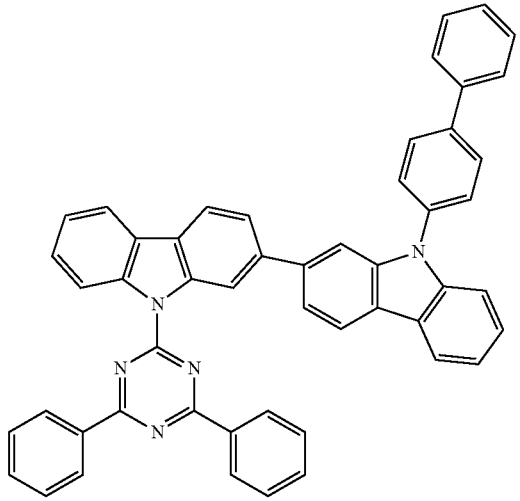

[D-2]

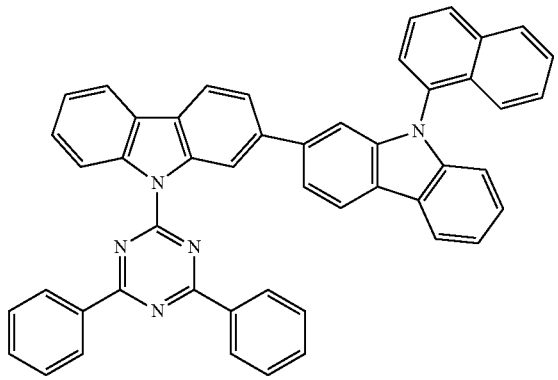

[D-3]

[D-4]
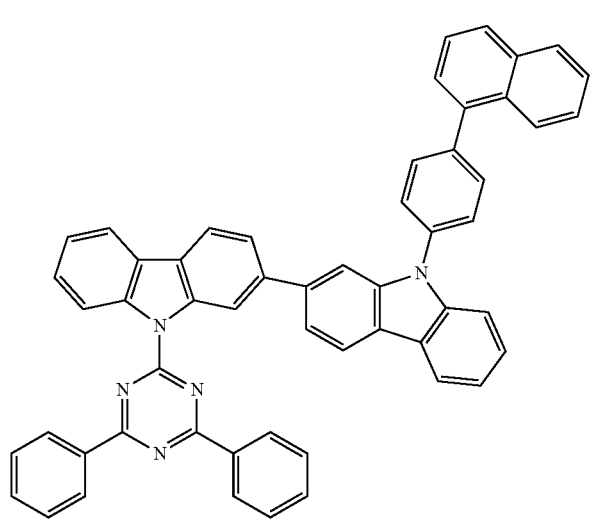
[D-5]
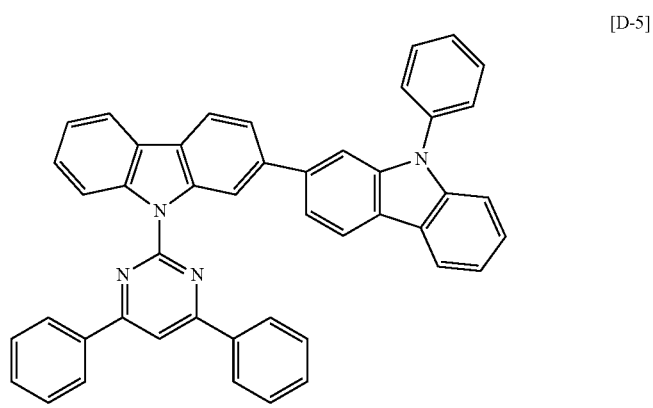
[D-6]
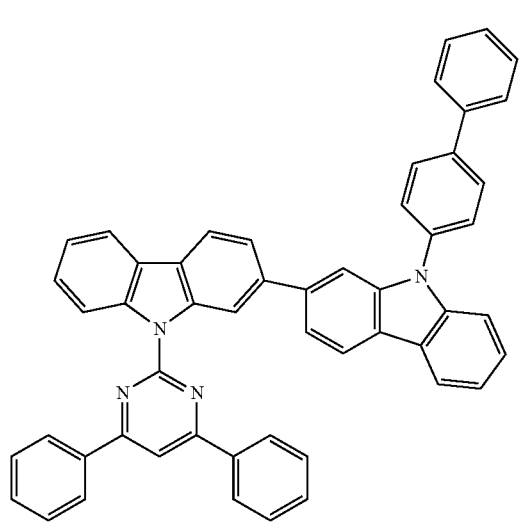

-continued
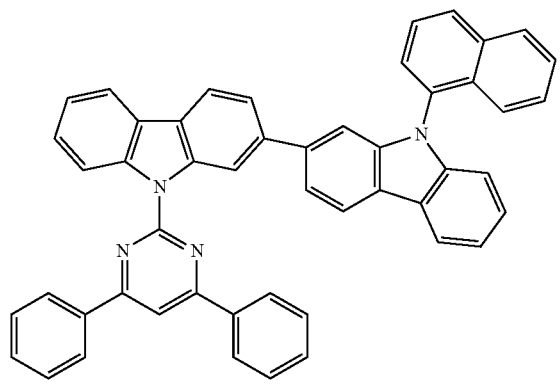
[D-7]
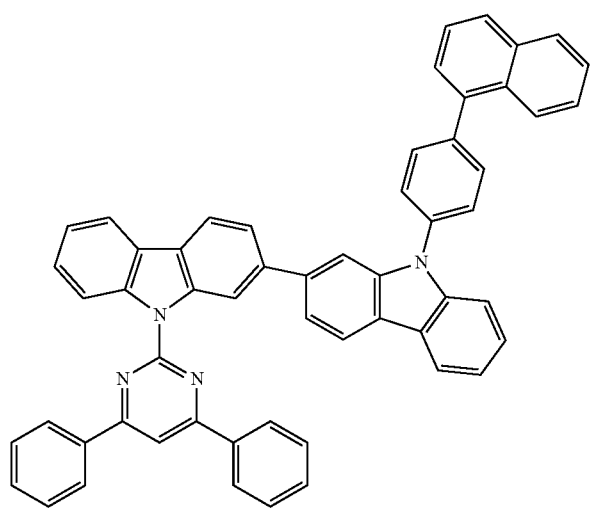
[D-8]
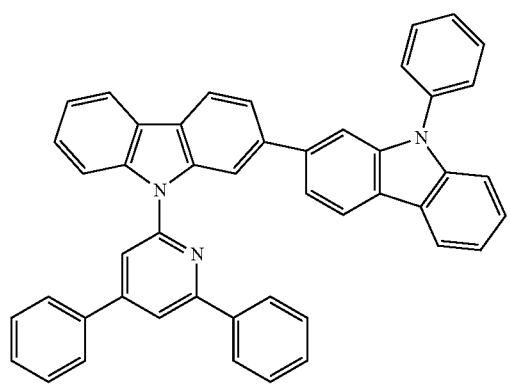
[D-9]

[D-10]
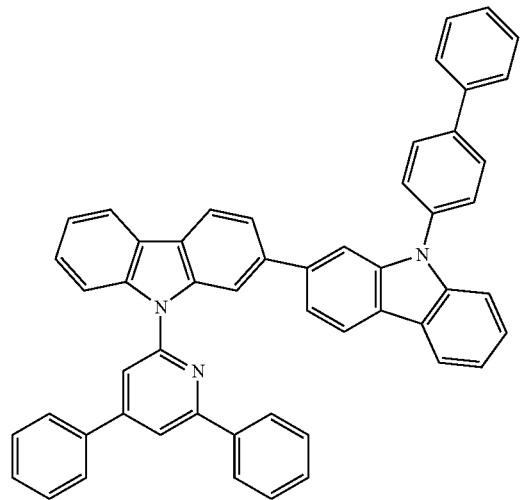
[D-11]
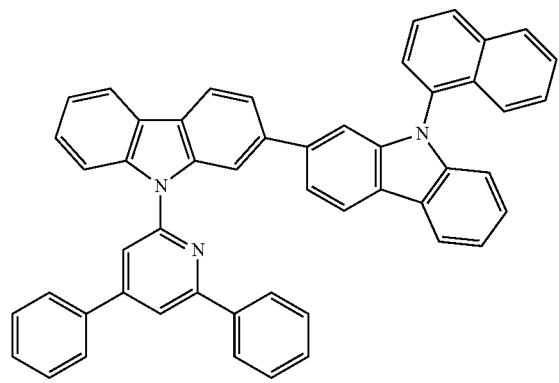
[D-12]
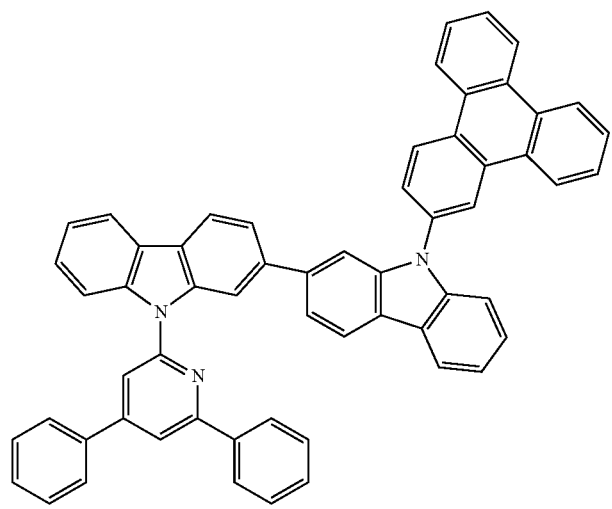

[D-13]
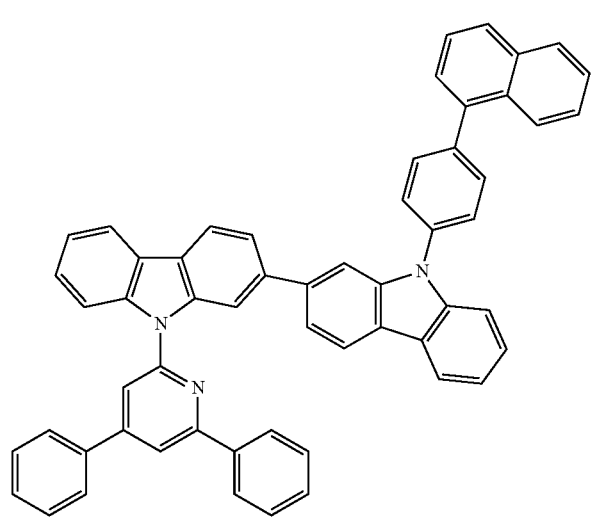
[D-14]
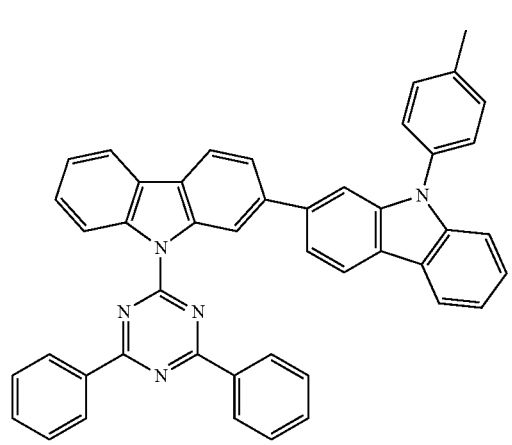
[D-15]
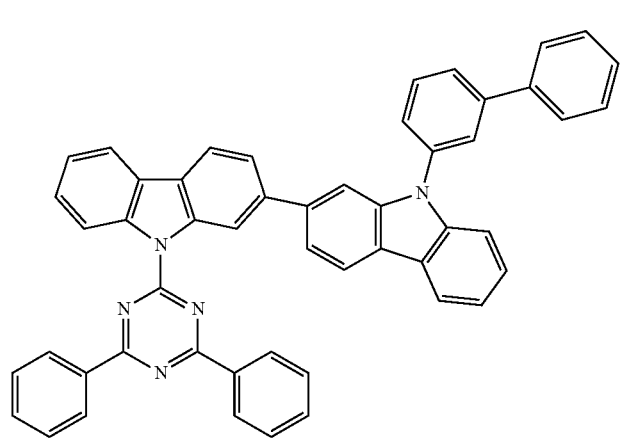

[D-16]
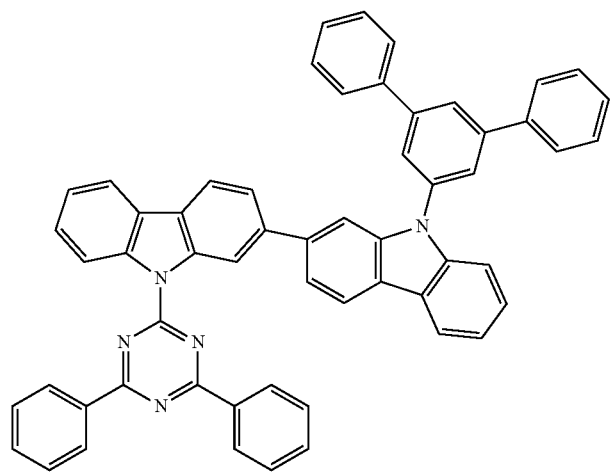
[D-17]
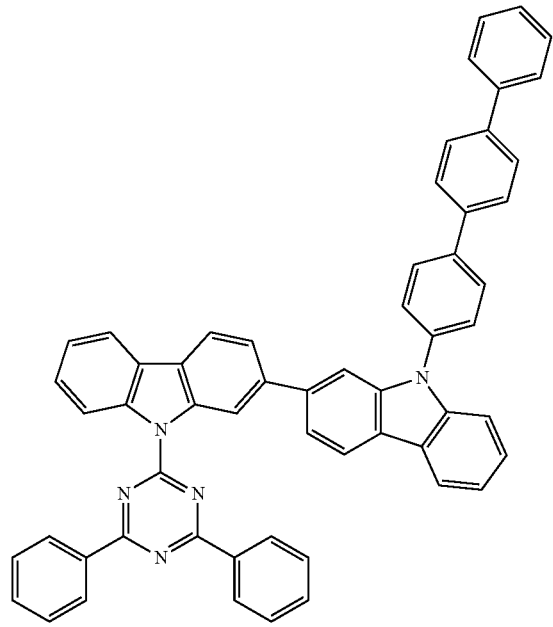
[D-18]
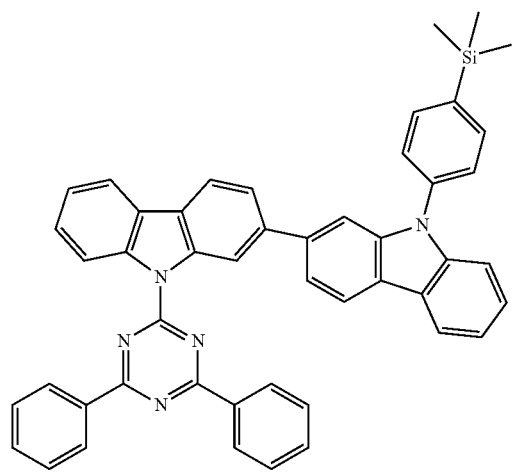

[D-19]
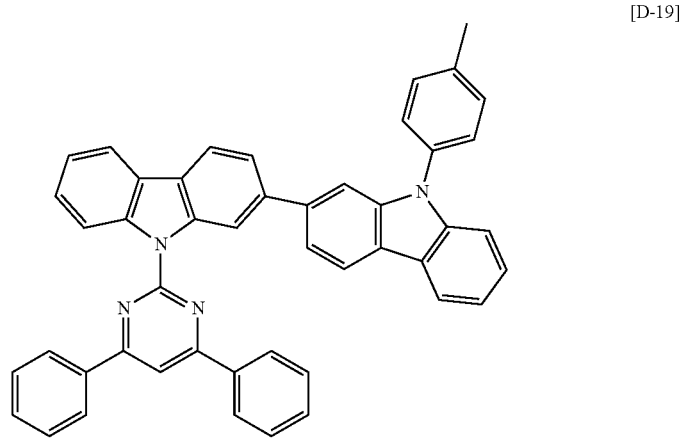
[D-20]
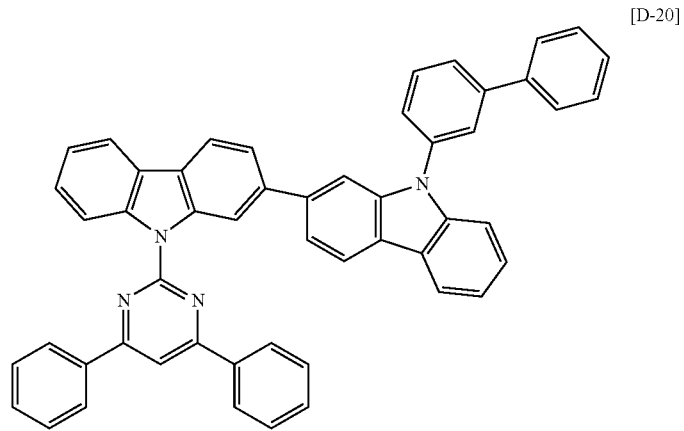
[D-21]
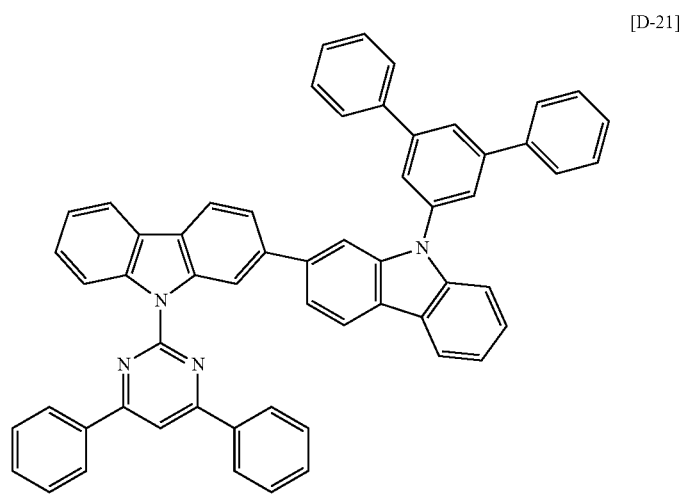

[D-22]
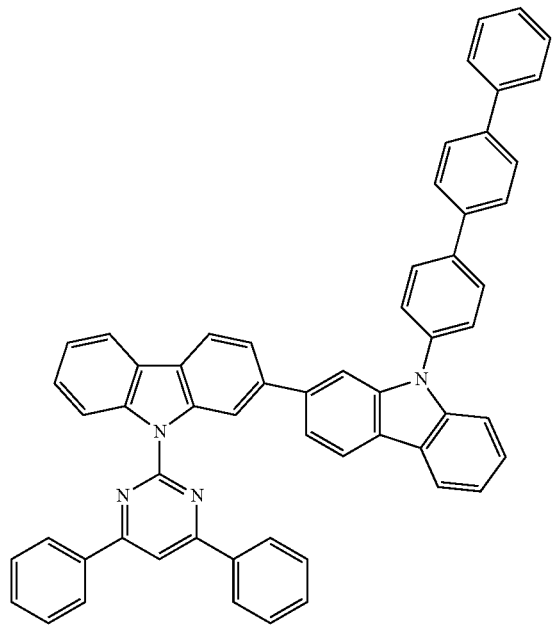
[D-23]
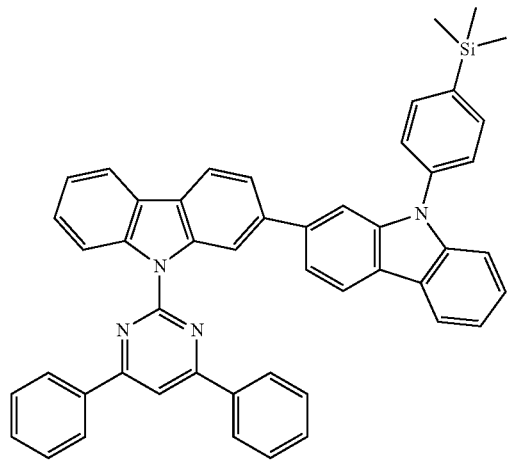
[D-24]
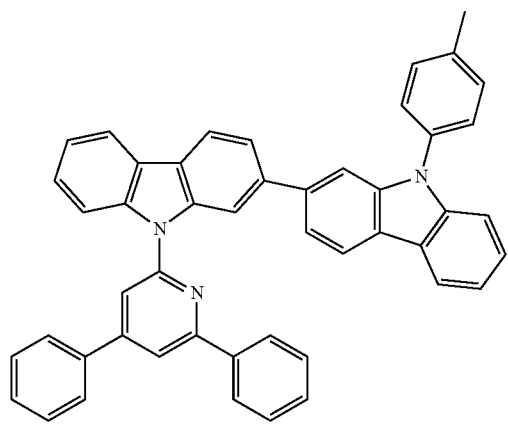

-continued
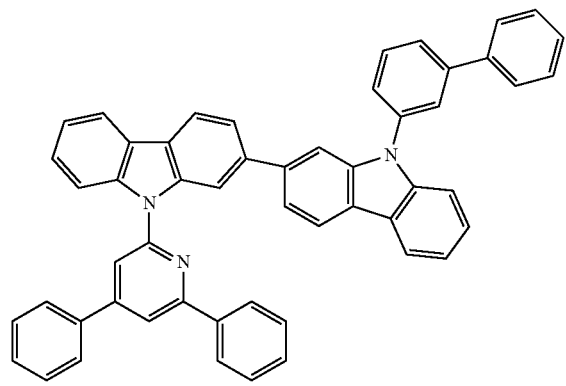
[D-25]
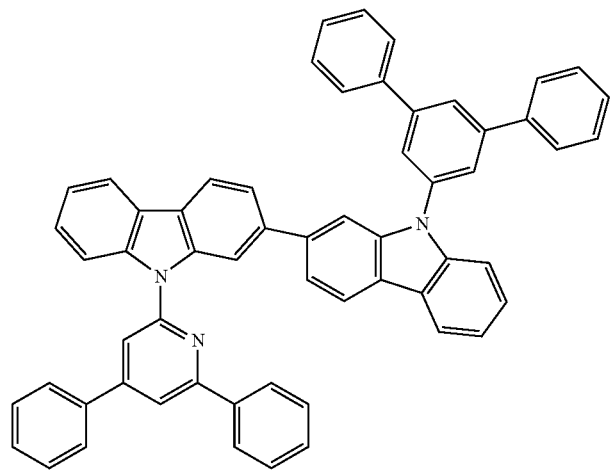
[D-26]
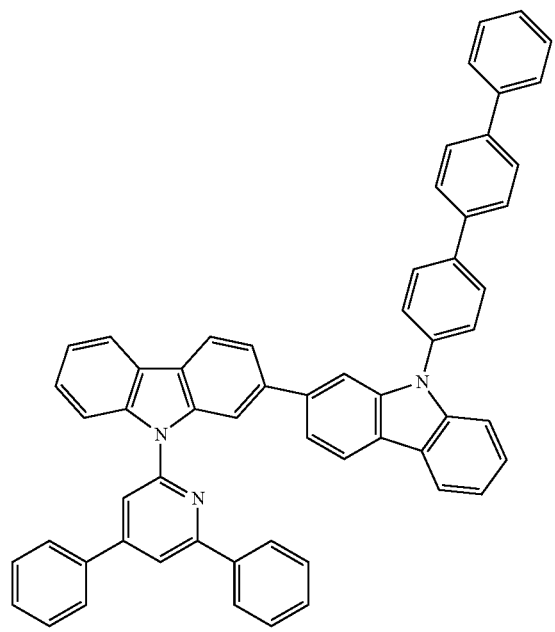
[D-27]

-continued
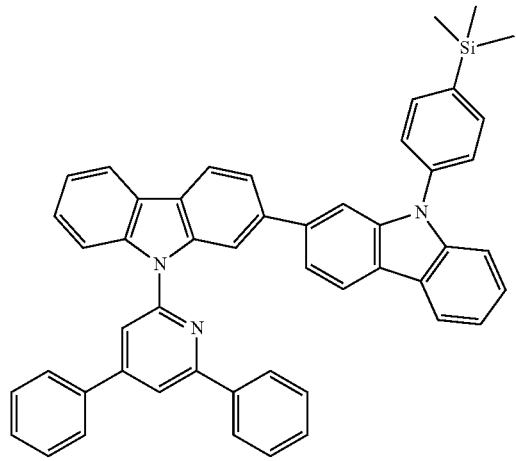
[D-28]
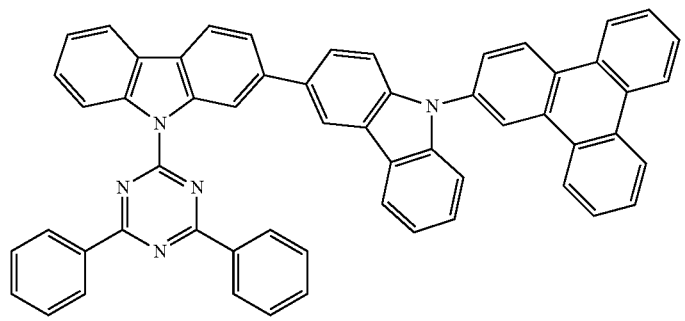
[D-29]
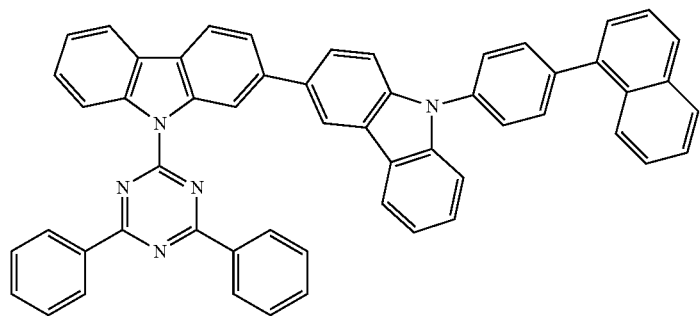
[D-30]
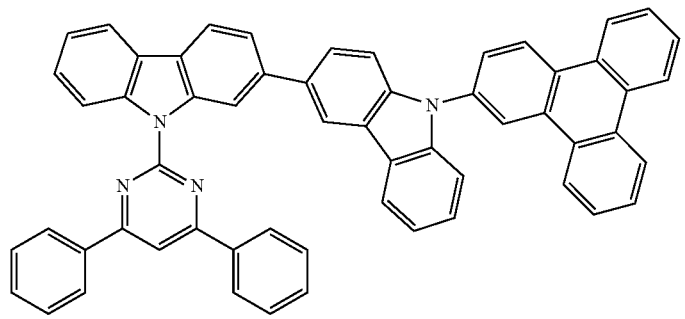
[D-31]

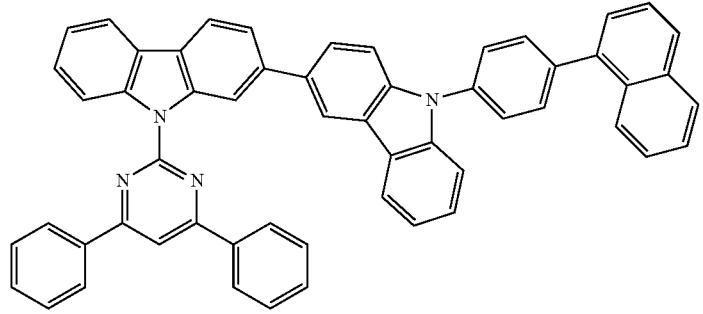
[D-32]
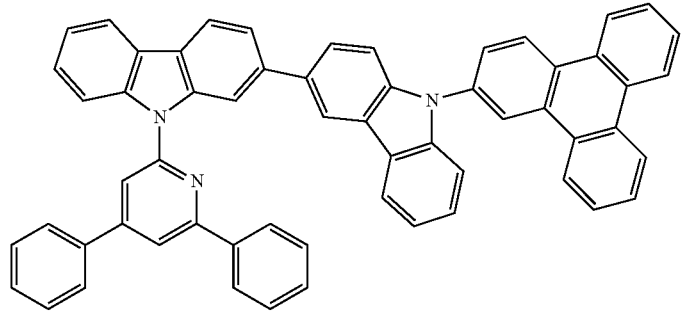
[D-33]
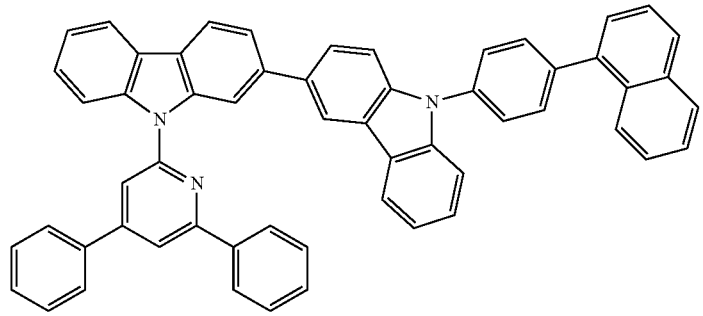
[D-34]
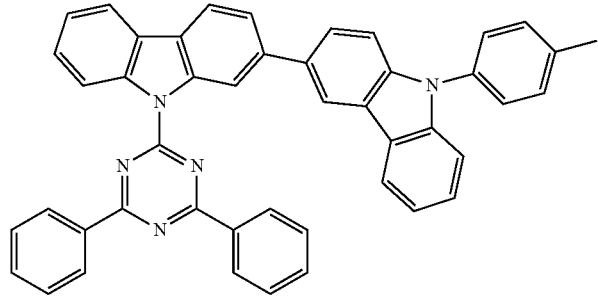
[D-35]
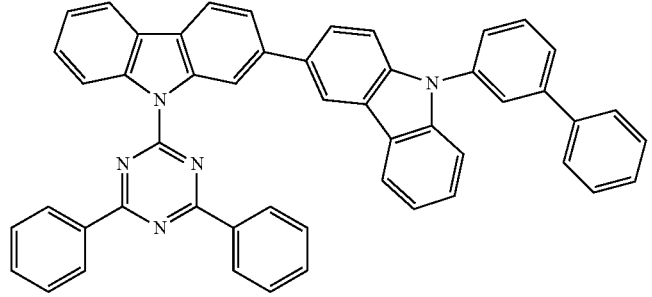
[D-36]

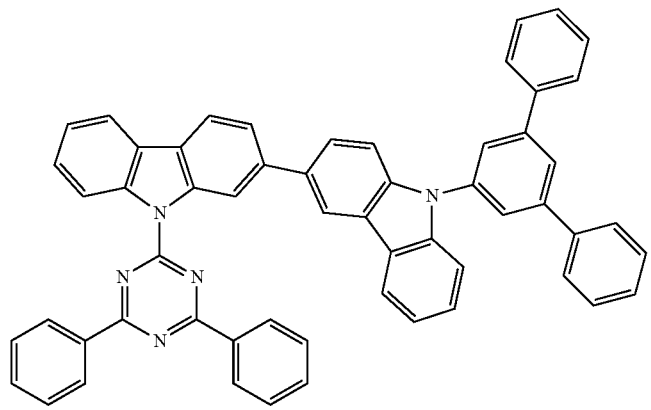

-continued
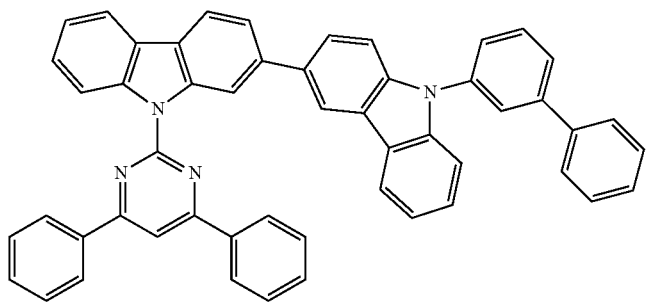
[D-41]
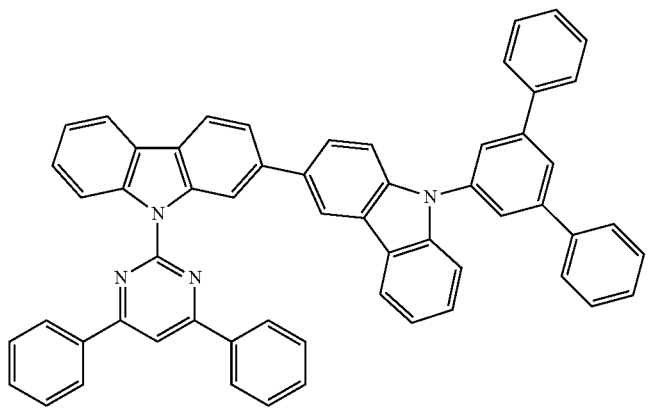
[D-42]
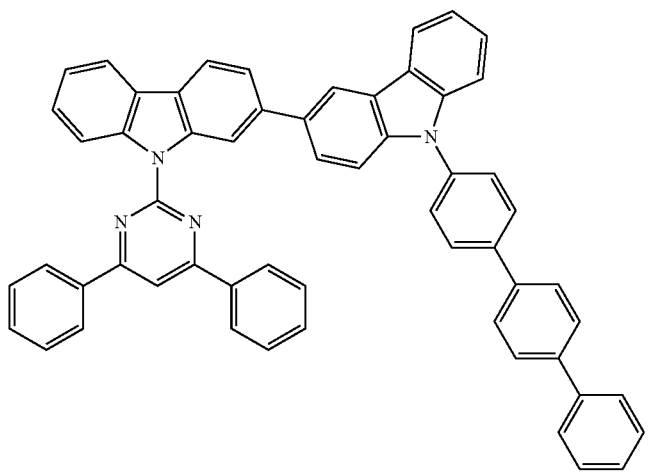
[D-43]
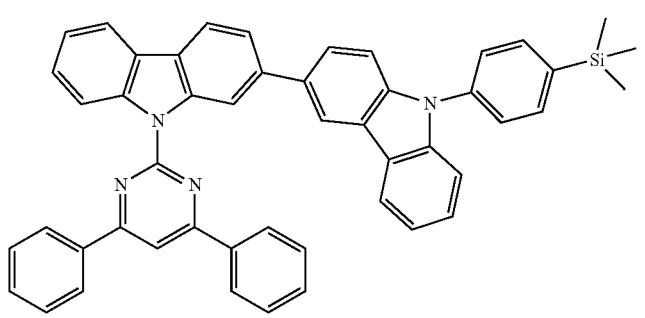
[D-44]

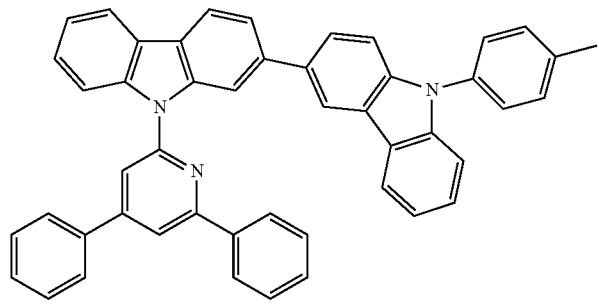
[D-45]
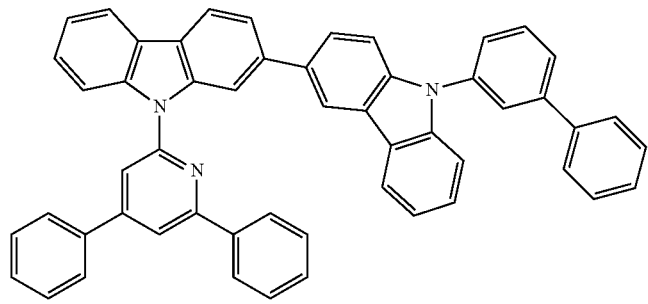
[D-46]
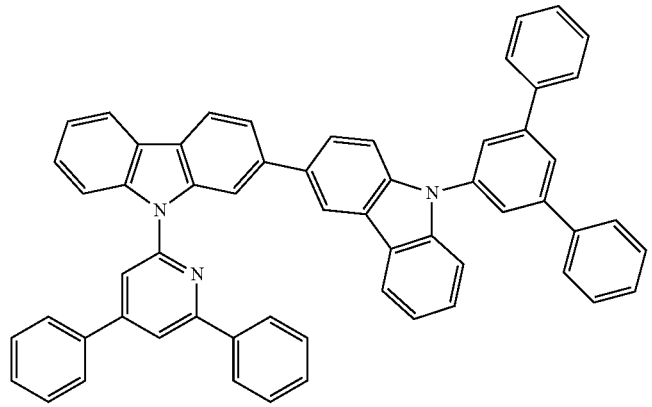
[D-47]
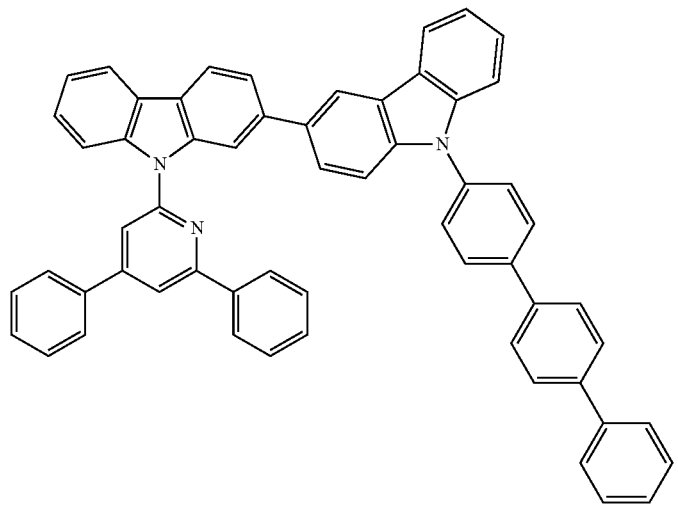
[D-48]

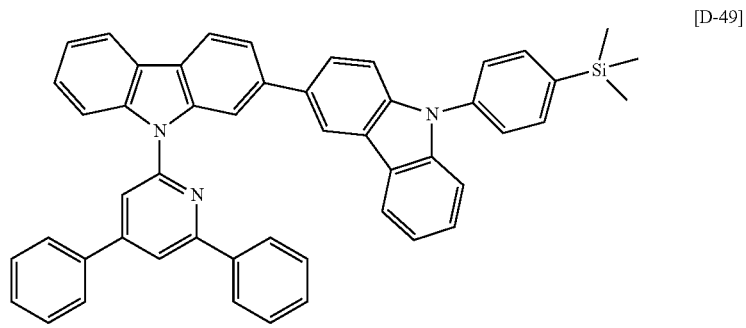
[D-49]
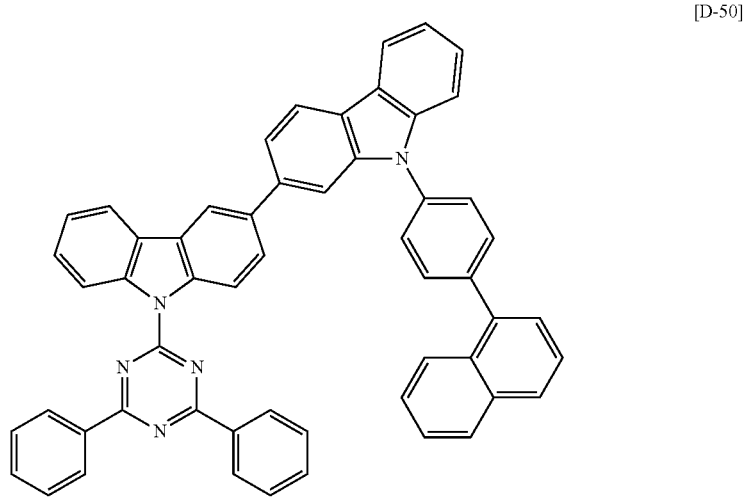
[D-50]
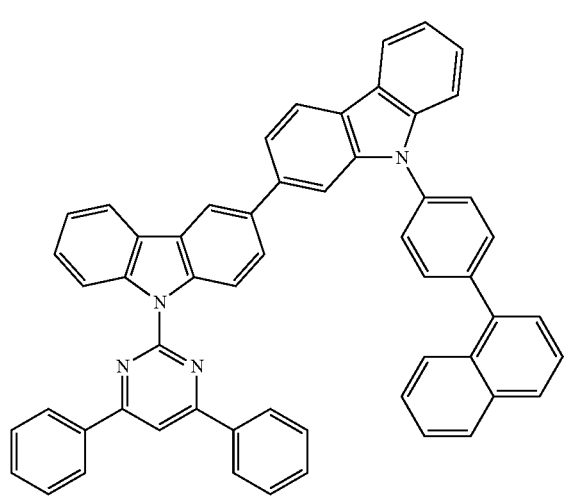
[D-51]

[D-52]
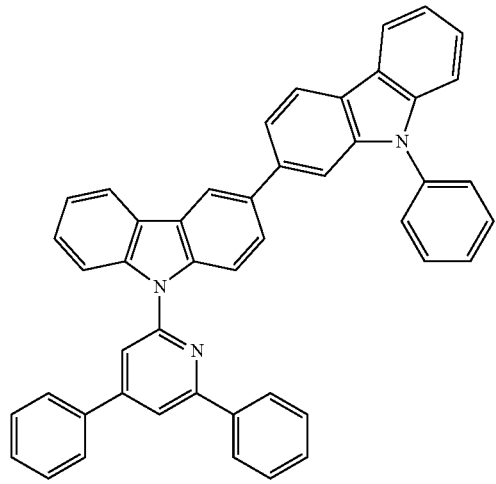
[D-53]
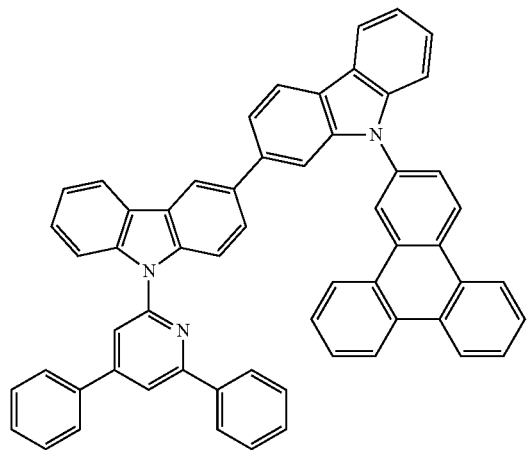
[D-54]
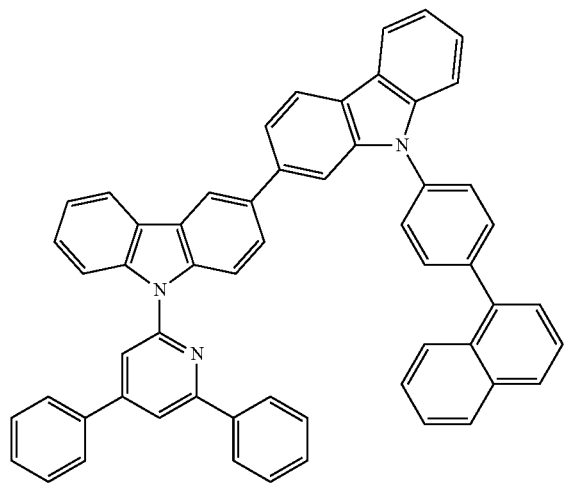

[D-55]
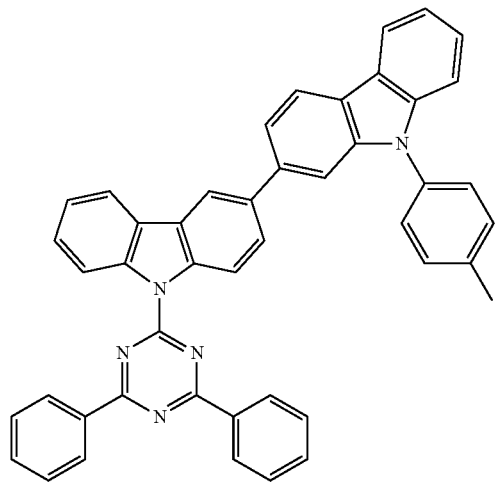
[D-56]
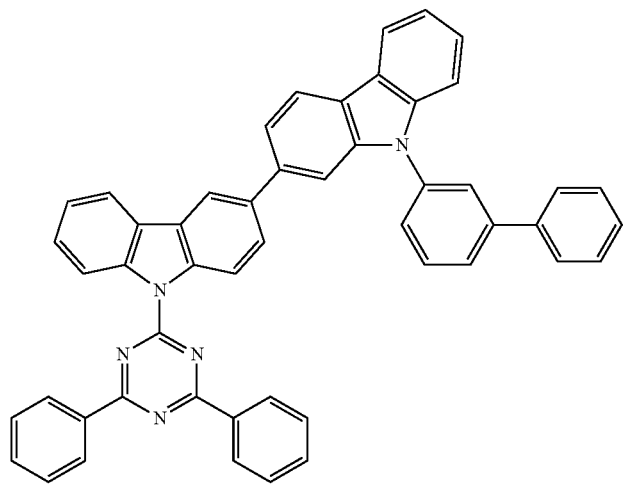
[D-57]
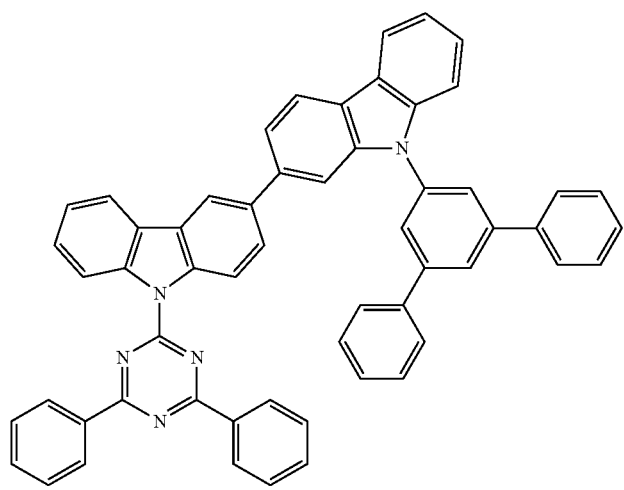

[D-58]
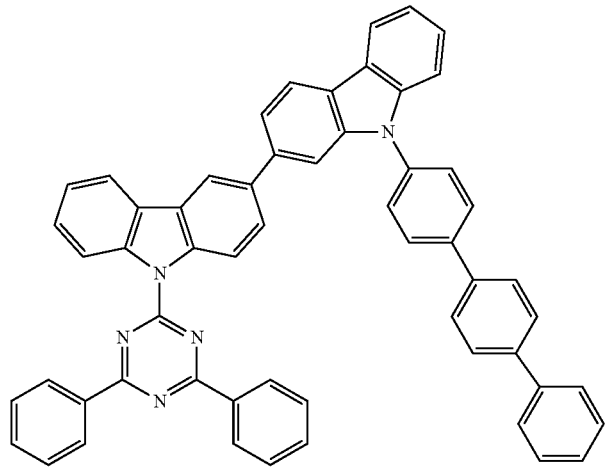
[D-59]
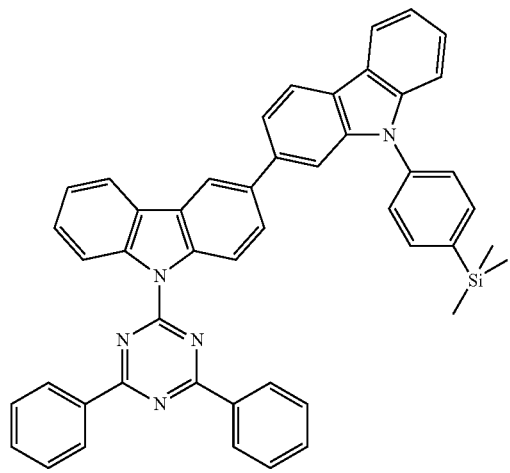
[D-60]
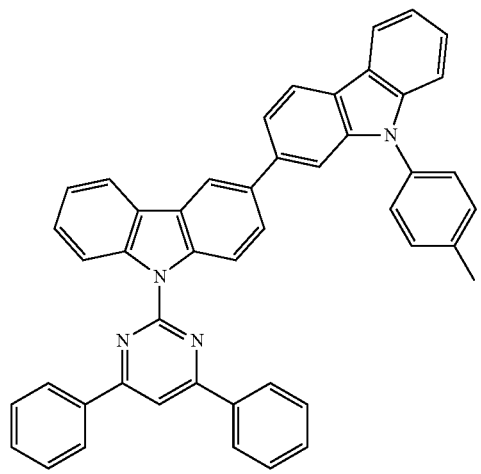

[D-61]
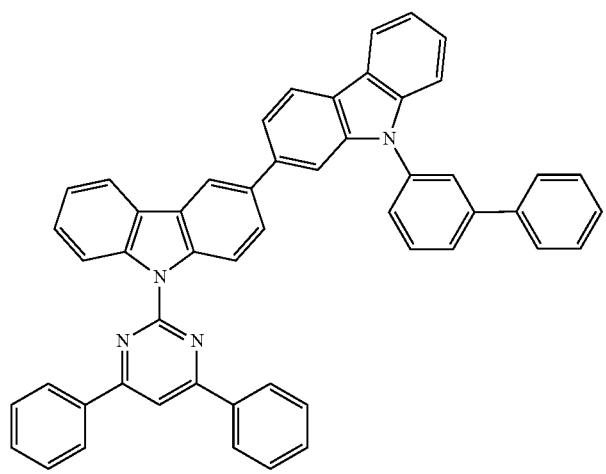
[D-62]
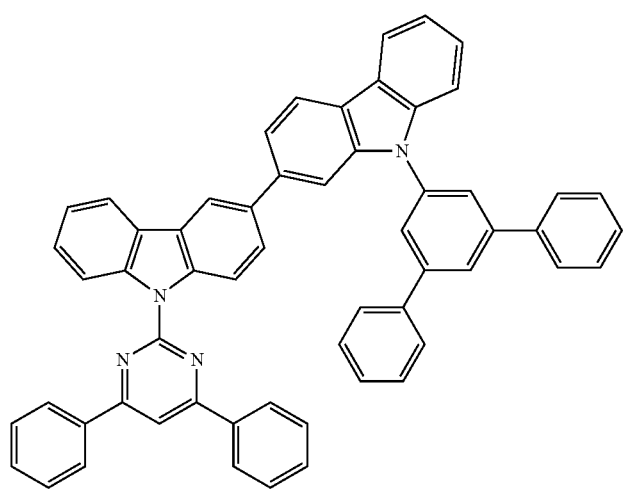
[D-63]
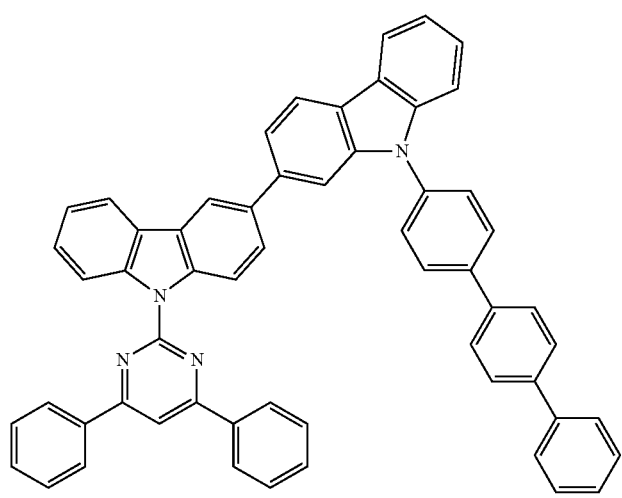

[D-64]
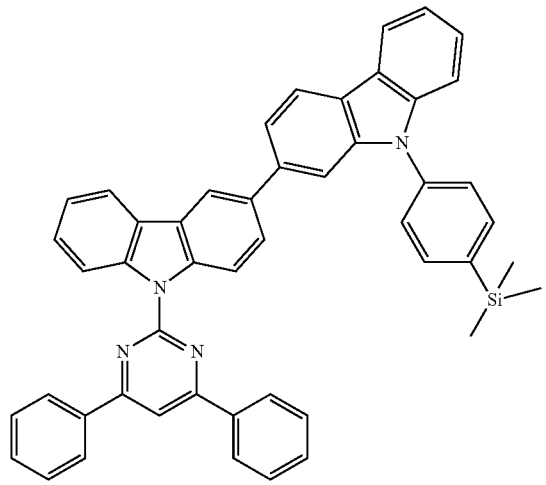
[D-65]
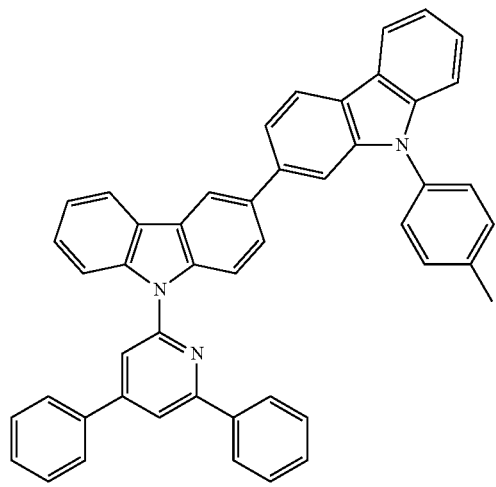
[D-66]
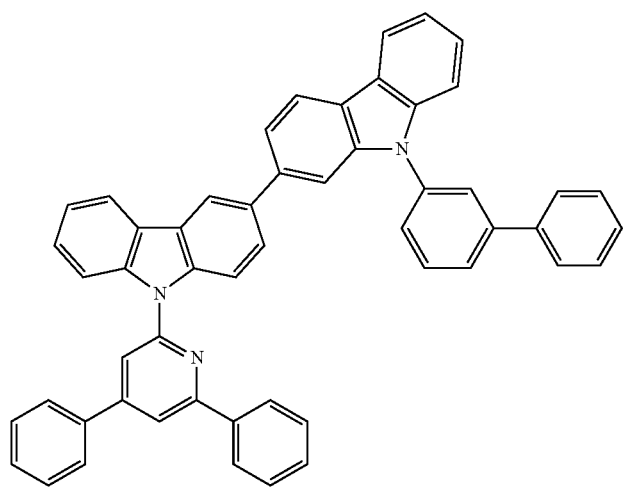

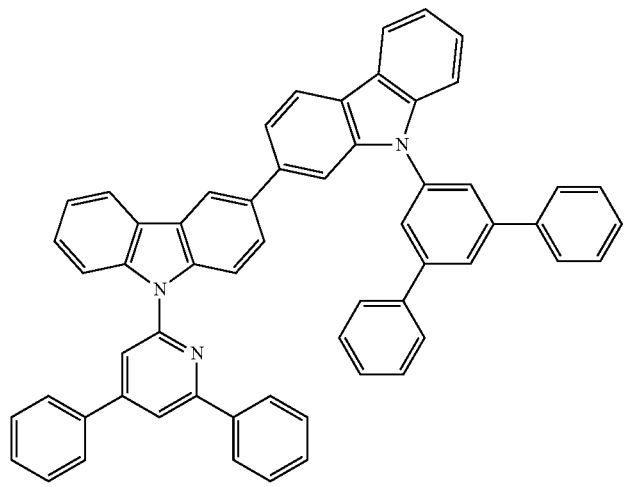
[D-67]
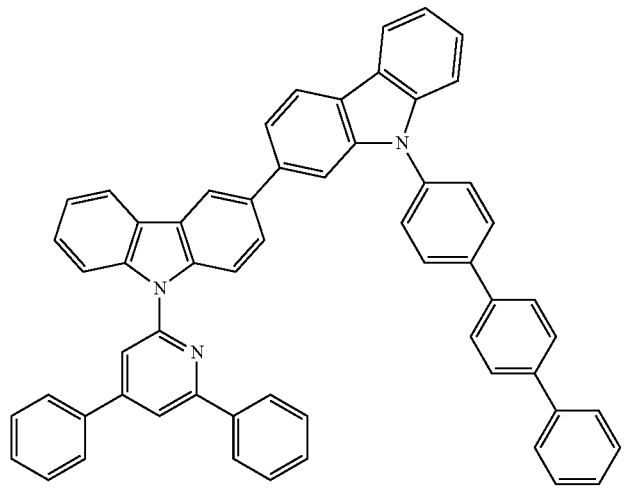
[D-68]
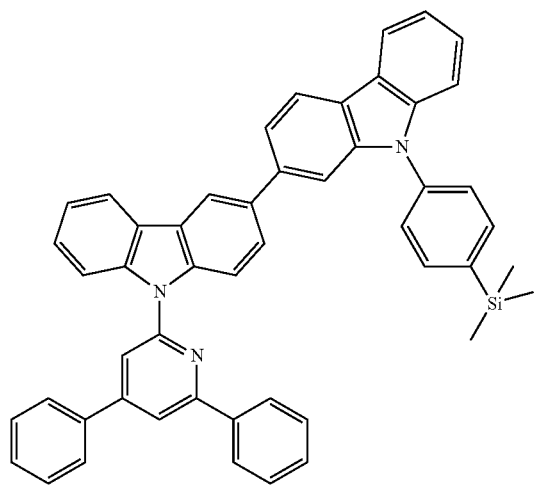
[D-69]

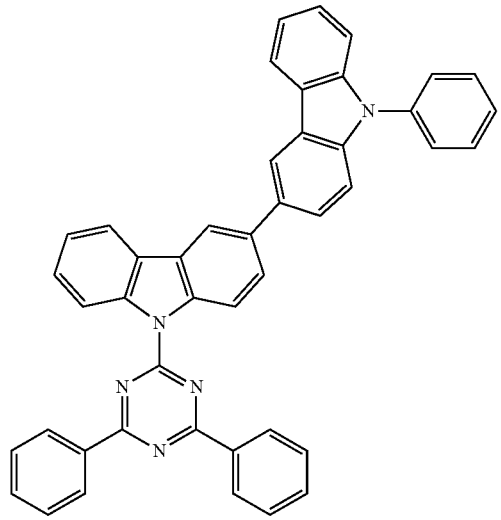
[D-70]
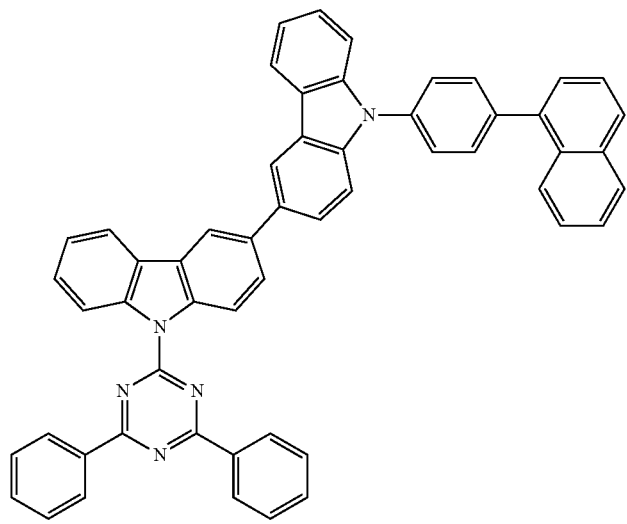
[D-71]
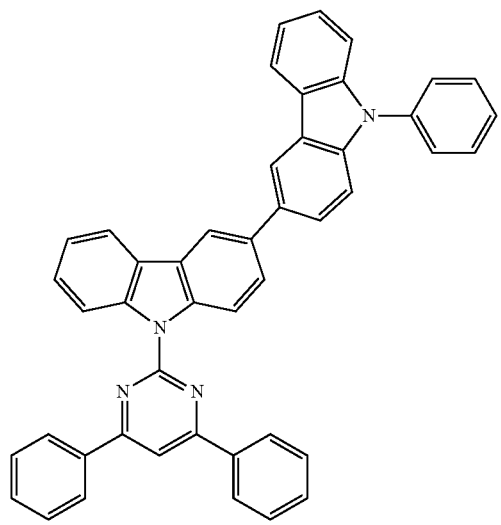
[D-72]

[D-73]
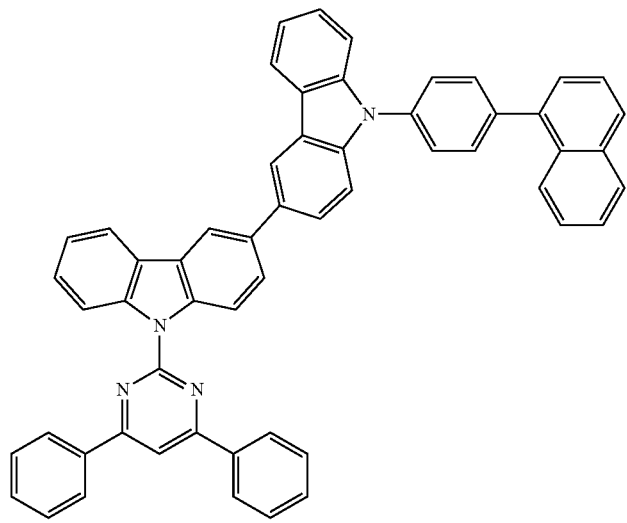
[D-74]
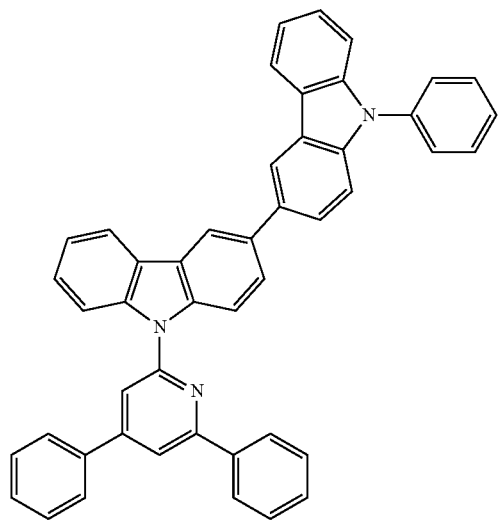
[D-75]
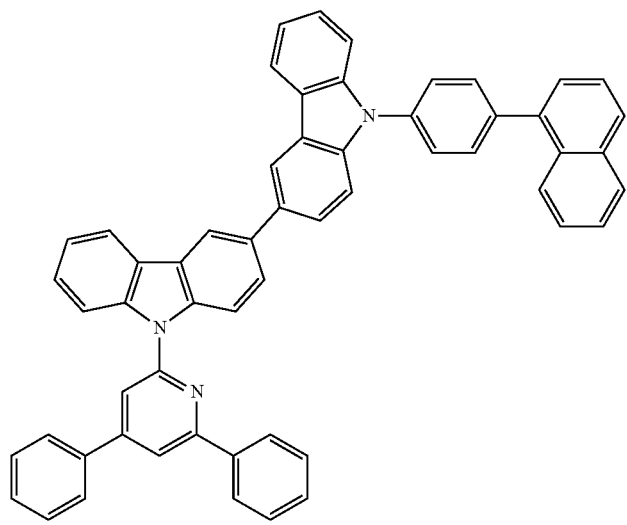

-continued
[D-76]
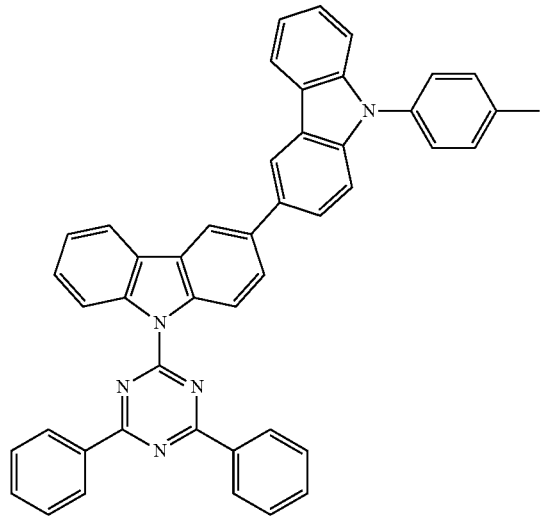
[D-77]
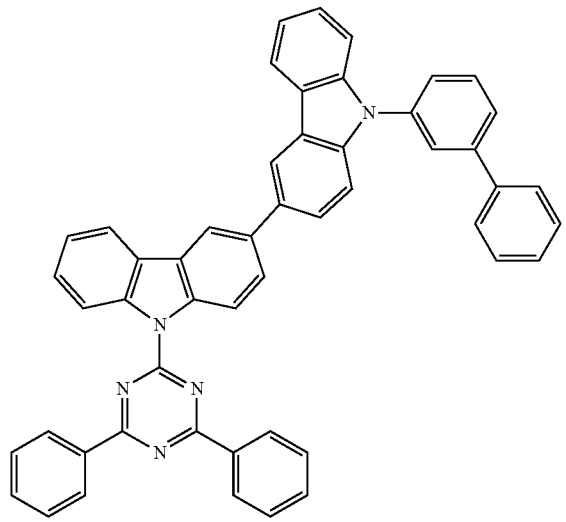
[D-78]
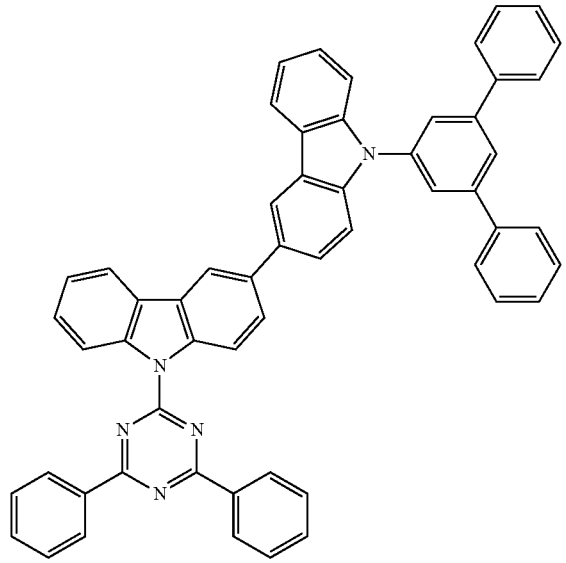

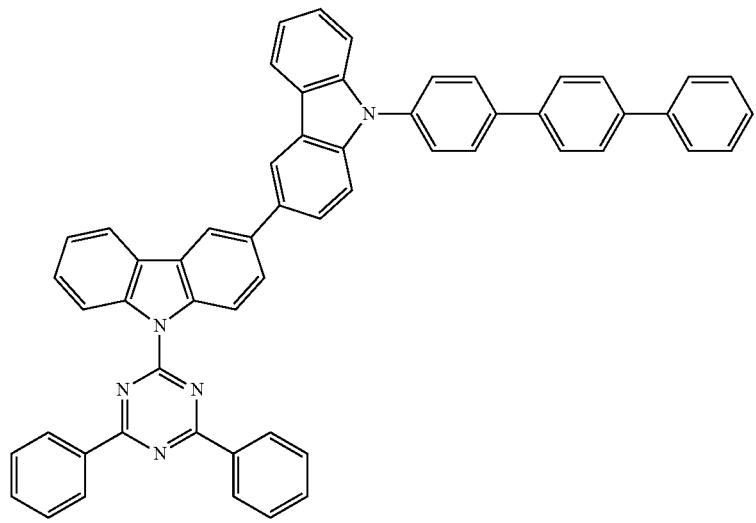
[D-79]
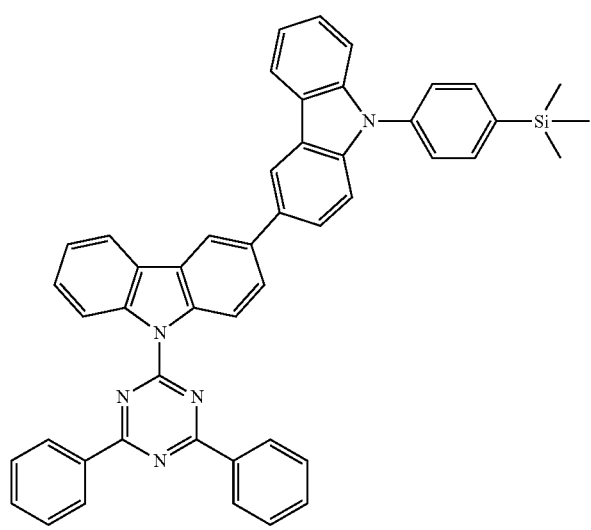
[D-80]
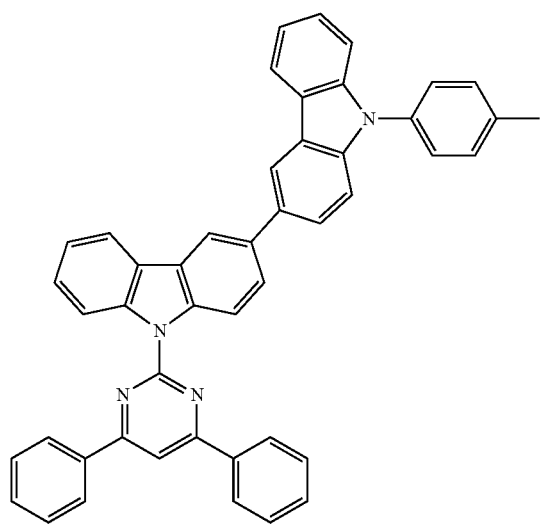
[D-81]

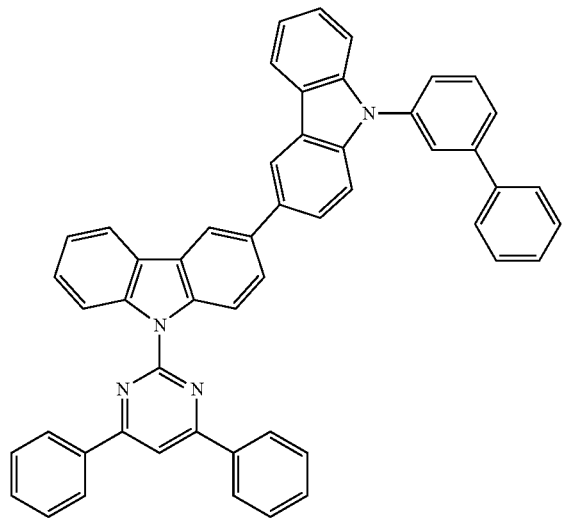
[D-82]
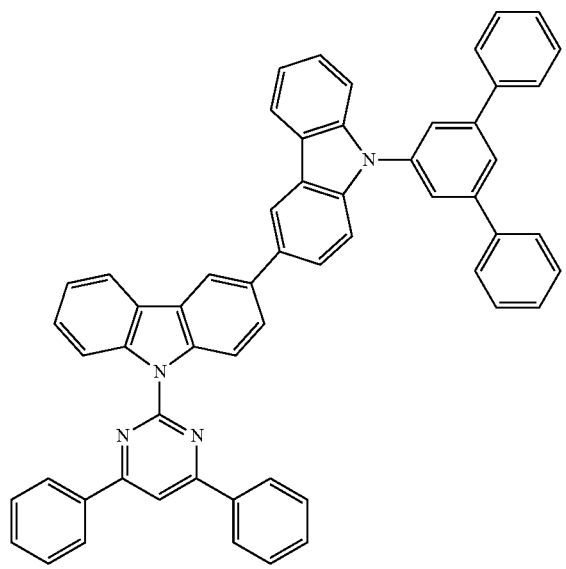
[D-83]
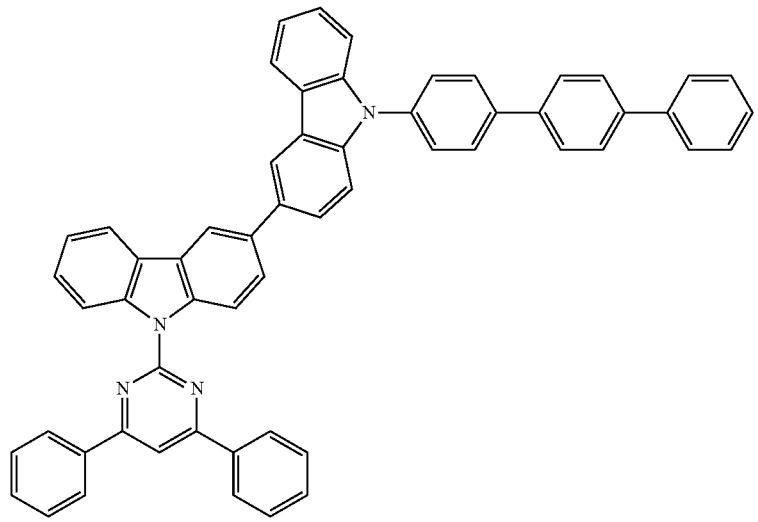
[D-84]

-continued
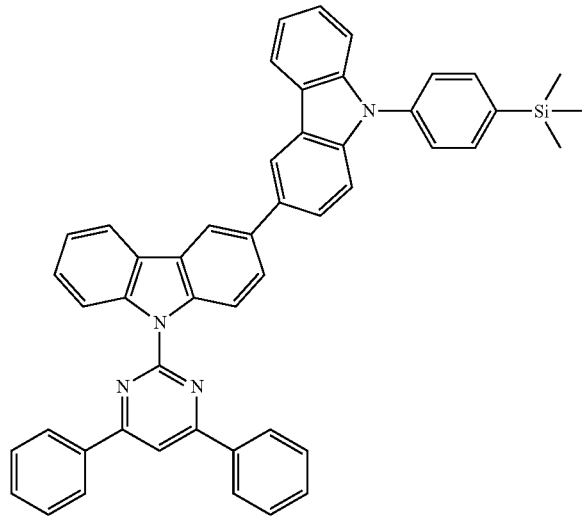
[D-85]
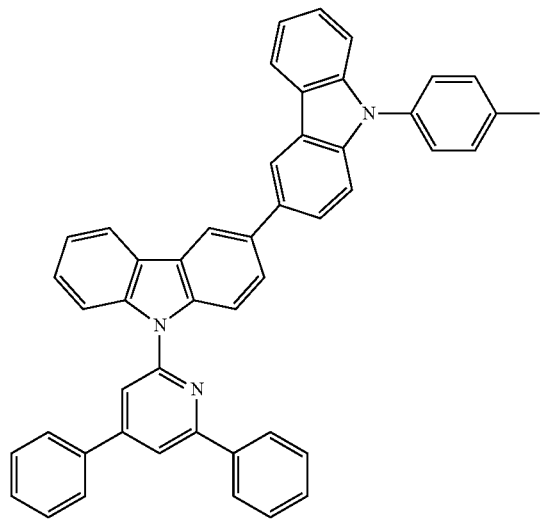
[D-86]
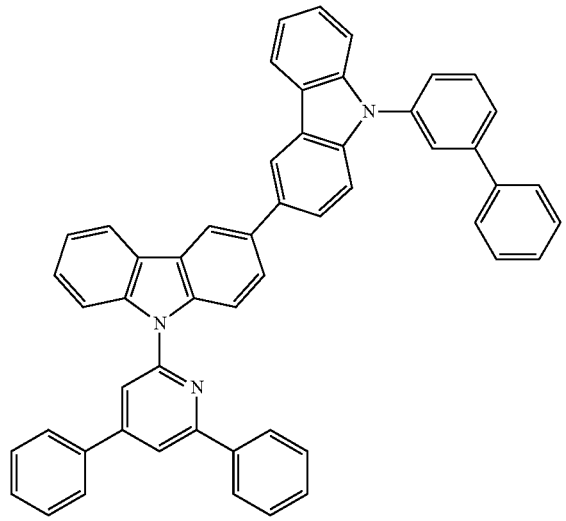
[D-87]

[D-88]
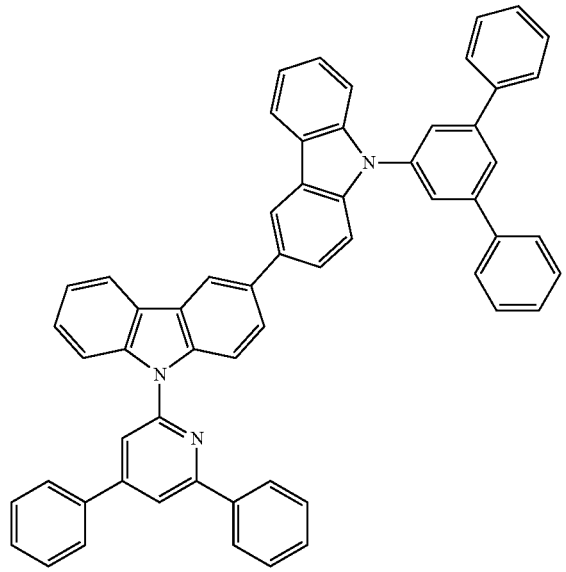
[D-89]
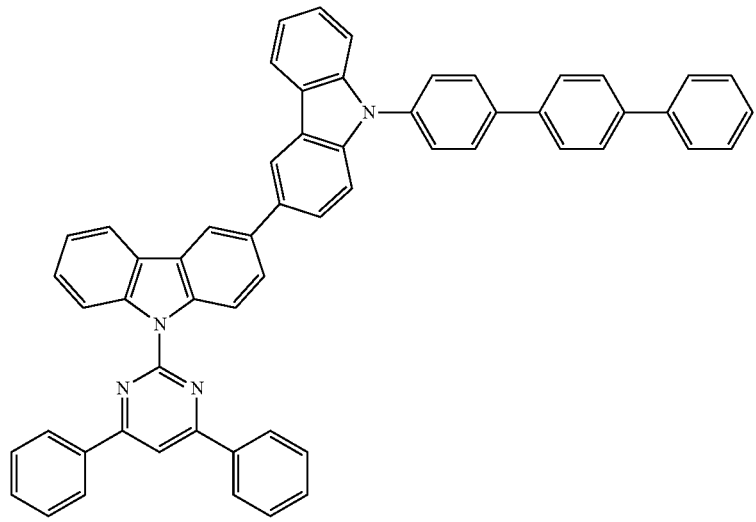
[D-90]
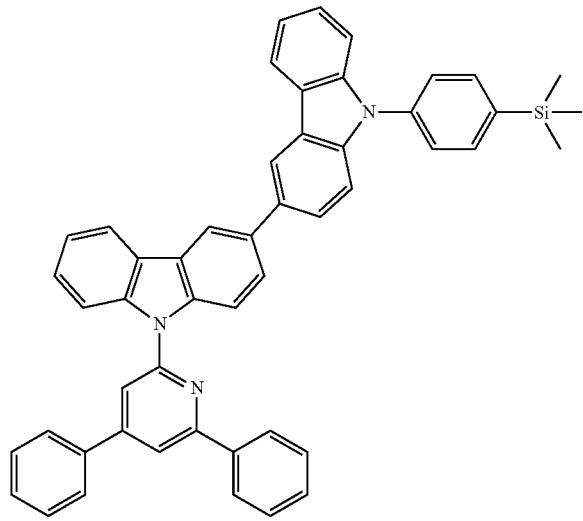

-continued
[D-91]
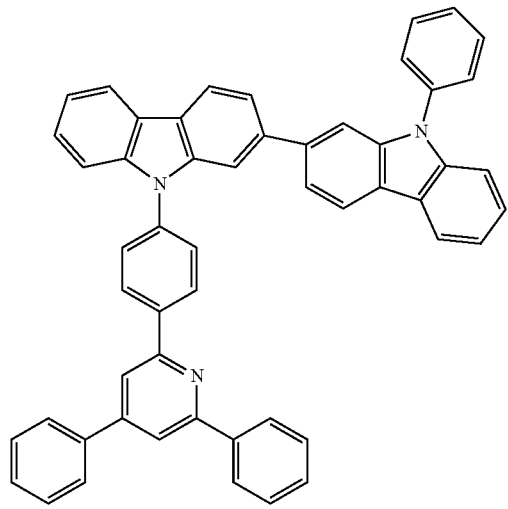
[D-92]
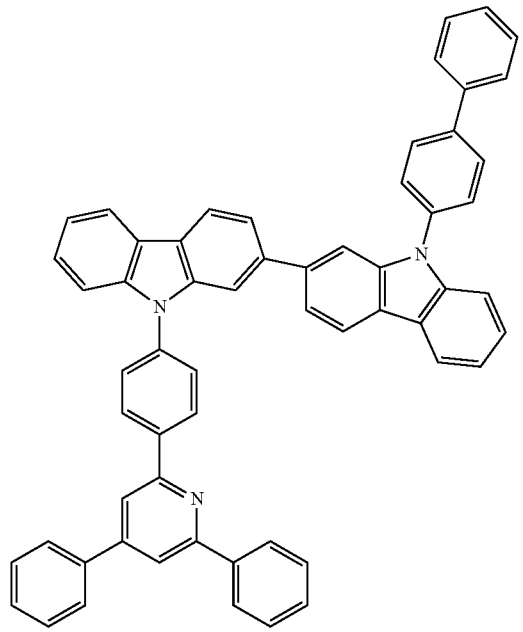
[D-93]
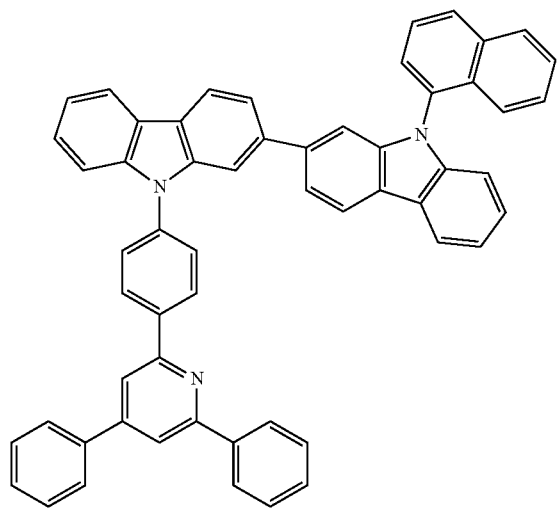

[D-94]
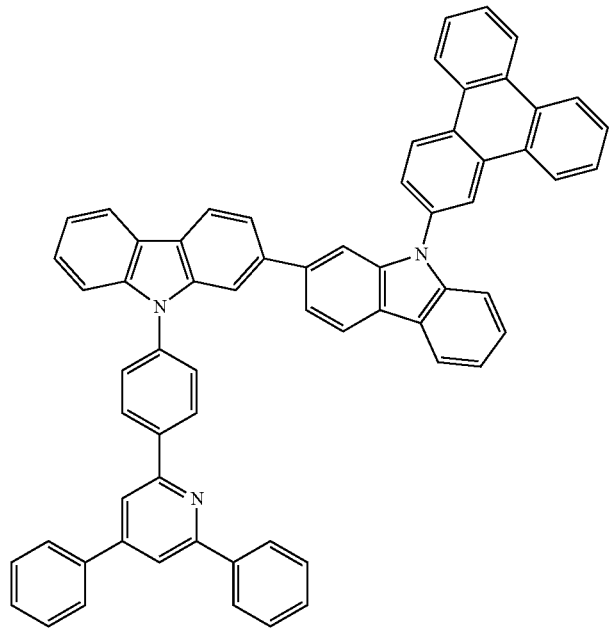
[D-95]
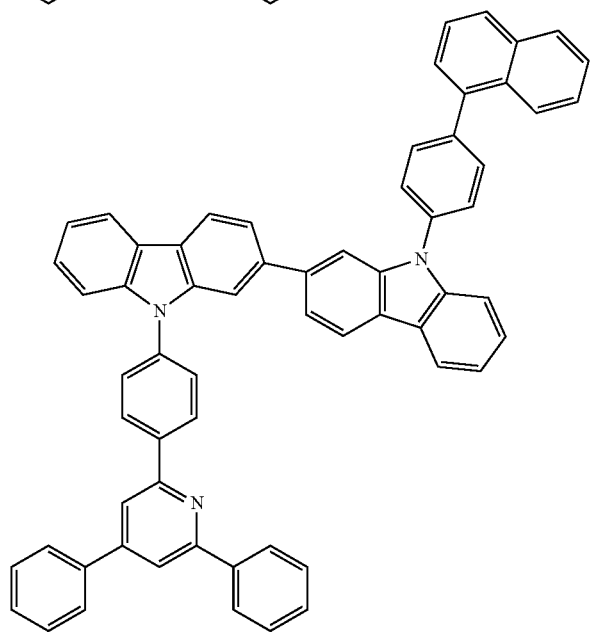
[D-96]
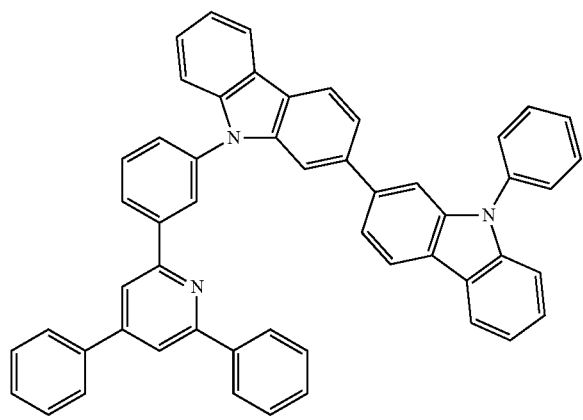

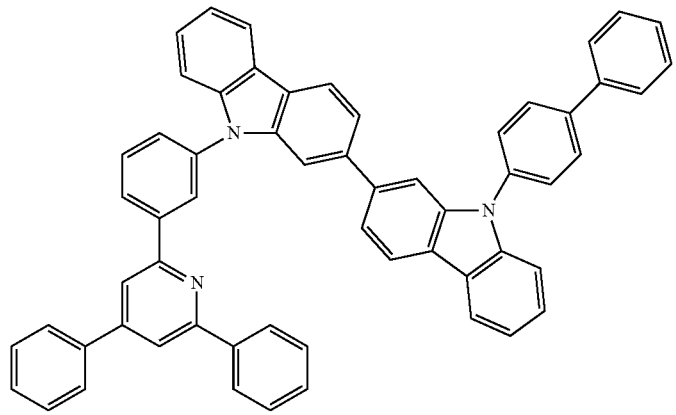
[D-97]
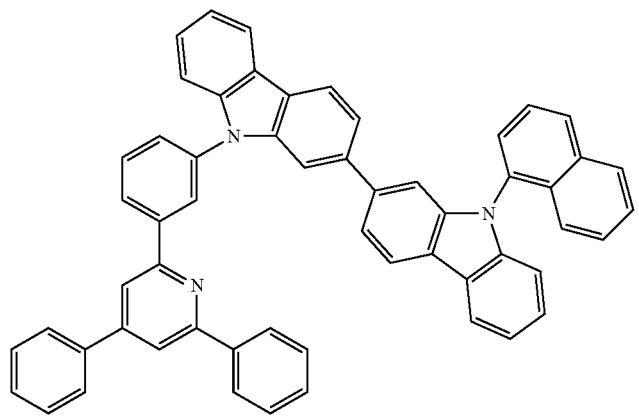
[D-98]
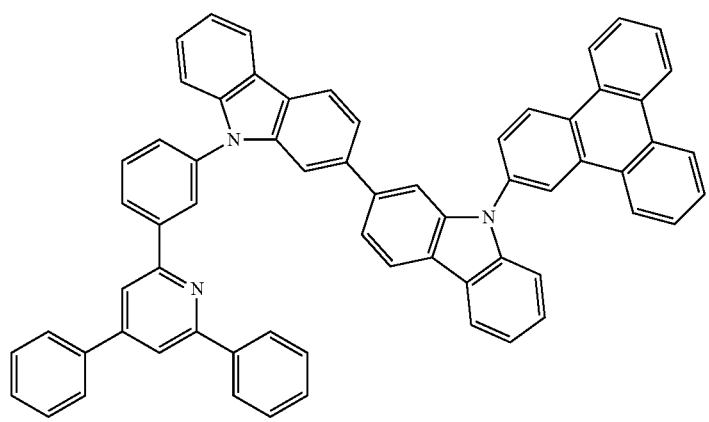
[D-99]

-continued
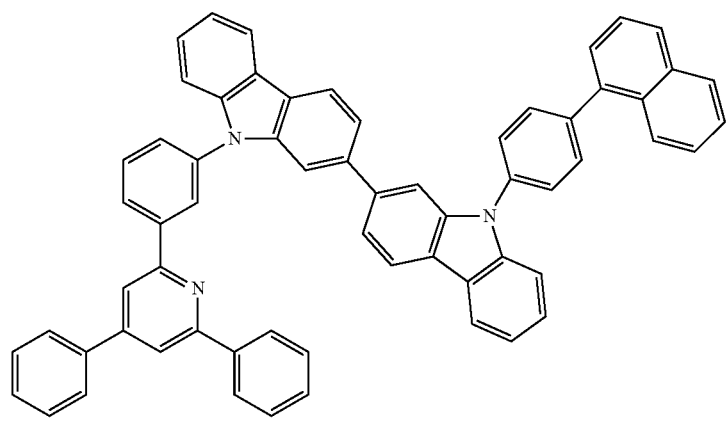
[D-100]
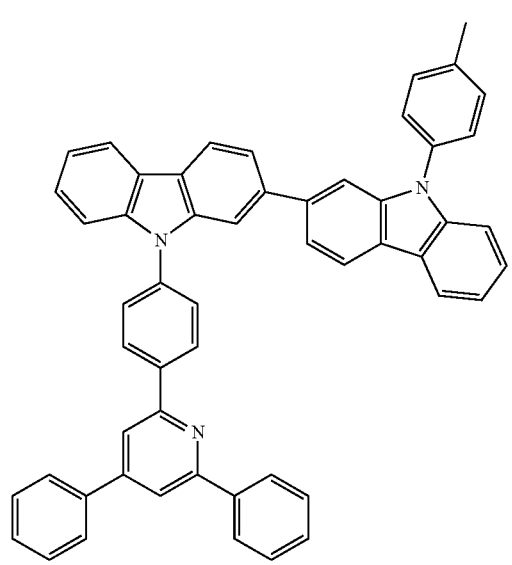
[D-101]
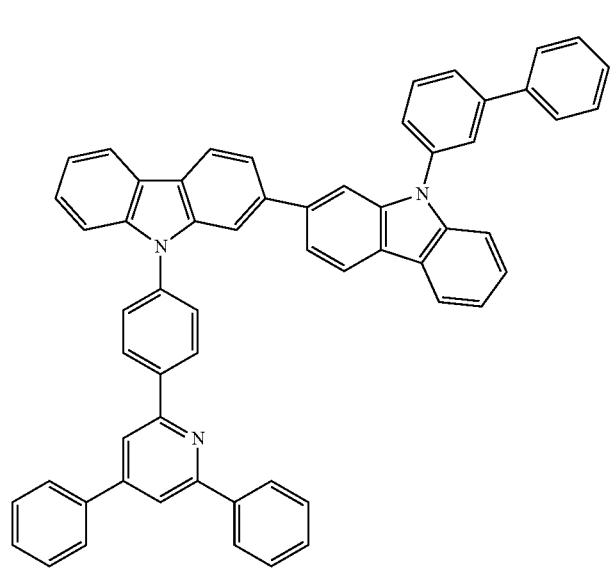
[D-102]

[D-103]
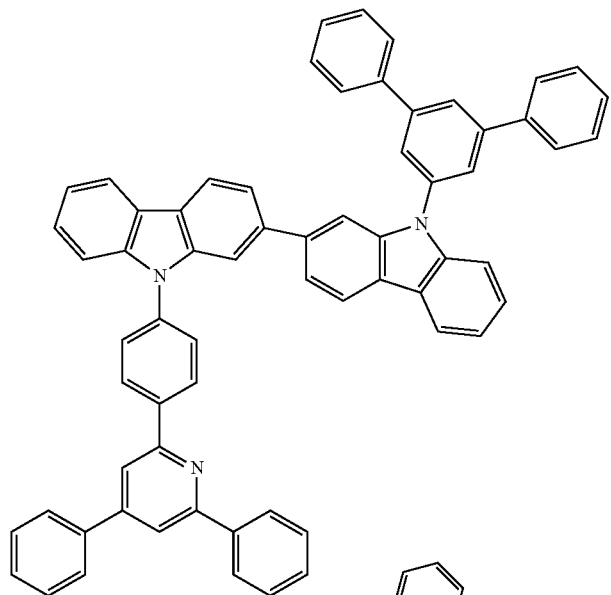
[D-104]
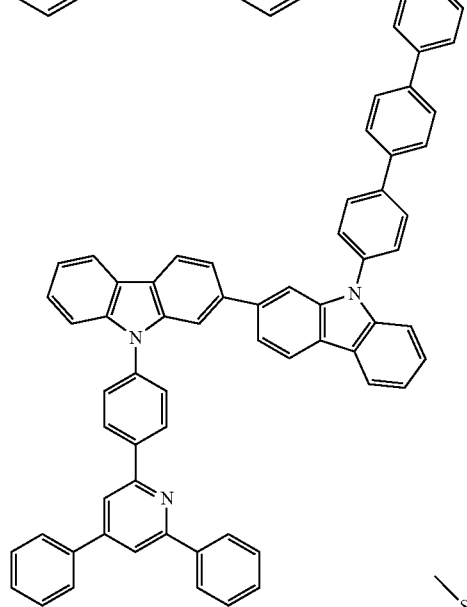
[D-105]
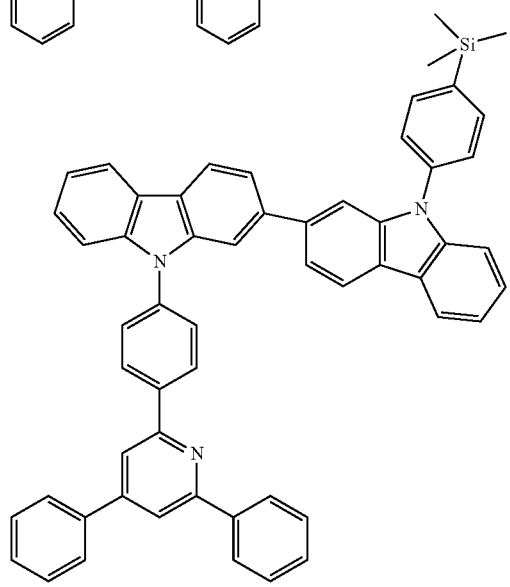

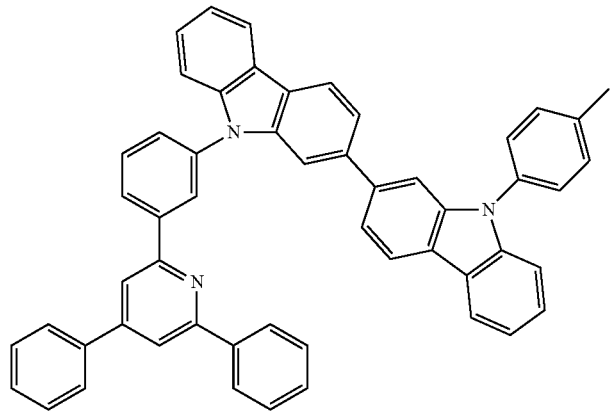
[D-106]
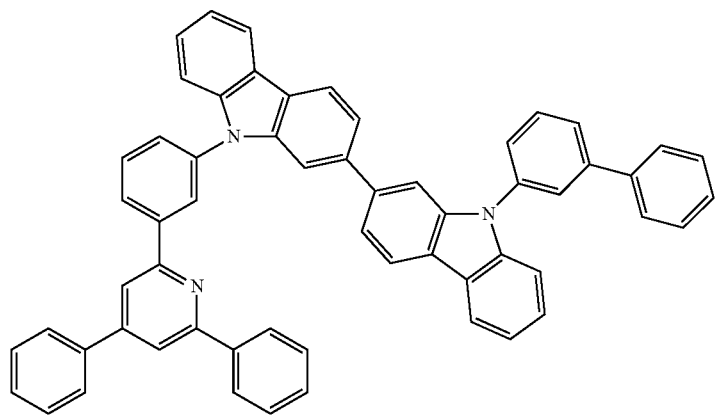
[D-107]
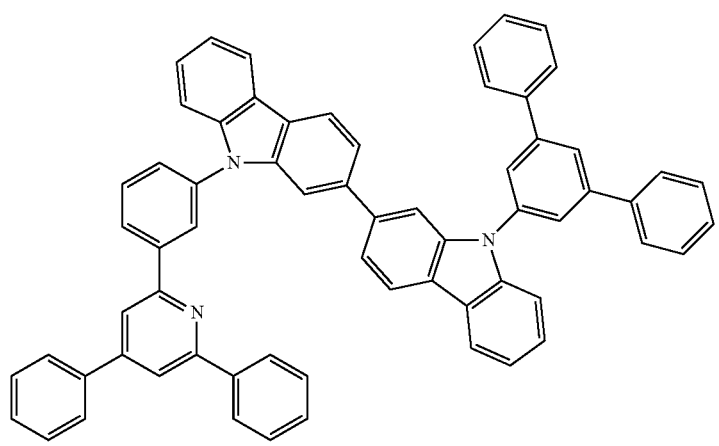
[D-108]

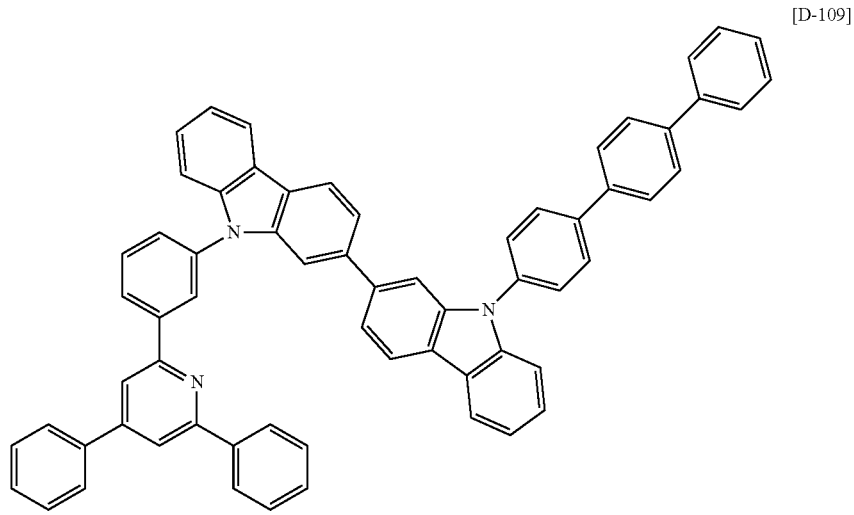
[D-109]
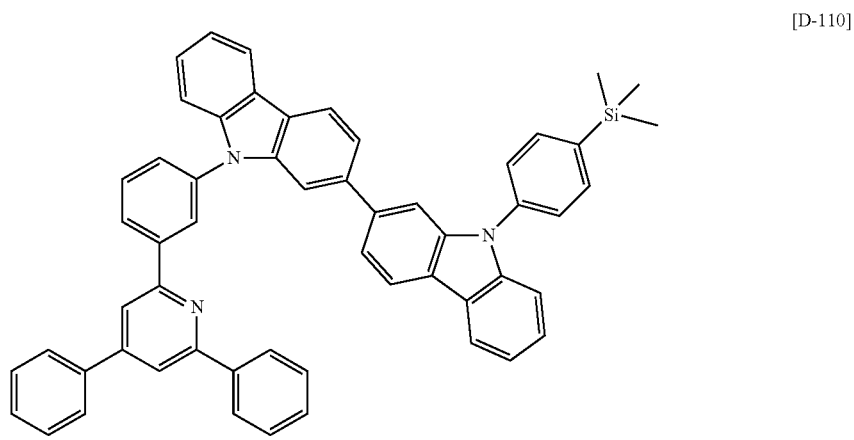
[D-110]
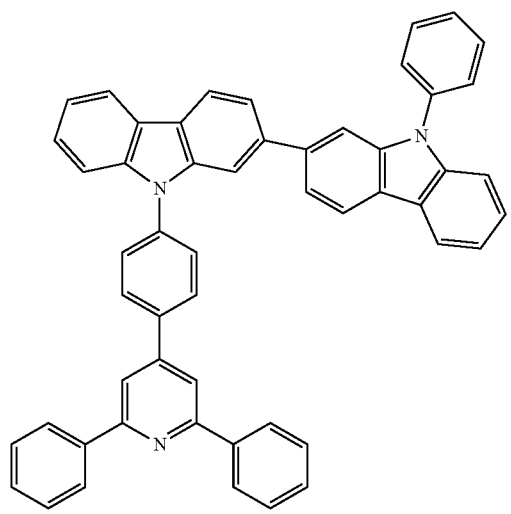
[D-111]

-continued
[D-112]
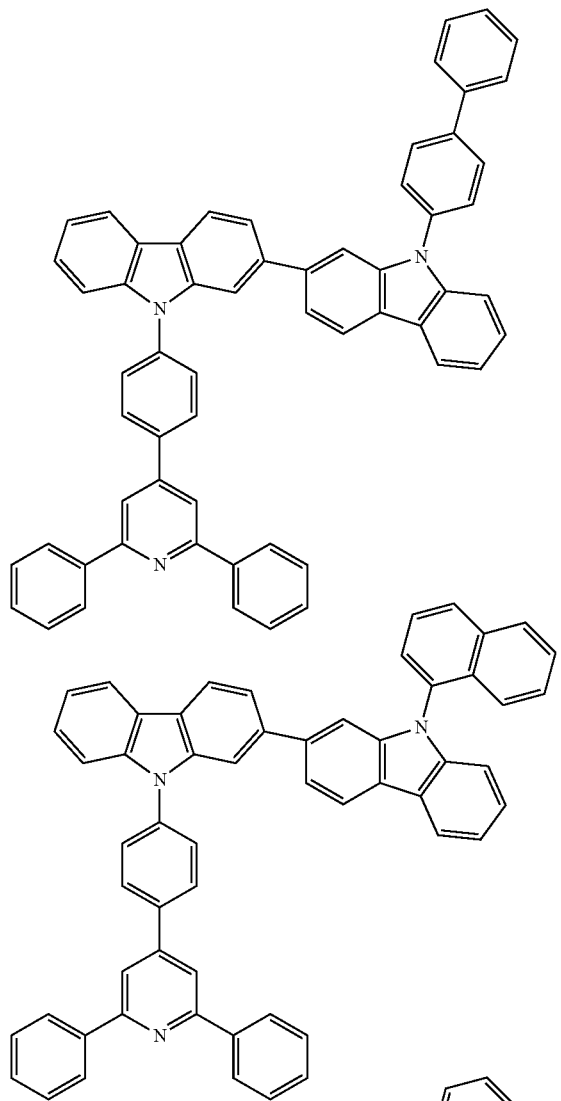
[D-113]
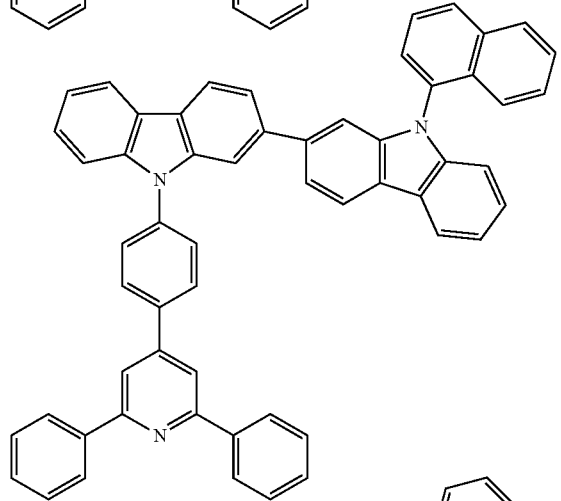
[D-114]
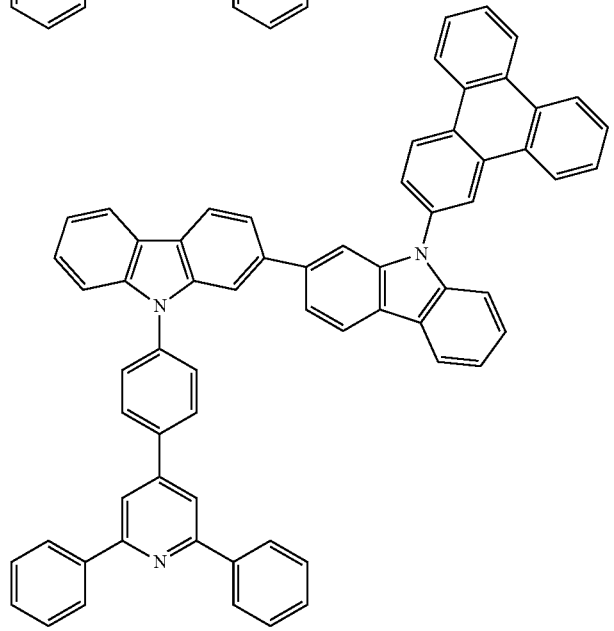

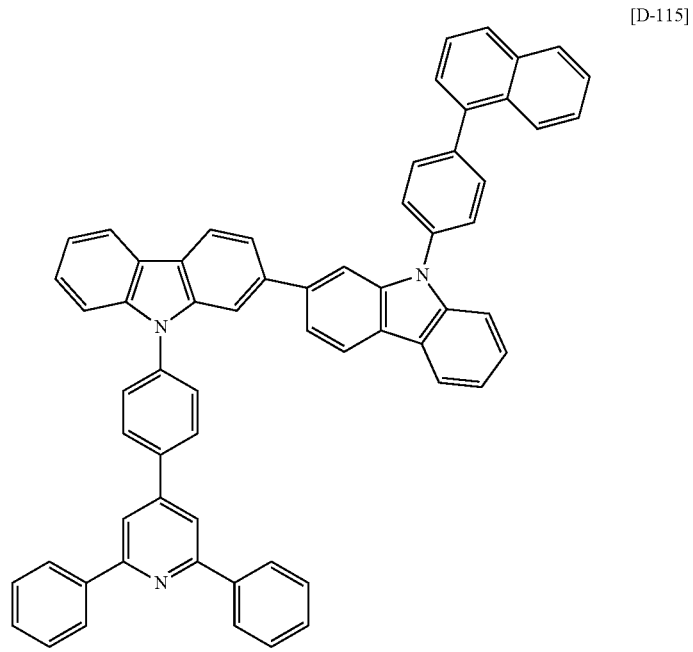
[D-115]
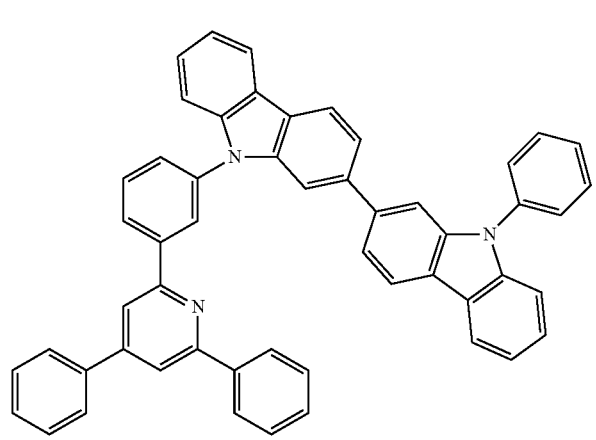
[D-116]
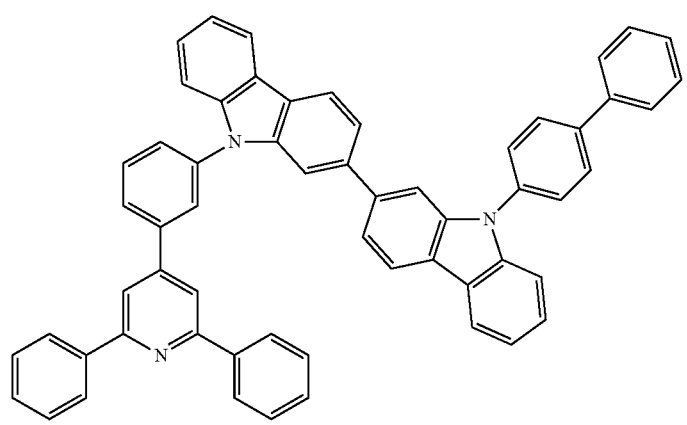
[D-117]

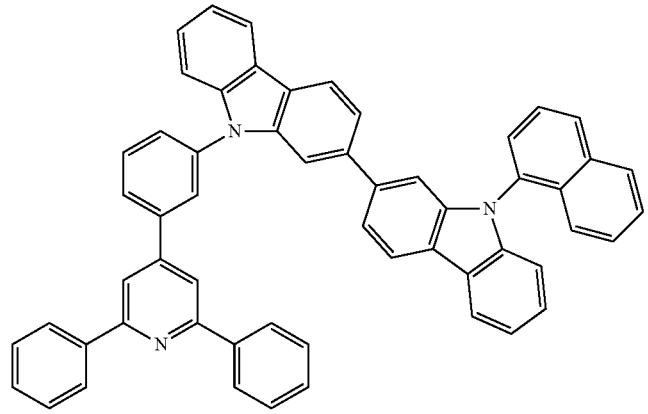
[D-118]
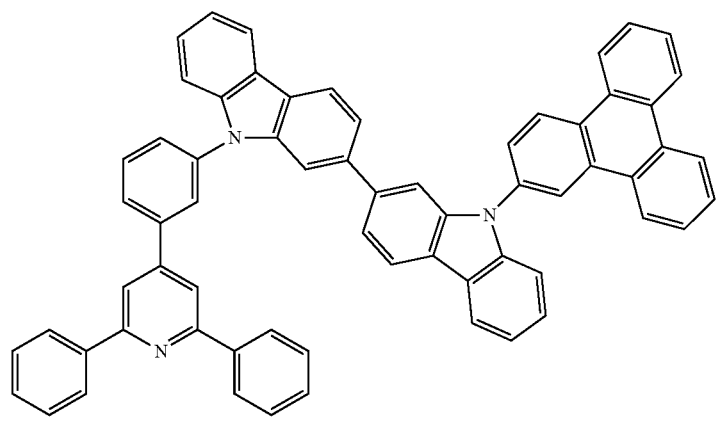
[D-119]
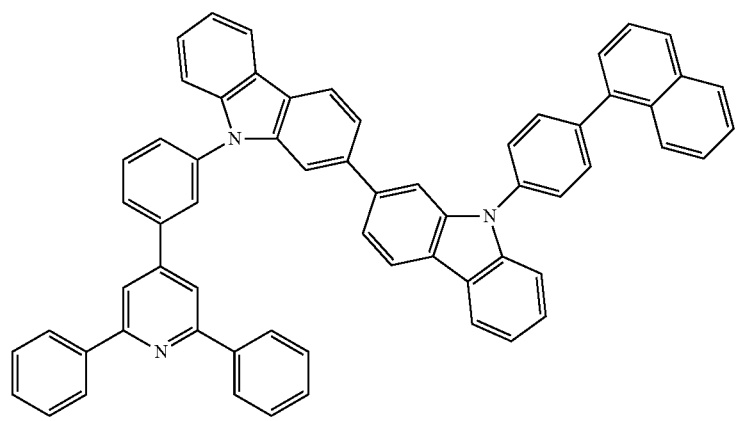
[D-120]

[D-121]
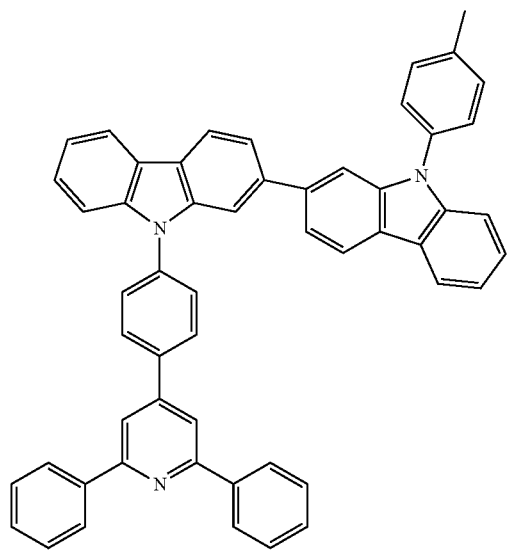
[D-122]
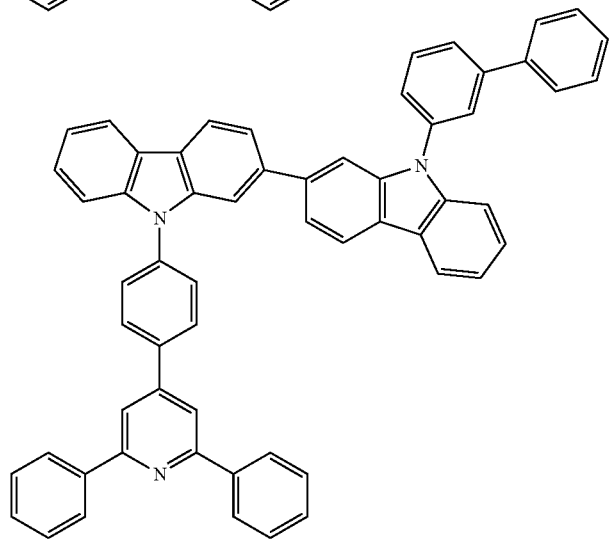
[D-123] [D-124]
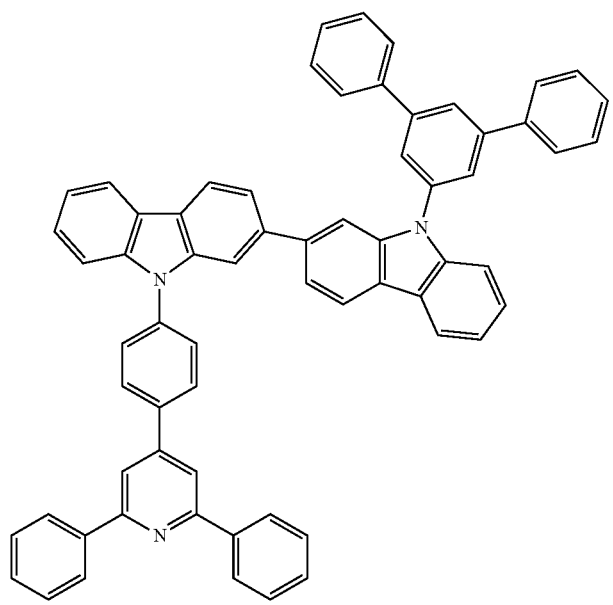

[D-125]
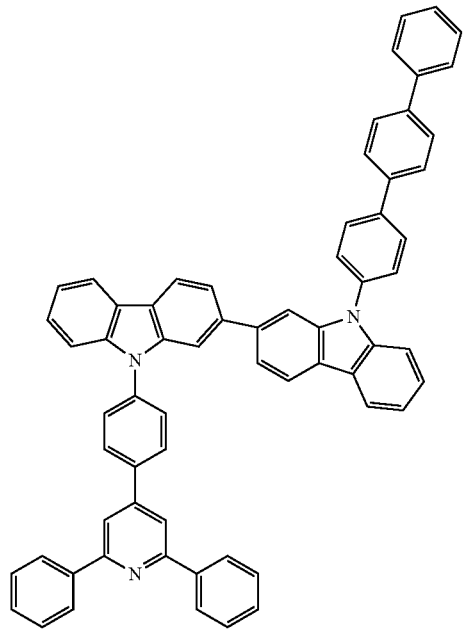
[D-126]
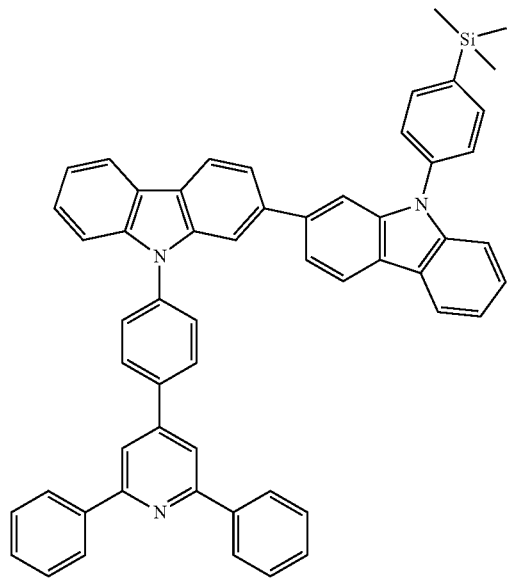
[D-127]
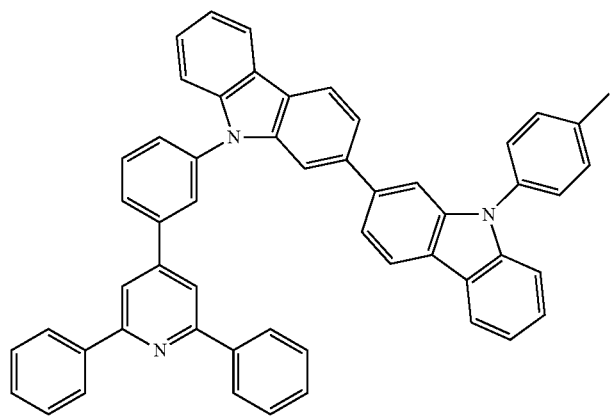

-continued
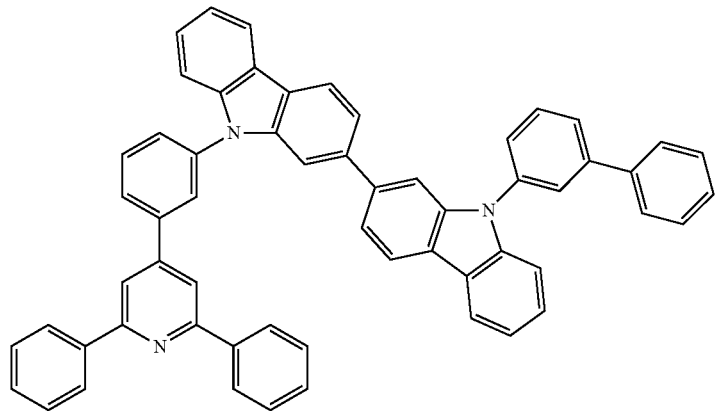
[D-128]
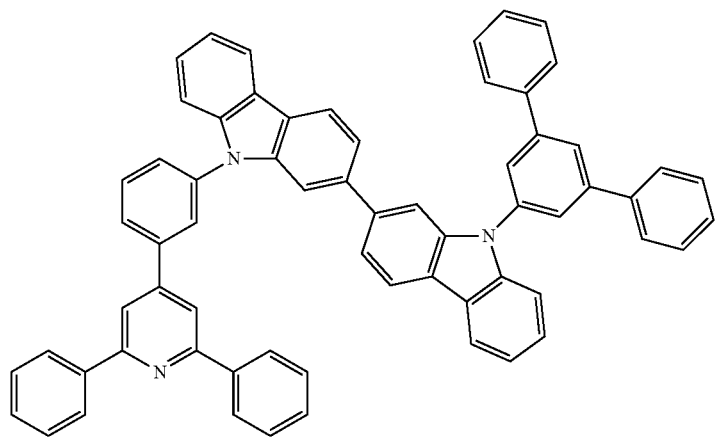
[D-129]
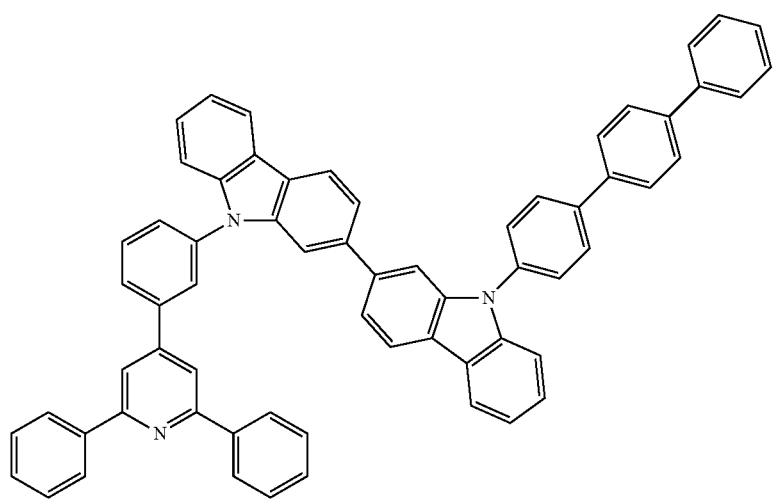
[D-130]

[D-131]
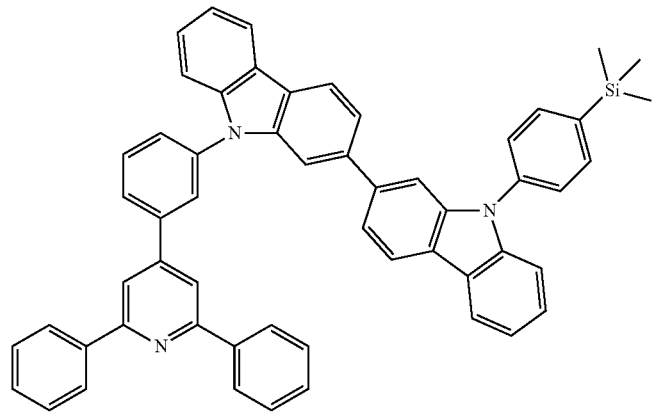
[D-132]
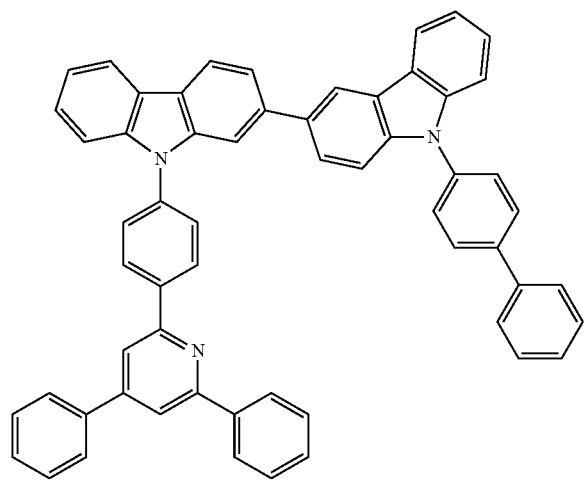
[D-133]
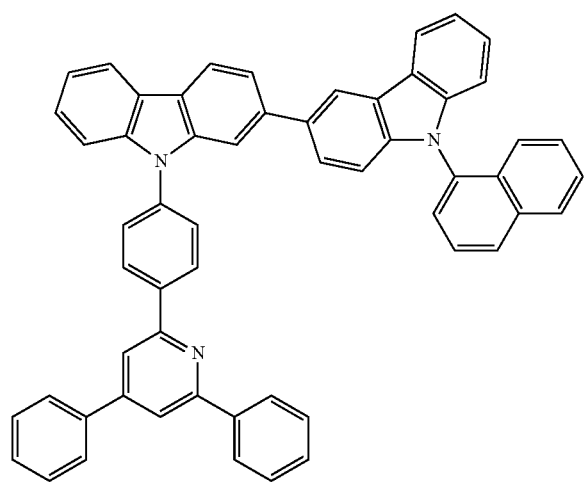

[D-134]
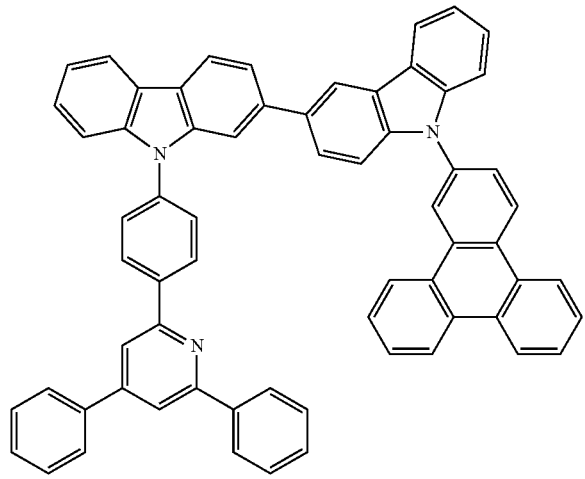
[D-135]
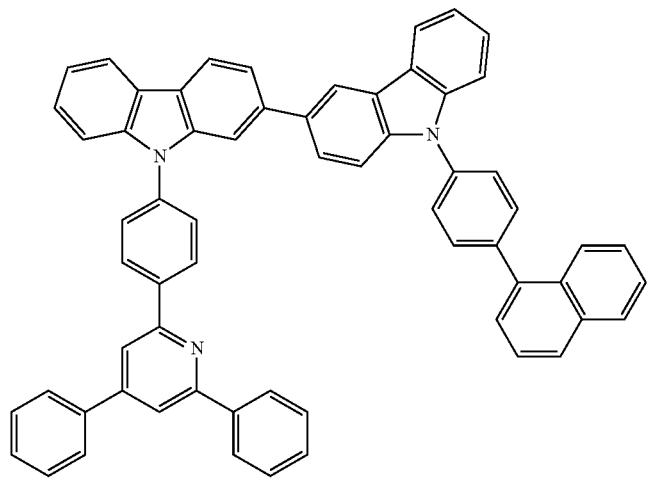
[D-136]
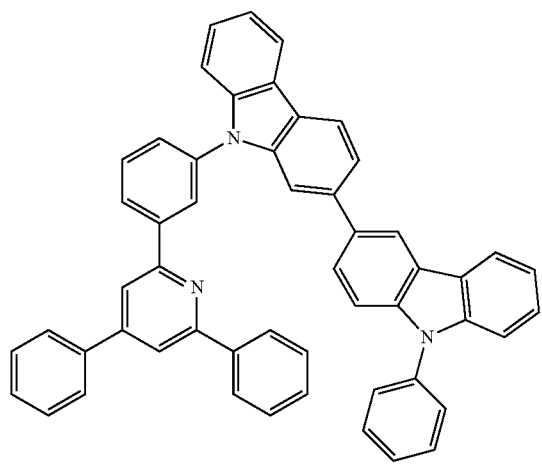

[D-137]
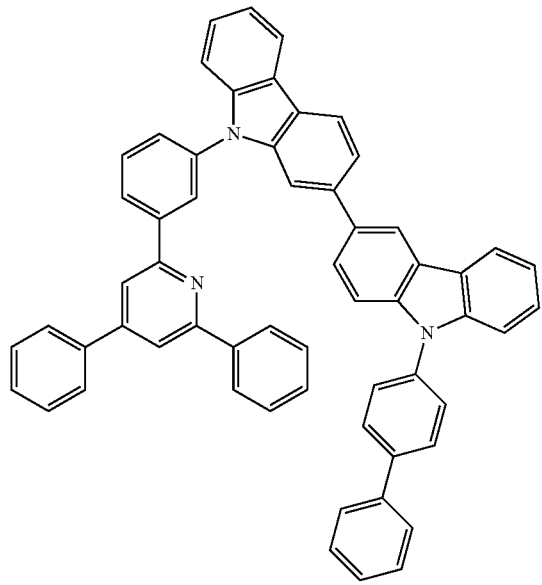
[D-138]
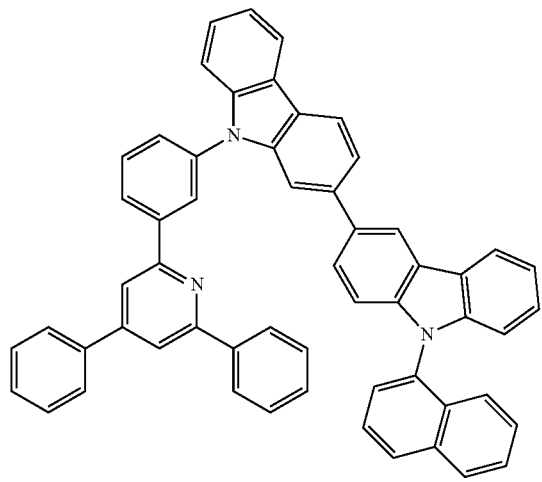
[D-139]
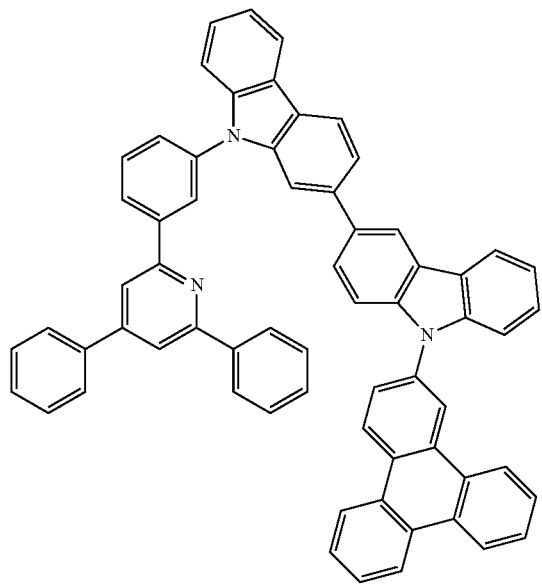

-continued
[D-140]
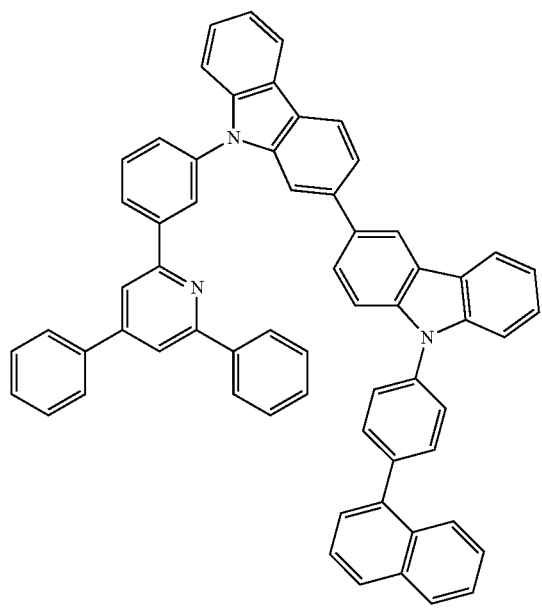
[D-141]
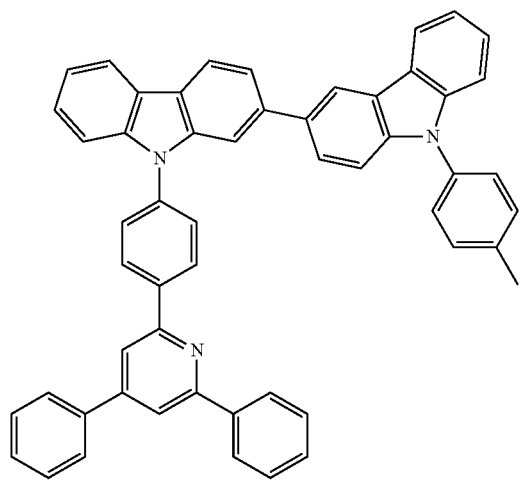
[D-142]
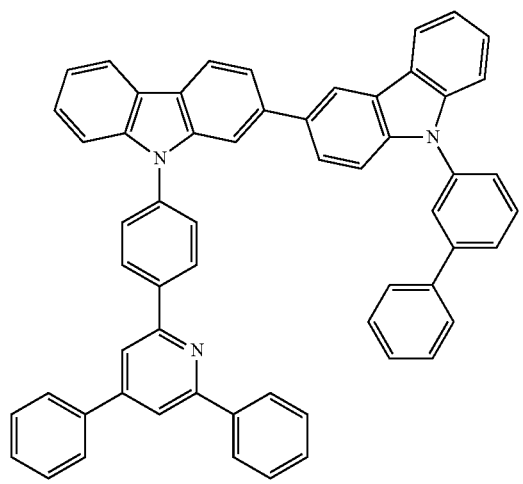

[D-143]
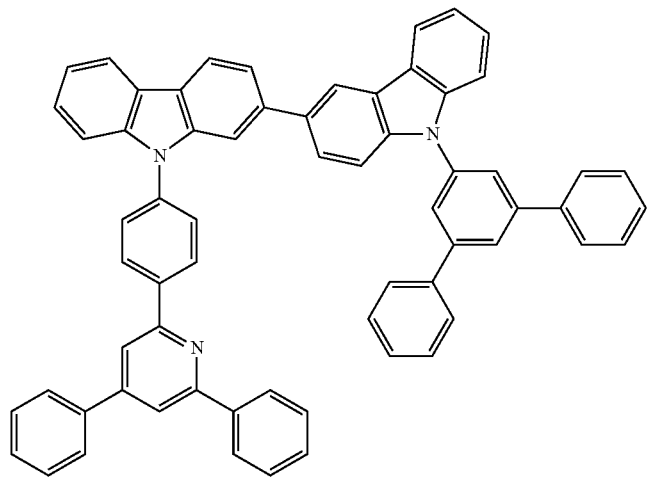
[D-144]
[D-145]
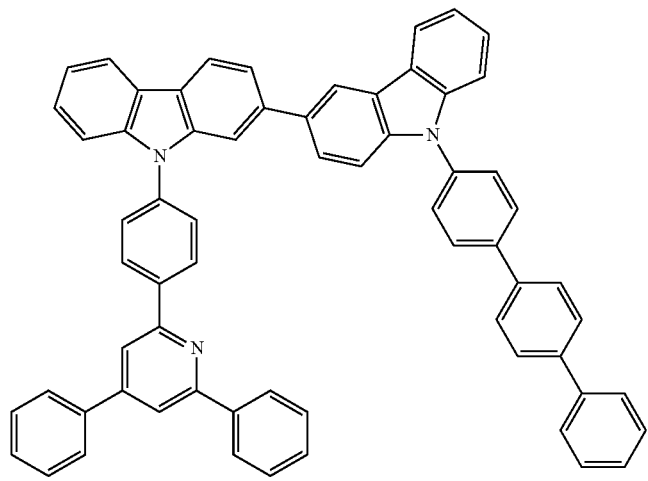
[D-146]
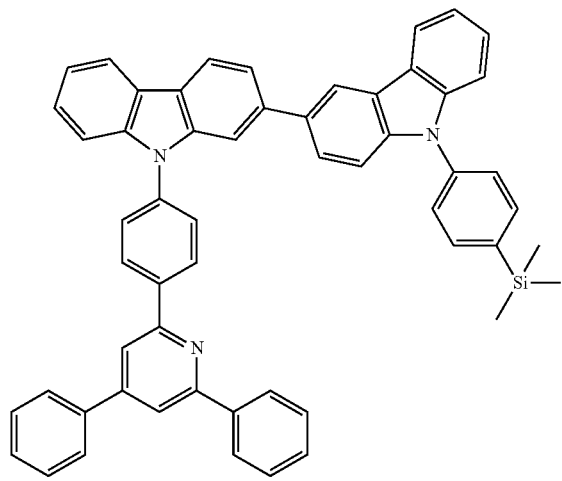

-continued
[D-147]
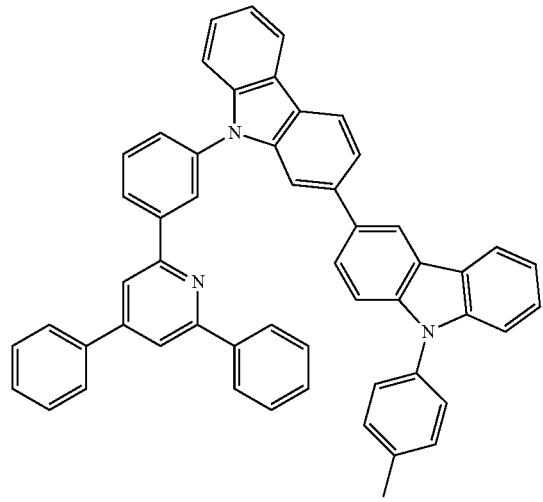
[D-148]
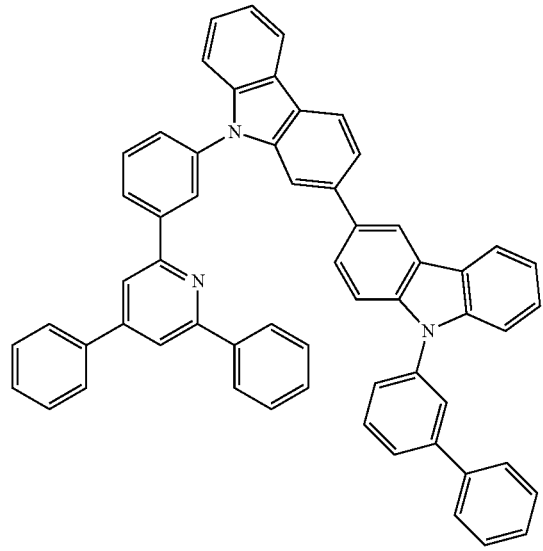
[D-149]
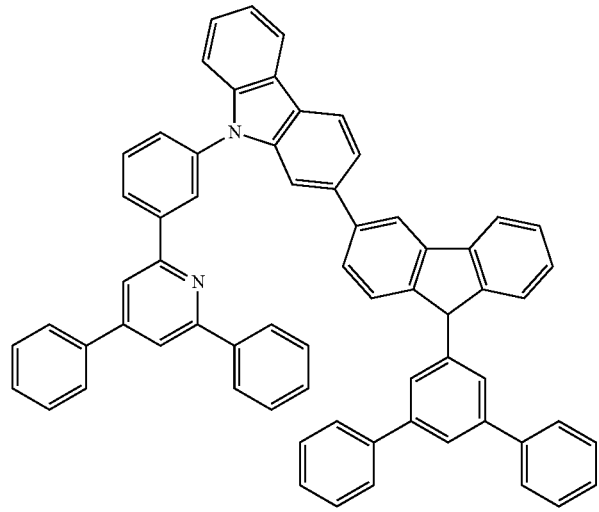

-continued
[D-150]
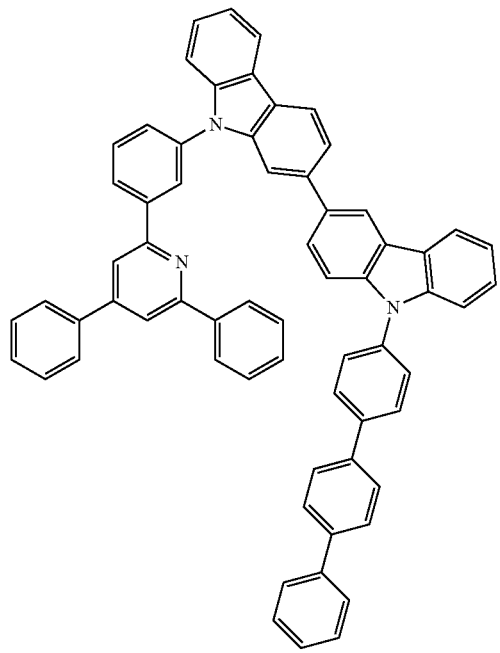
[D-151]
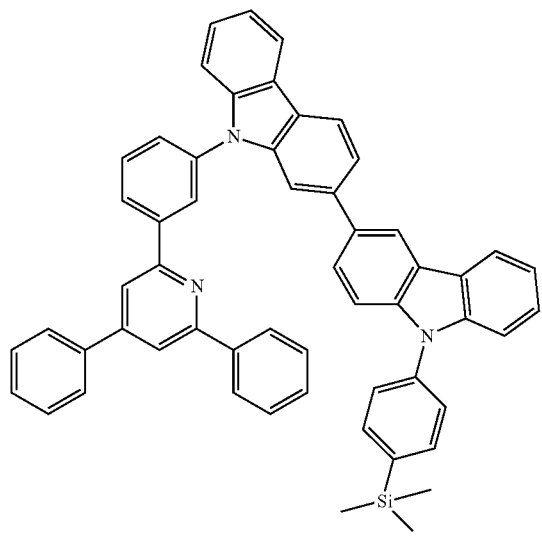
[D-152]
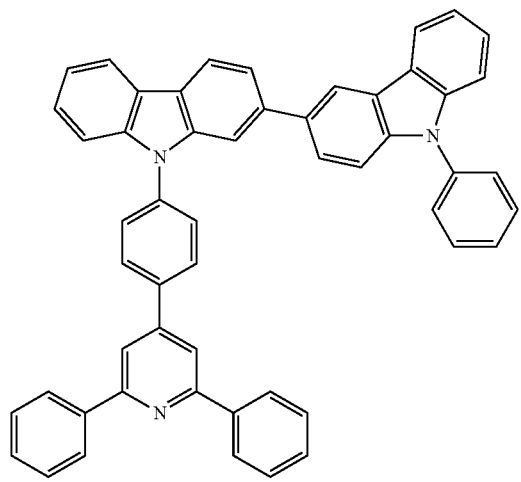

[D-153]
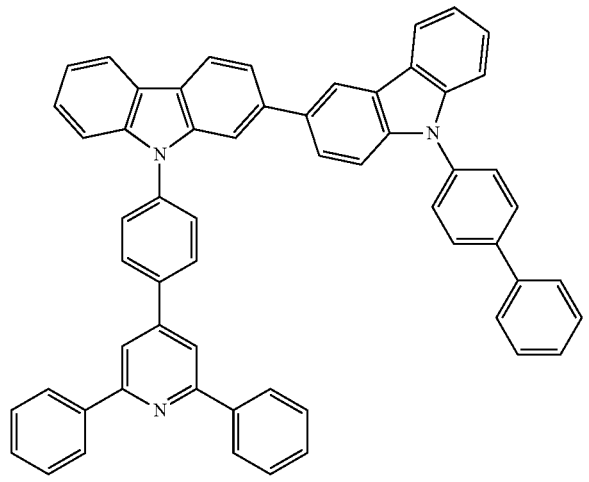
[D-154]
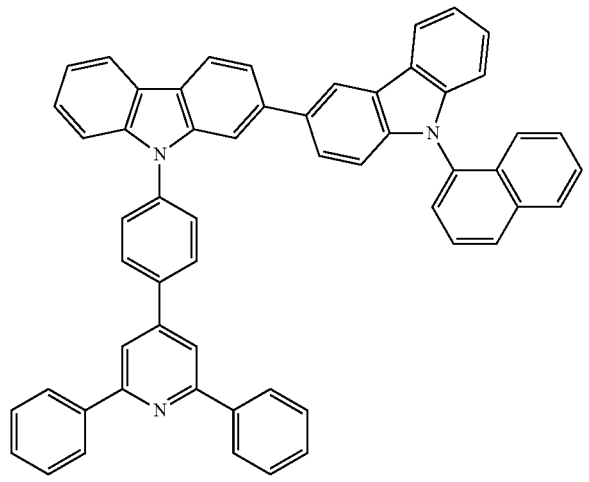
[D-155]
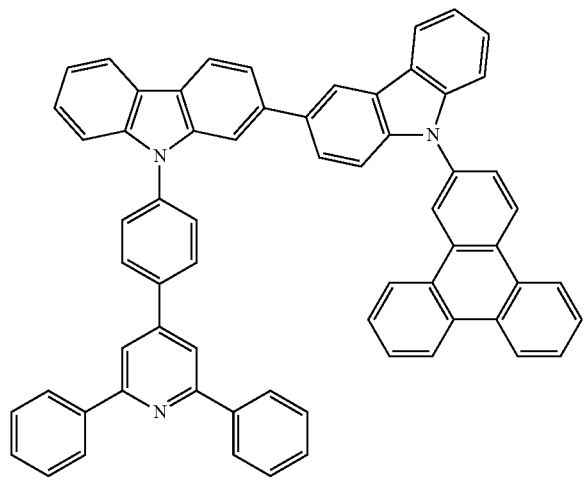

-continued
[D-156]
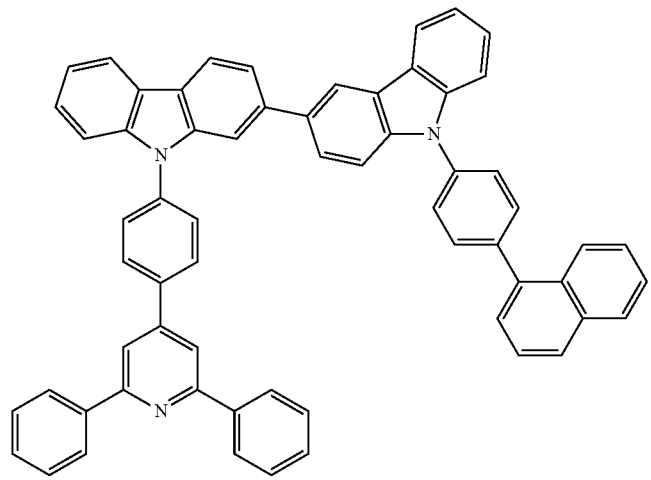
[D-157]
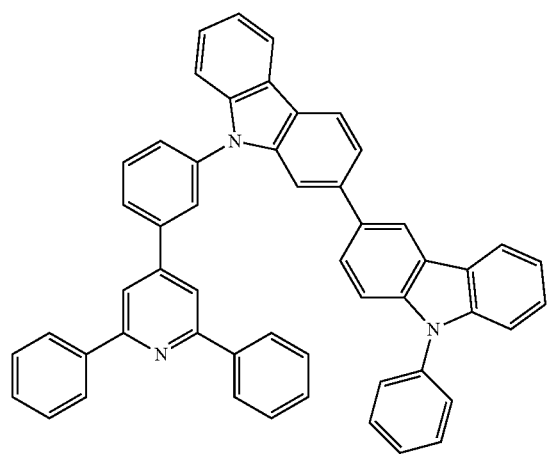
[D-158]
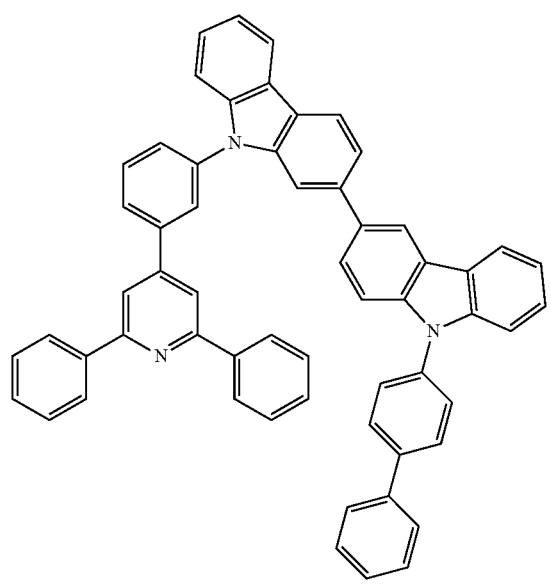

[D-159]
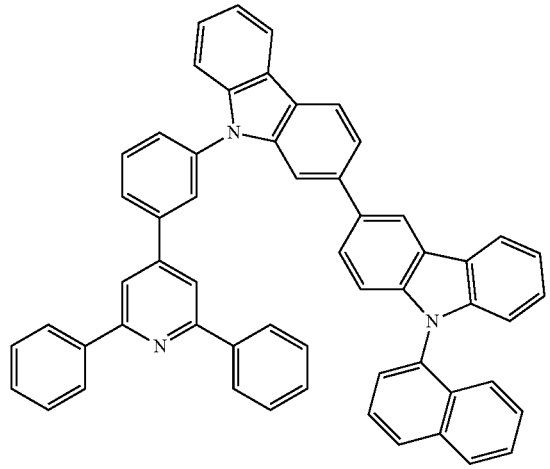
[D-160]
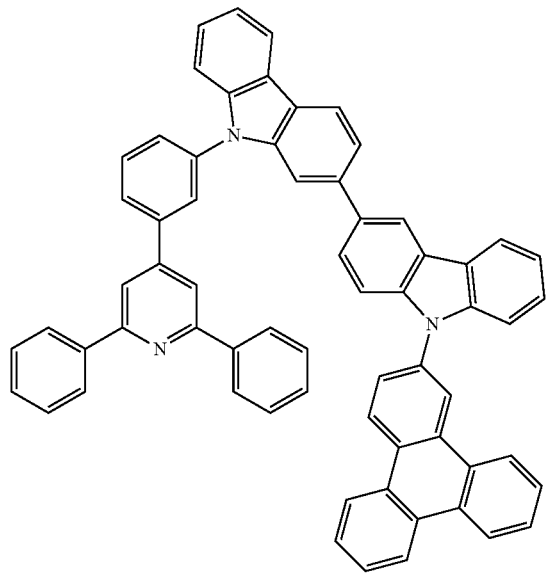
[D-161]
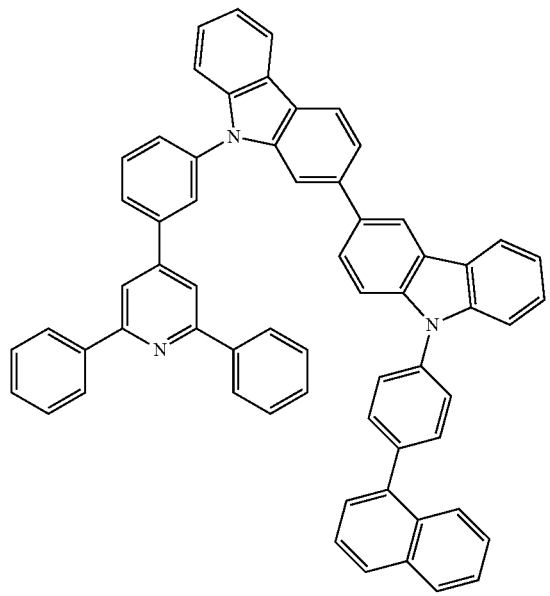

-continued
[D-162]
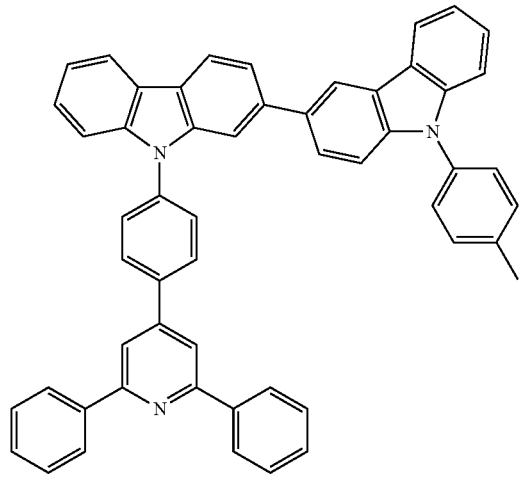
[D-163]
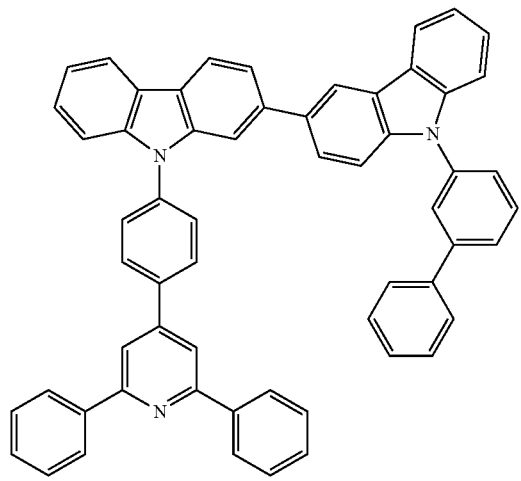
[D-164]
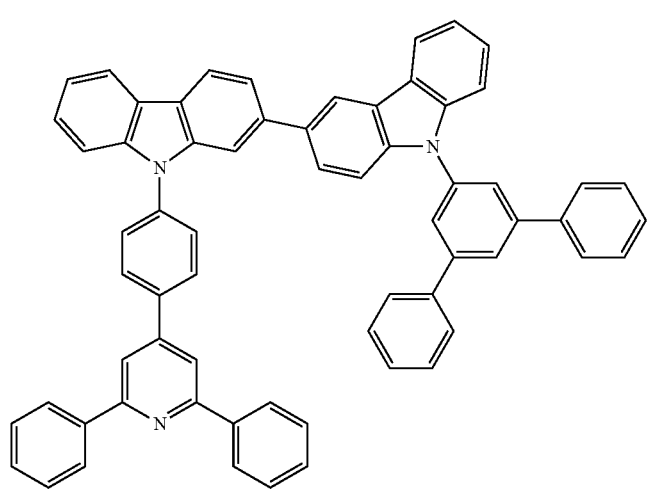

-continued
[D-165]
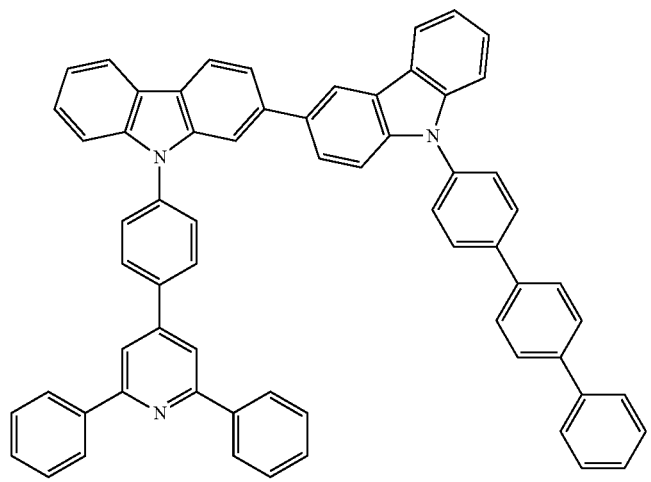
[D-166]
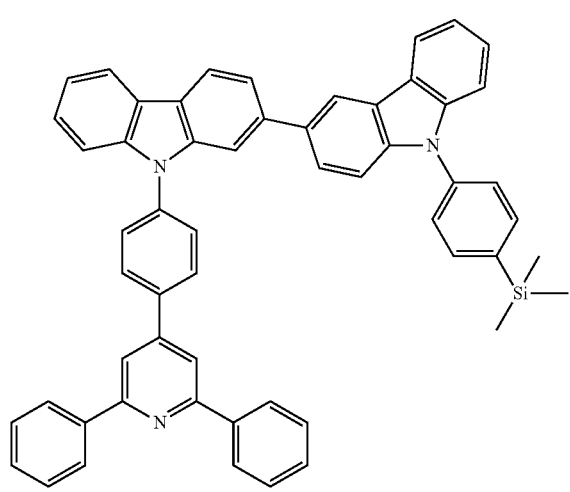
[D-167]
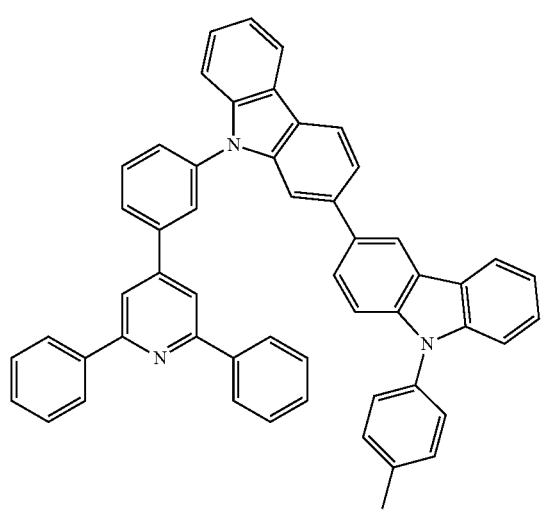

[D-168]
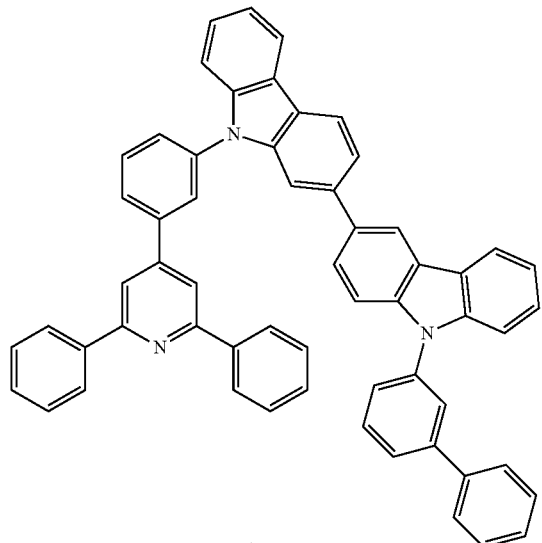
[D-169]
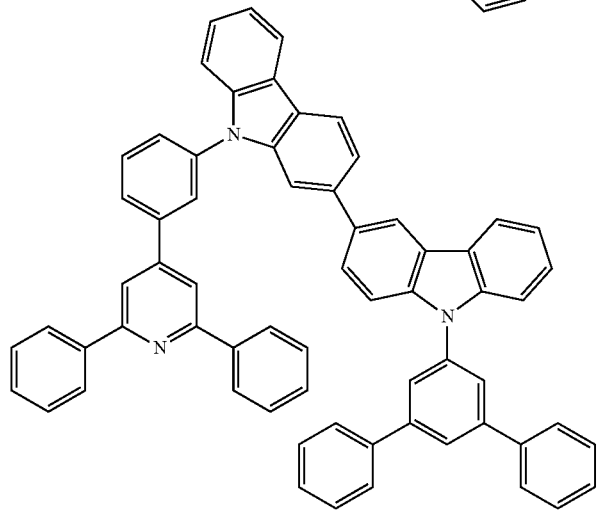
[D-170]
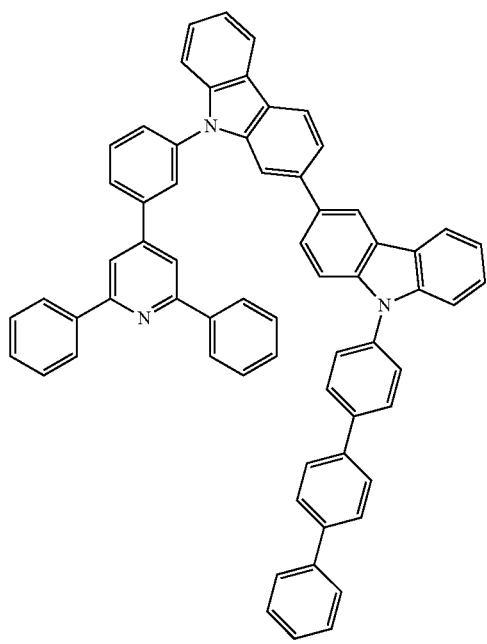

-continued
[D-171]
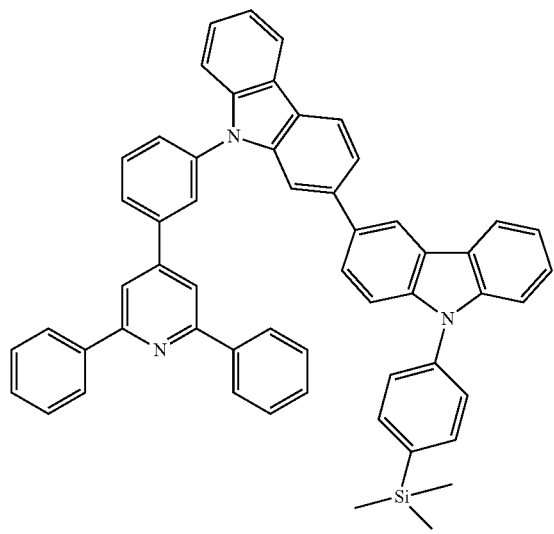
[D-172]
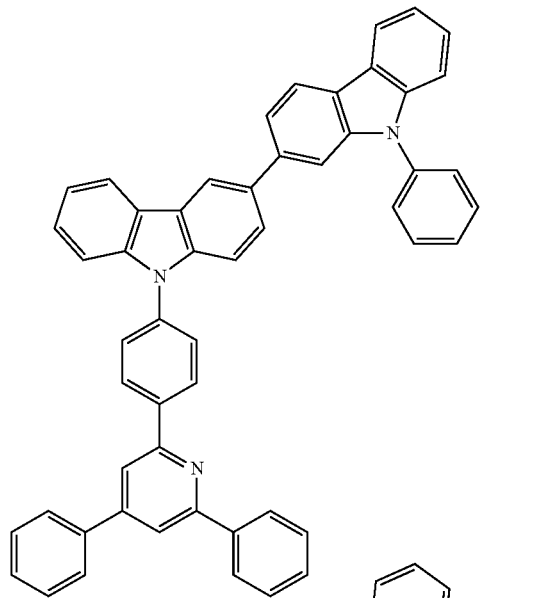
[D-173]
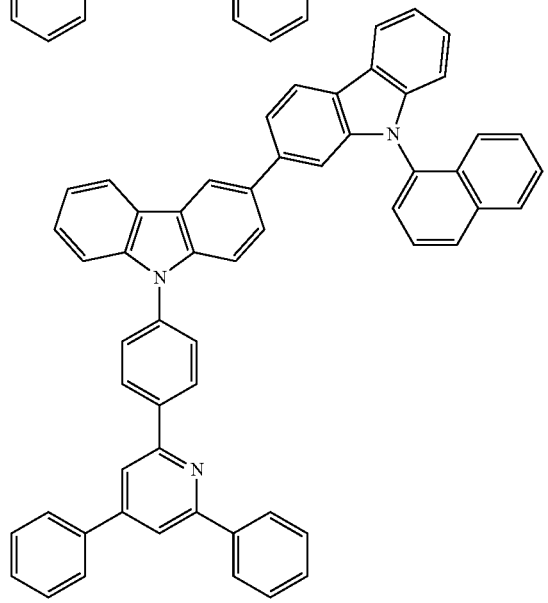

-continued
[D-174]
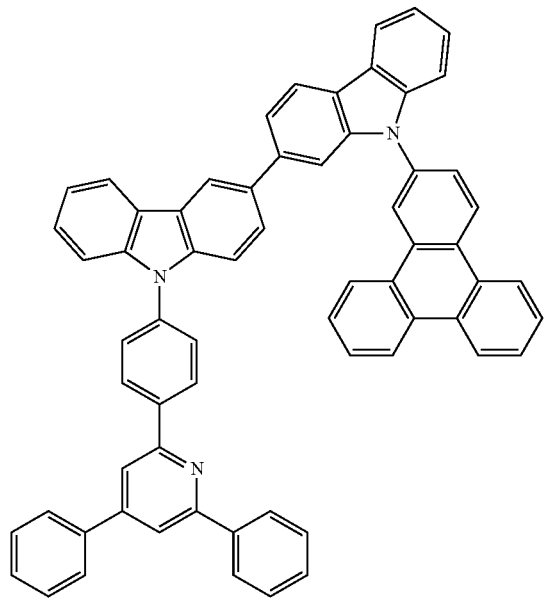
[D-185]
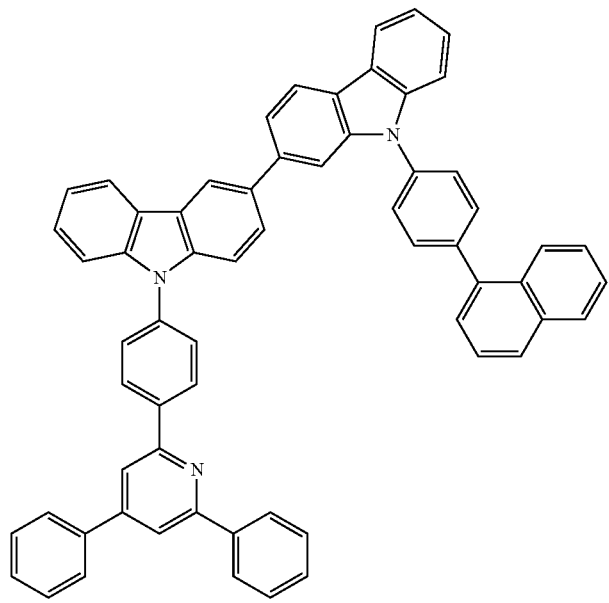
[D-176]
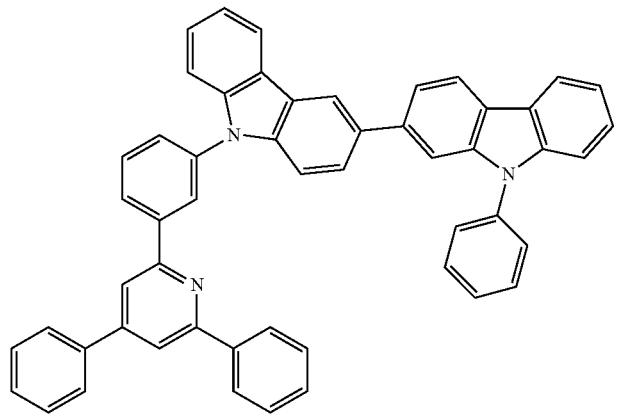

-continued
[D-177]
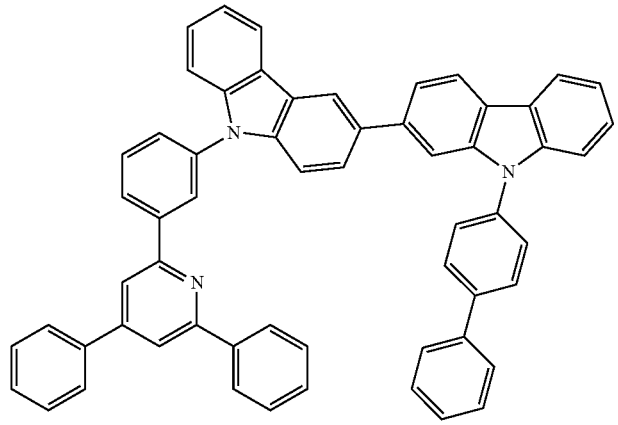
[D-178]
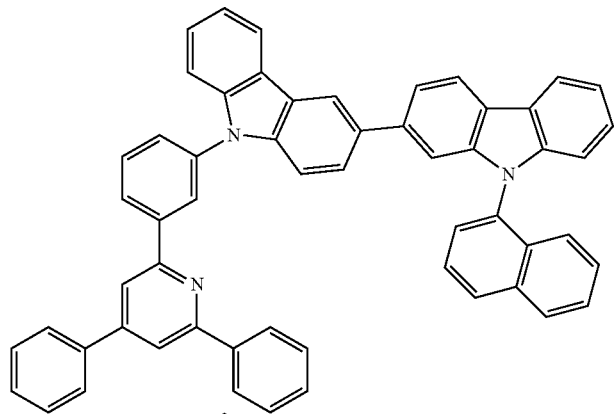
[D-179]
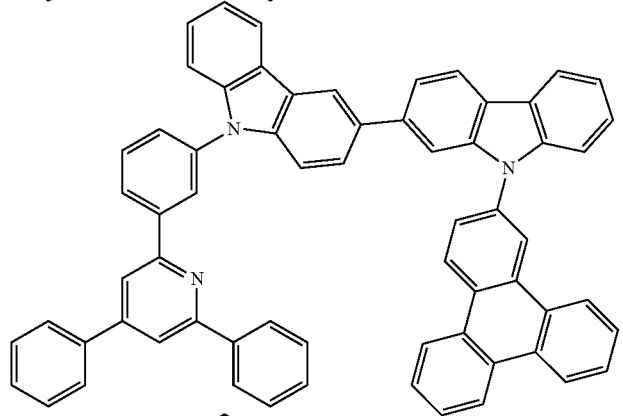
[D-180]
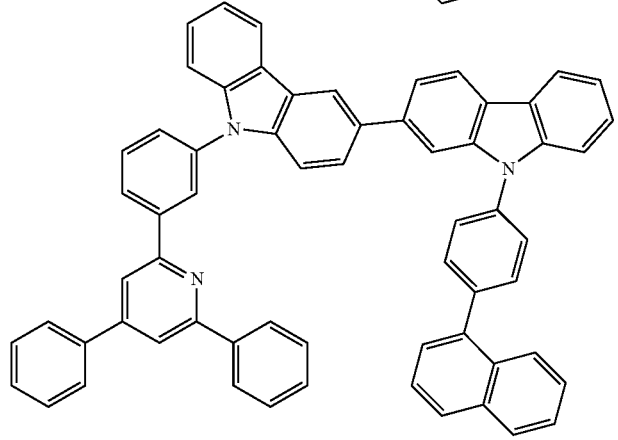

-continued
[D-181]
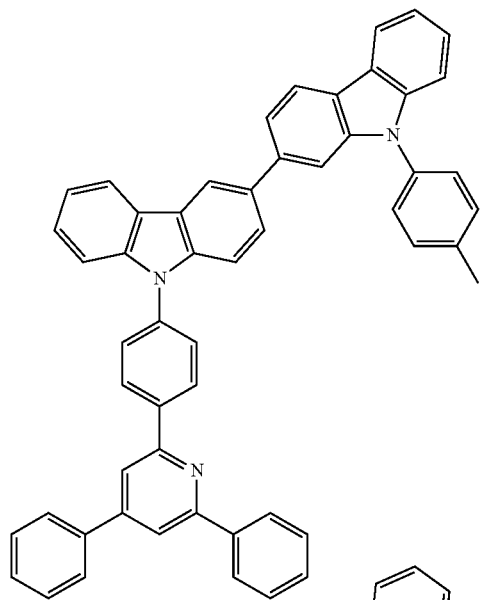
[D-1821]
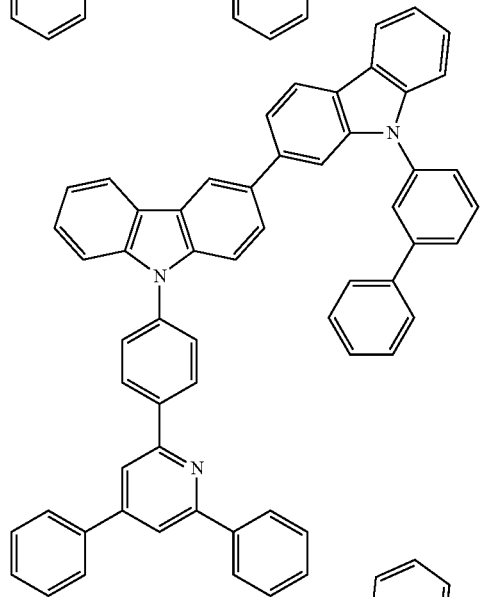
[D-183]
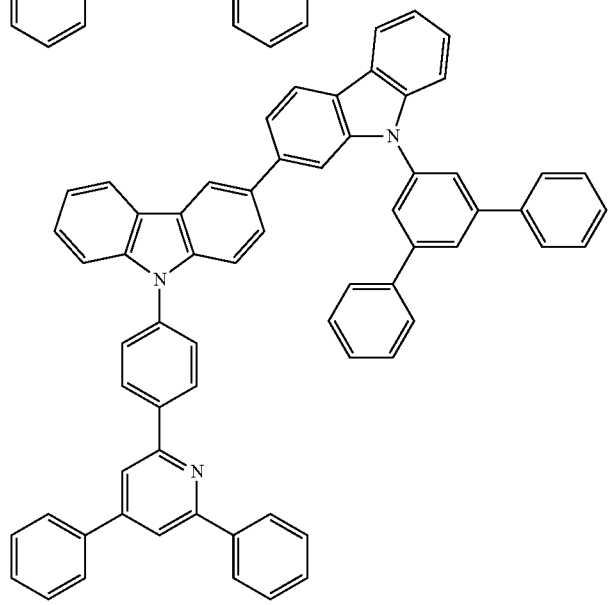

-continued
[D-184]
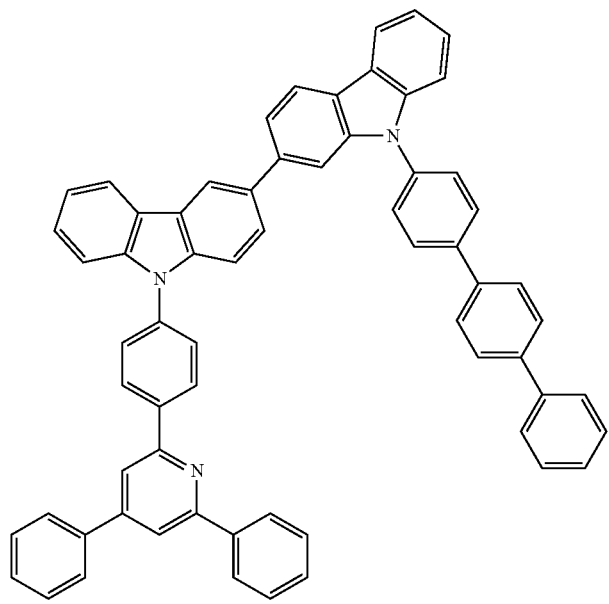
[D-185]
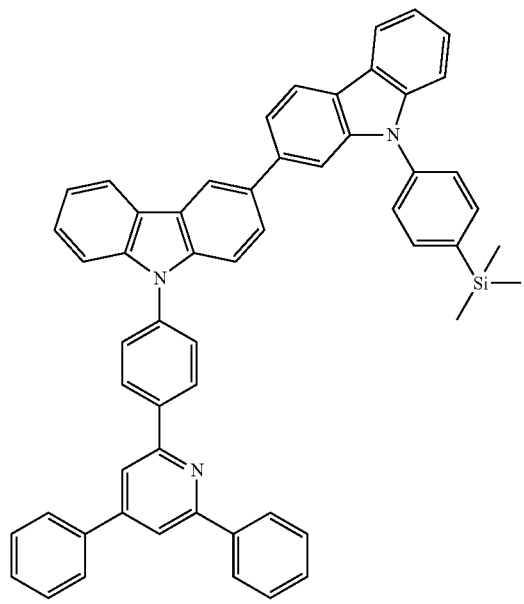
[D-186]
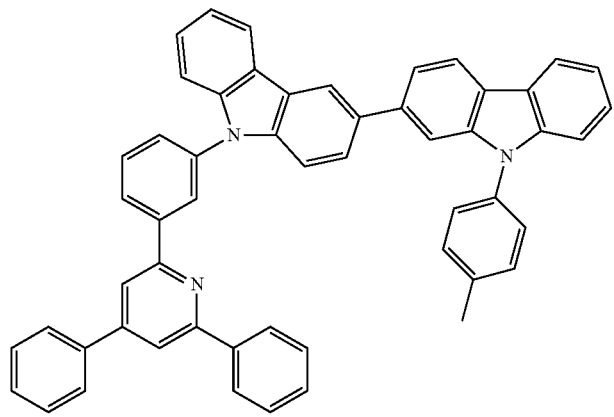

[D-187]
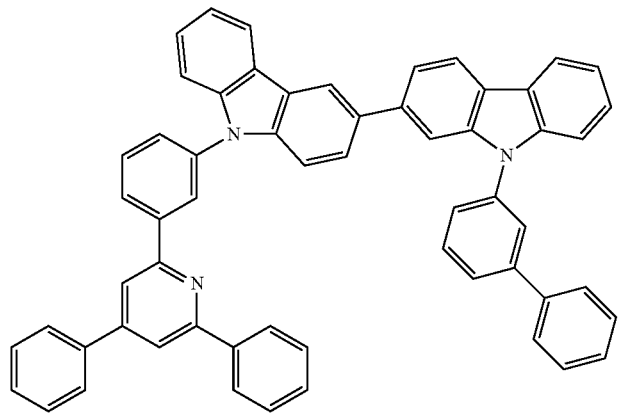
[D-188]
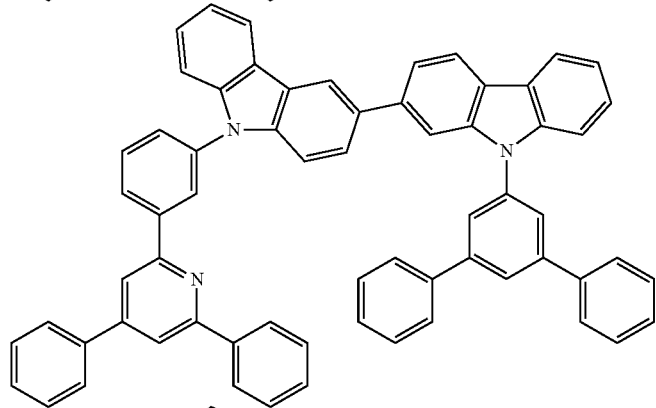
[D-189]
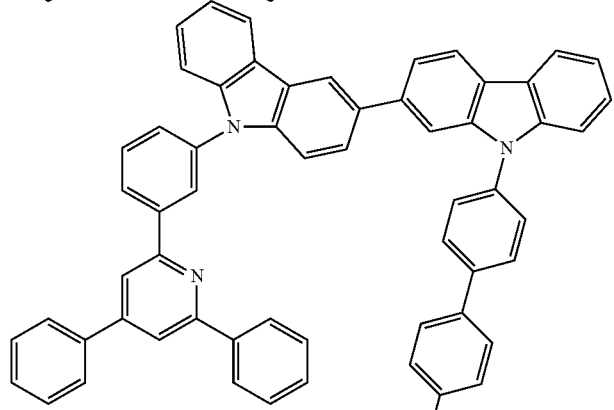
[D-190]
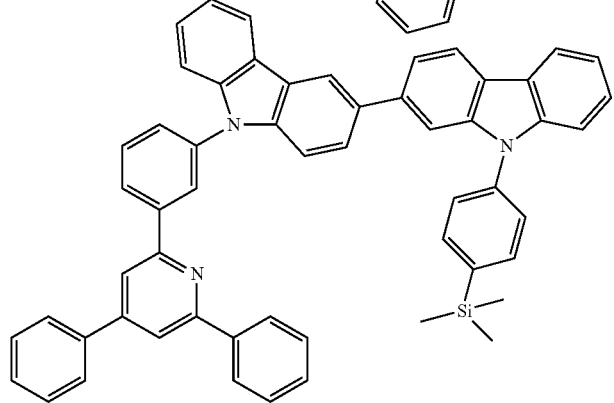

-continued
[D-191]
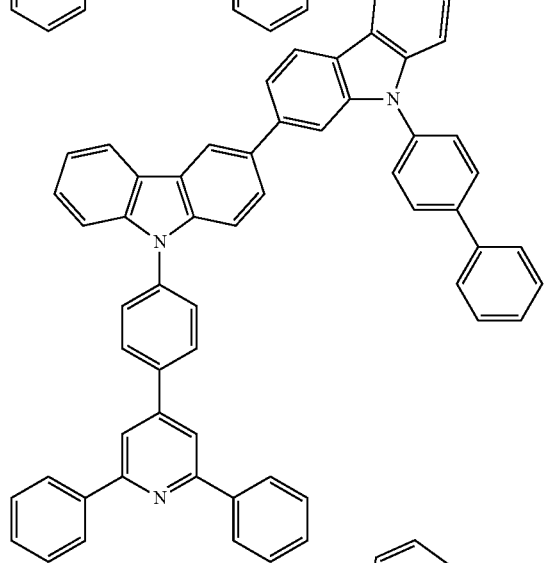
[D-192]
[D-193]
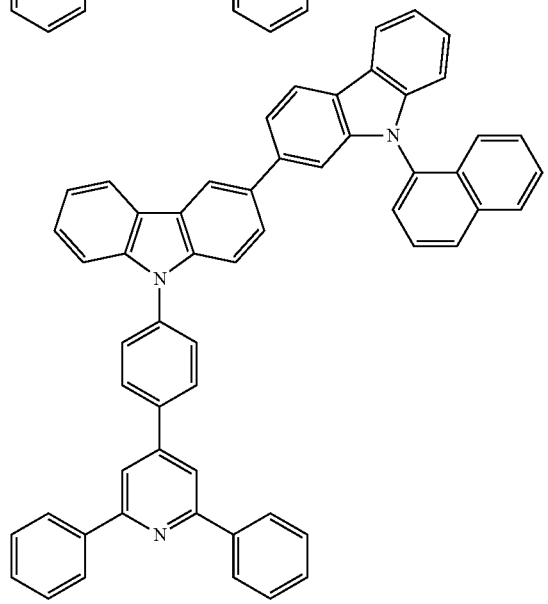

[D-194]
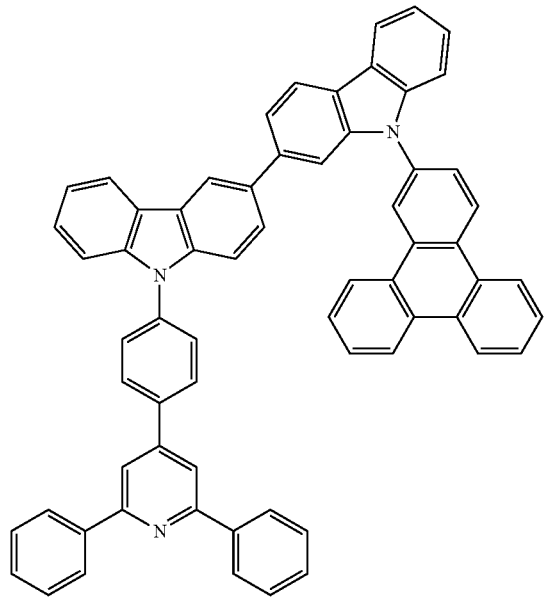
[D-195]
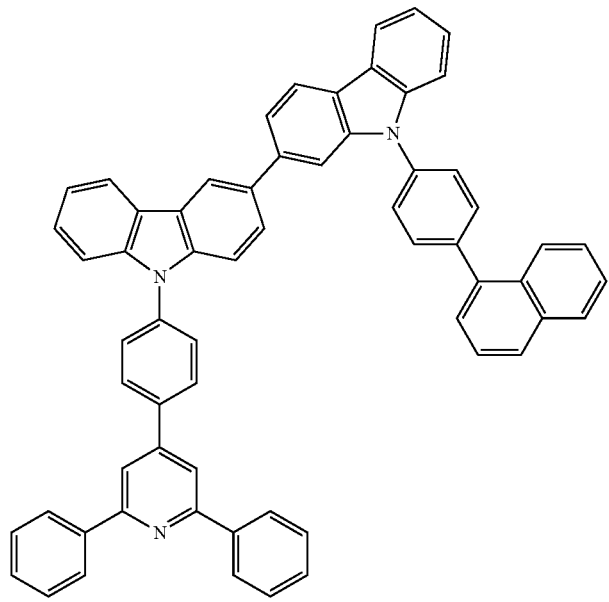
[D-196]
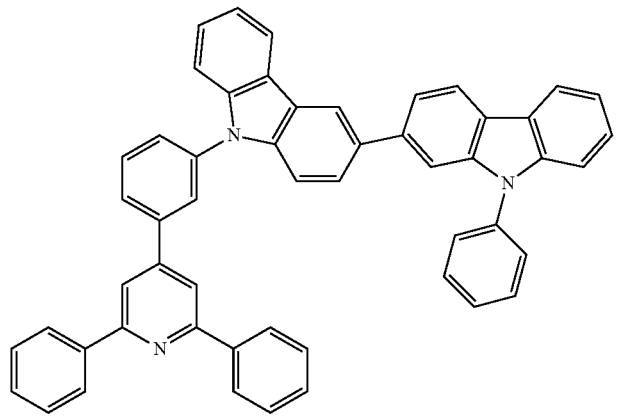

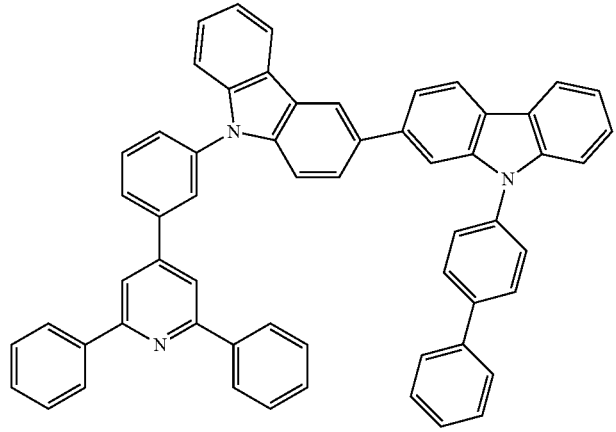
[D-197]
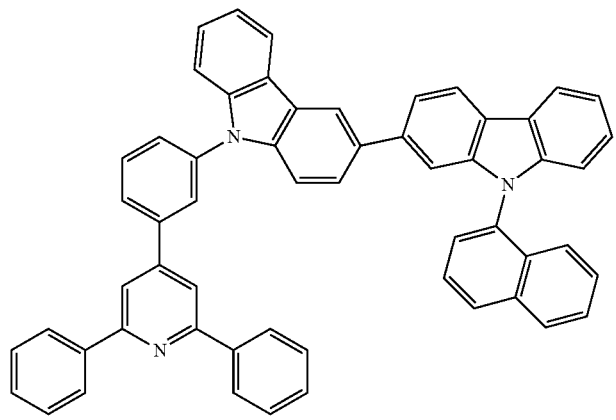
[D-198]
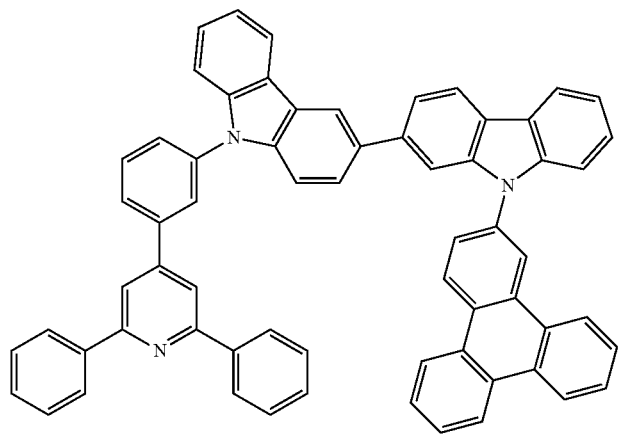
[D-199]

-continued
[D-200]
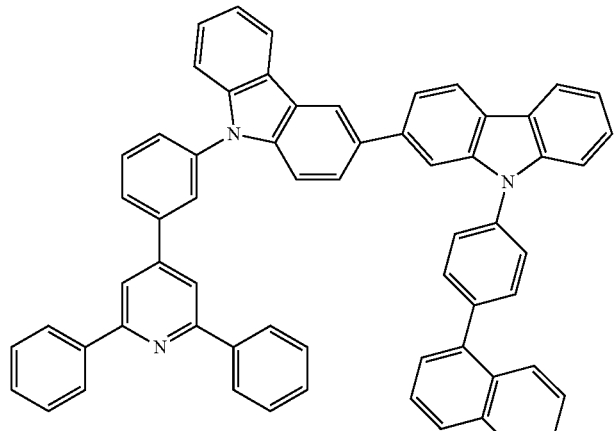
[D-201]
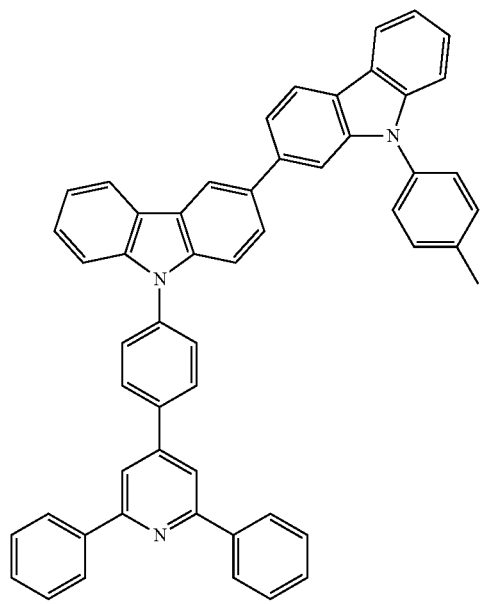
[D-202]
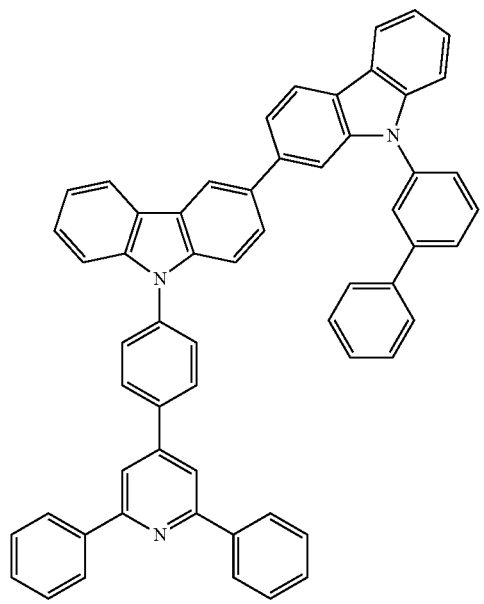

-continued
[D-203]
[D-204]
[D-205]
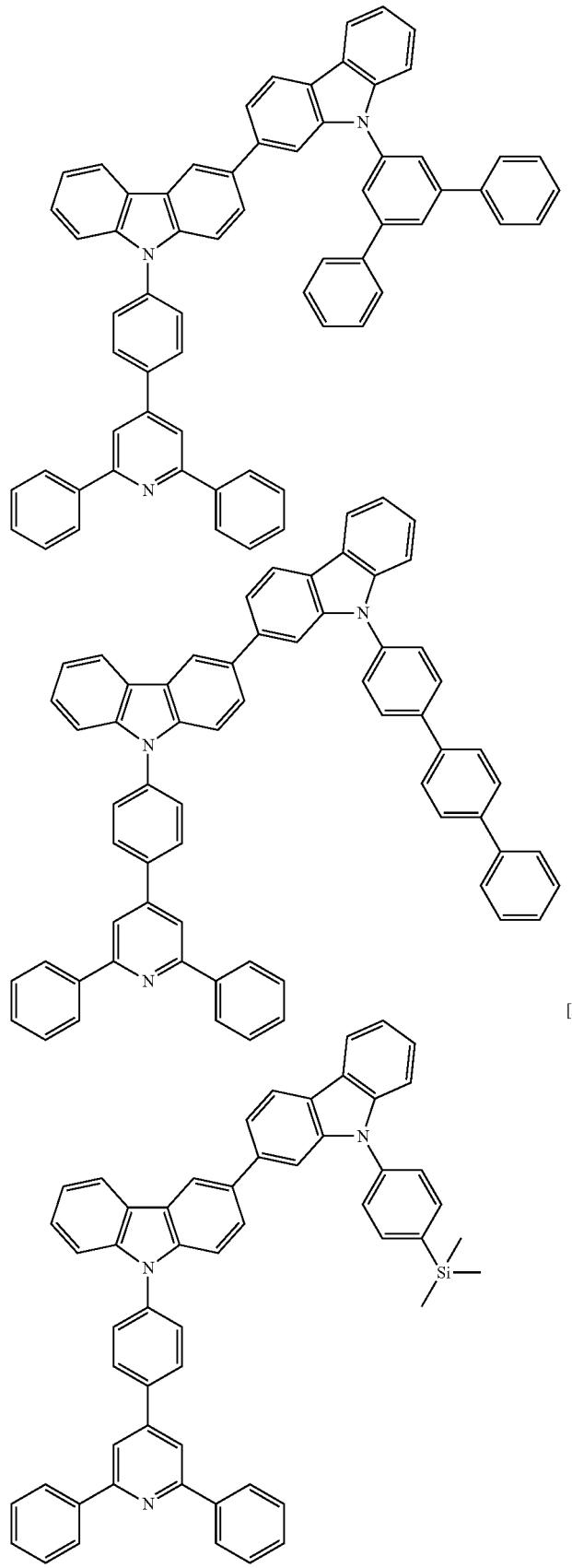

[D-206]
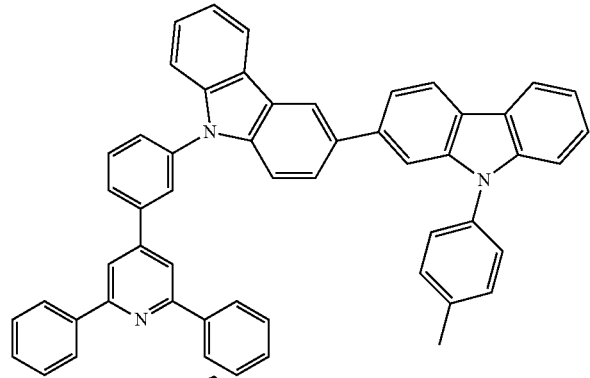
[D-207]
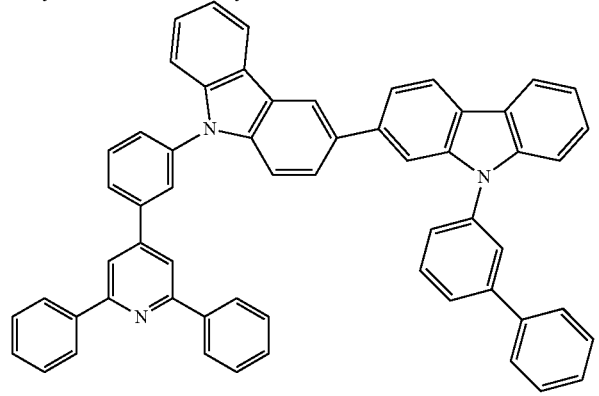
[D-208]
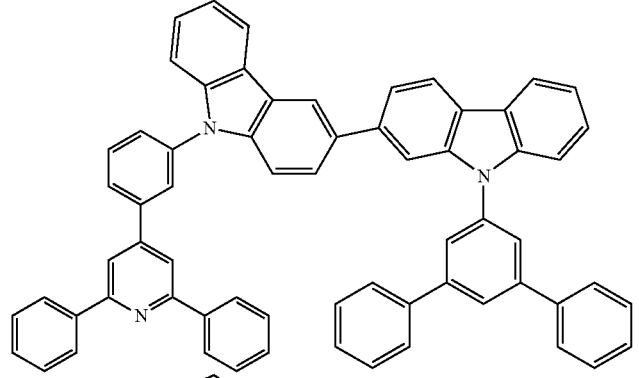
[D-209]
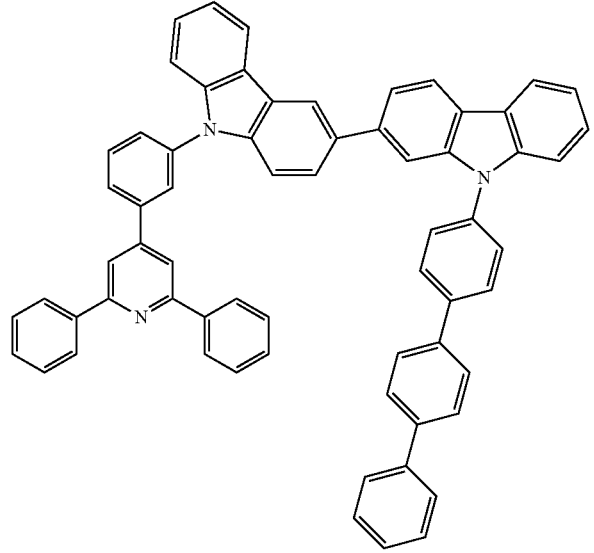

[D-210]
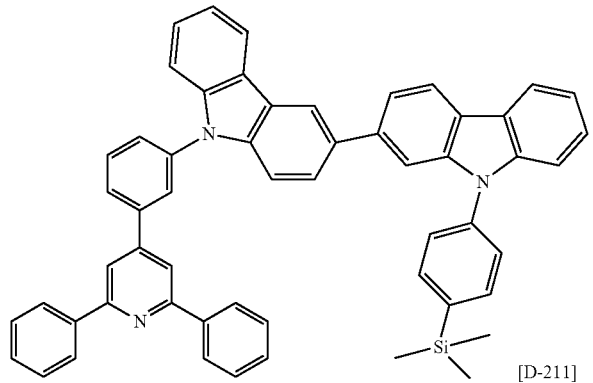
[D-211]
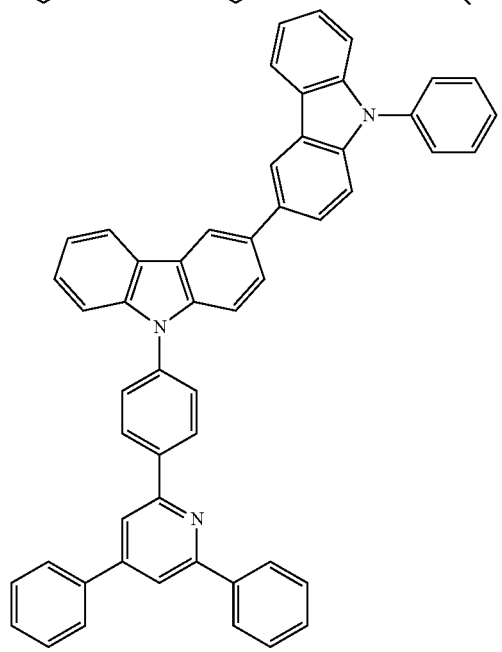
[D-212]
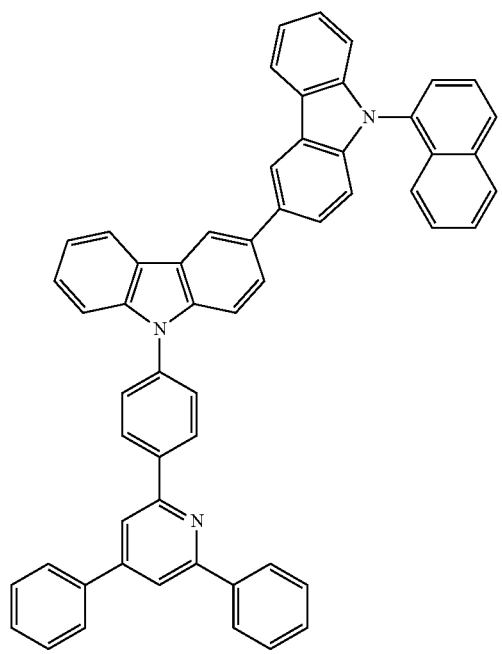

[D-213]
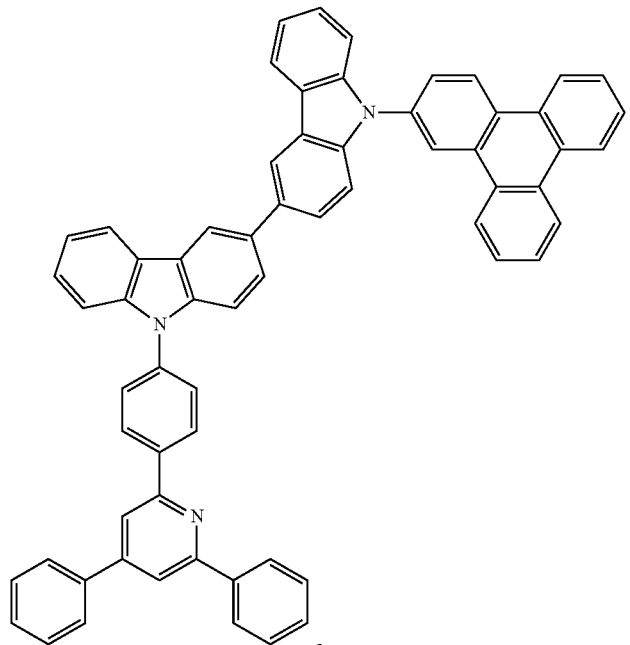
[D-214]
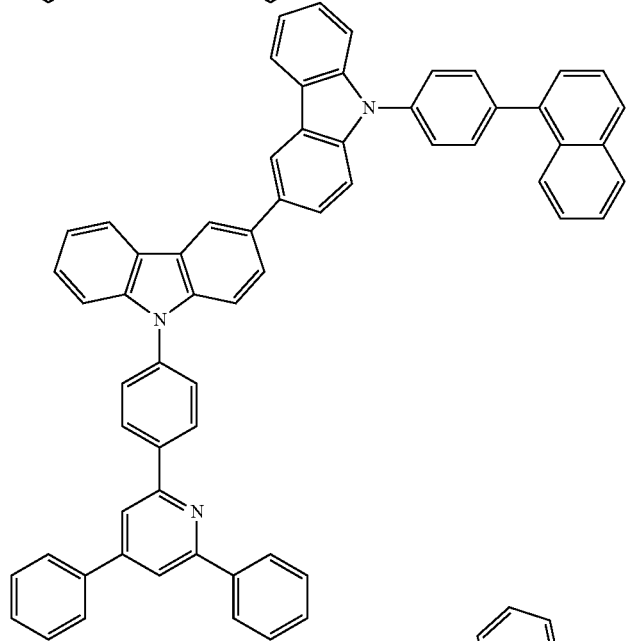
[D-215]
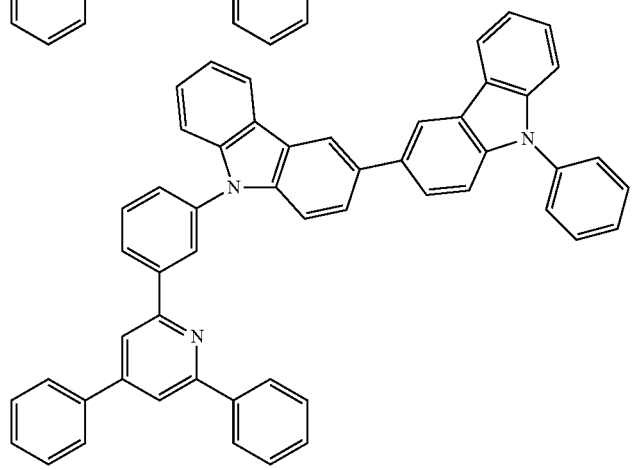

[D-216]
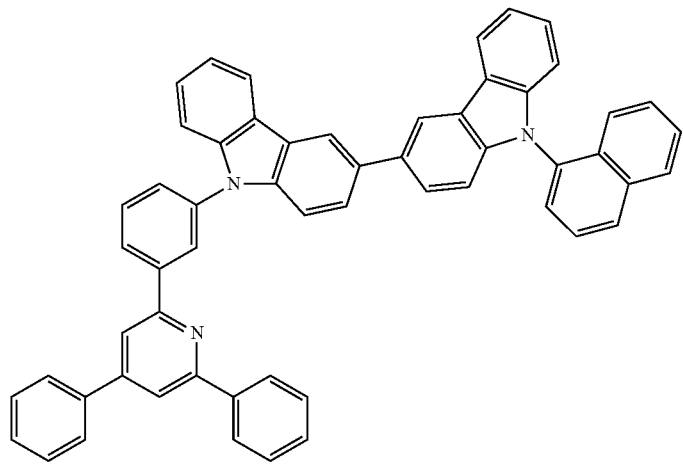
[D-217]
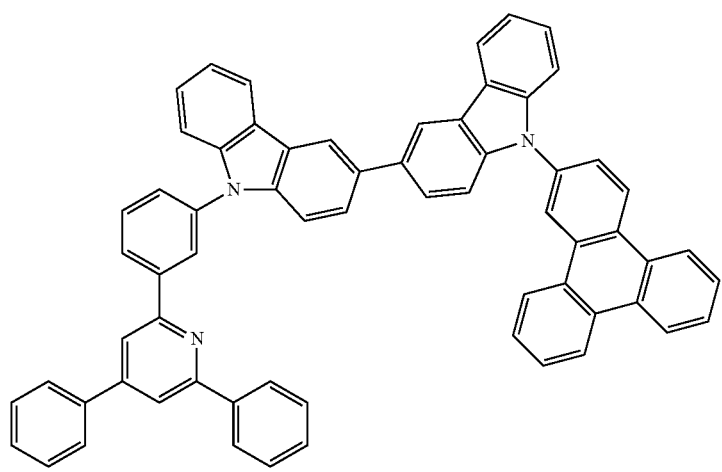
[D-218]
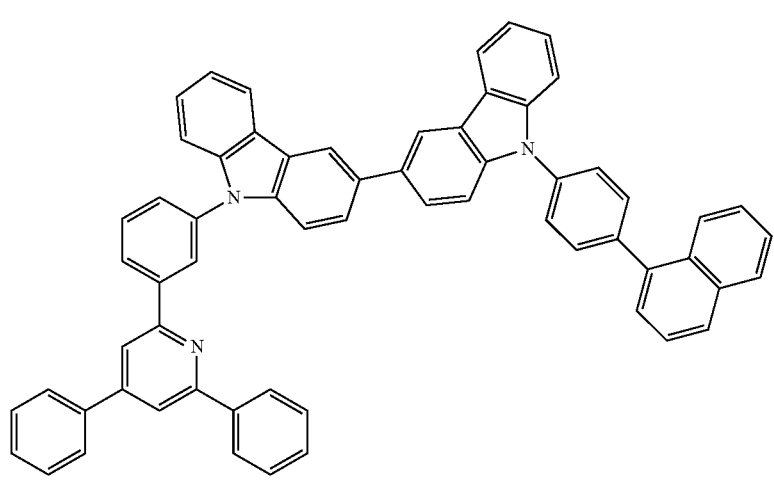

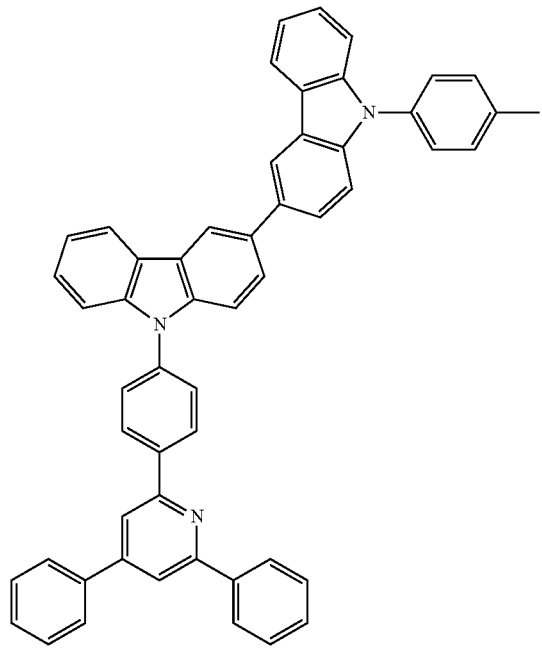
[D-219]
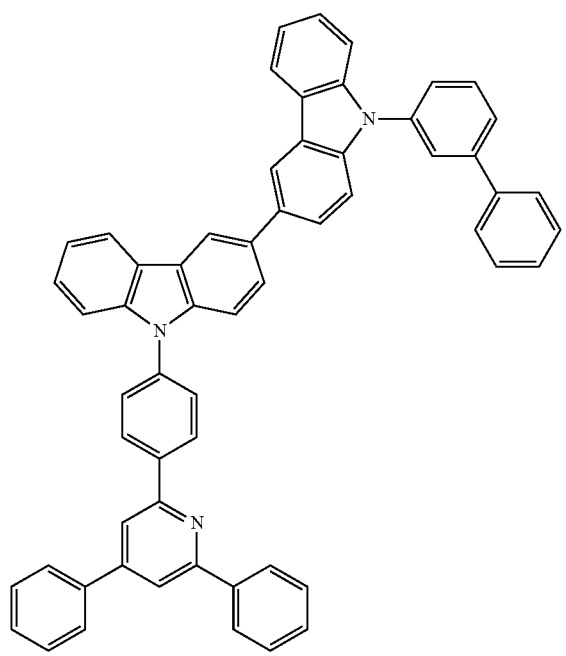
[D-220]

[D-221]
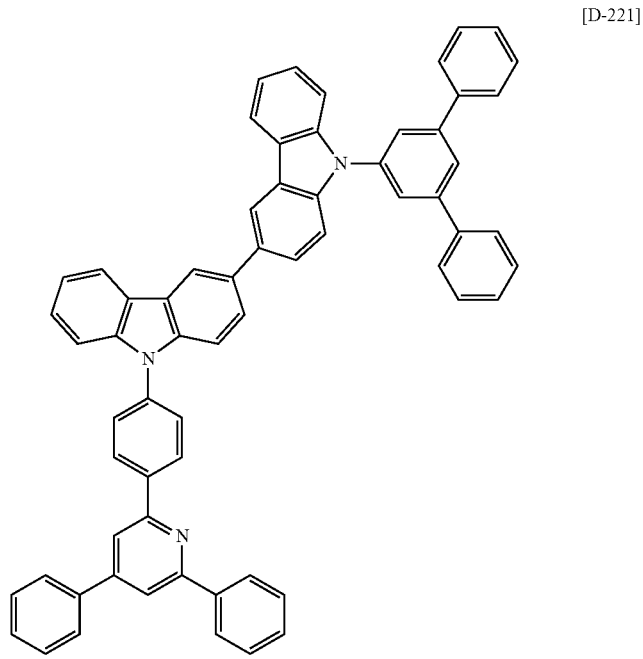
[D-222]
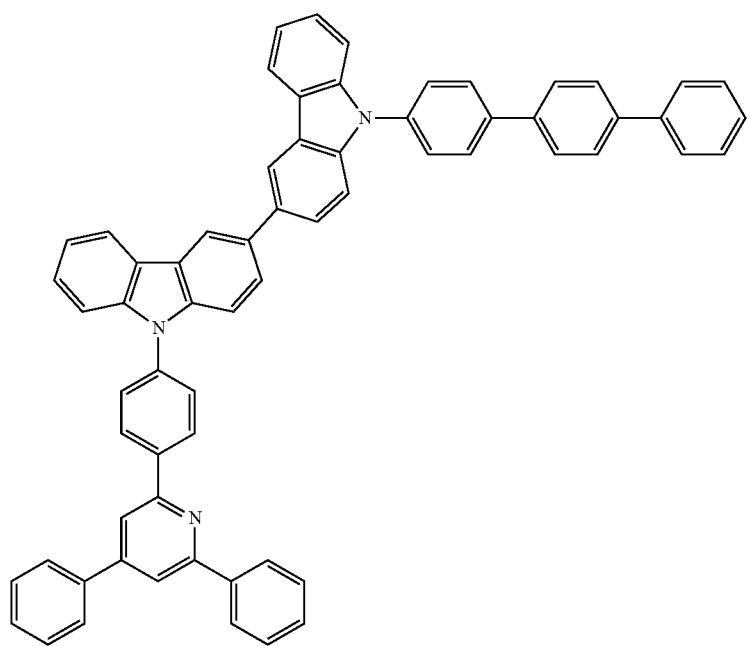

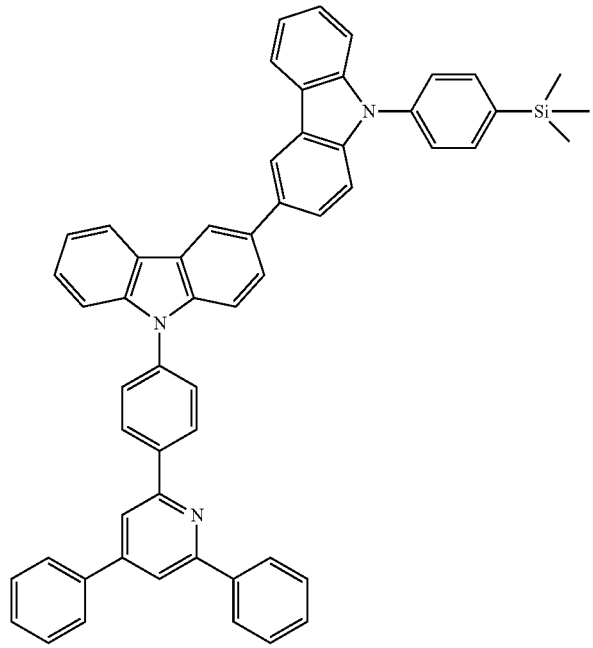
[D-223]
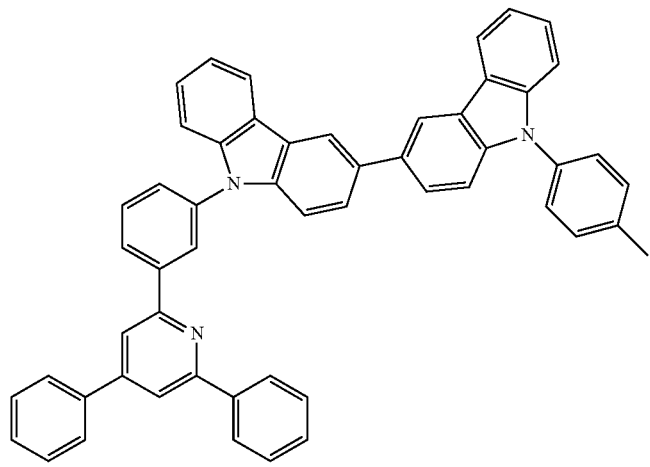
[D-224]
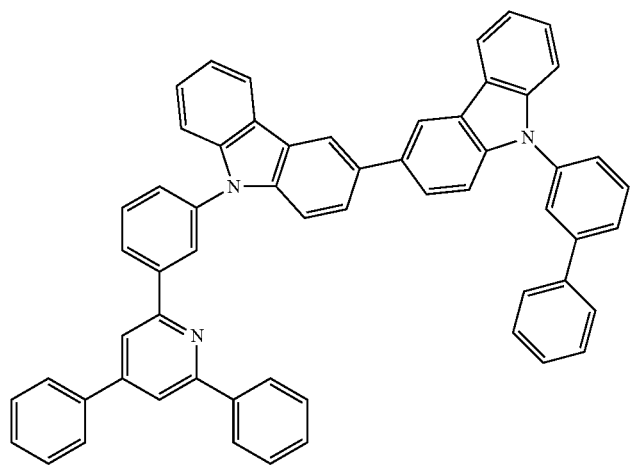
[D-225]

[D-226]
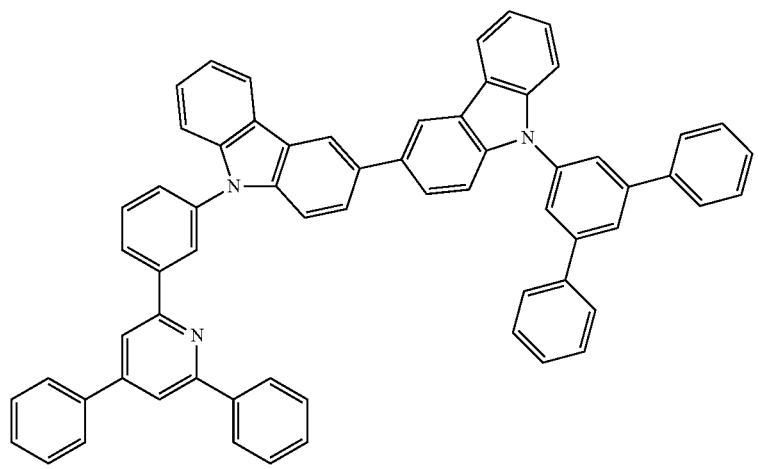
[D-227]
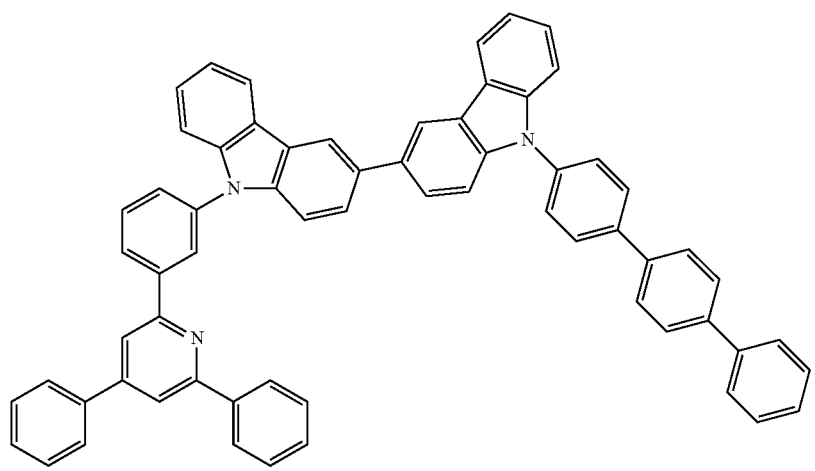
[D-228]
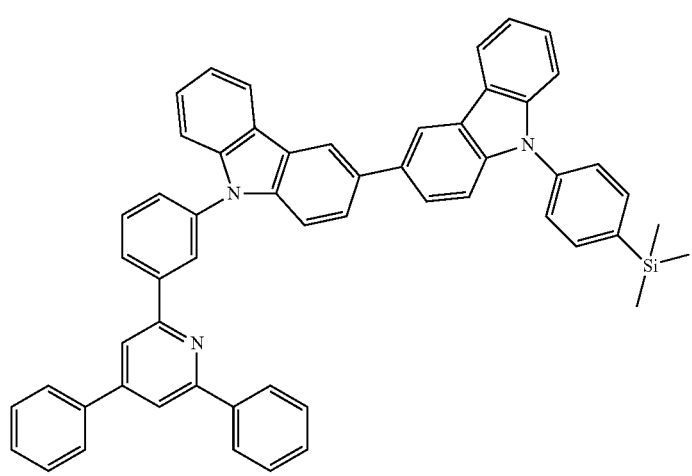

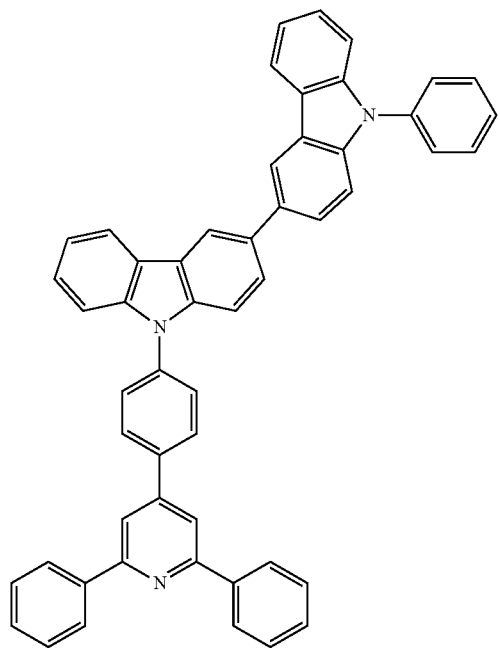
[D-229]
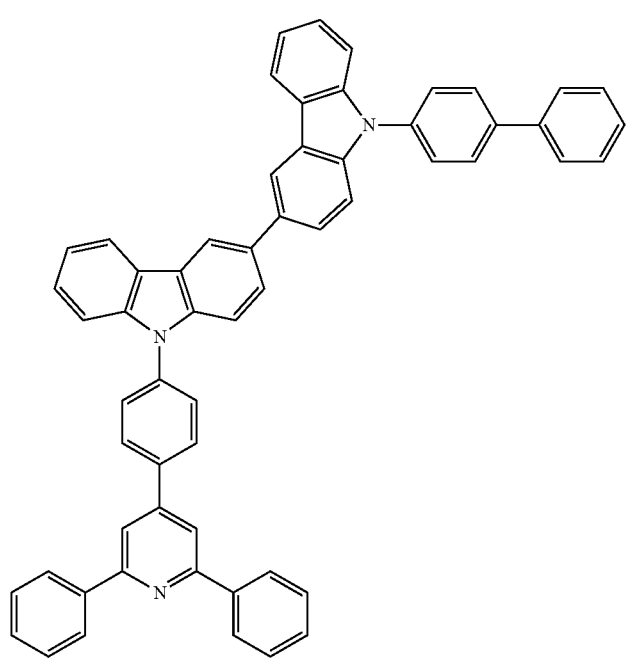
[D-230]

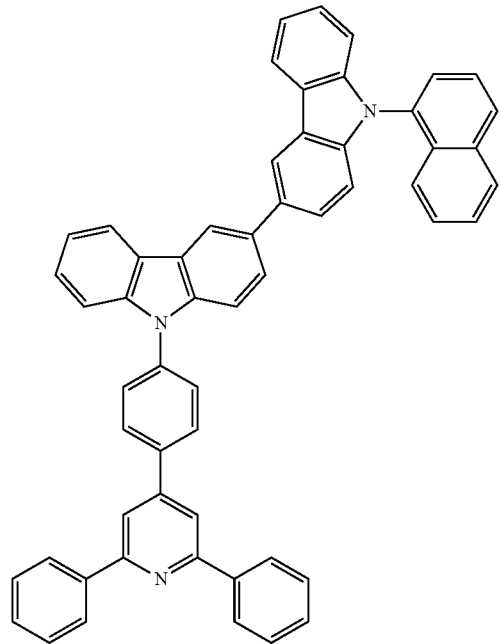
[D-231]
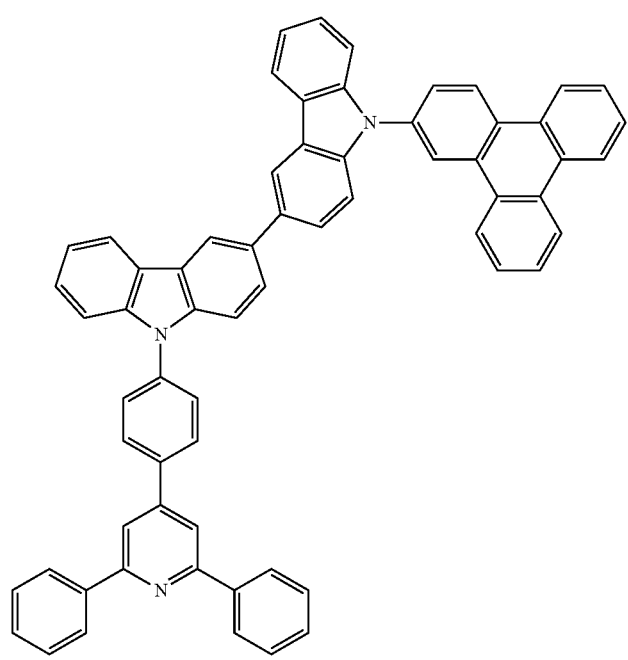
[D-232]

-continued
[D-233]
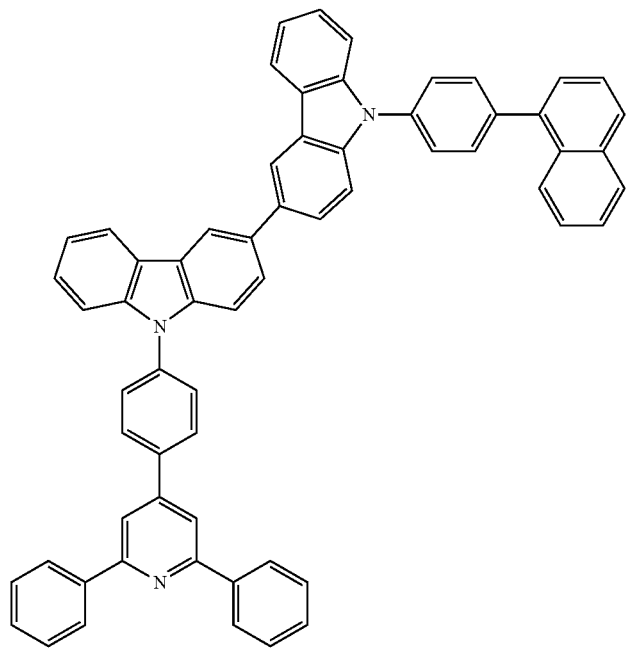
[D-234]
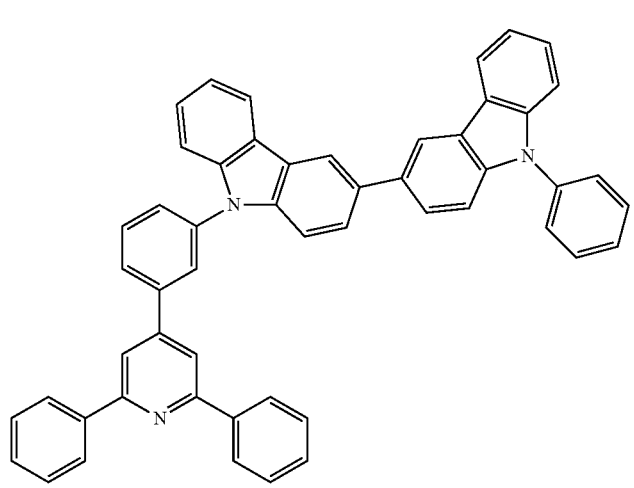
[D-235]
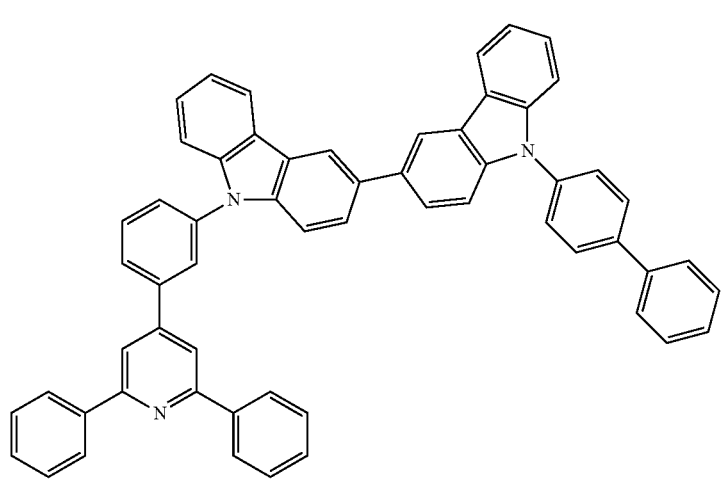

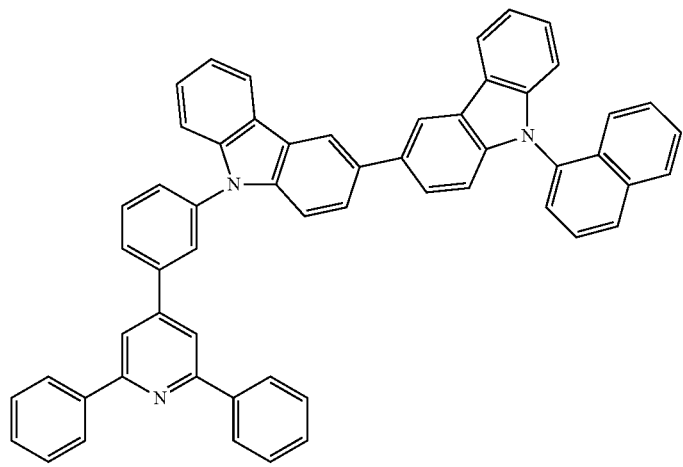
[D-236]
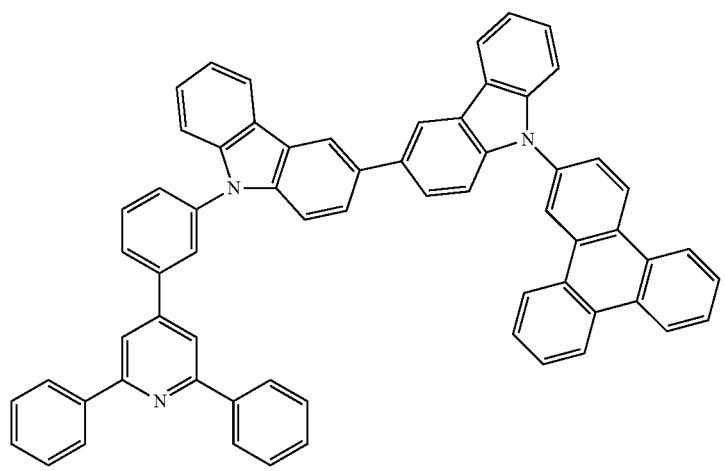
[D-237]
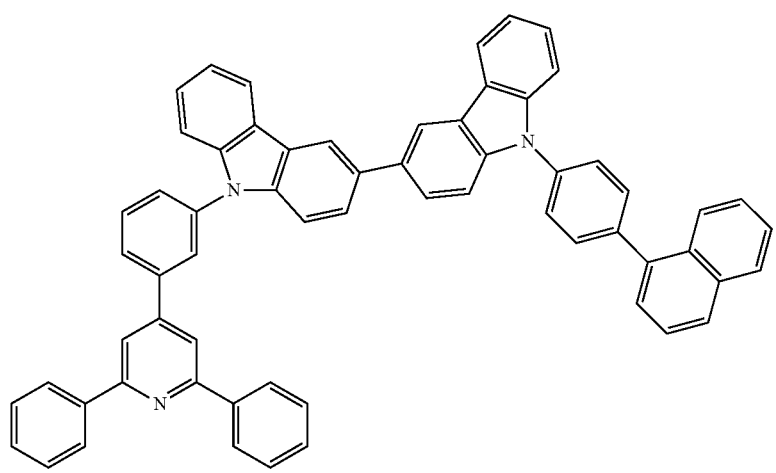
[D-238]

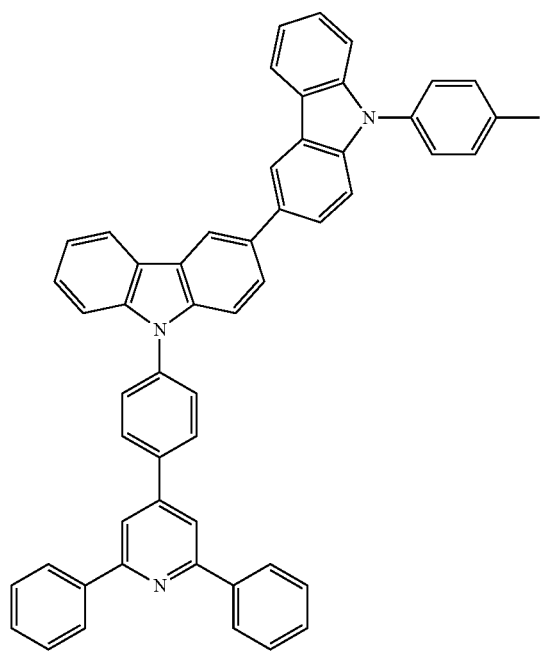
[D-239]
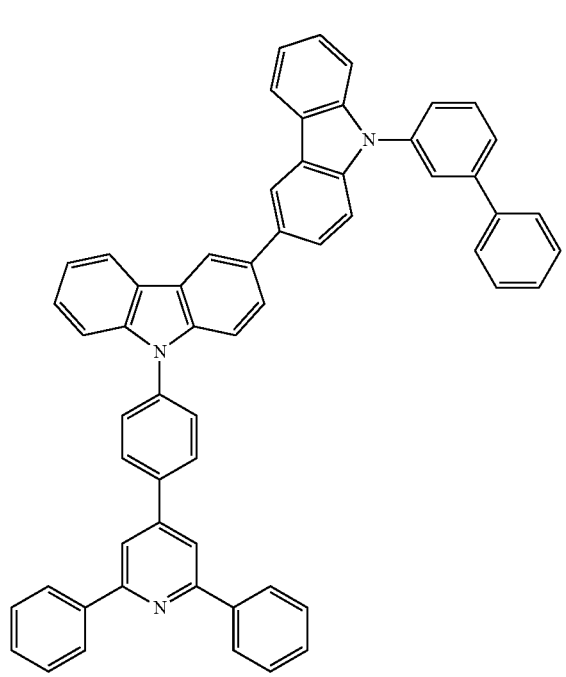
[D-240]

[D-241]
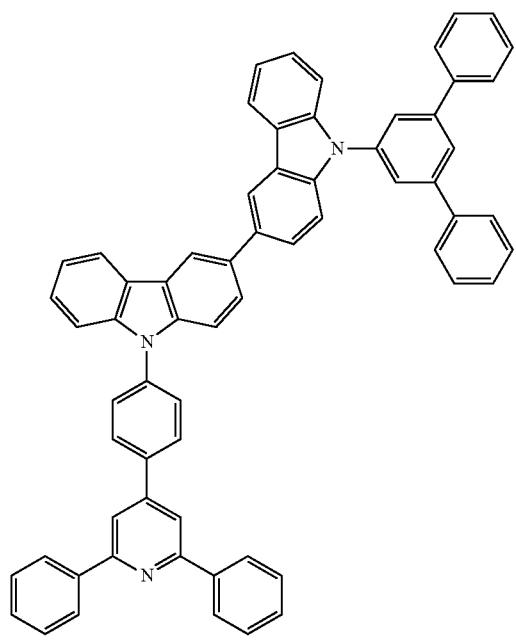
[D-242]
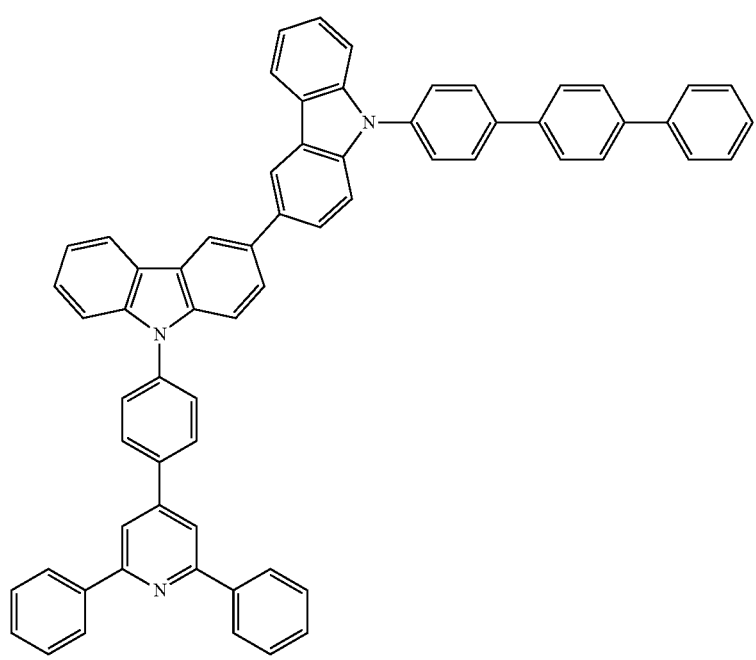

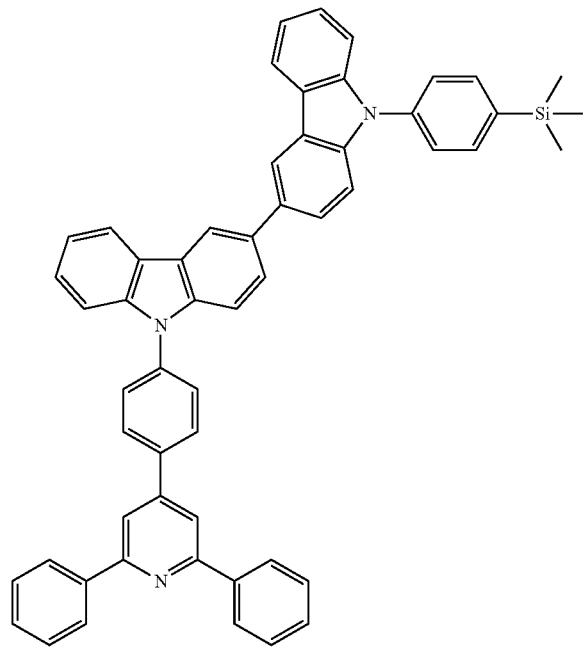
[D-243]
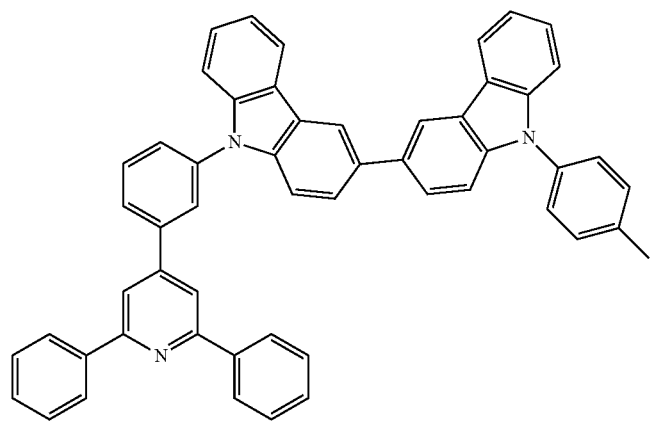
[D-244]
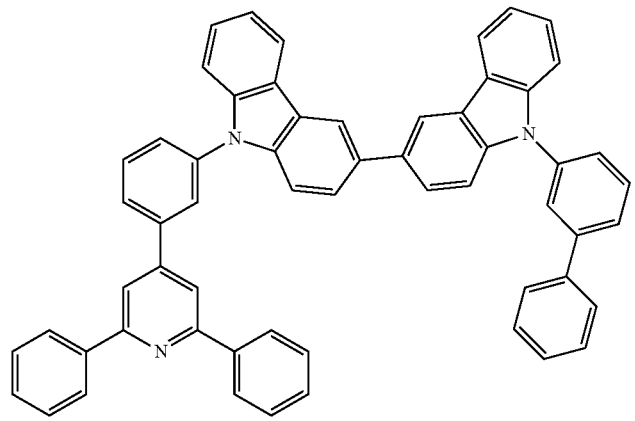
[D-245]

[D-246]
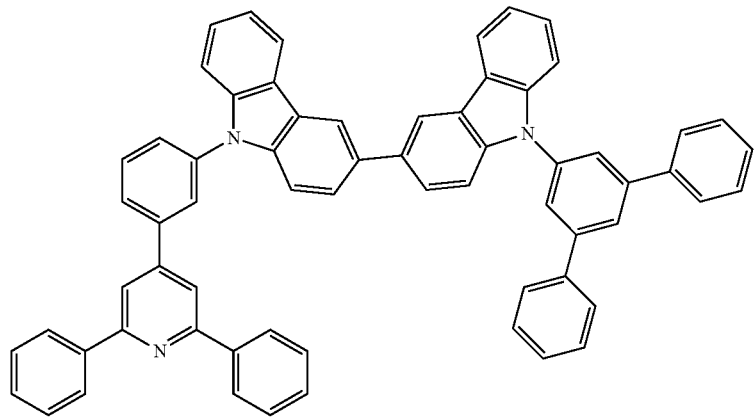
[D-247]
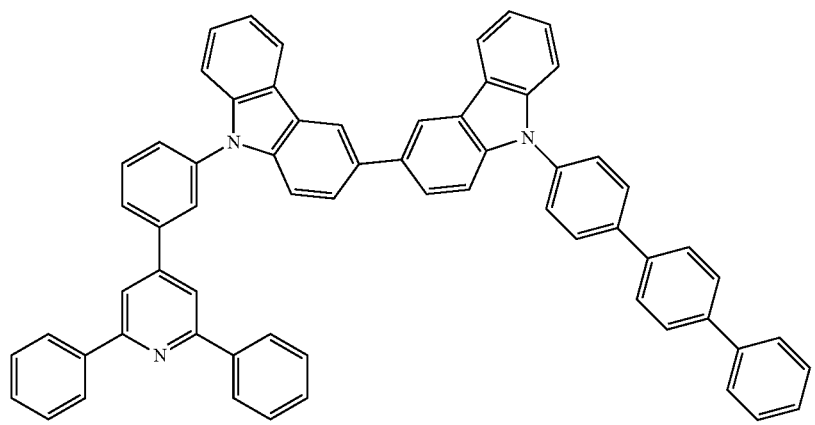
[D-248]
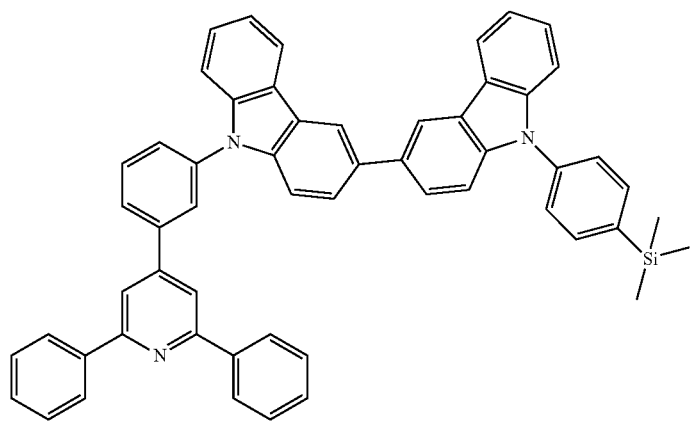

-continued
[D-249]
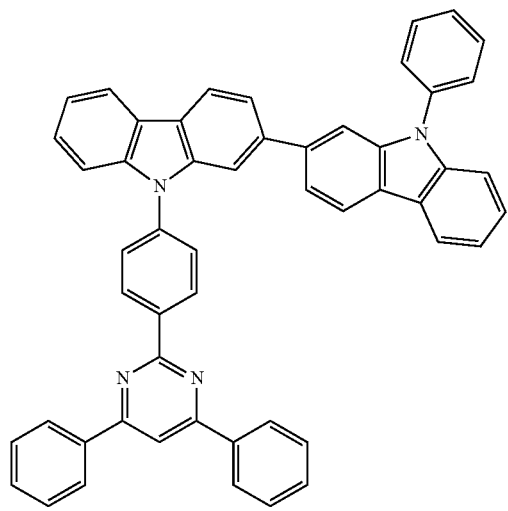
[D-250]
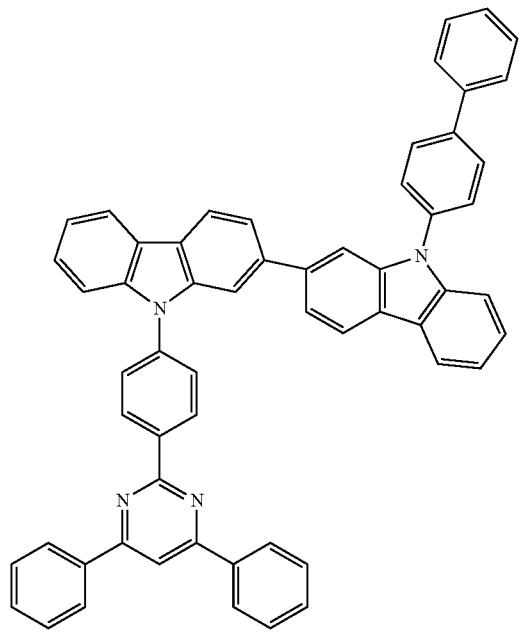
[D-251]
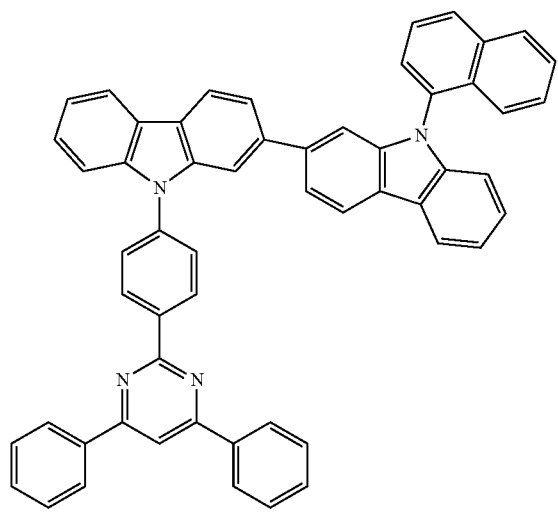

[D-252]
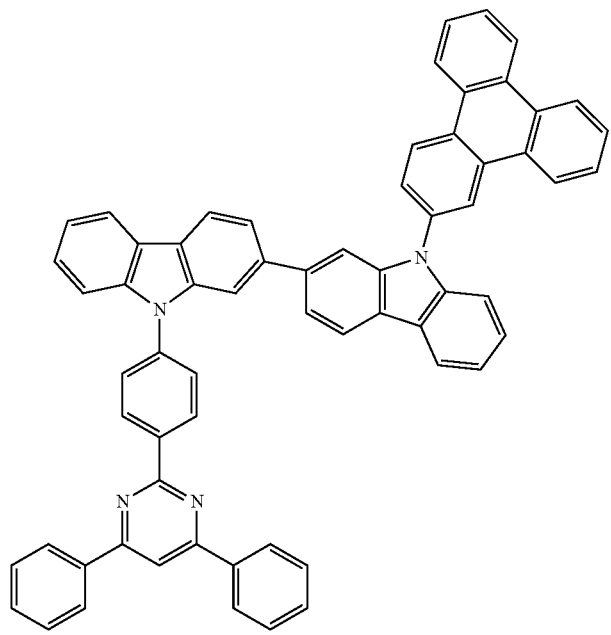
[D-253]
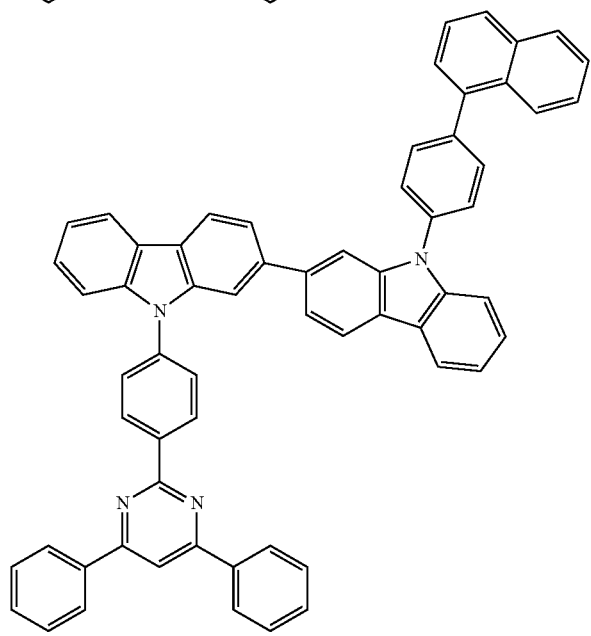
[D-254]
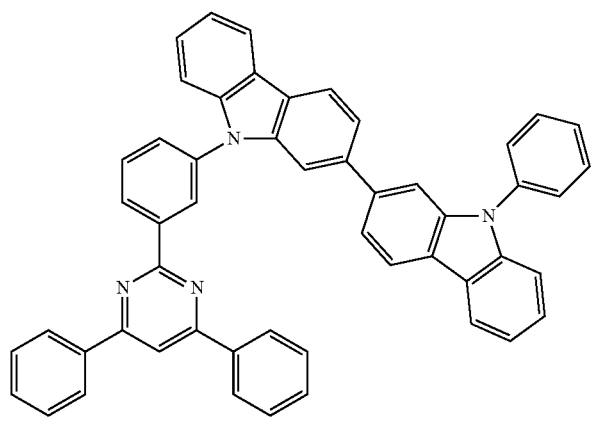

[D-255]
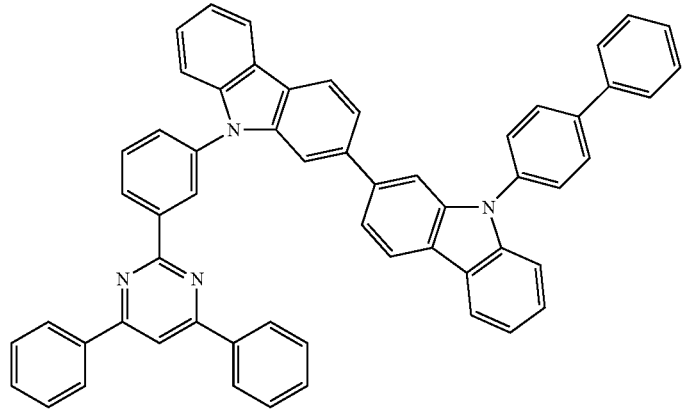
[D-256]
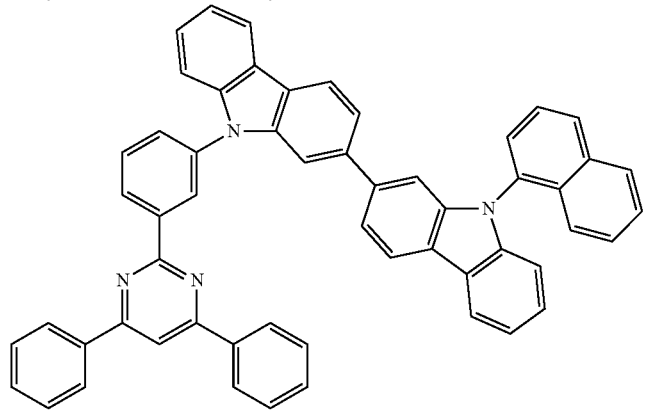
[D-257]
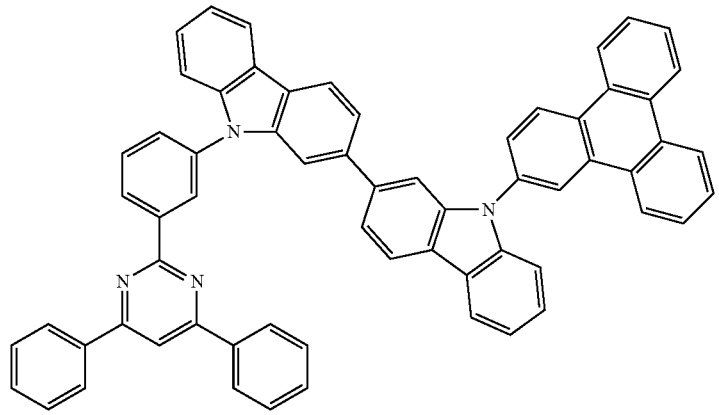
[D-258]
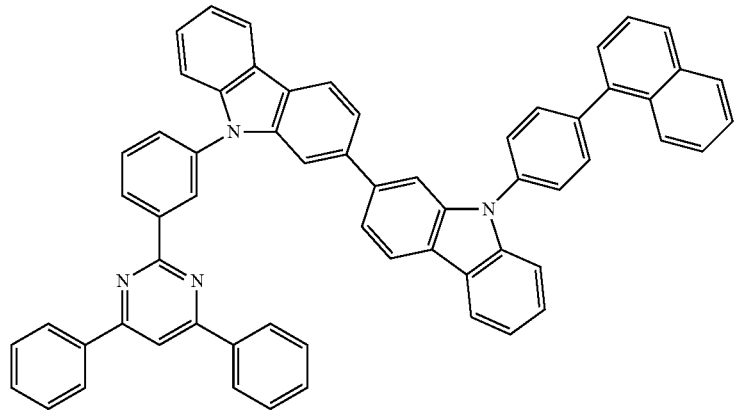

-continued
[D-259]
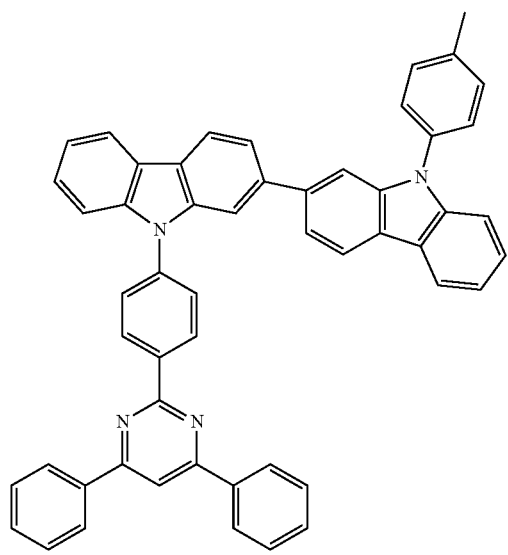
[D-260]
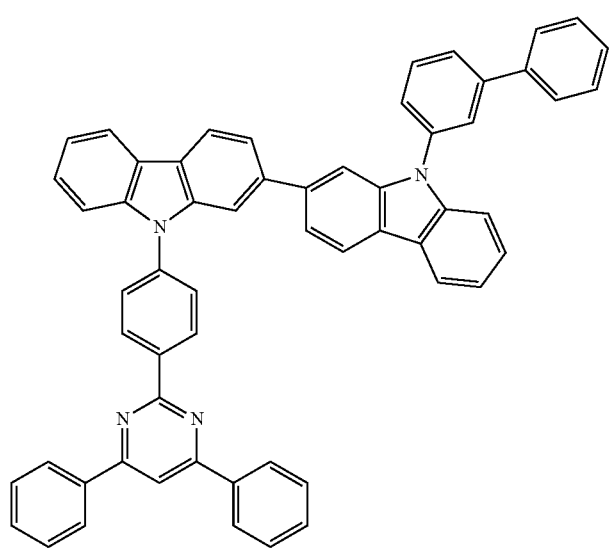
[D-261]
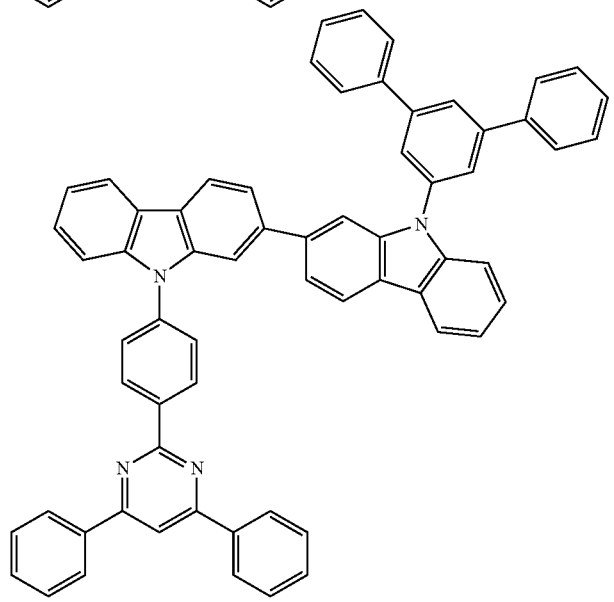

[D-262]
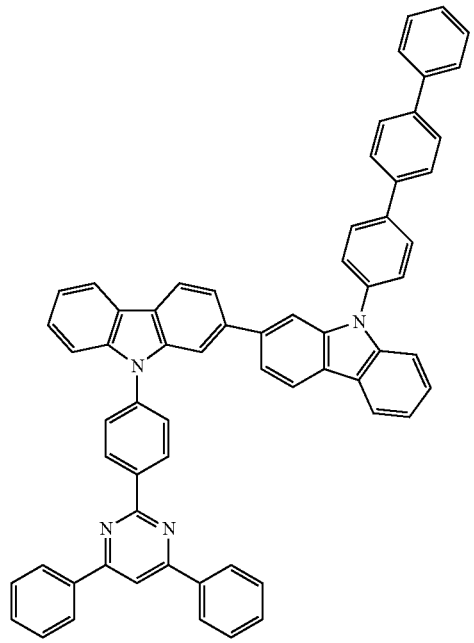
[D-263]
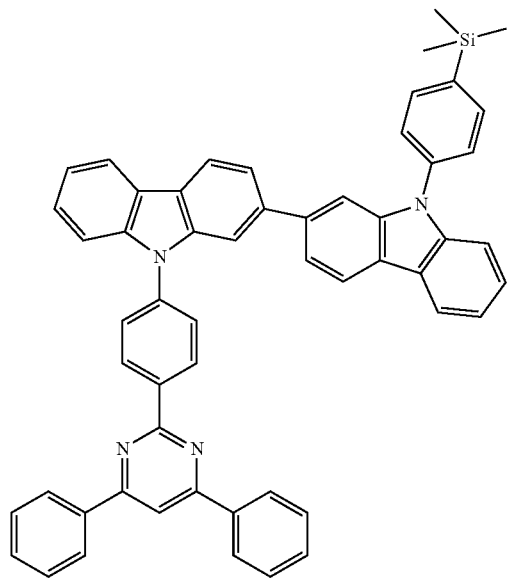
[D-264]
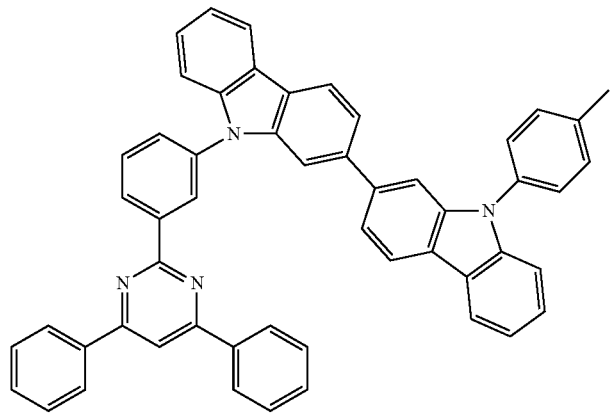

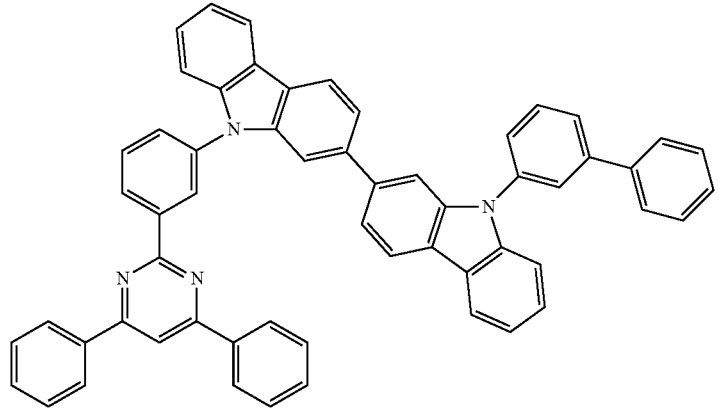
[D-265]
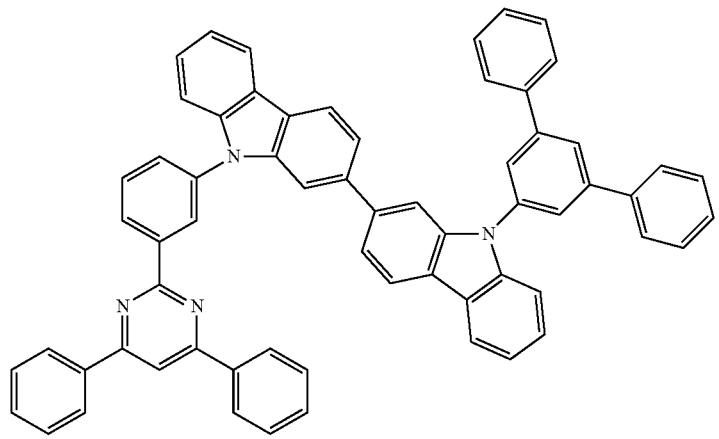
[D-266]
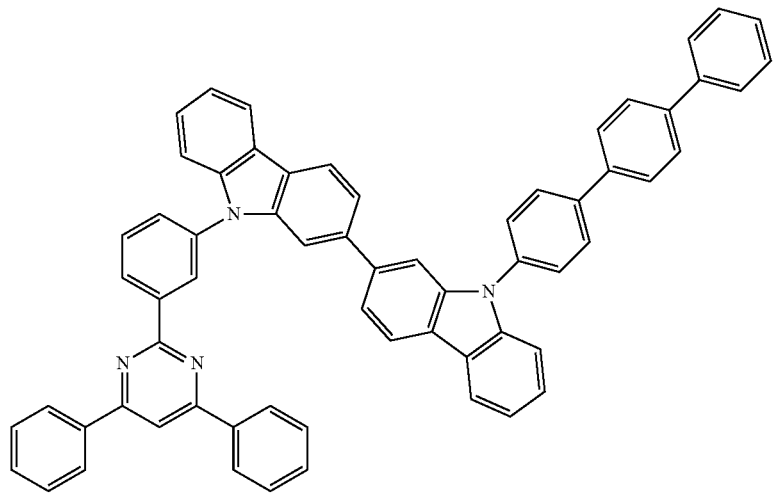
[D-267]

[D-268]
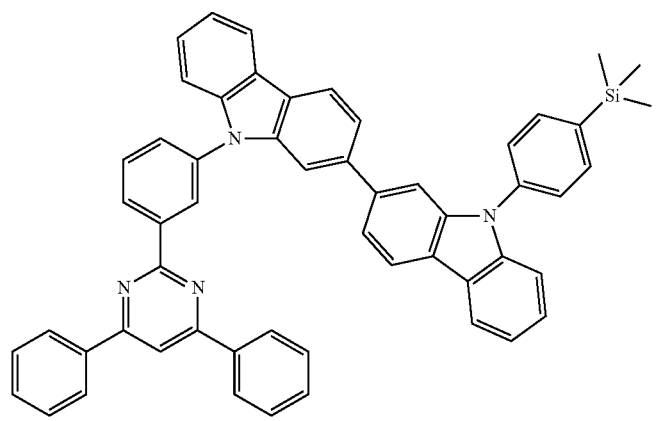
[D-269]
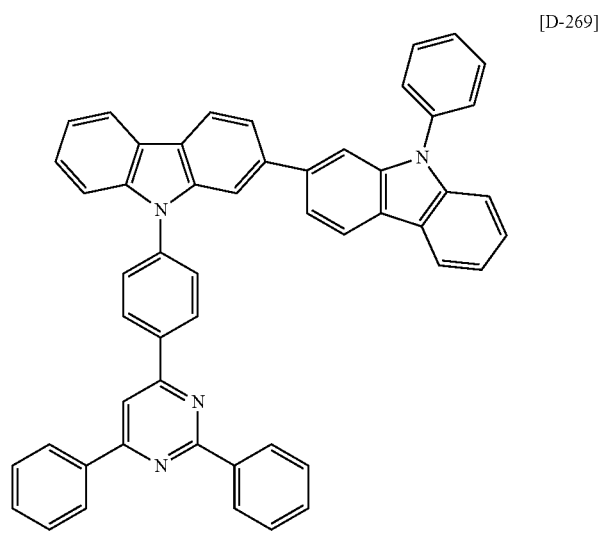
[D-270]
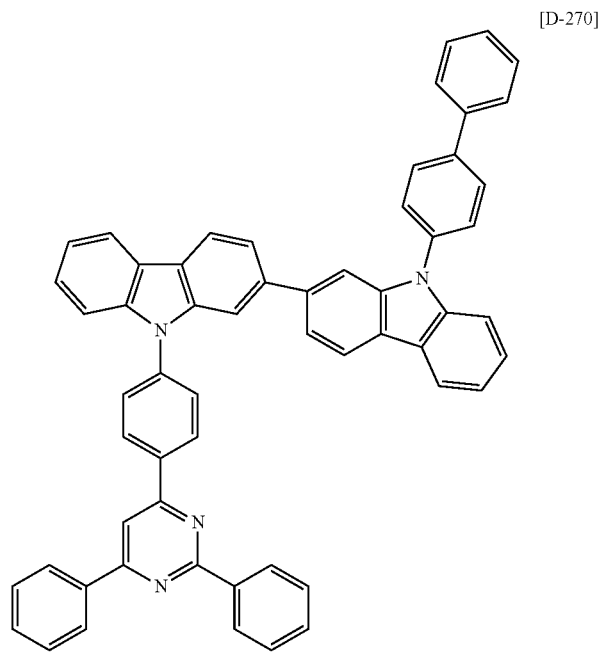

[D-271]
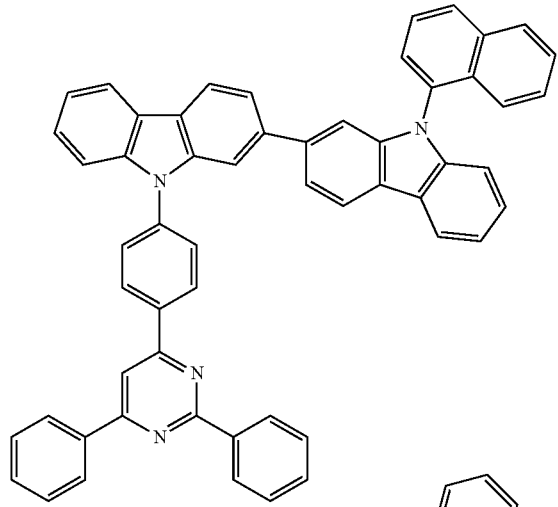
[D-272]
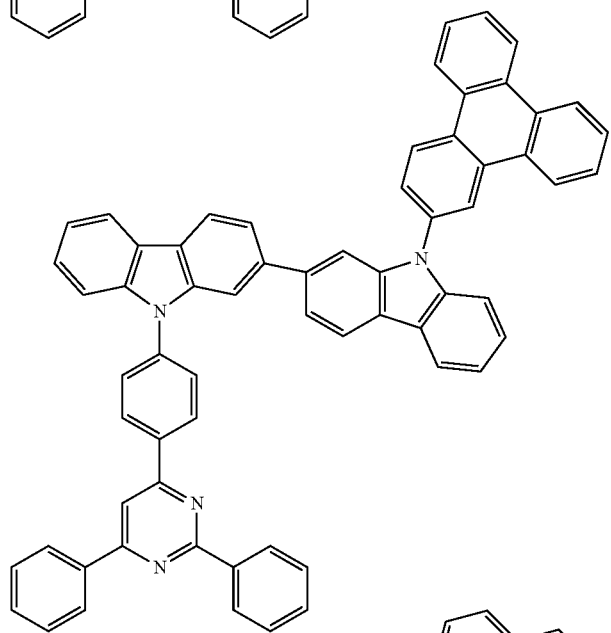
[D-273]
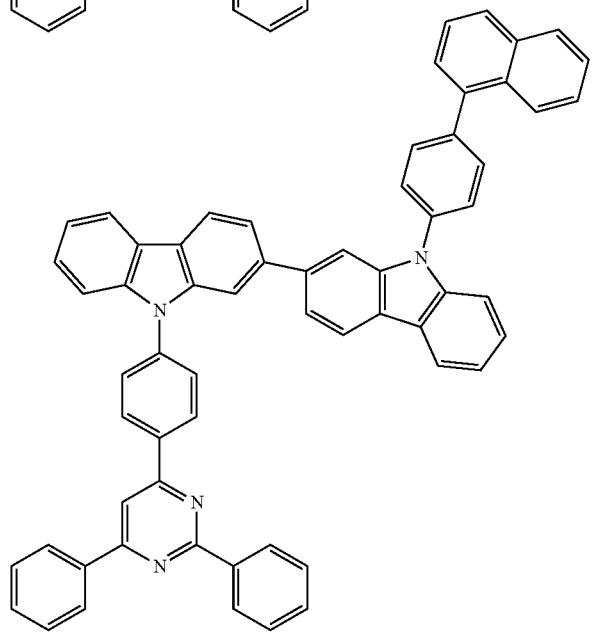

[D-274]
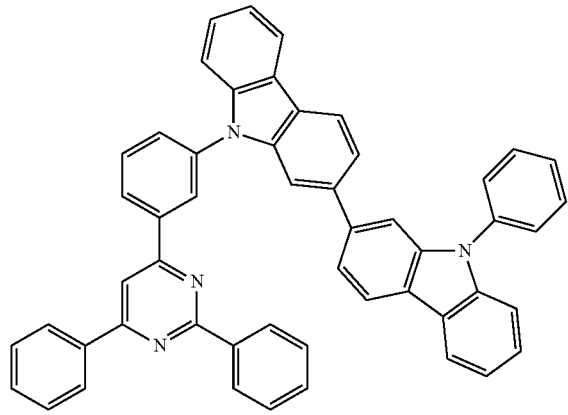
[D-275]
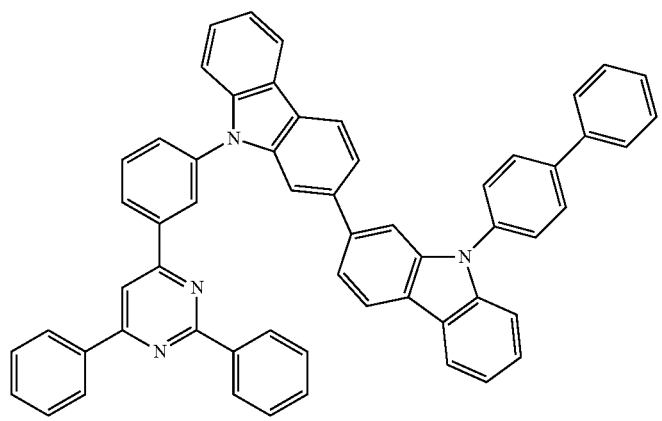
[D-276]
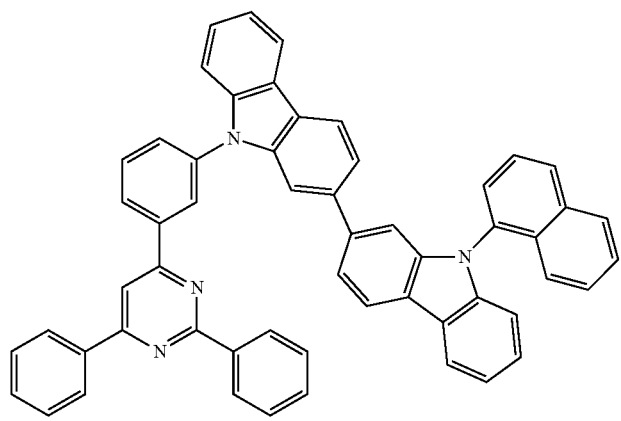

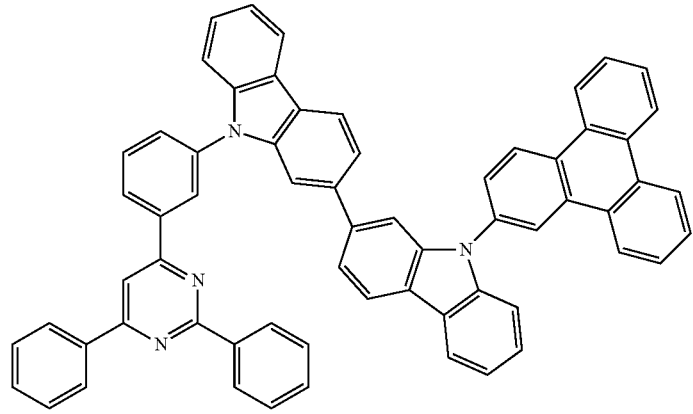
[D-277]
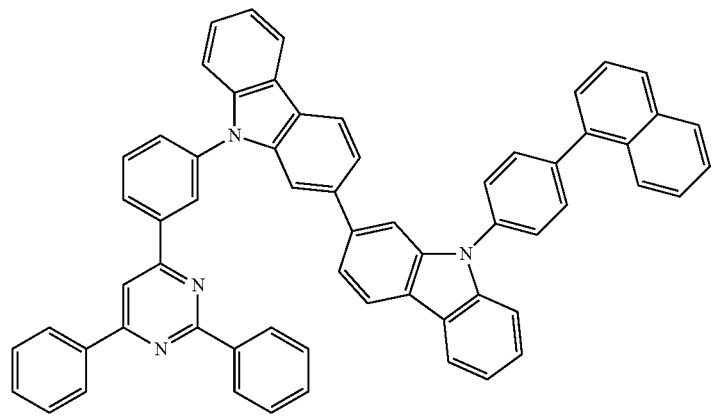
[D-278]
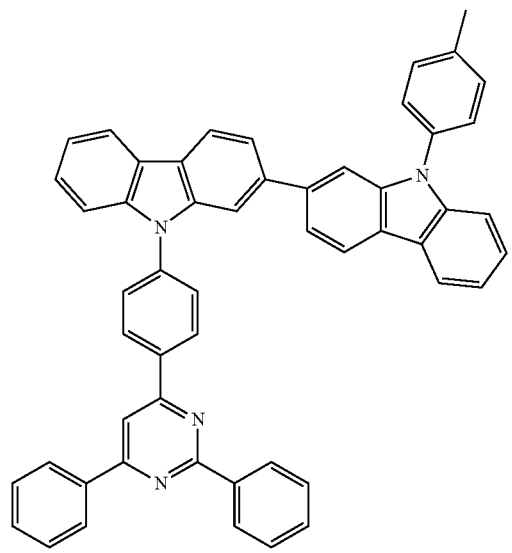
[D-279]

[D-280]
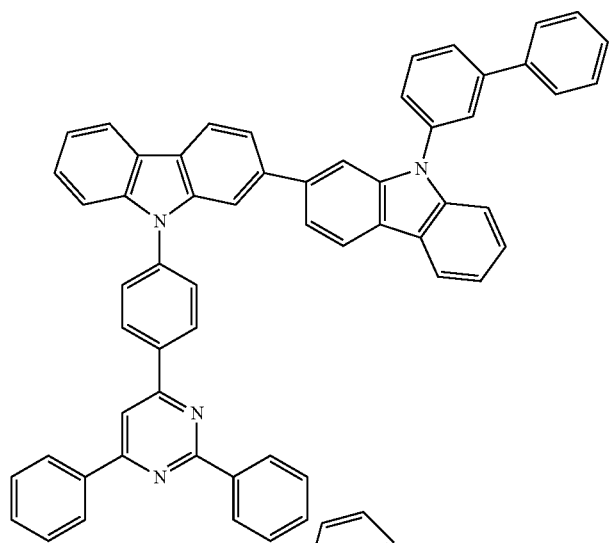
[D-281]
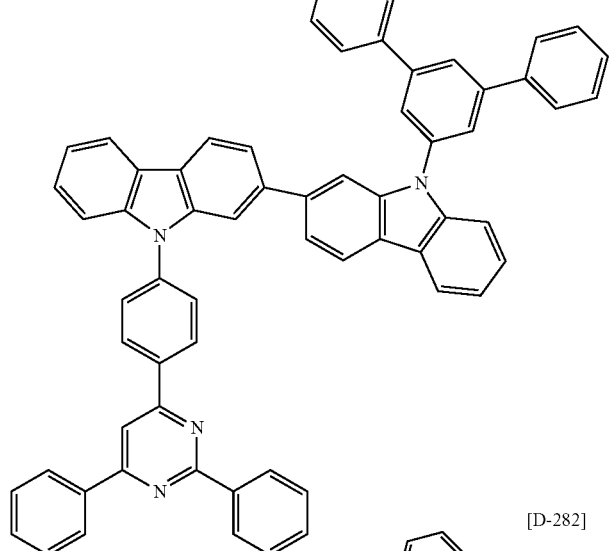
[D-282]
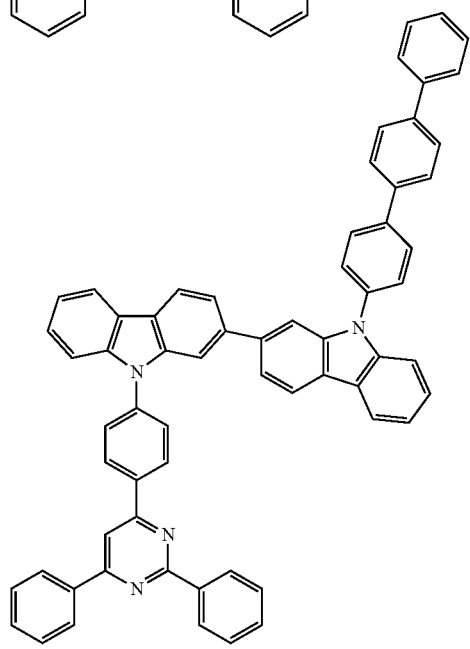

[D-283]
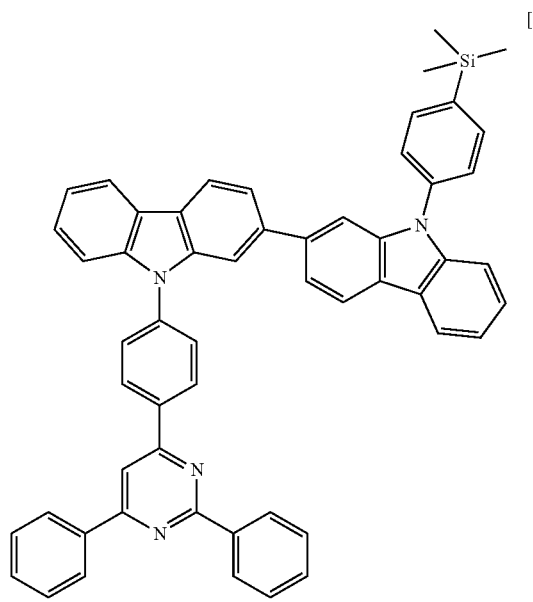
[D-284]
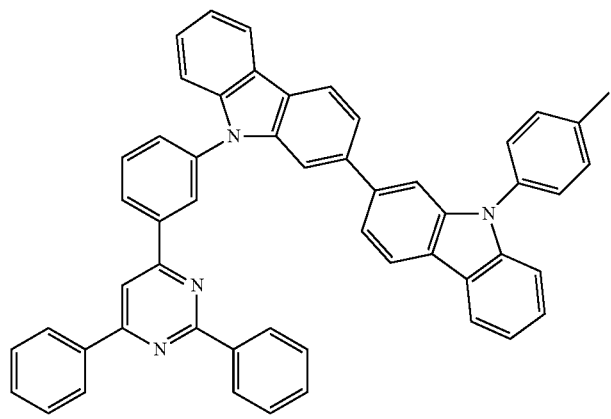
[D-285]
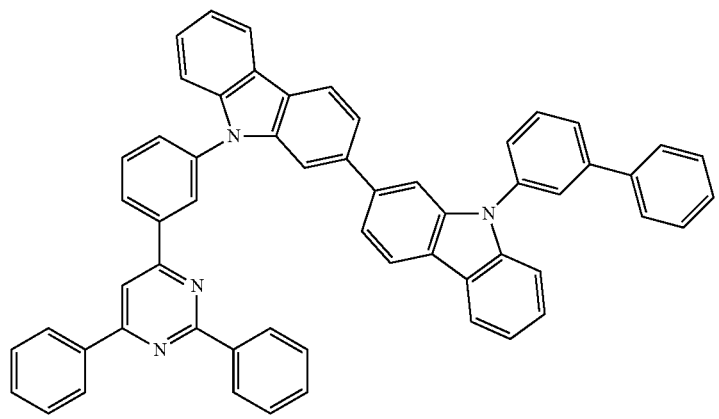

[D-286]
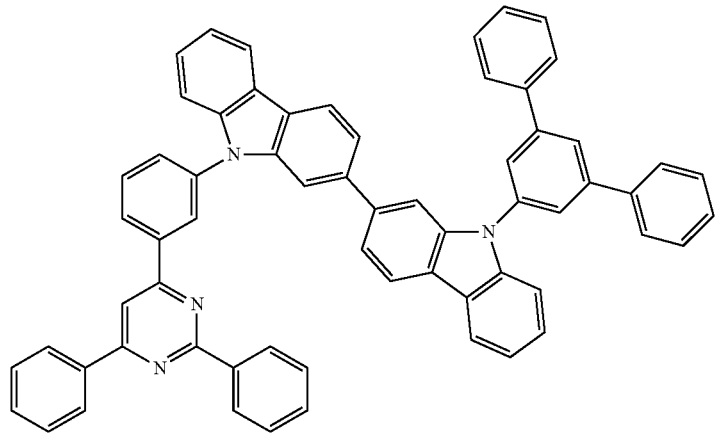
[D-287]
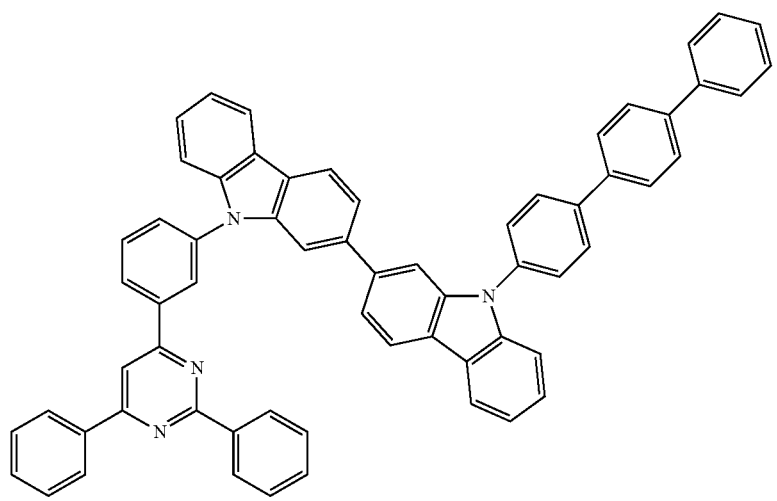
[D-288]
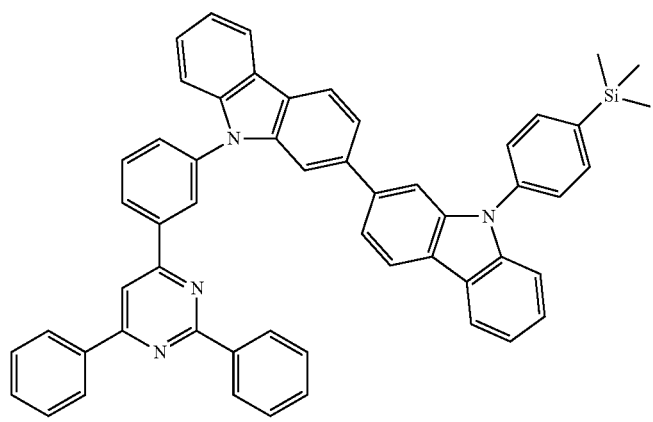

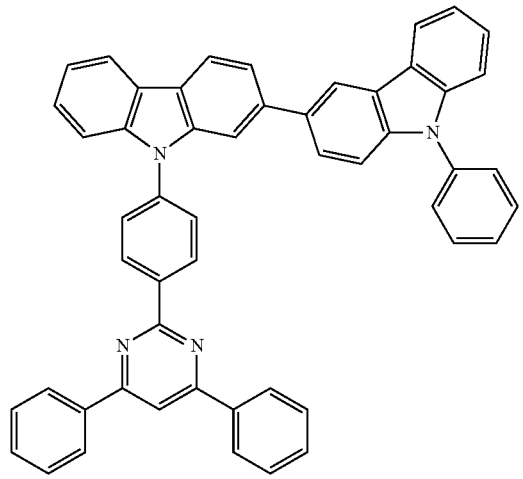
[D-289]
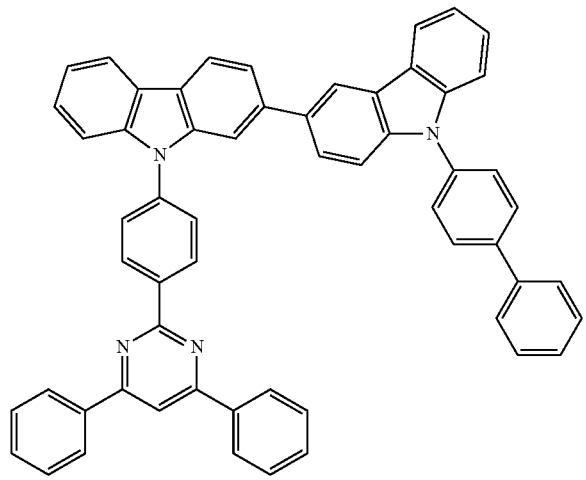
[D-290]
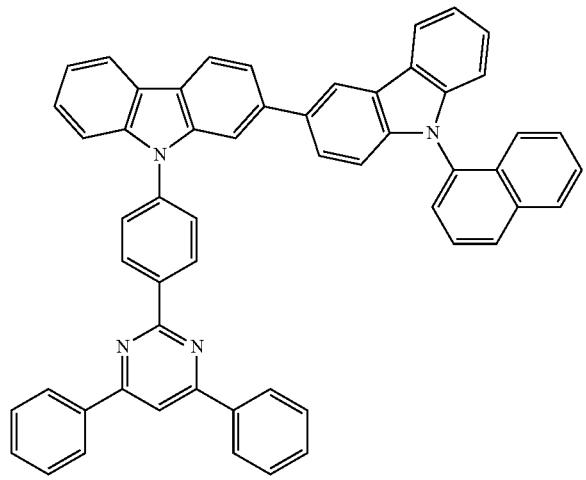
[D-291]

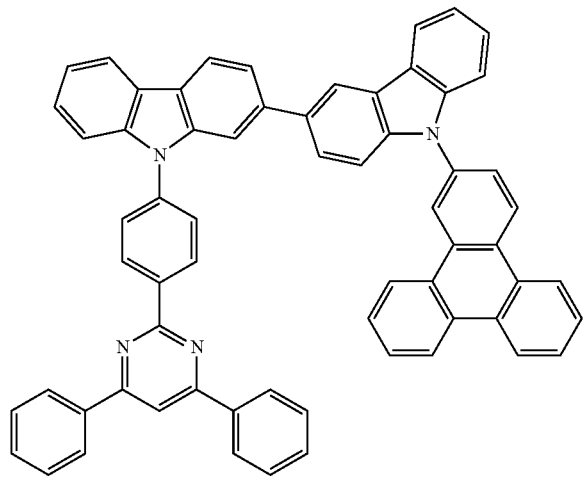
[D-292]
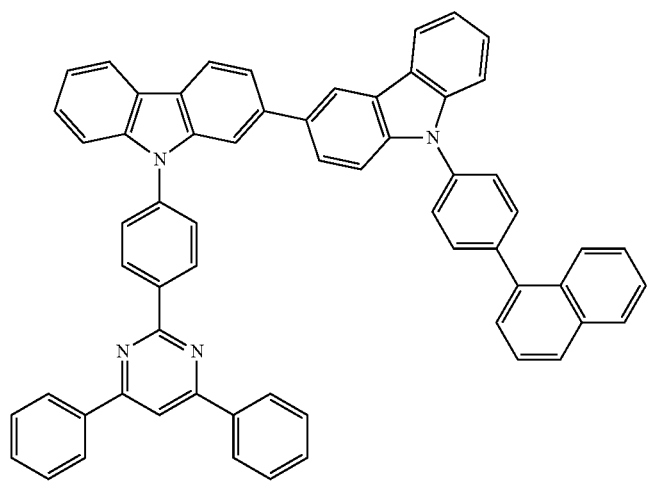
[D-293]
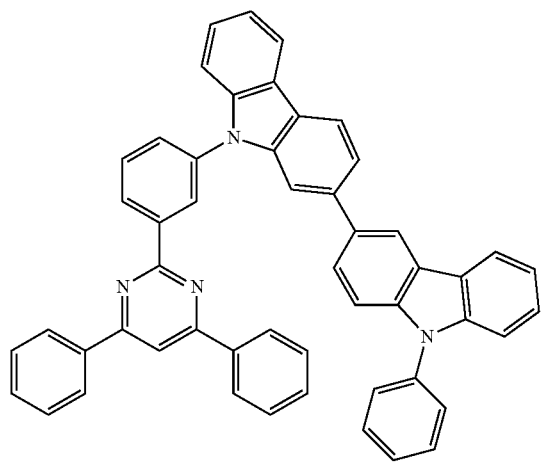
[D-294]

[D-295]
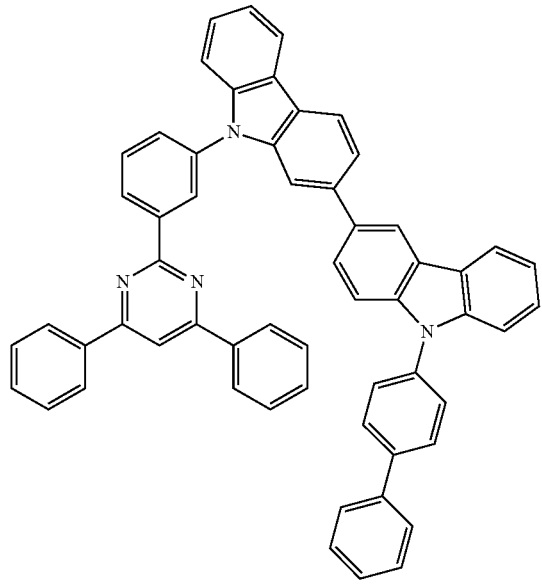
[D-296]
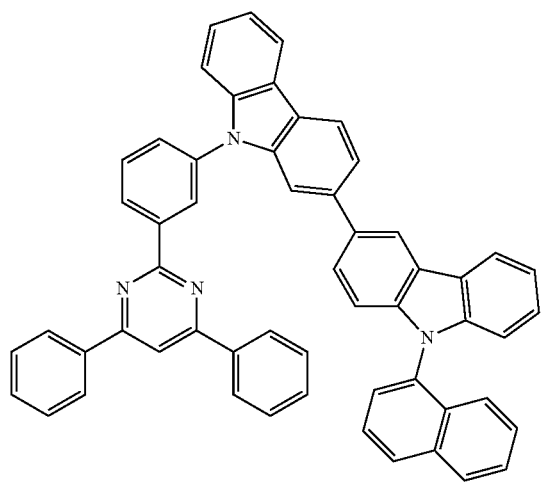
[D-297]
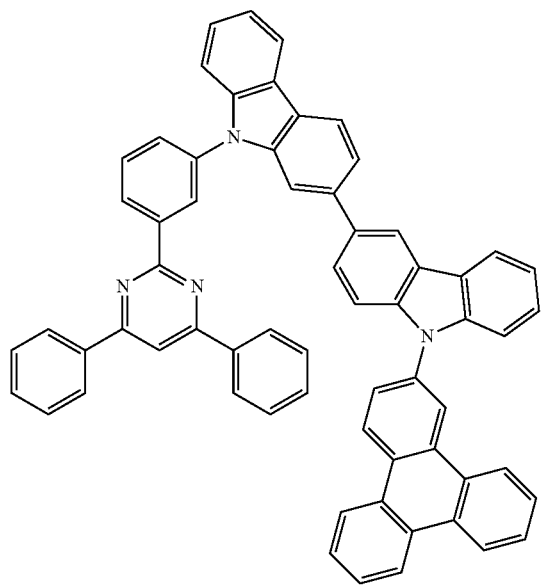

[D-298]
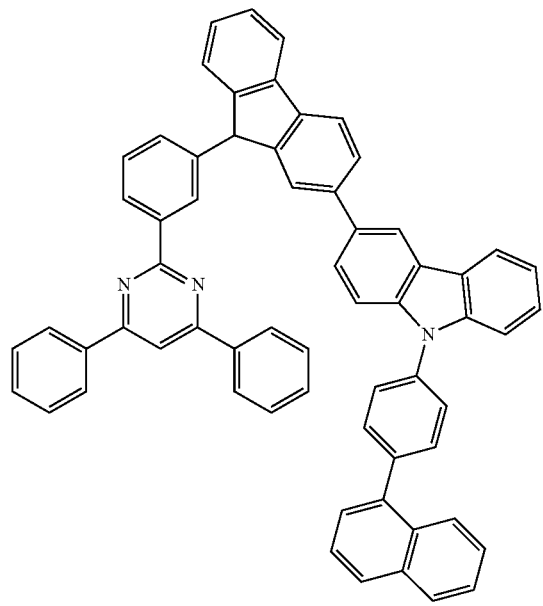
[D-299]
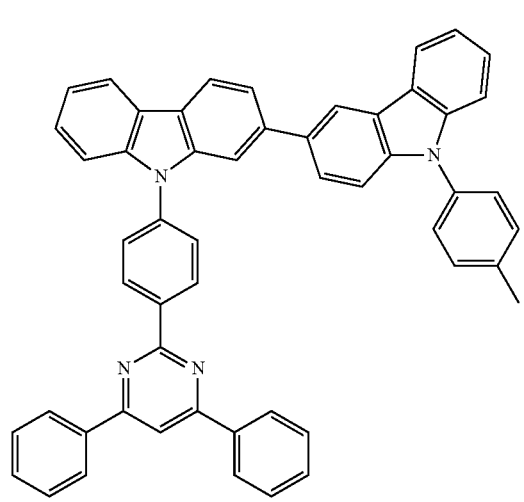
[D-300]
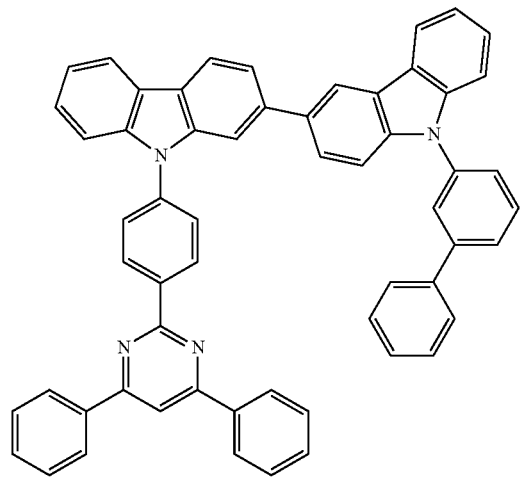

[D-301]
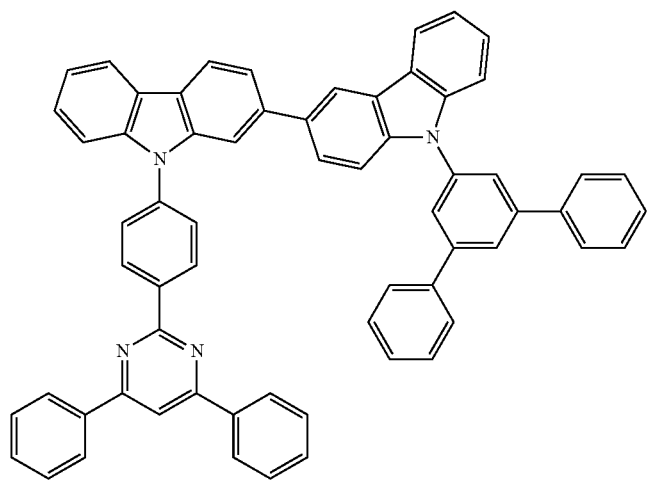
[D-302]
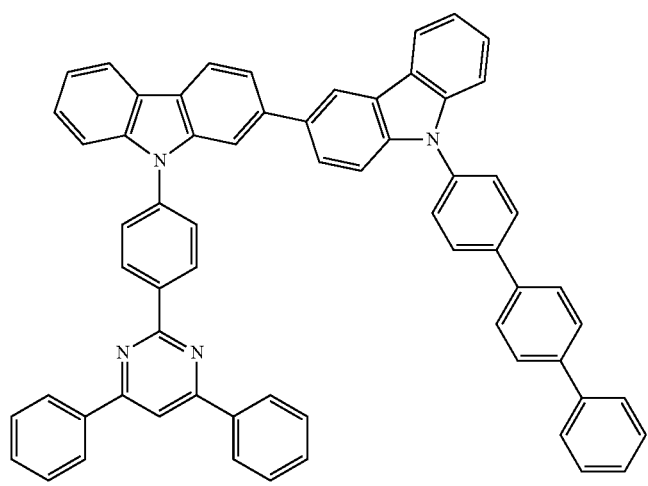
[D-303]
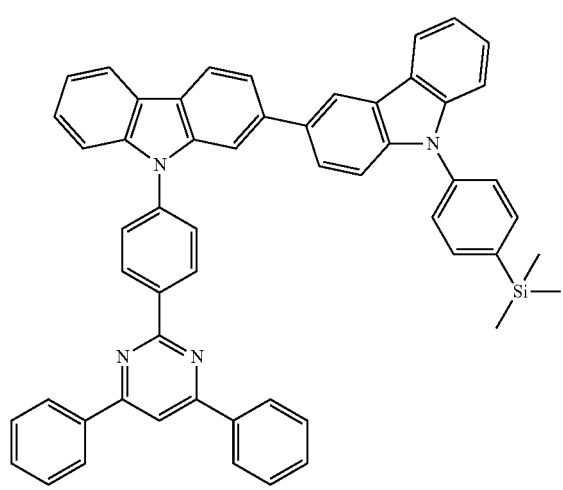

[D-304]
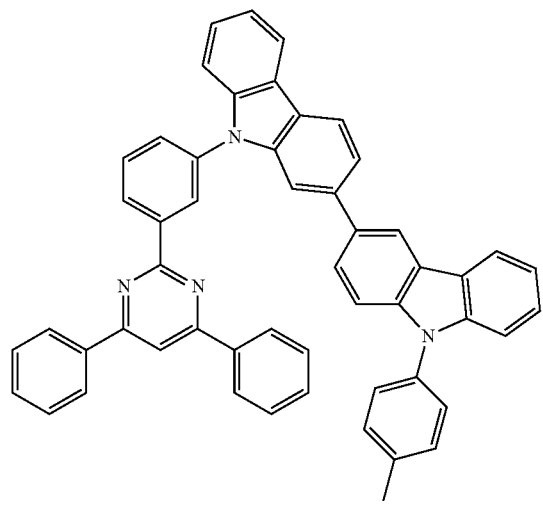
[D-305]
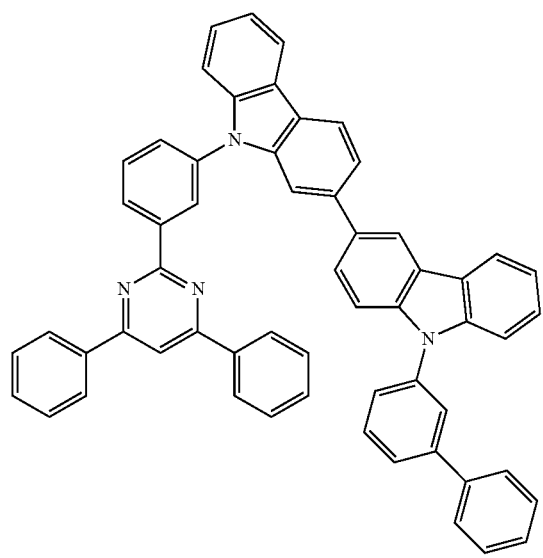
[D-306]
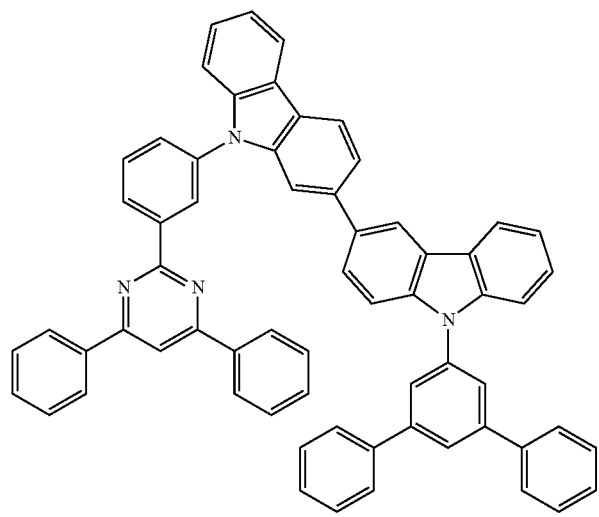

[D-307]
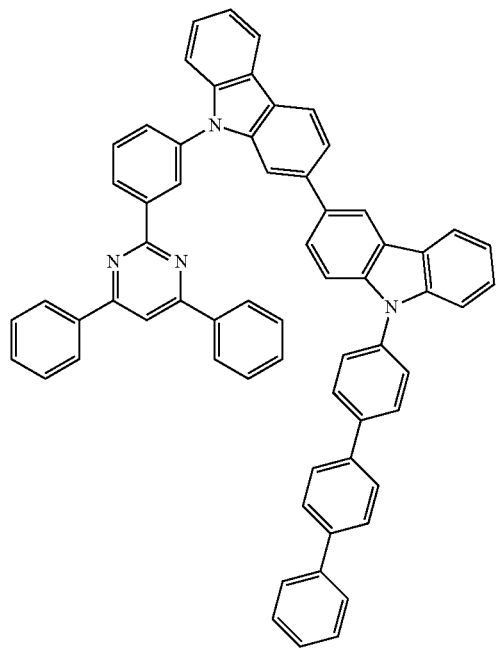
[D-308]
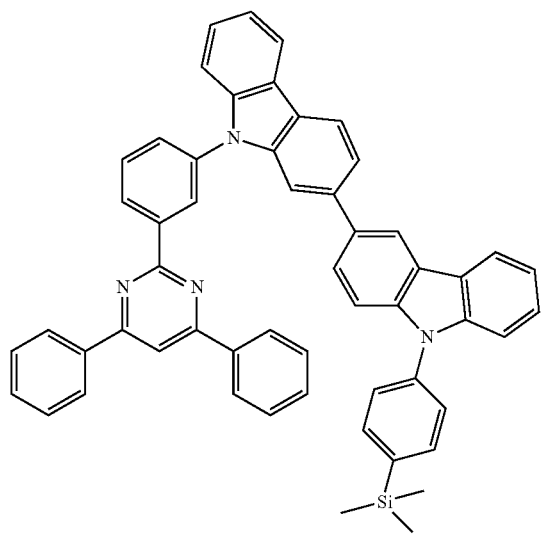
[D-309]
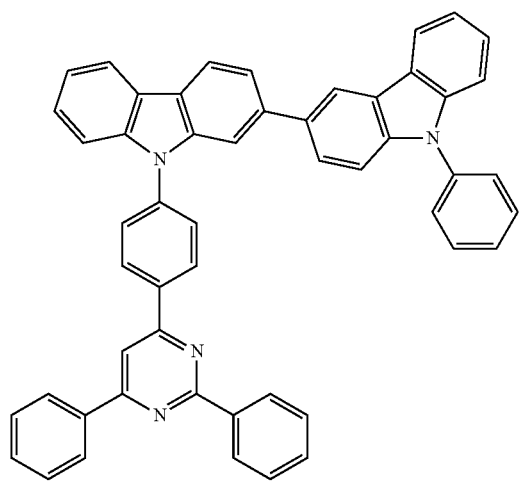

[D-310]
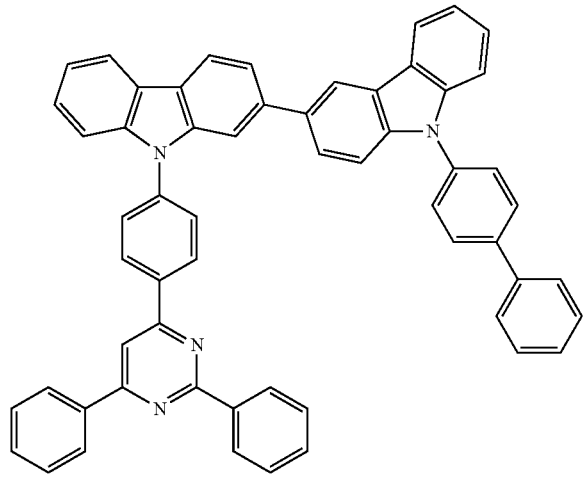
[D-311]
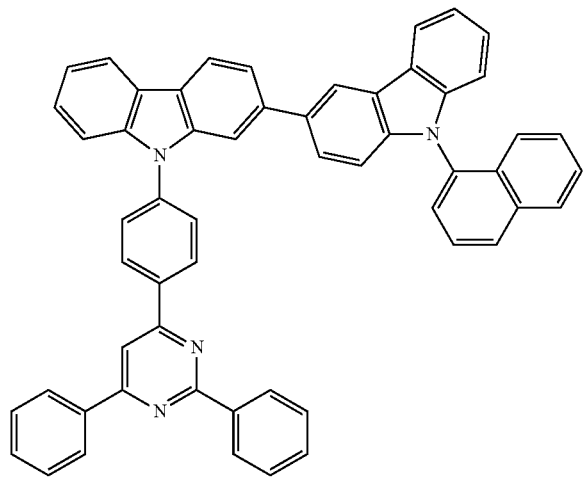
[D-312]
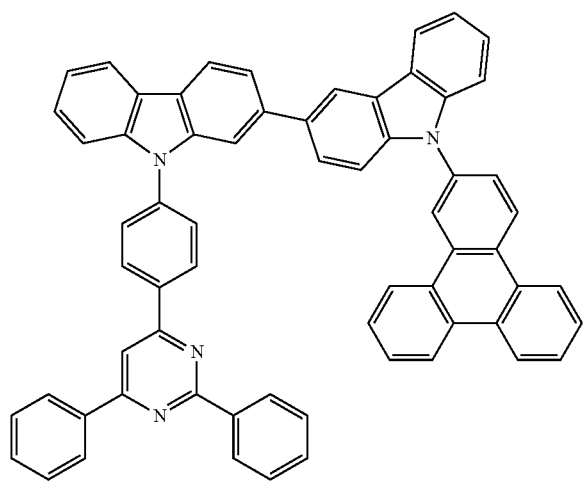

-continued
[D-313]
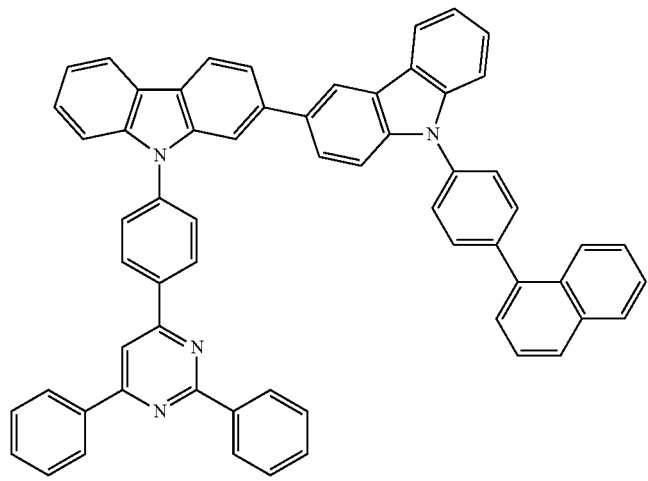
[D-314]
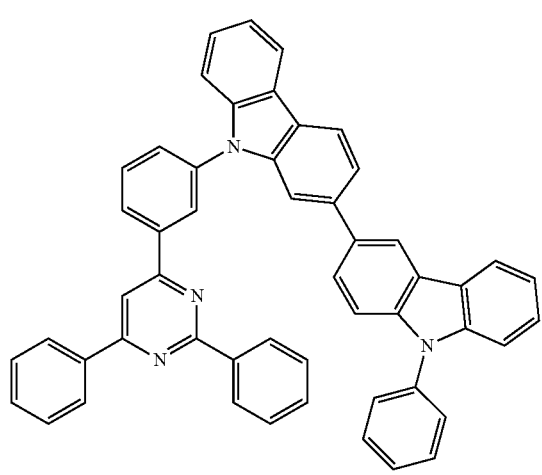
[D-315]
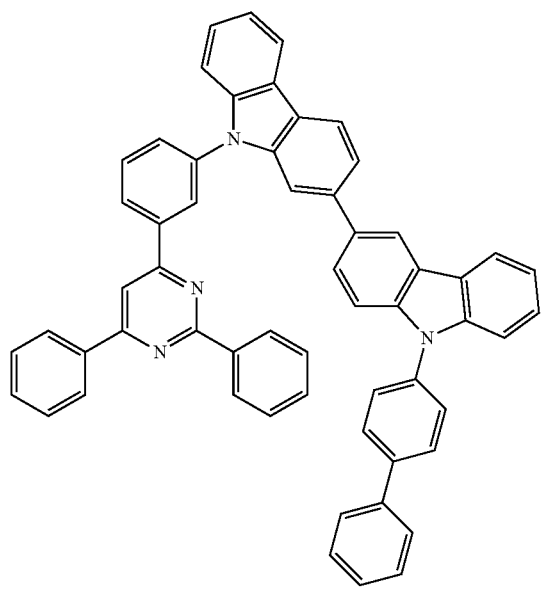

[D-316]
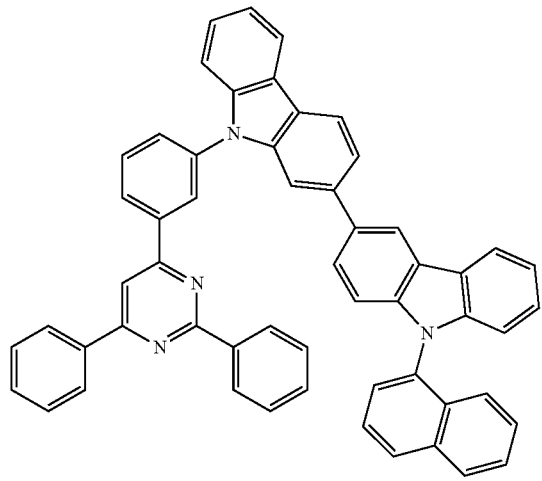
[D-317]
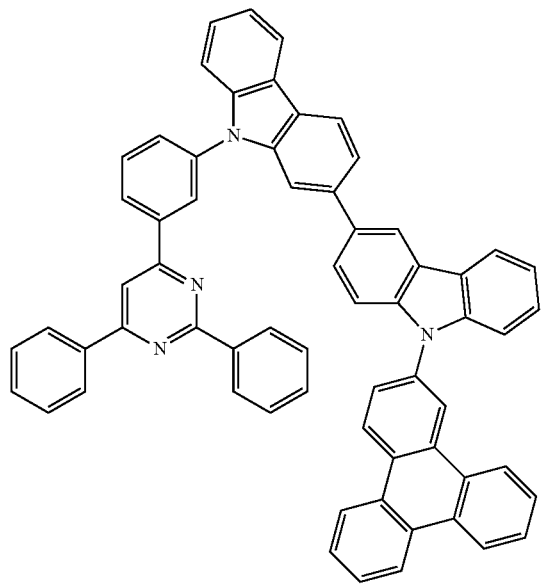
[D-318]
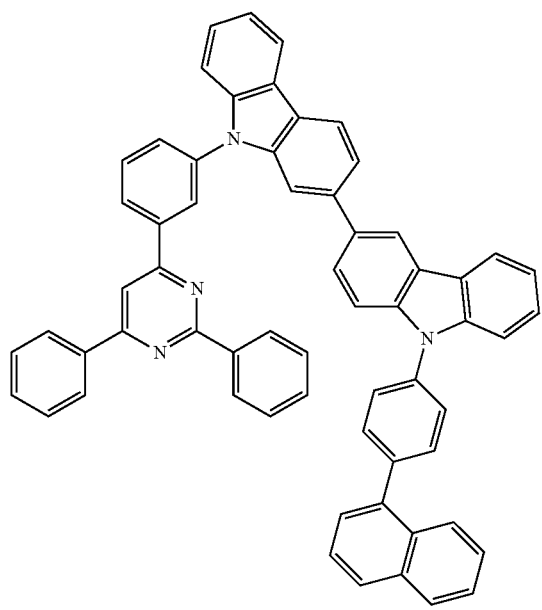

[D-319]
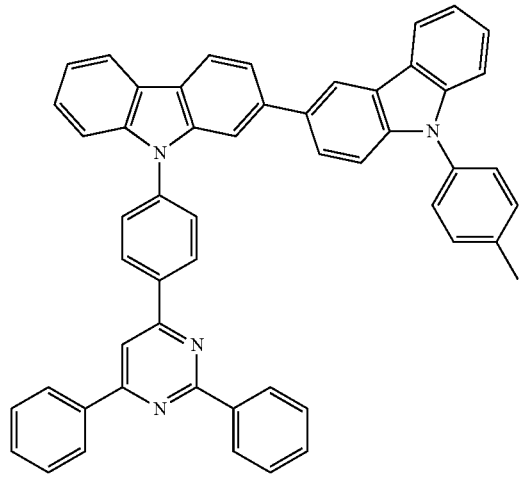
[D-320]
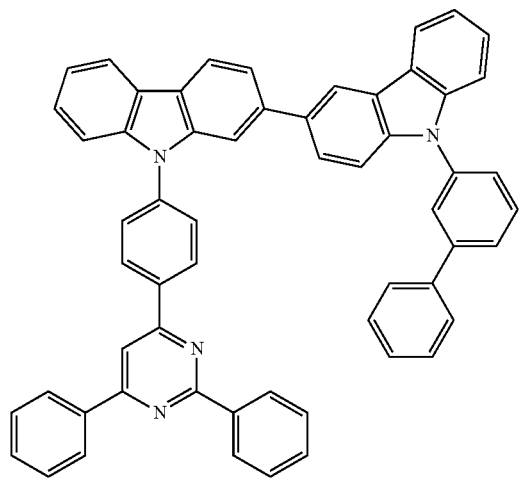
[D-321]
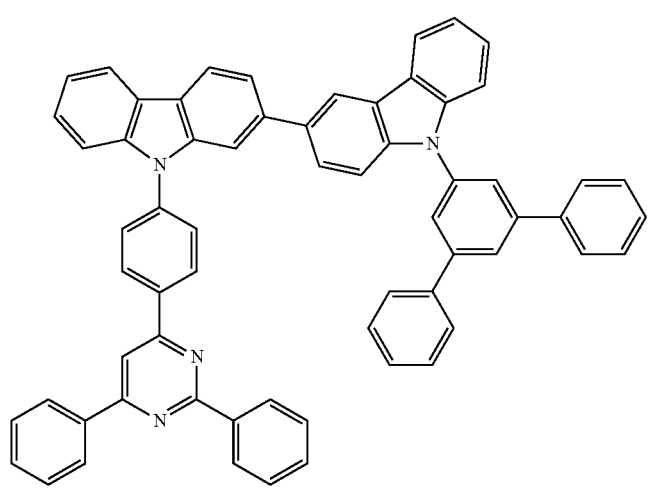

[D-322]
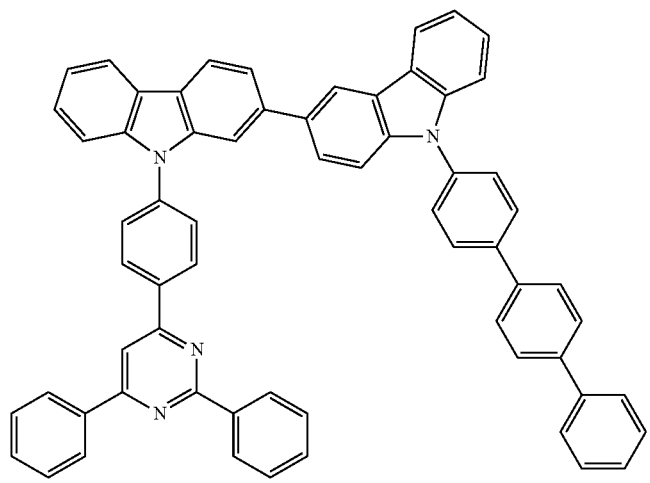
[D-323]
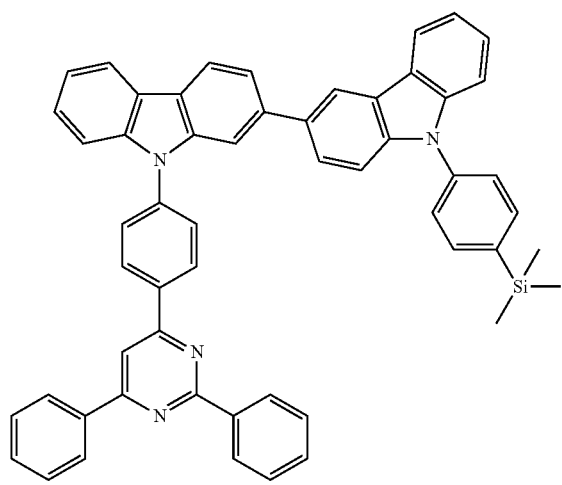
[D-324]
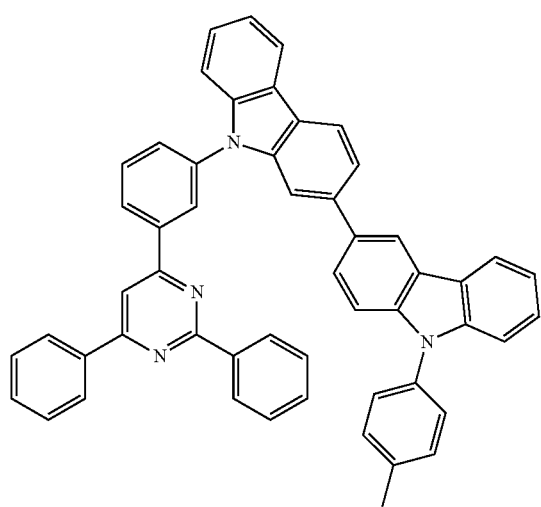

[D-325]
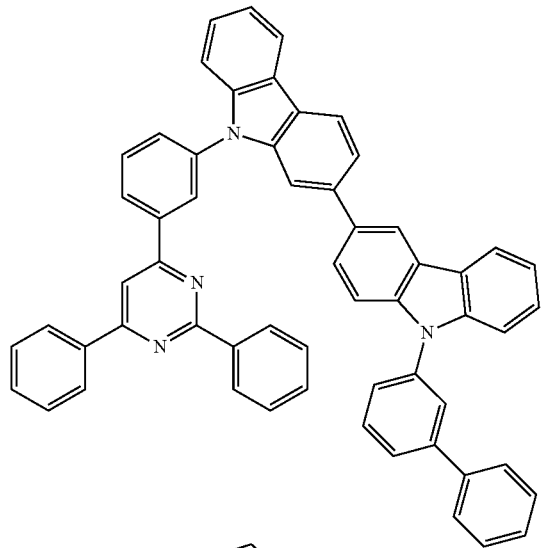
[D-326]
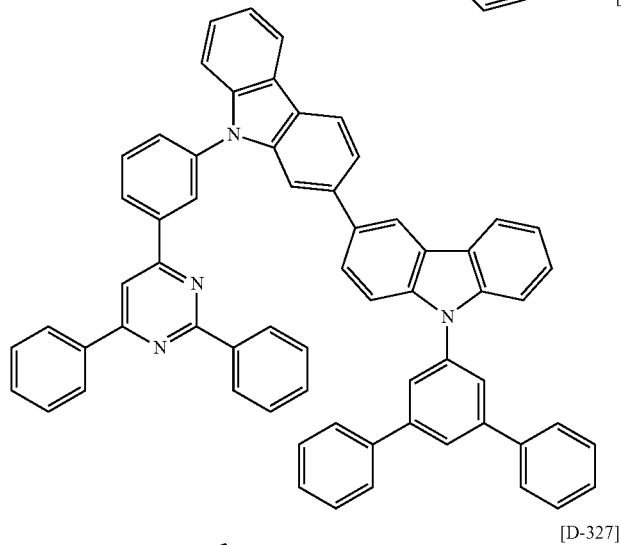
[D-327]
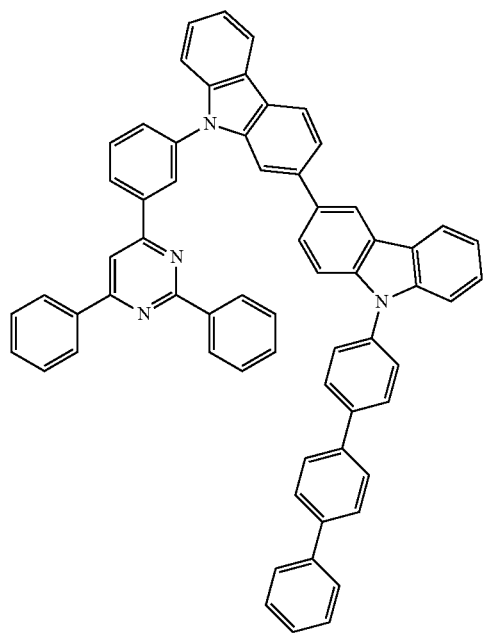

-continued
[D-328]
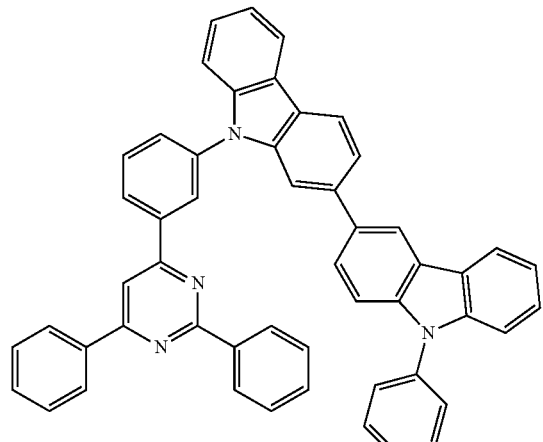
[D-329]
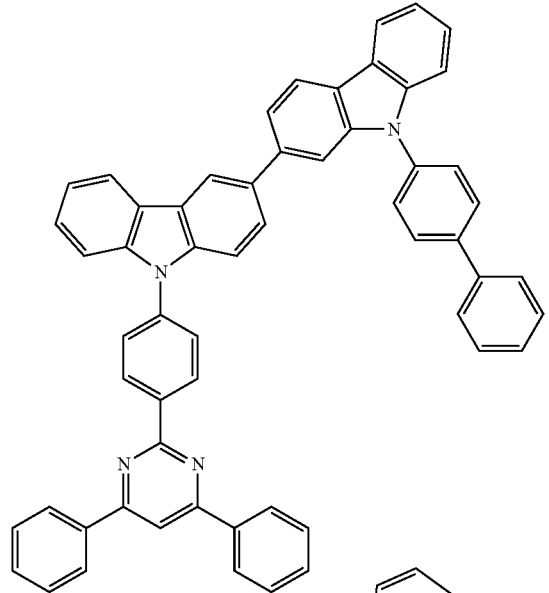
[D-330]
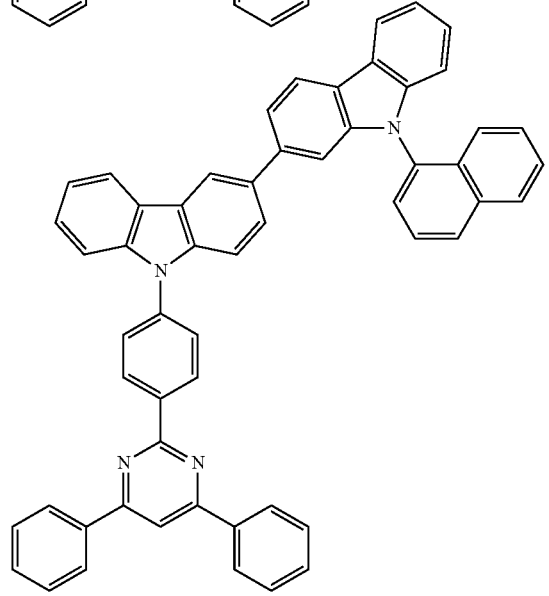

[D-331]
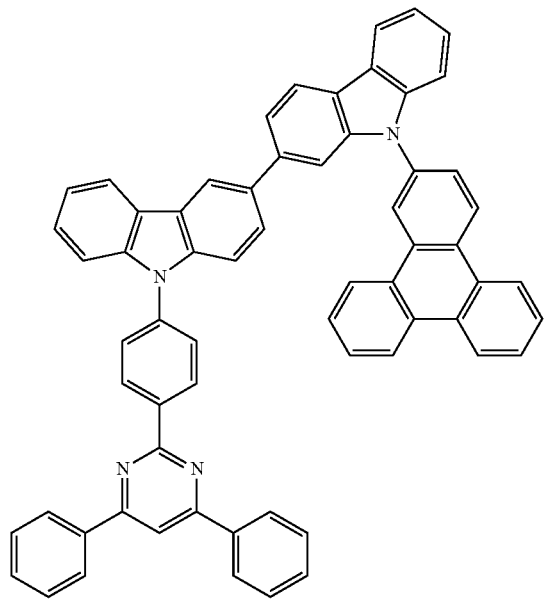
[D-332]
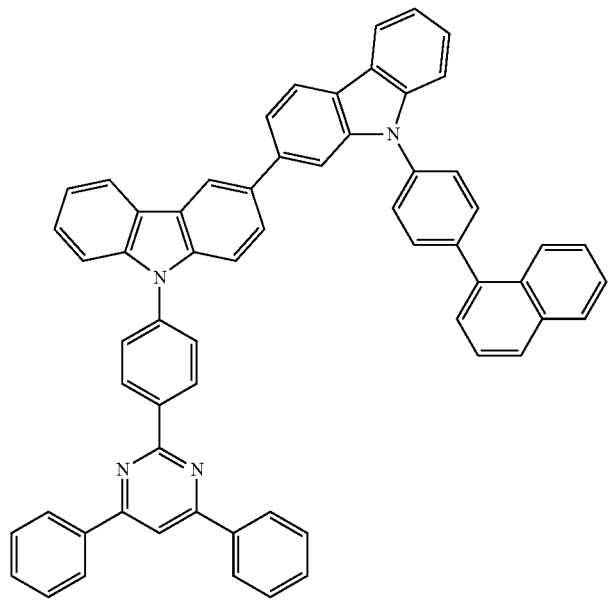
[D-333]
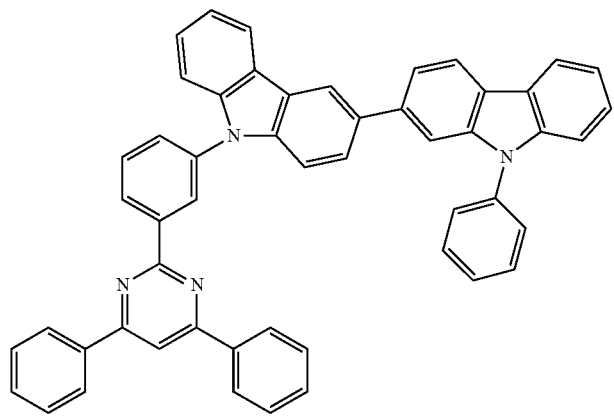

-continued
[D-334]
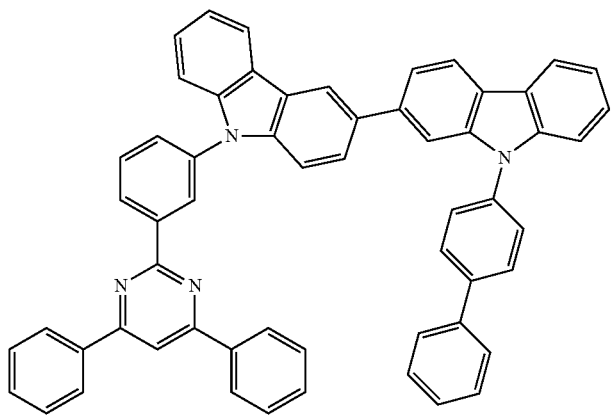
[D-335]
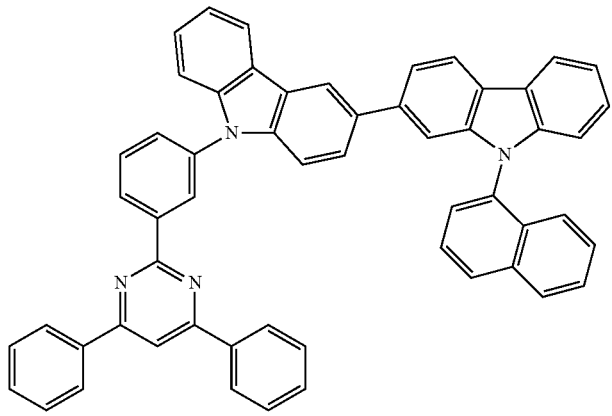
[D-336]
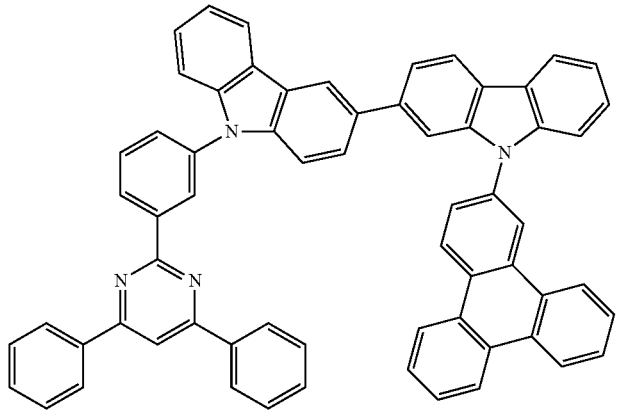
[D-337]
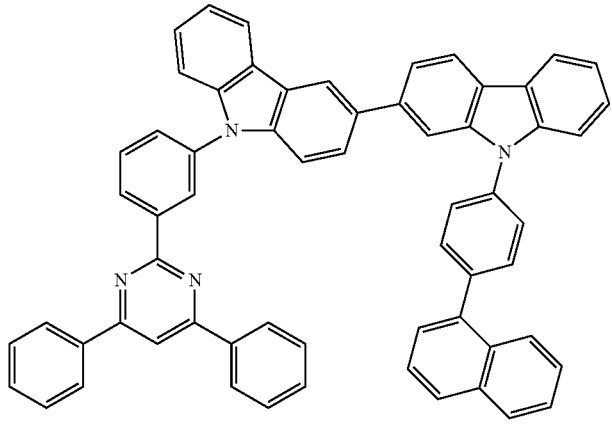

-continued
[D-338]
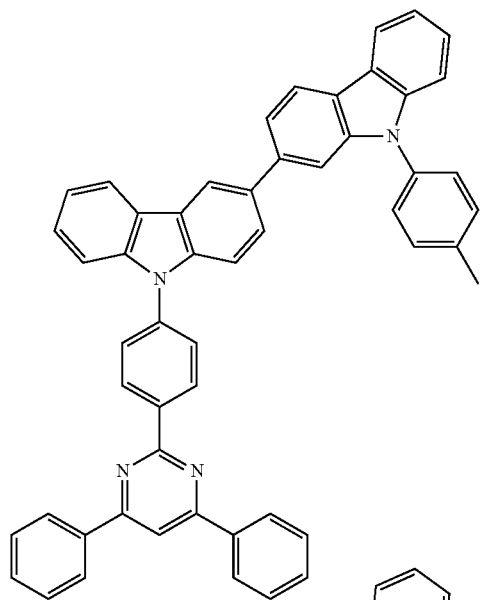
[D-339]
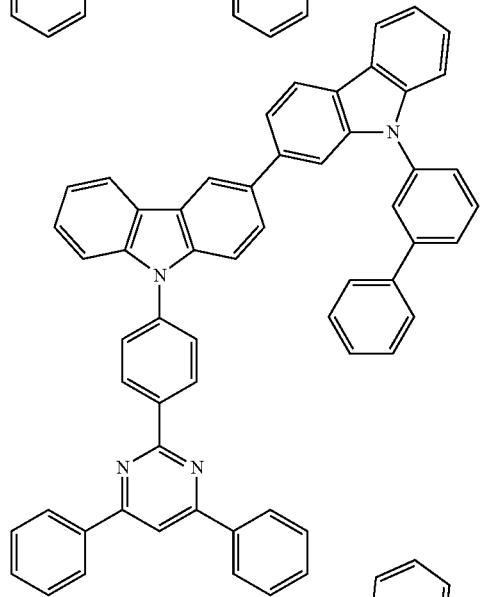
[D-340]
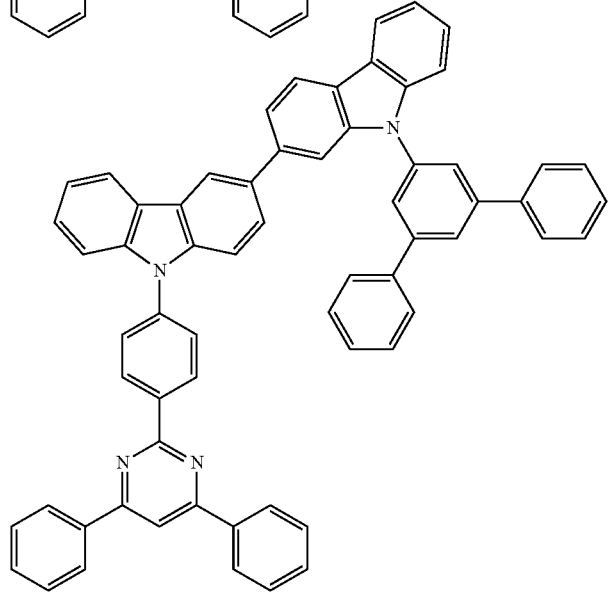

[D-341]
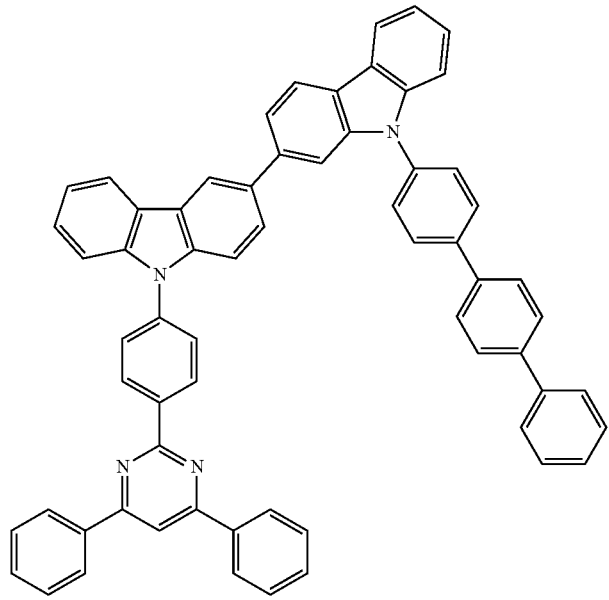
[D-342]
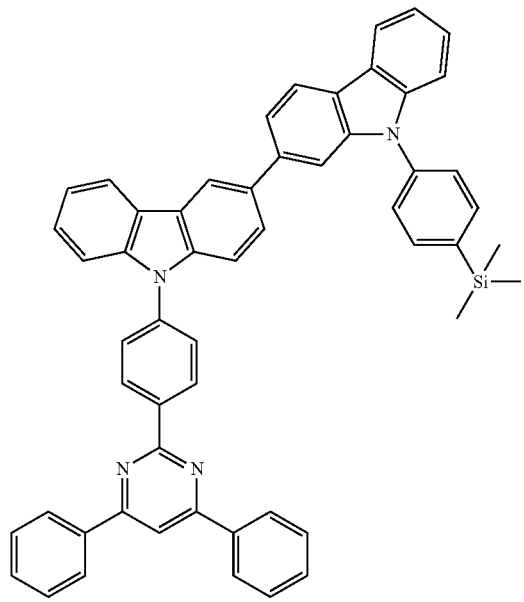
[D-343]
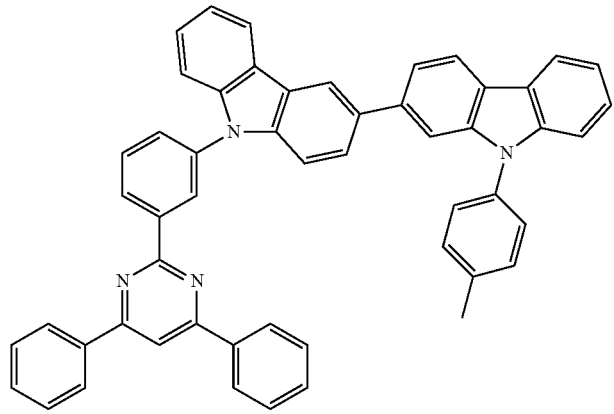

[D-344]
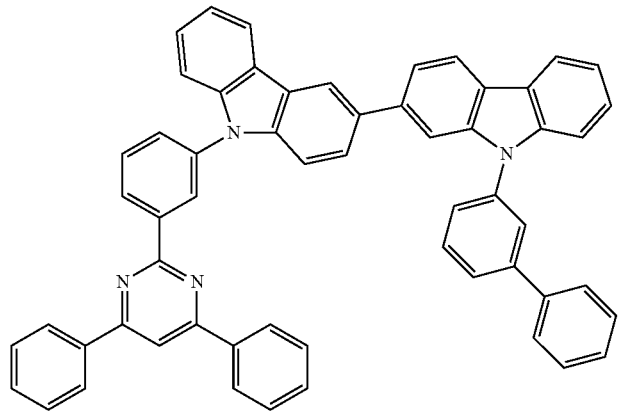
[D-345]
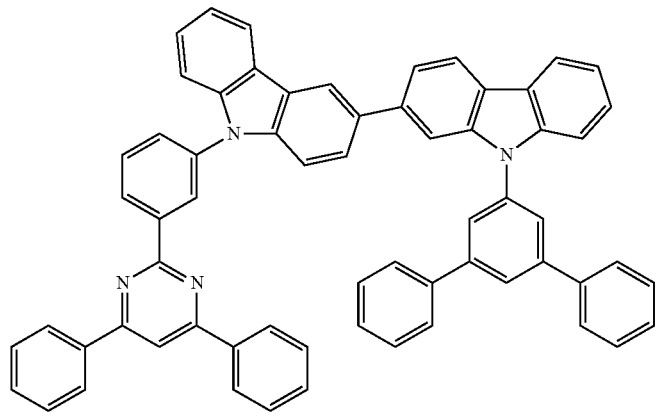
[D-346]
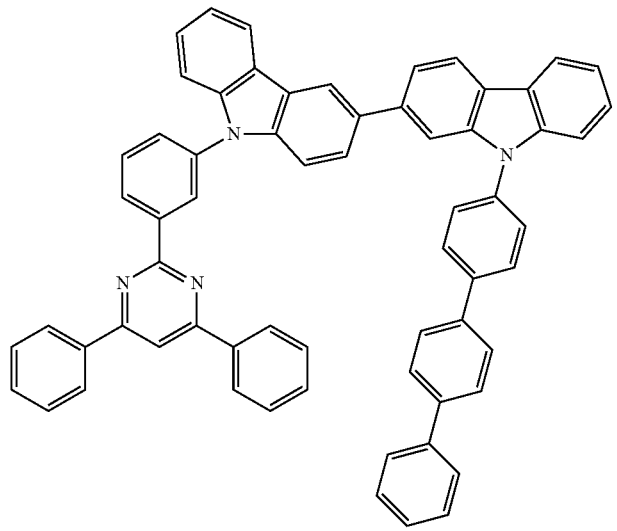

[D-347]
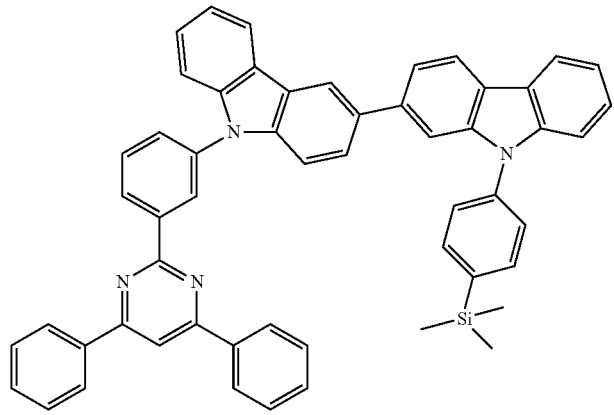
[D-348]
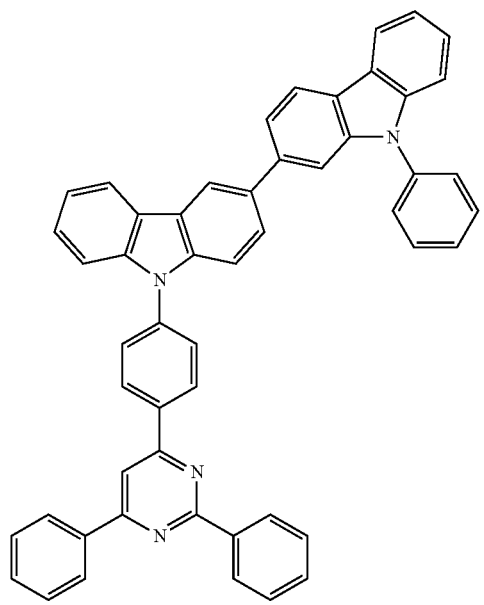
[D-349]
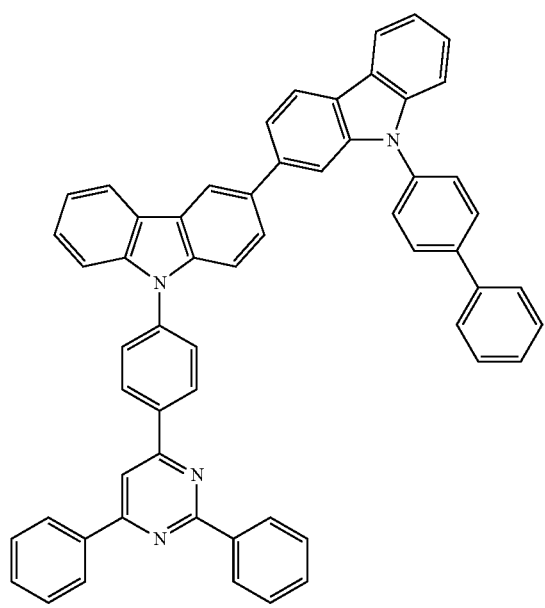

[D-350]
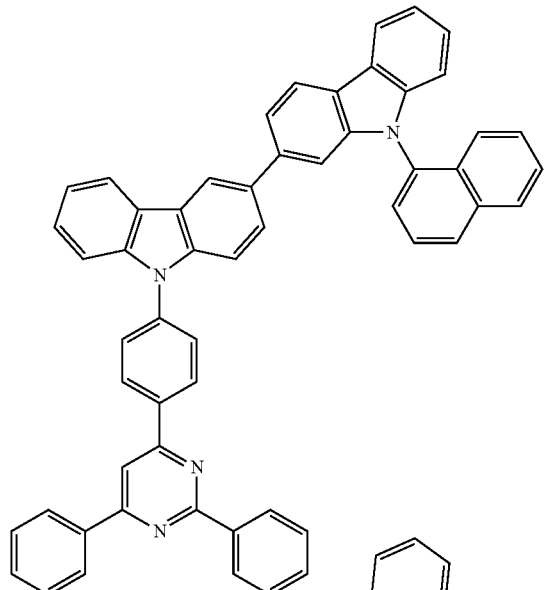
[D-351]
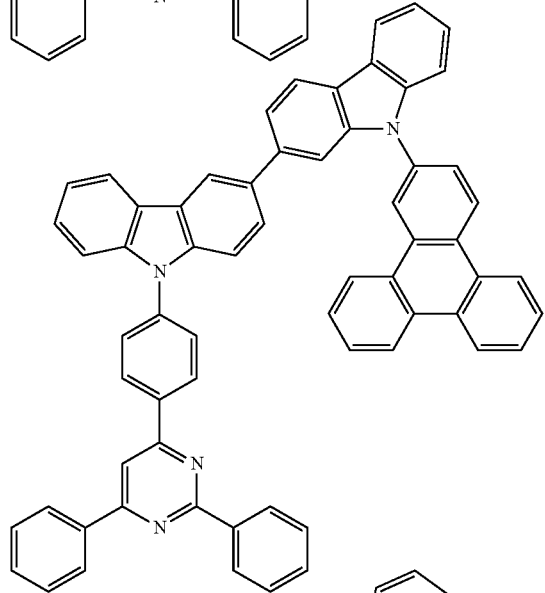
[D-352]
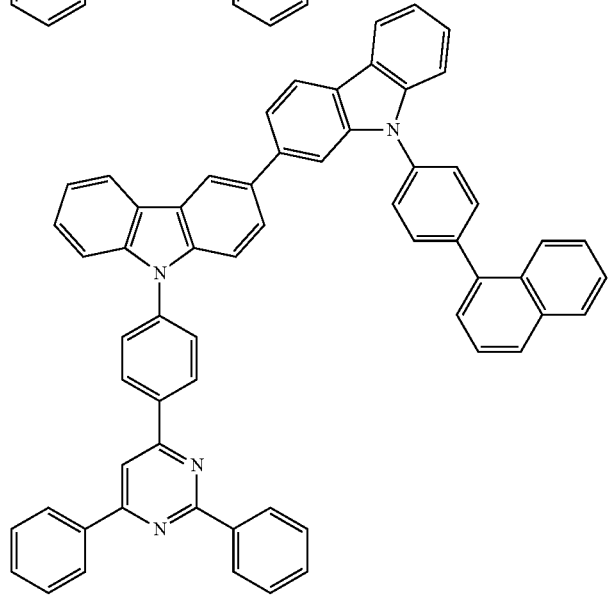

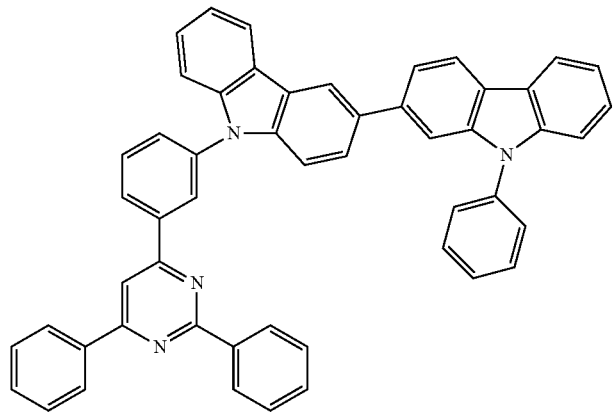
[D-353]
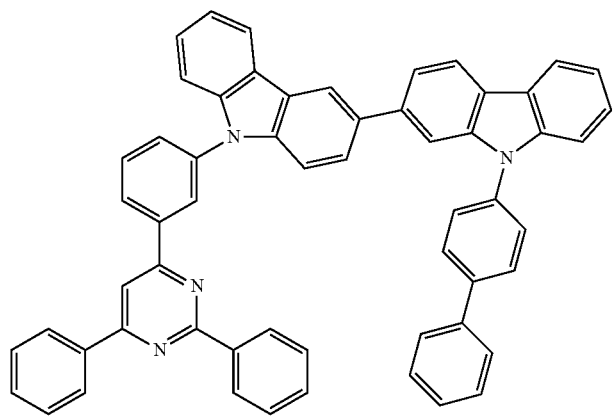
[D-354]
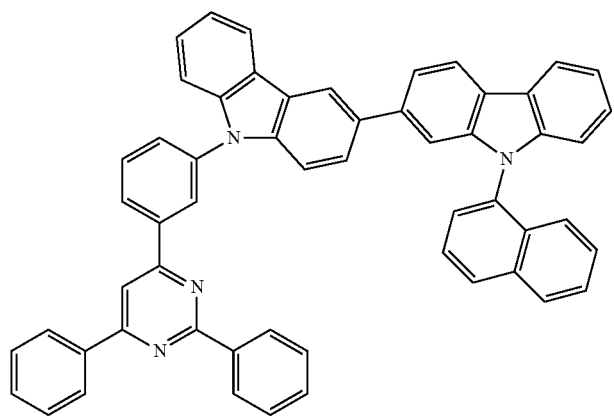
[D-355]

-continued
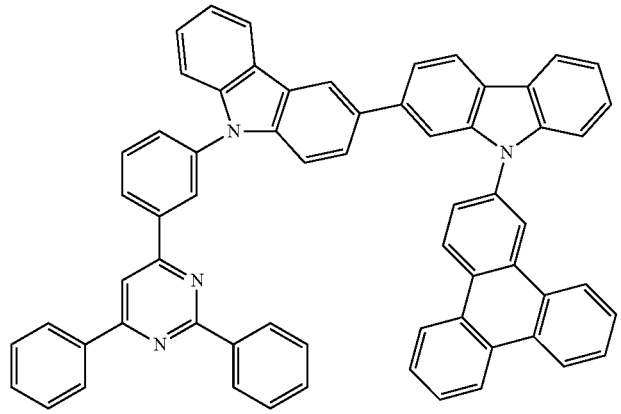
[D-356]
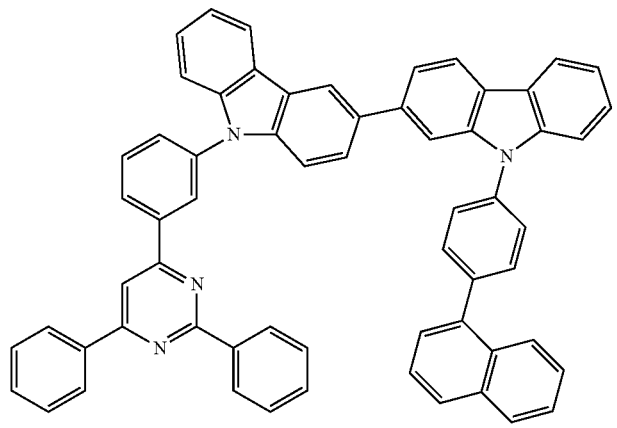
[D-357]
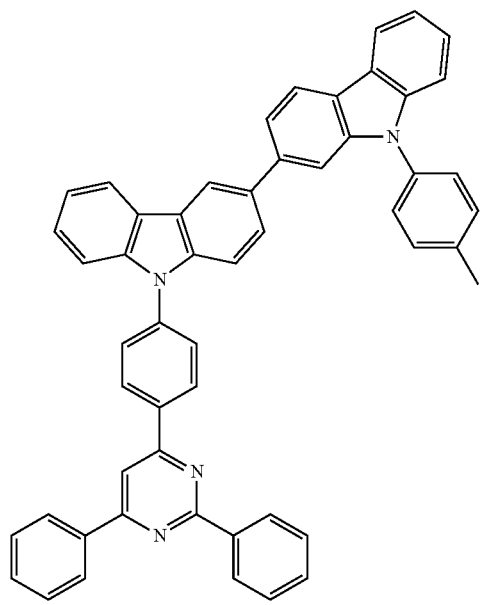
[D-358]

[D-359]
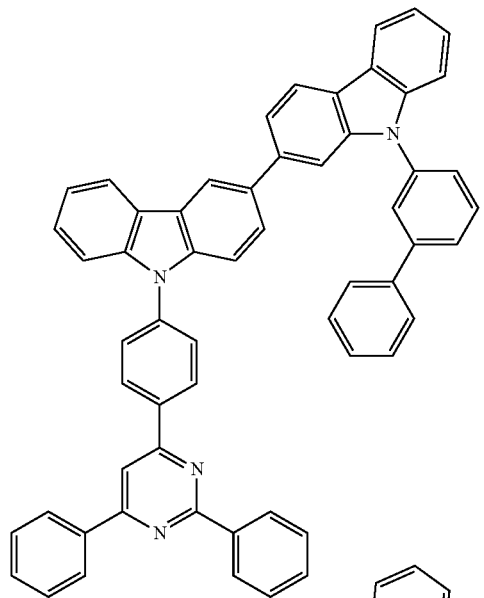
[D-360]
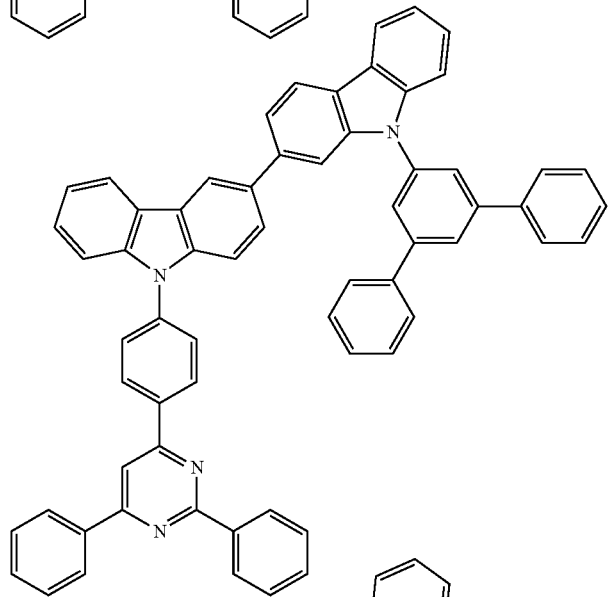
[D-361]
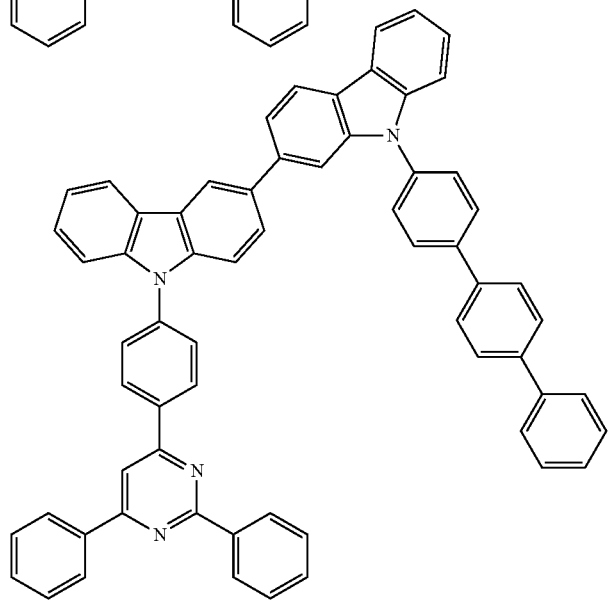

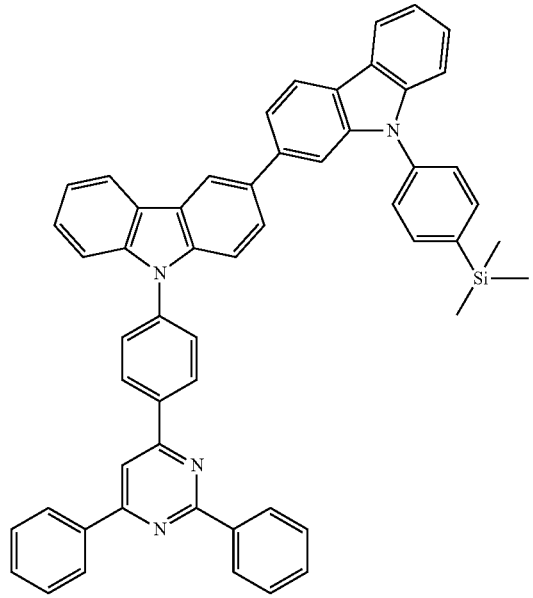
[D-362]
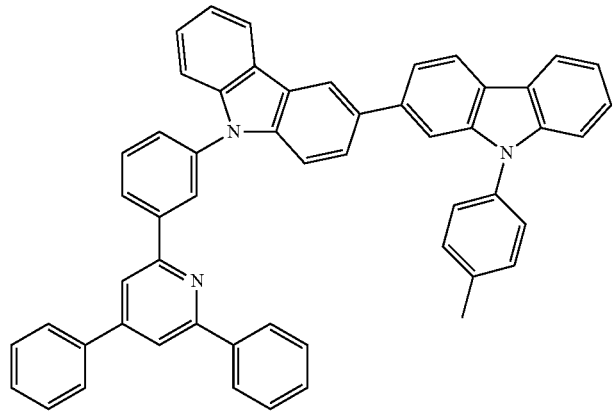
[D-363]
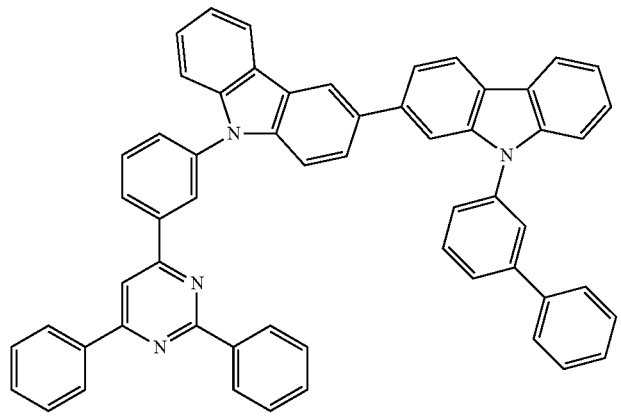
[D-364]

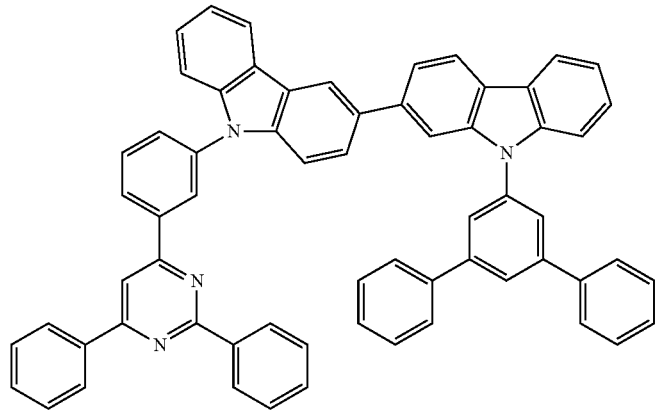
[D-365]
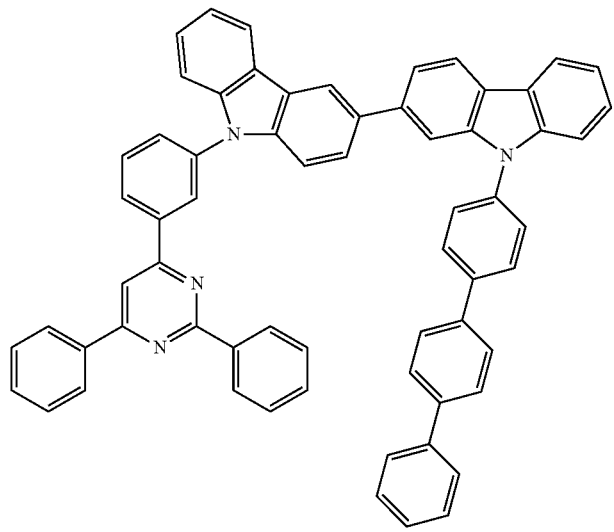
[D-366]
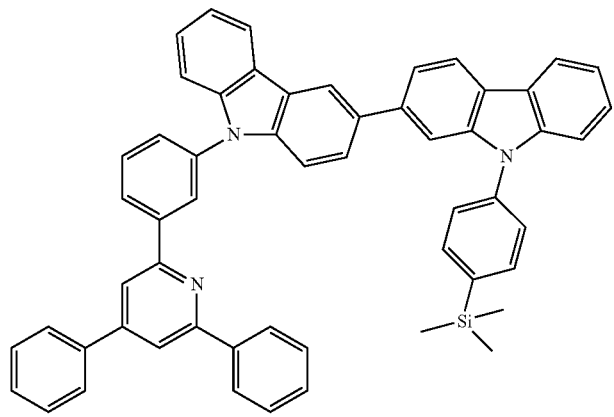
[D-367]

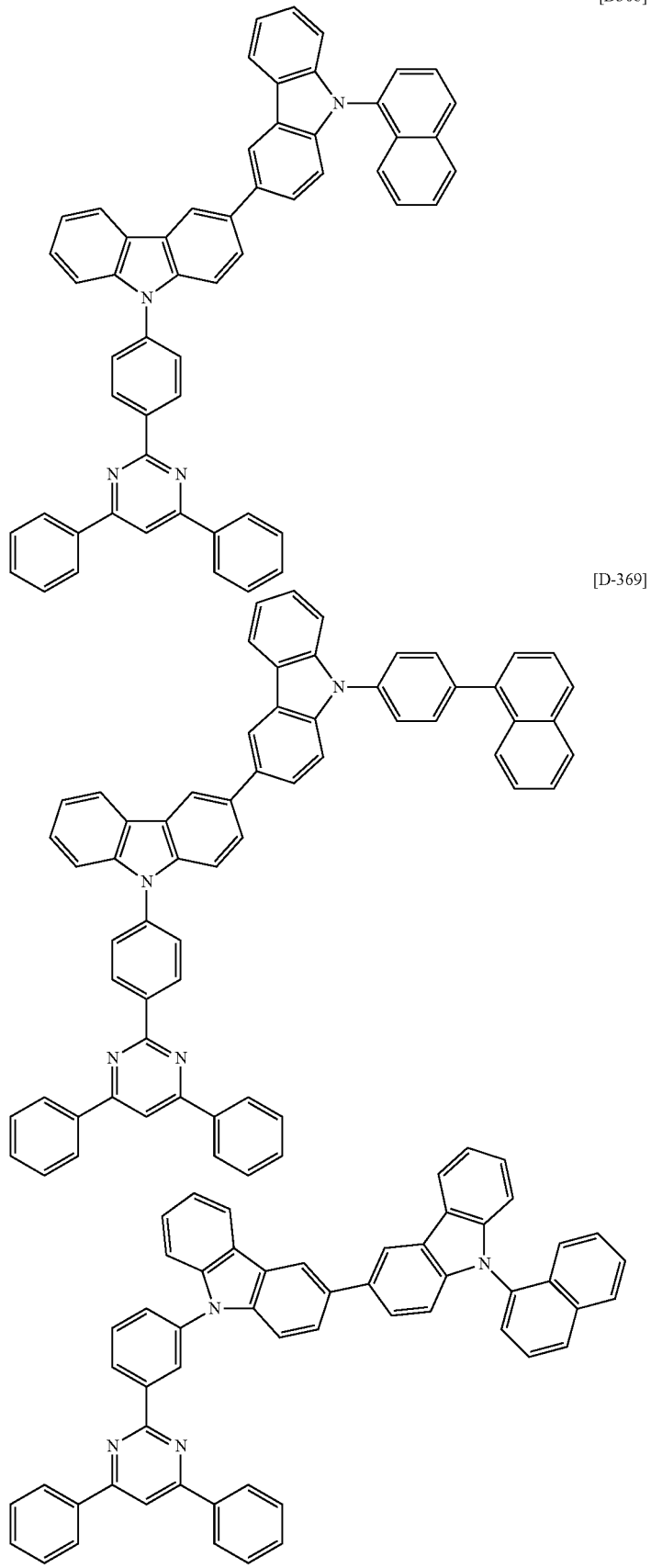

[D-371]
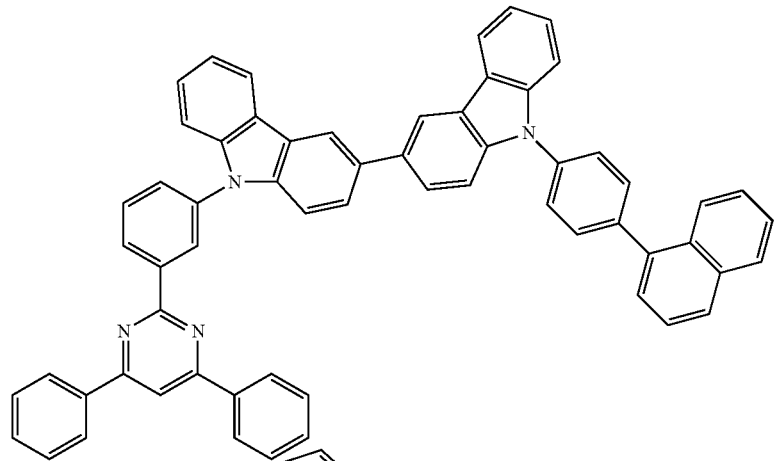
[D-372]
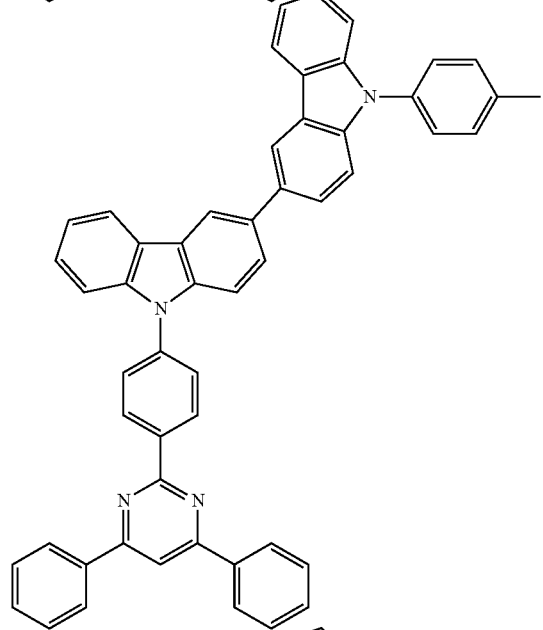
[D-373]
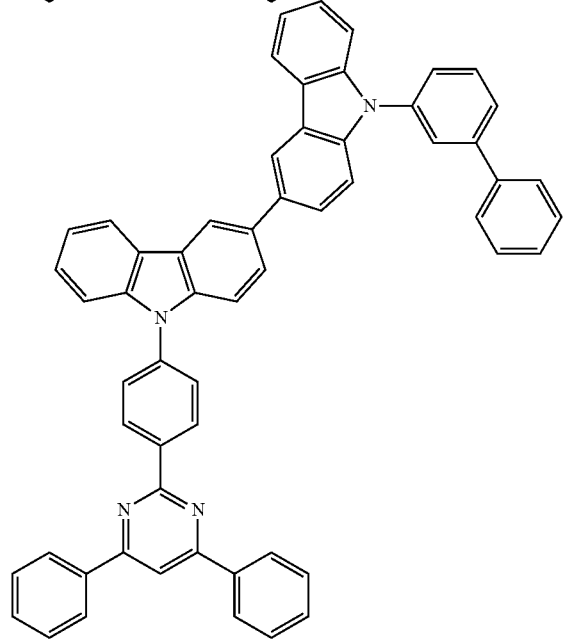

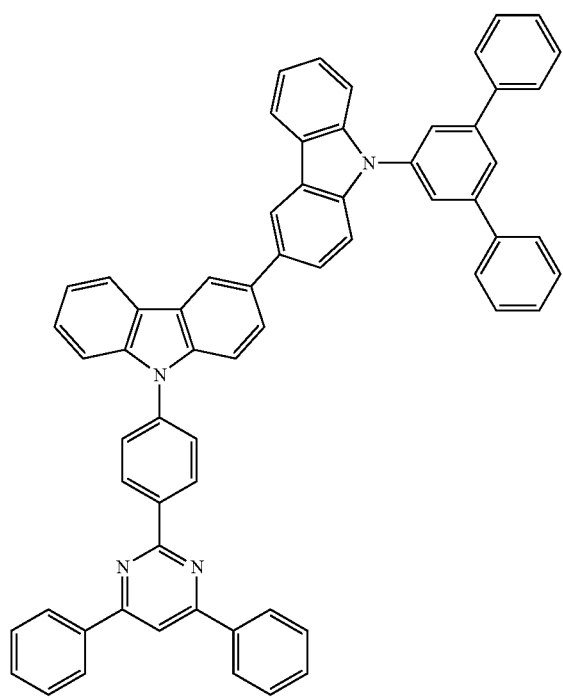
[D-374]
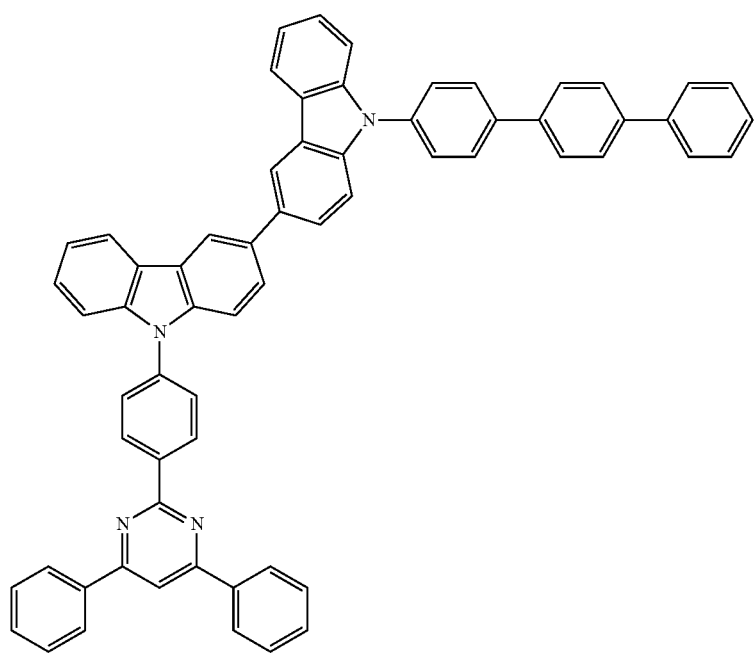
[D-375]

[D-376]
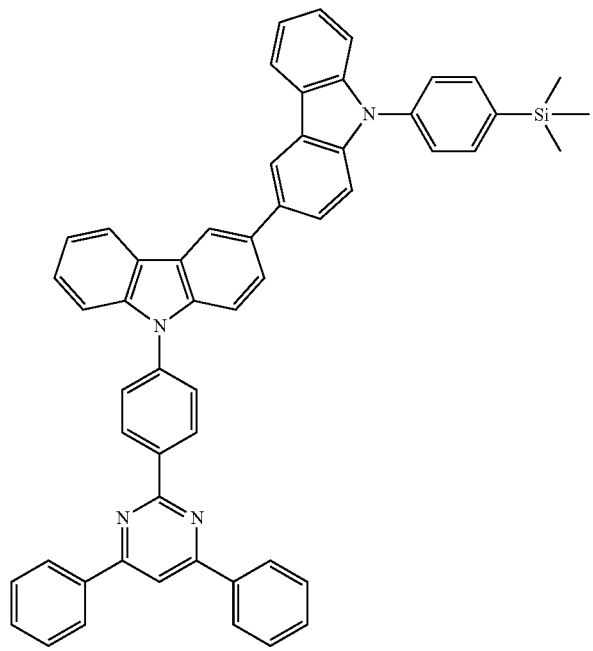
[D-377]
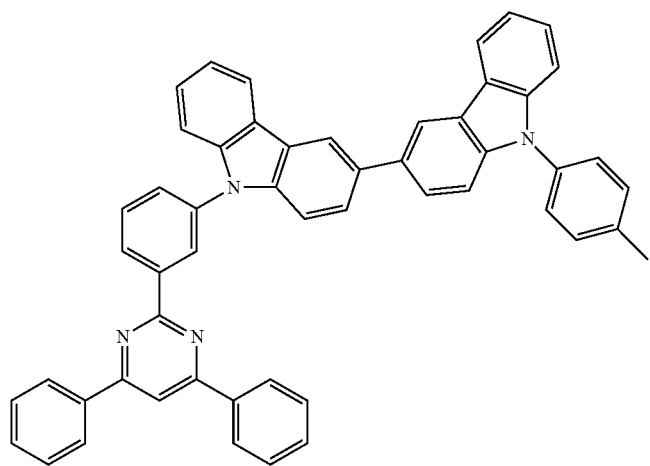
[D-378]
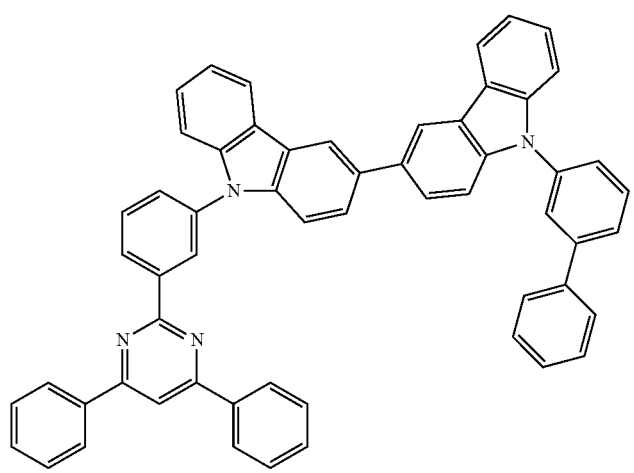

[D-379]
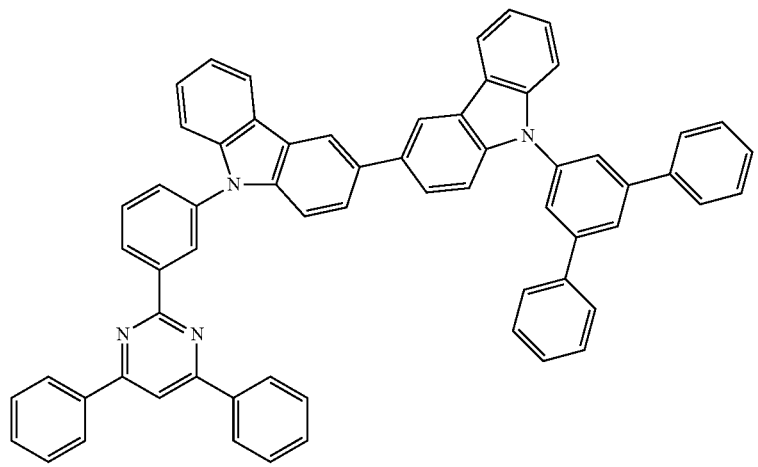
[D-380]
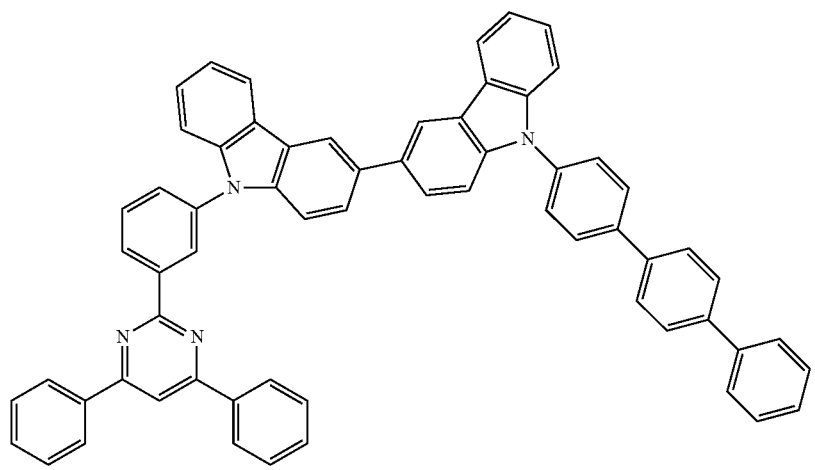
[D-381]
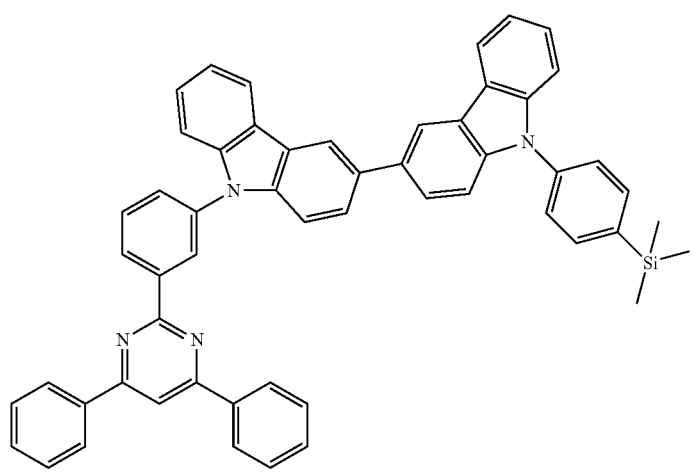

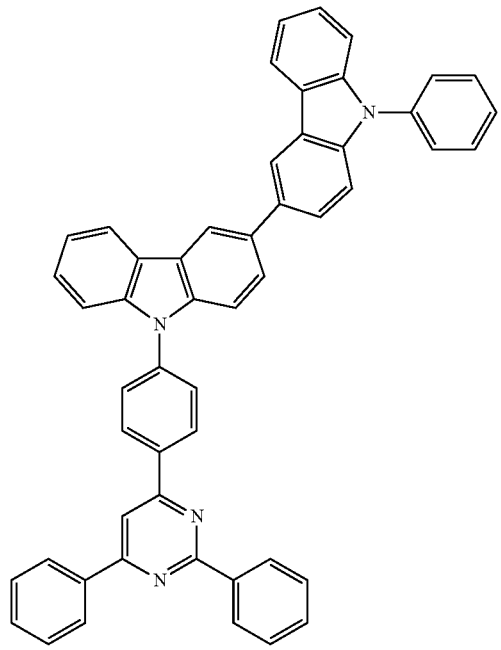
[D-382]
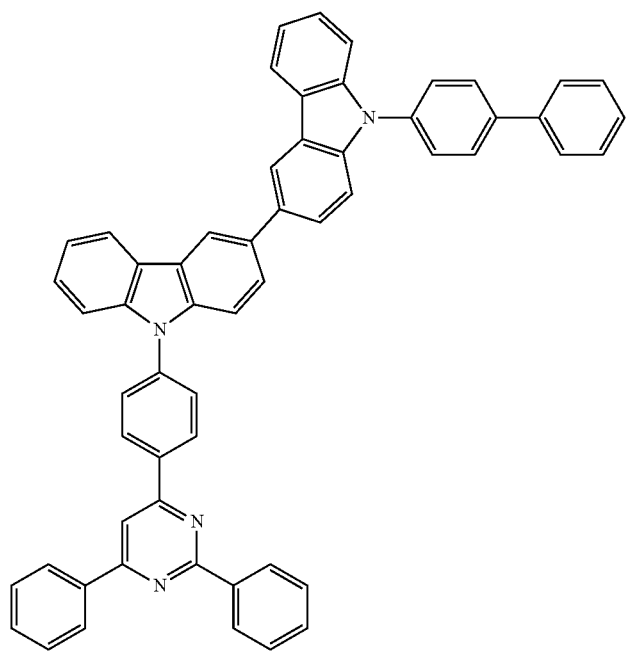
[D-383]

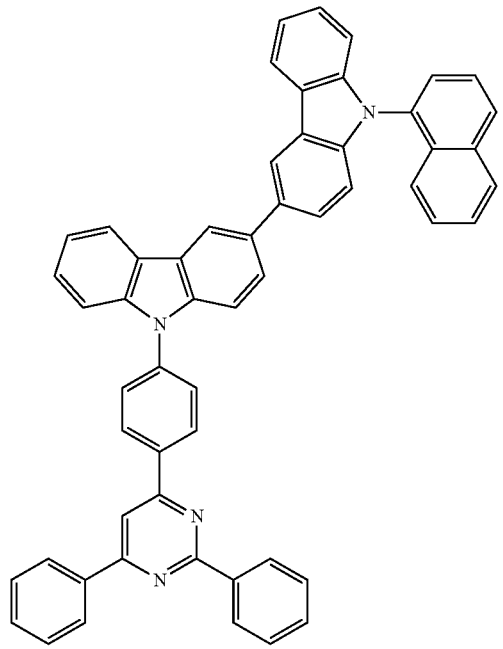
[D-384]
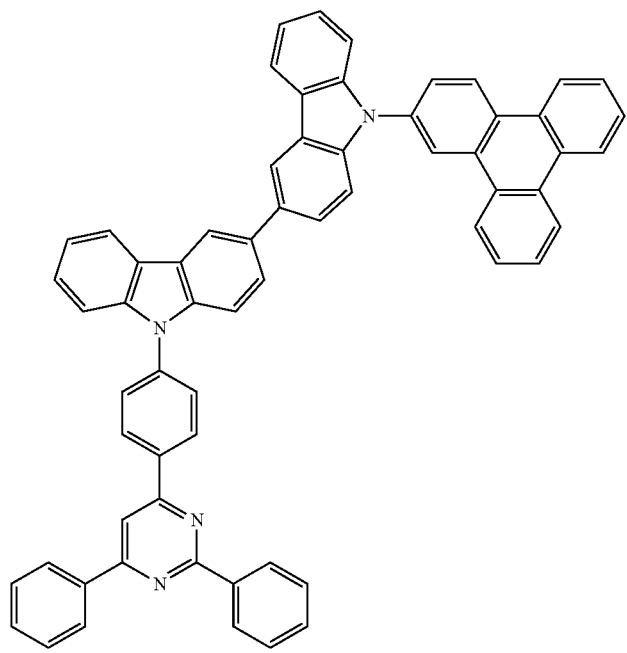
[D-385]

[D-386]
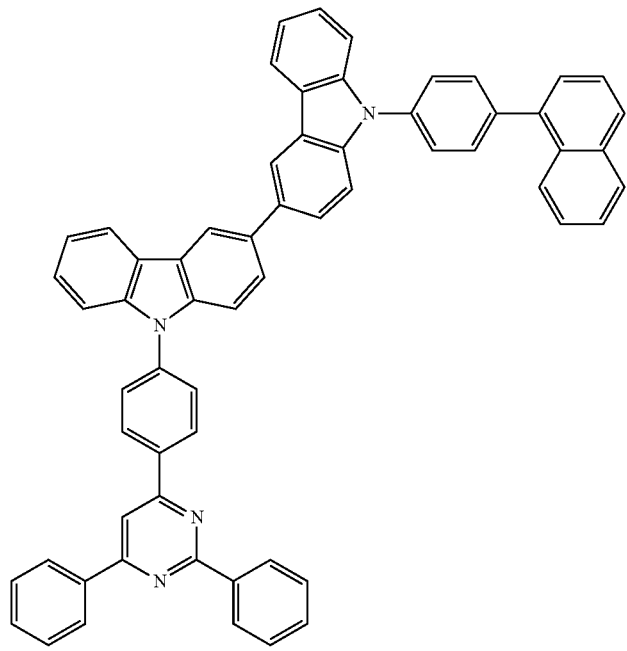
[D-387]
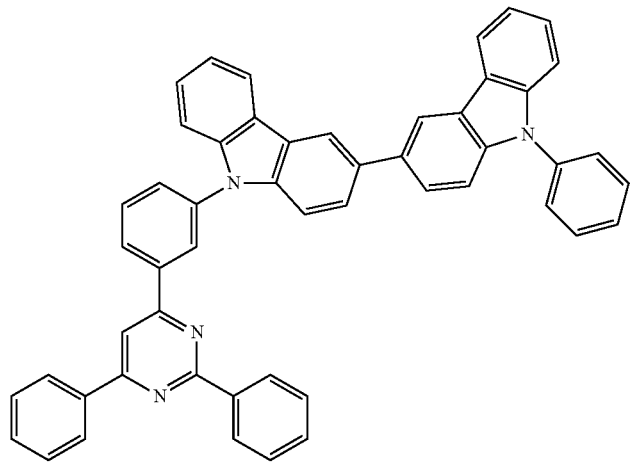
[D-388]
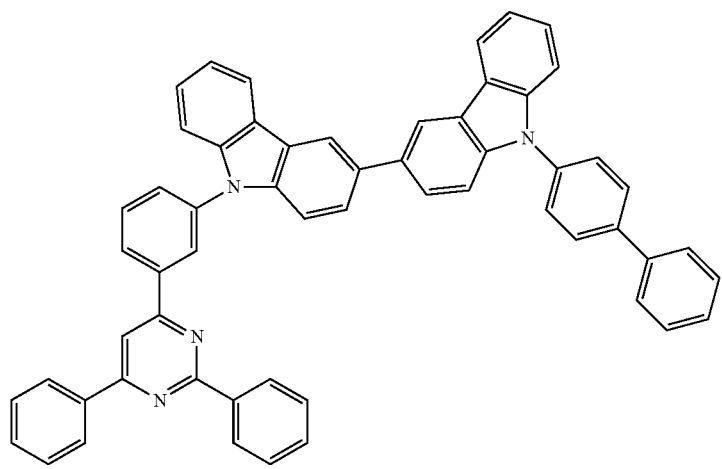

[D-389]
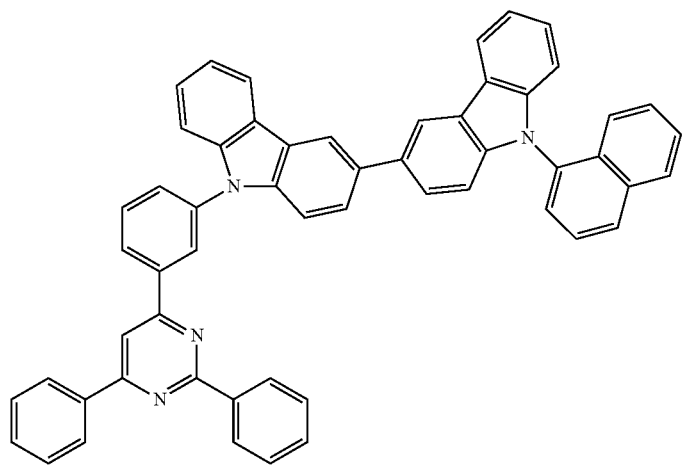
[D-390]
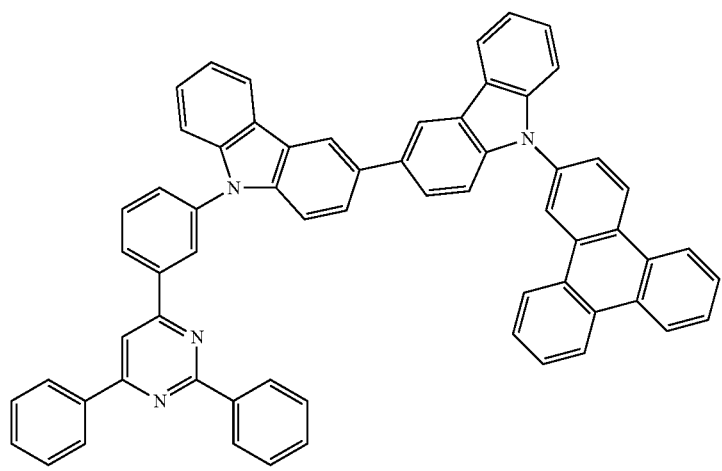
[D-391]
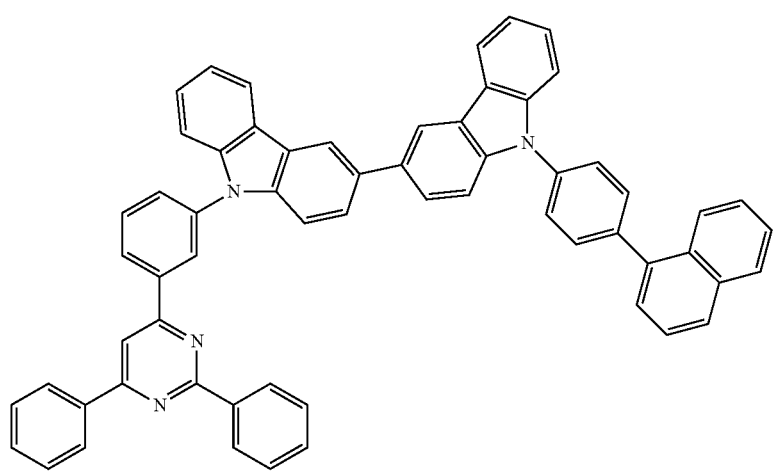

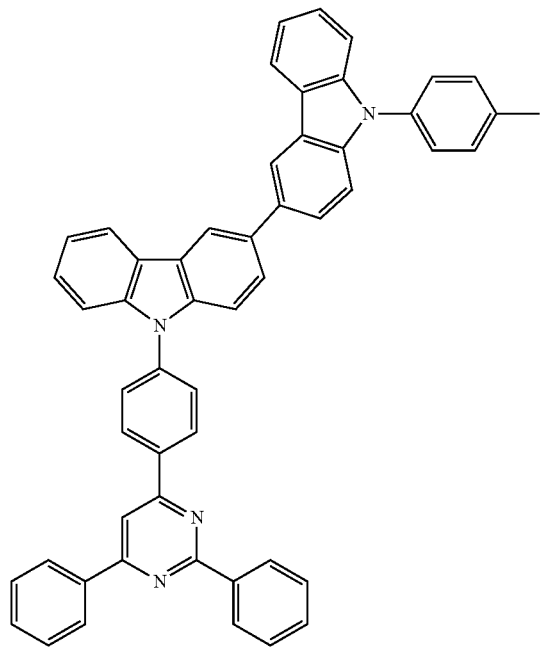
[D-392]
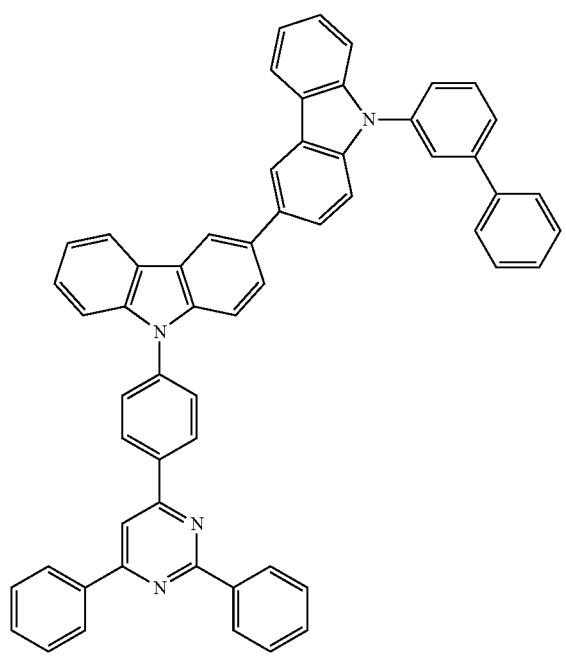
[D-393]

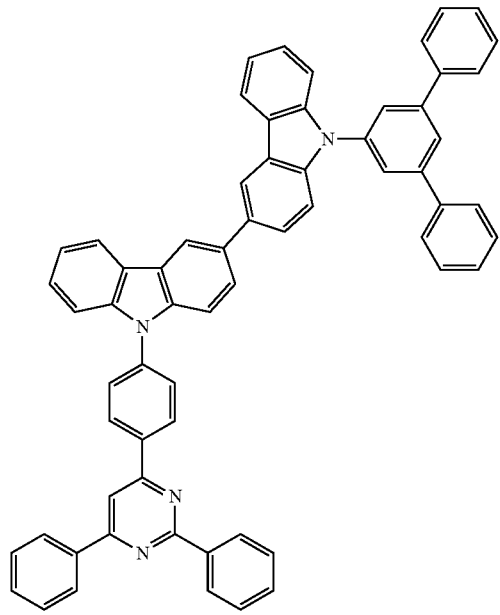
[D-394]
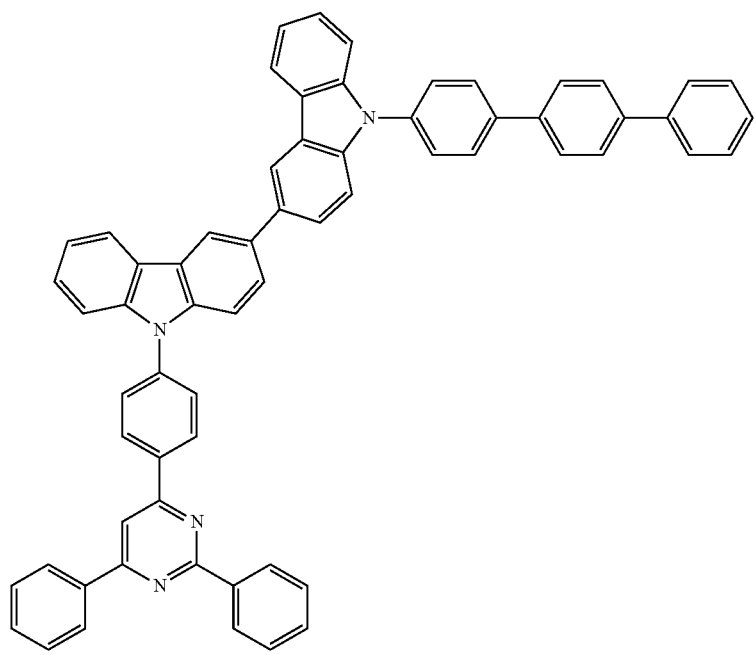
[D-395]

-continued
[D-396]
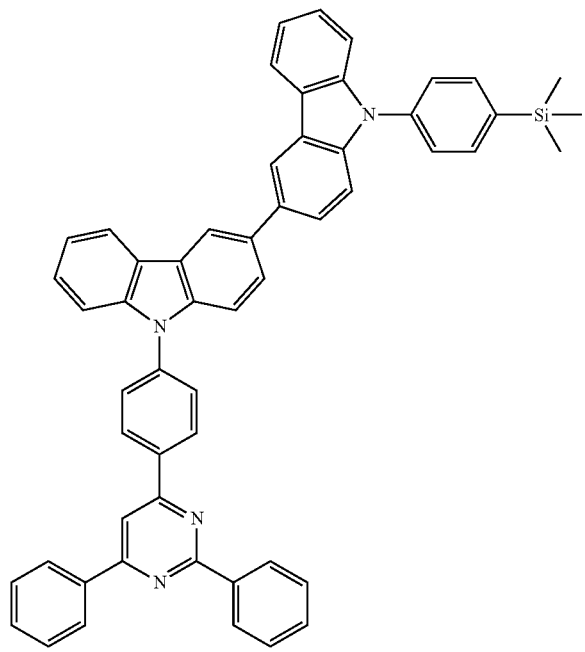
[D-397]
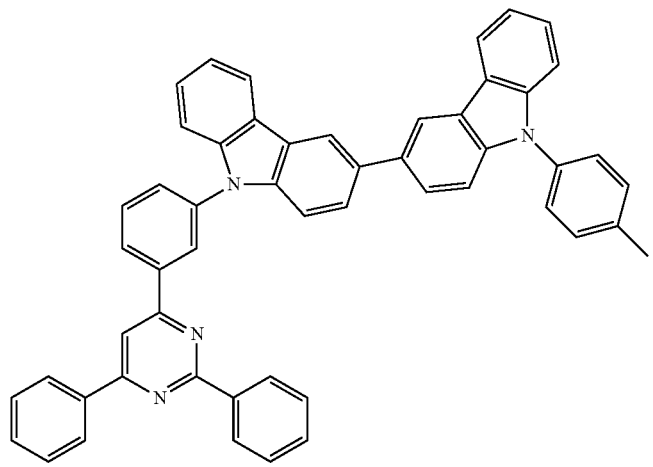
[D-398]
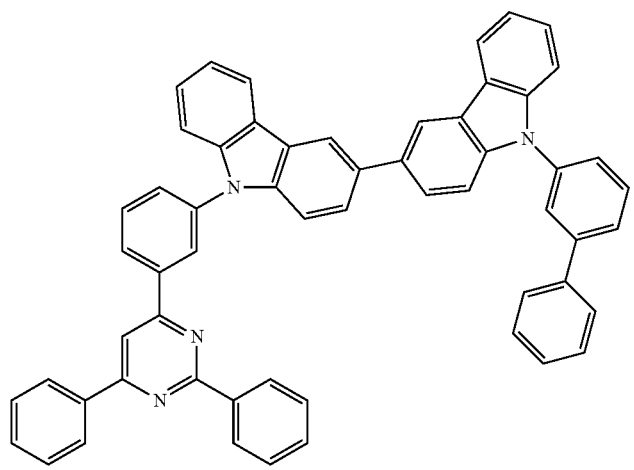

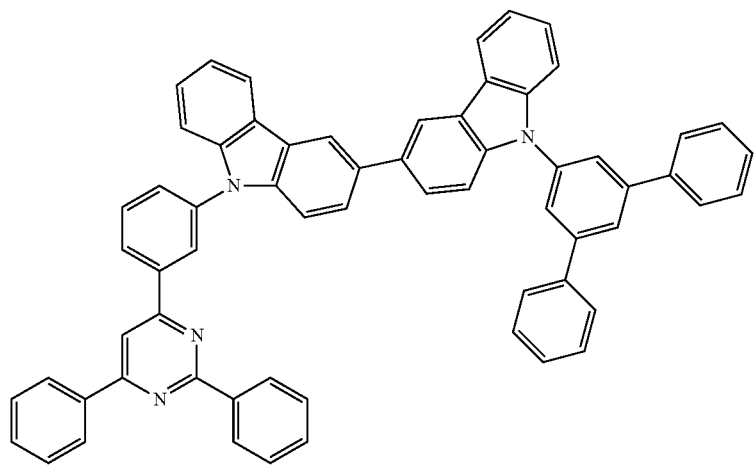
[D-399]
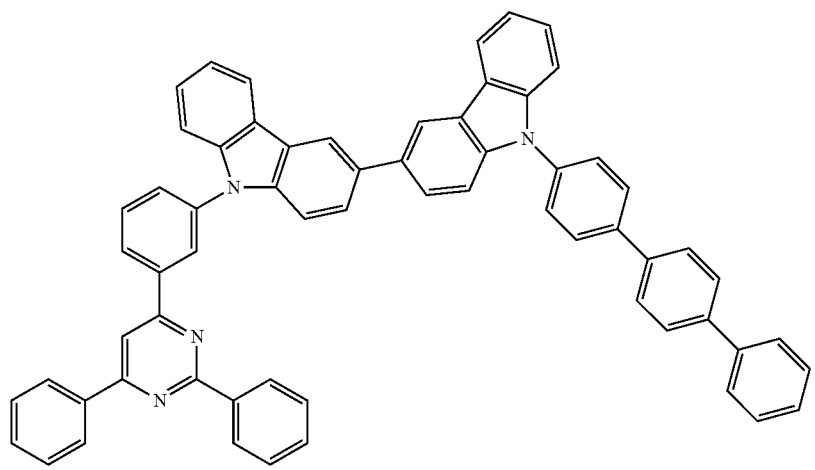
[D-400]
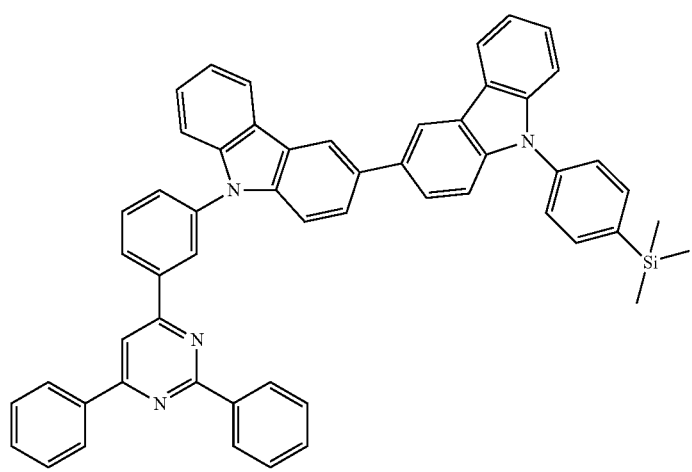
[D-401]

-continued
[D-402]
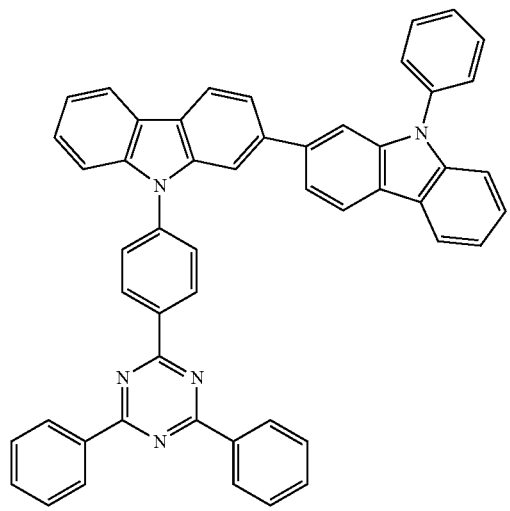
[D-403]
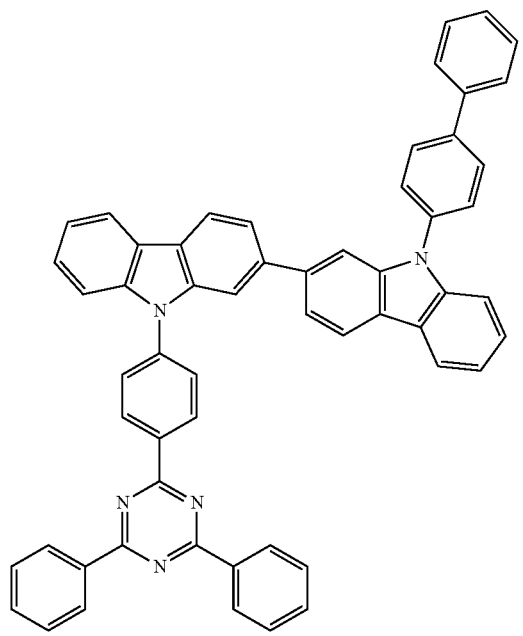
[D-404]
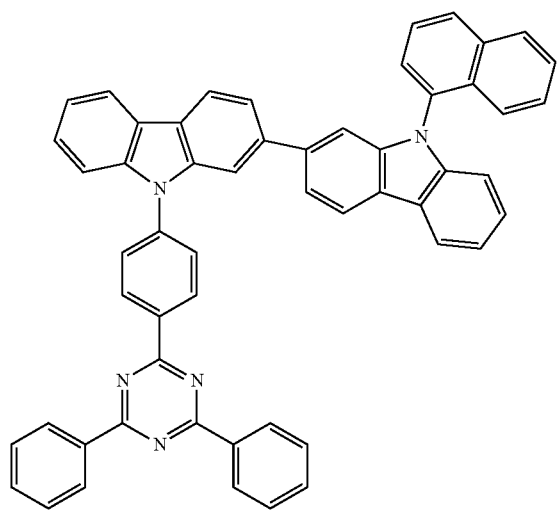

[D-405]
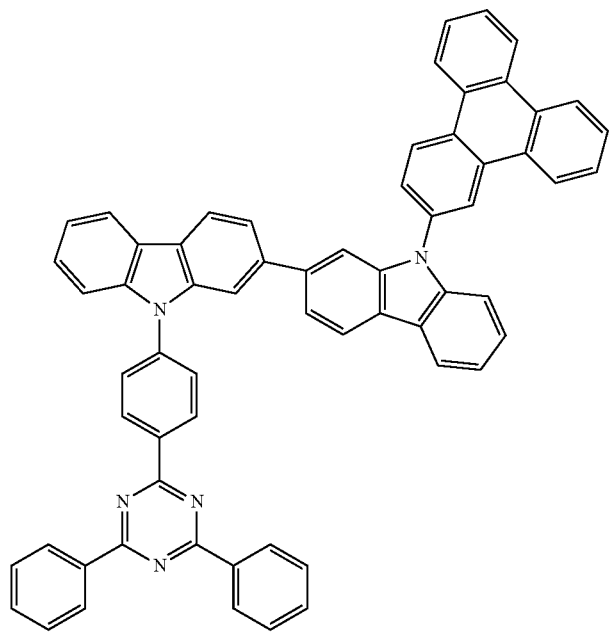
[D-406]
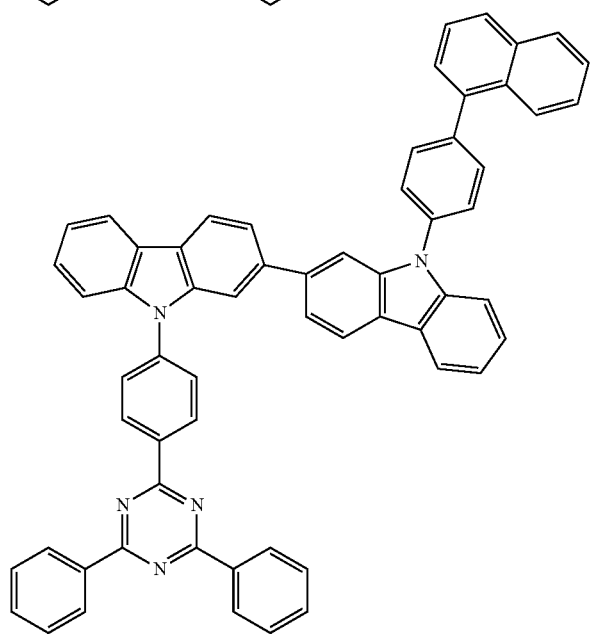
[D-407]
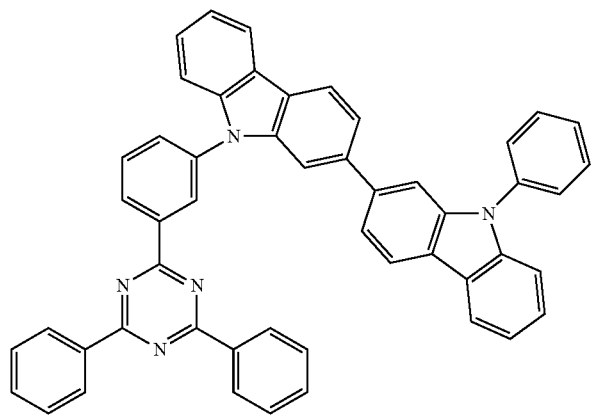

[D-408]
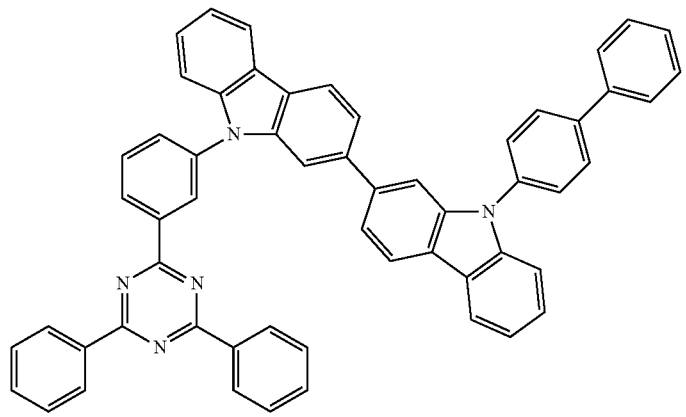
[D-409]
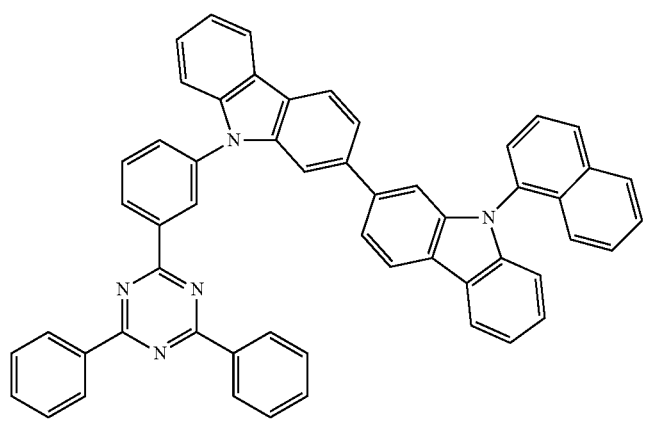
[D-410]
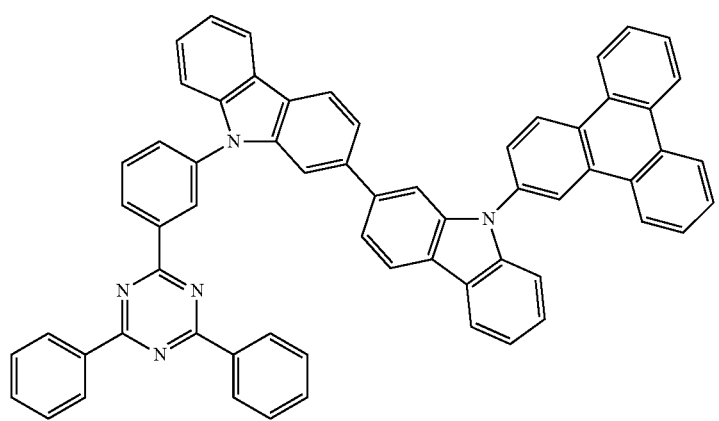
[D-411]
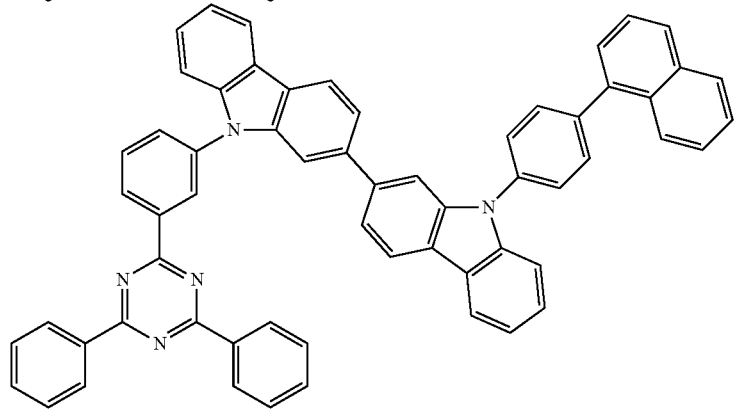

-continued
[D-412]
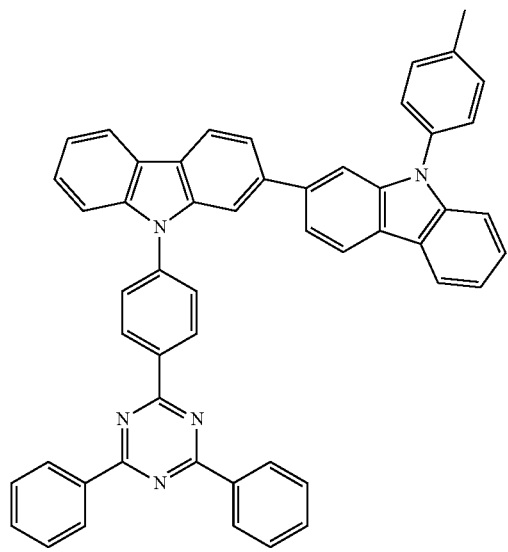
[D-413]
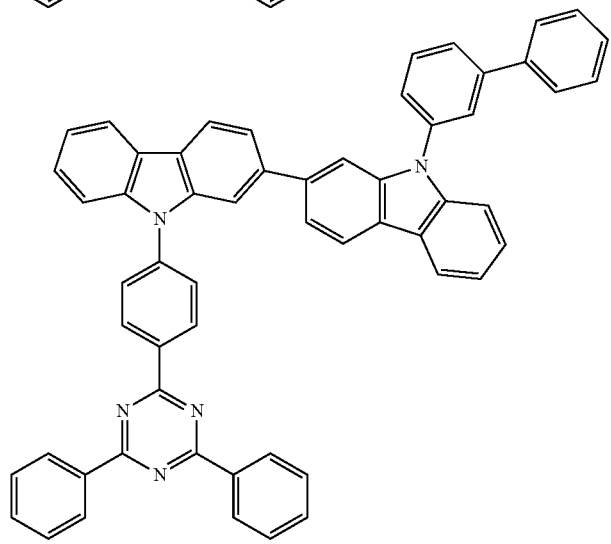
[D-414]
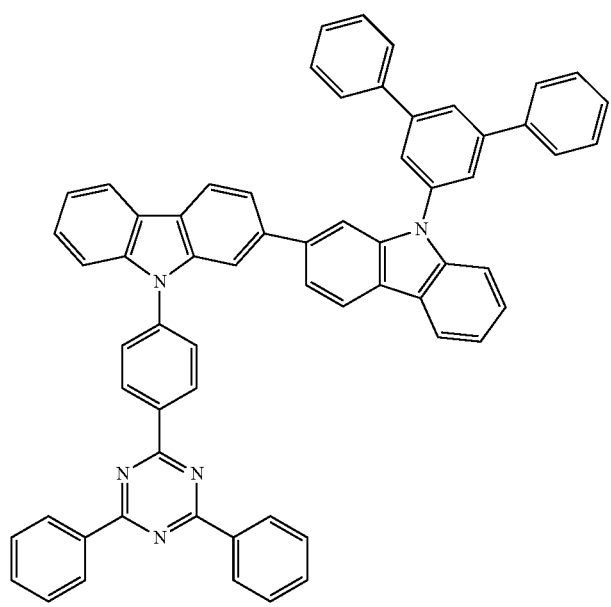

-continued
[D-415]
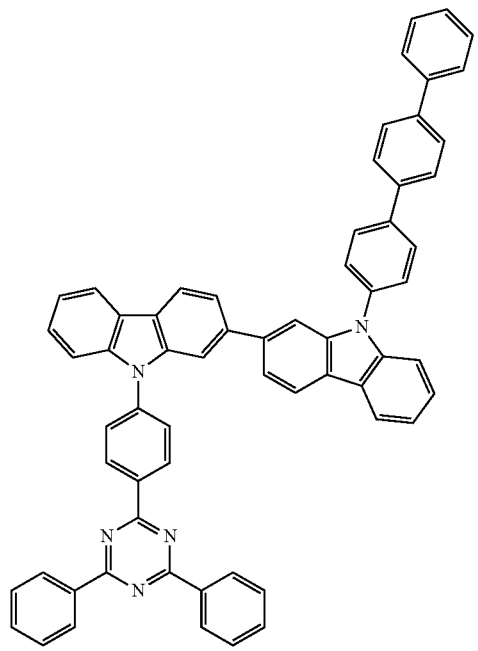
[D-416]
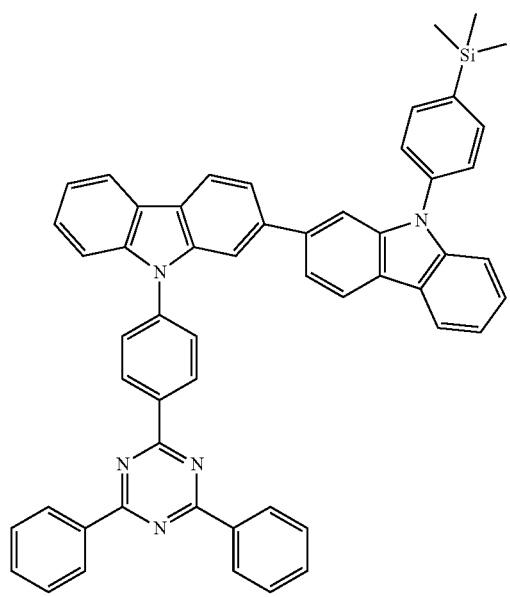
[D-417]
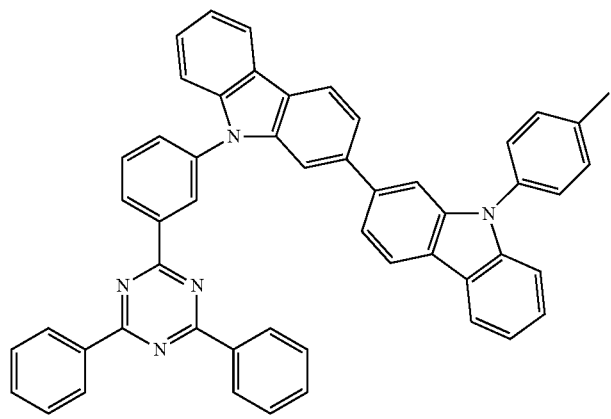

[D-418]
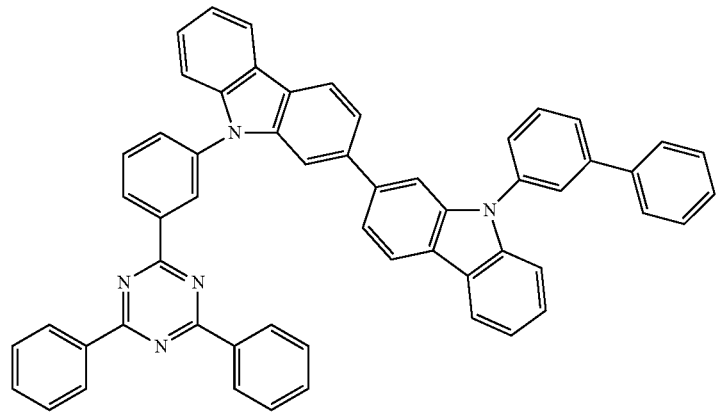
[D-419]
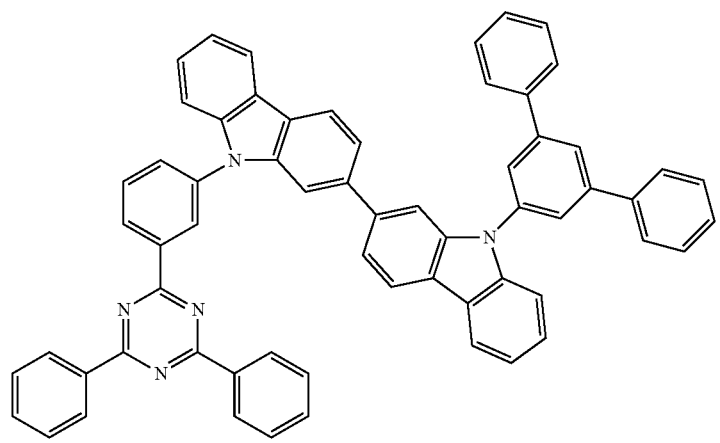
[D-420]
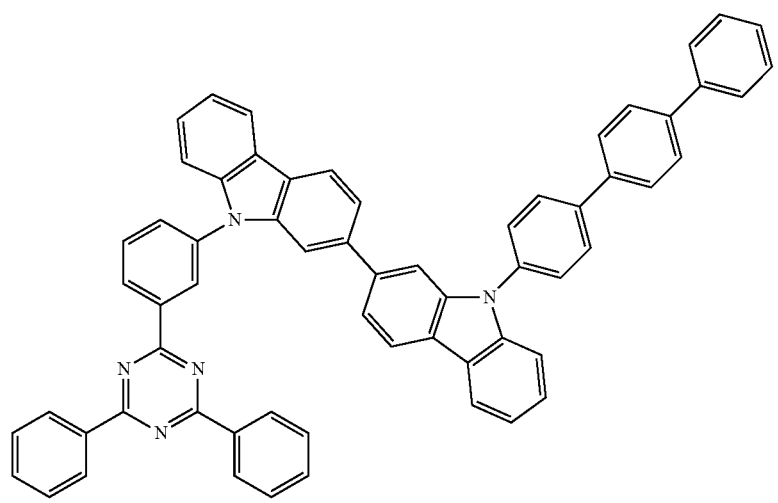

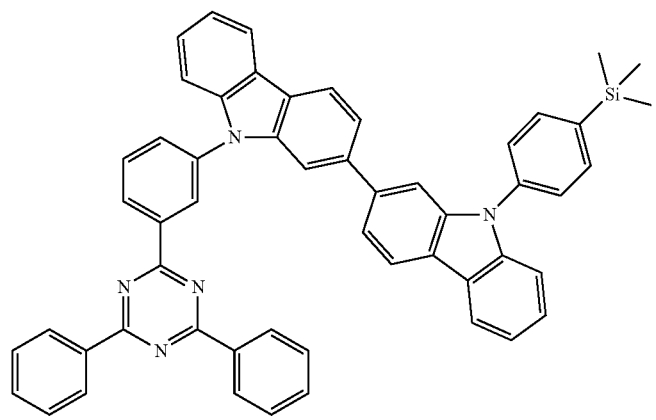
[D-421]
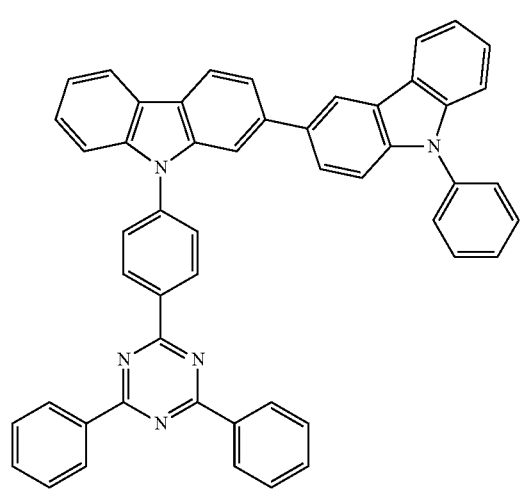
[D-422]
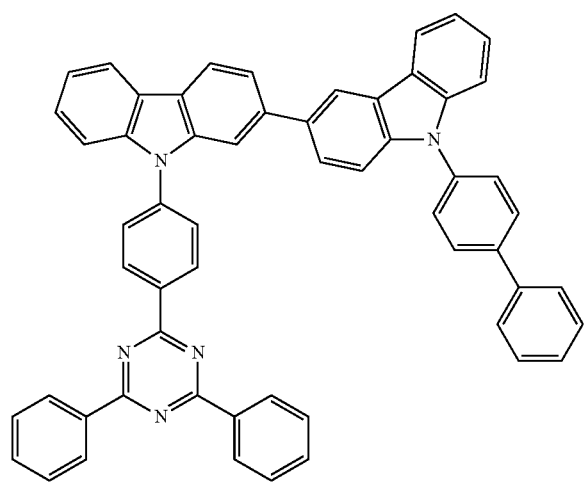
[D-423]

[D-424]
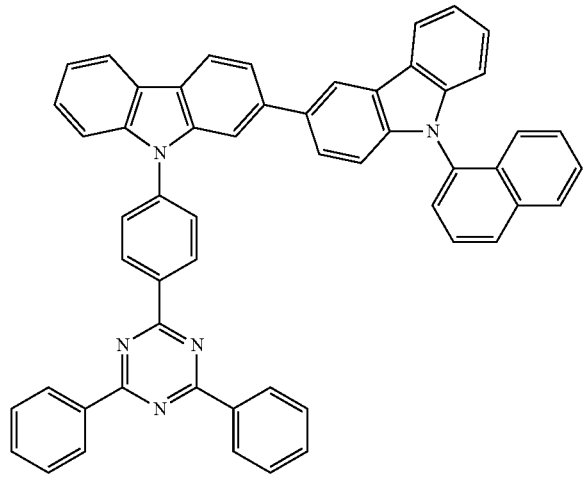
[D-425]
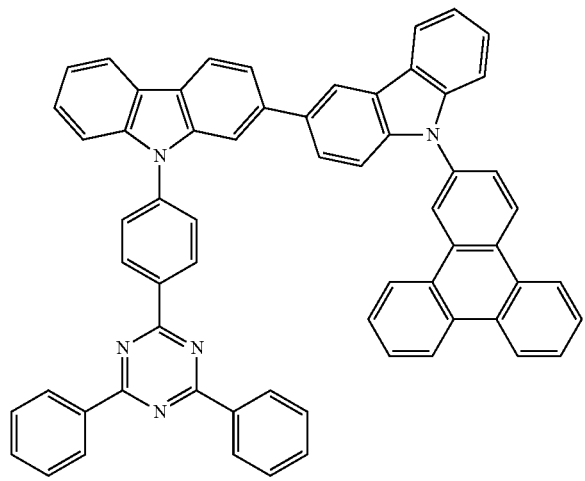
[D-426]
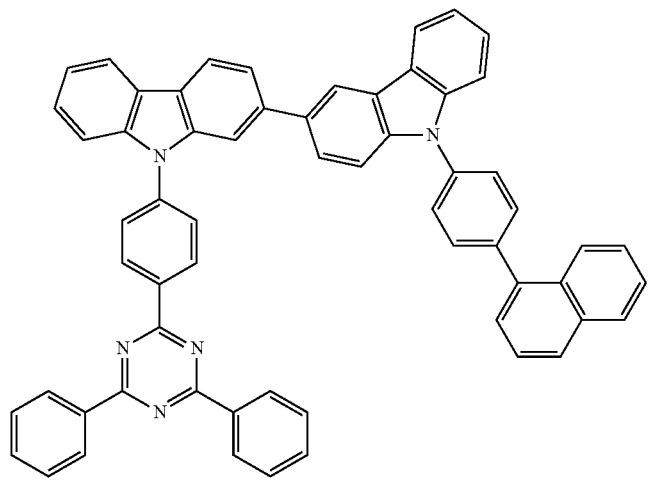

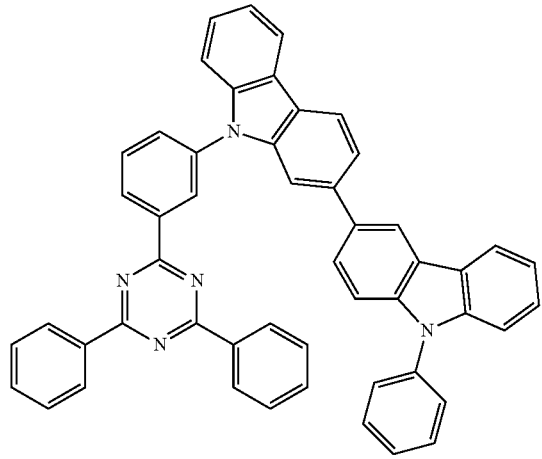
[D-427]
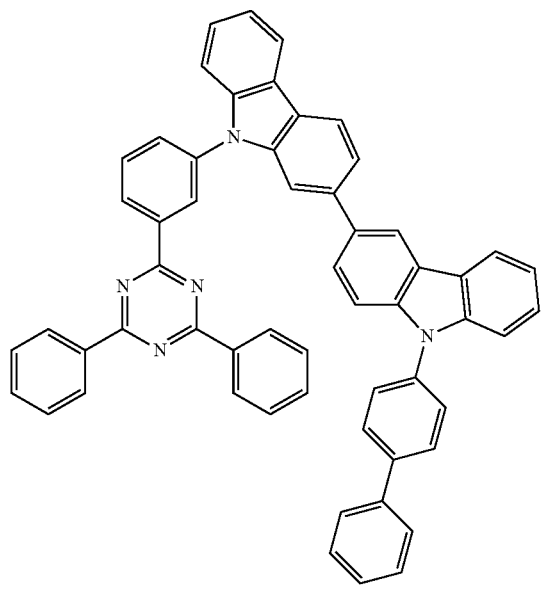
[D-428]
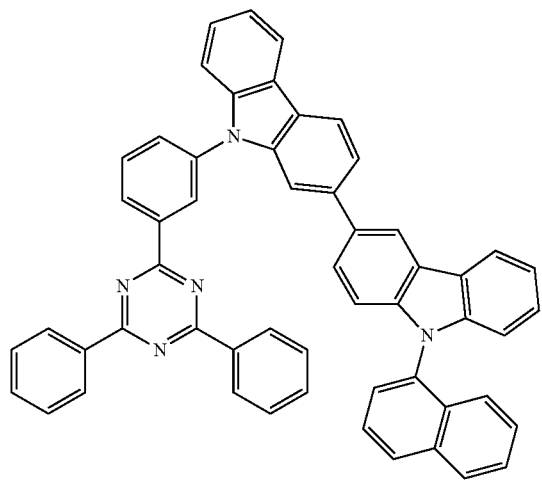
[D-429]

-continued
[D-430]
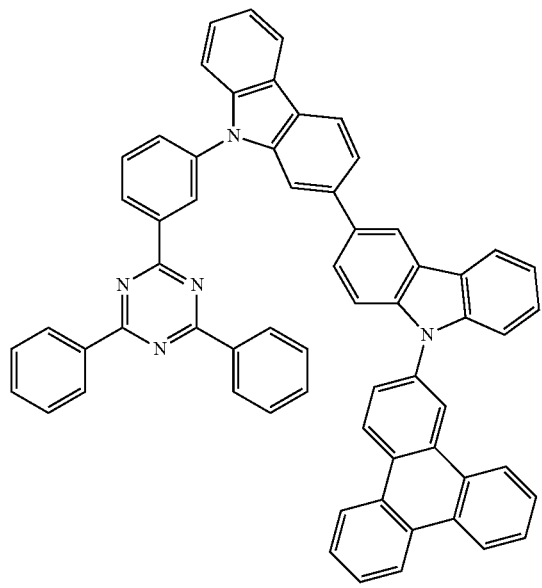
[D-431]
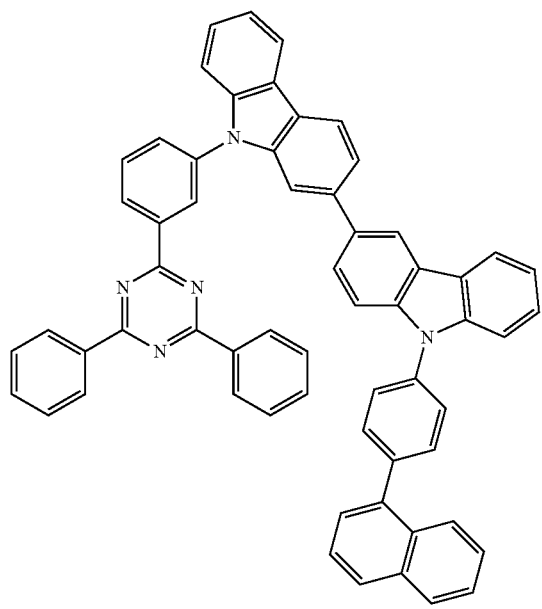
[D-432]
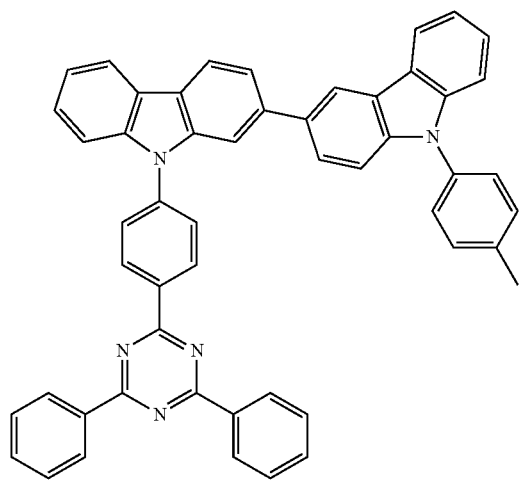

[D-433]
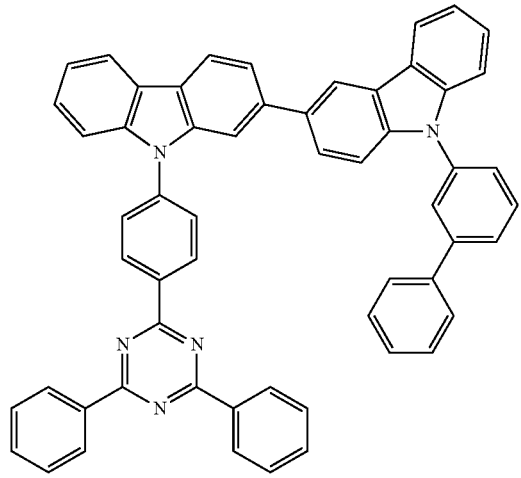
[D-434]
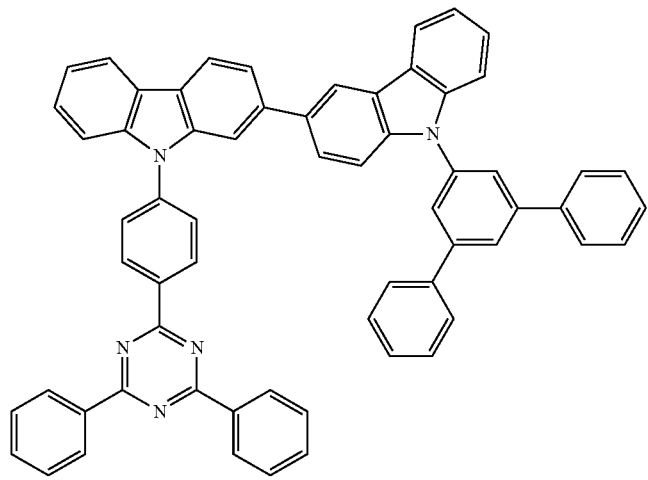
[D-435]
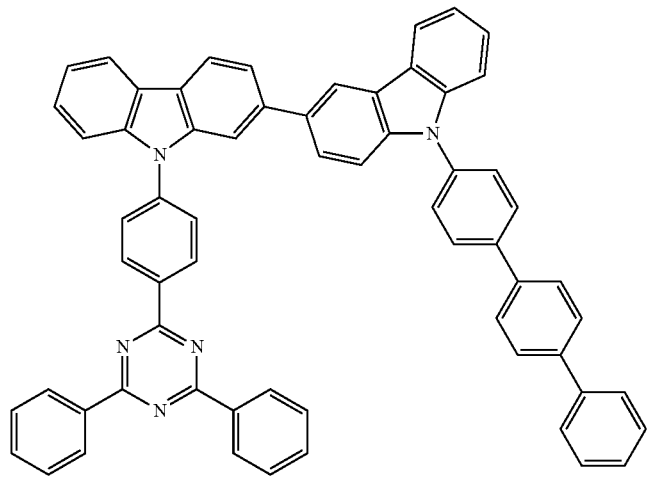

-continued
[D-436]
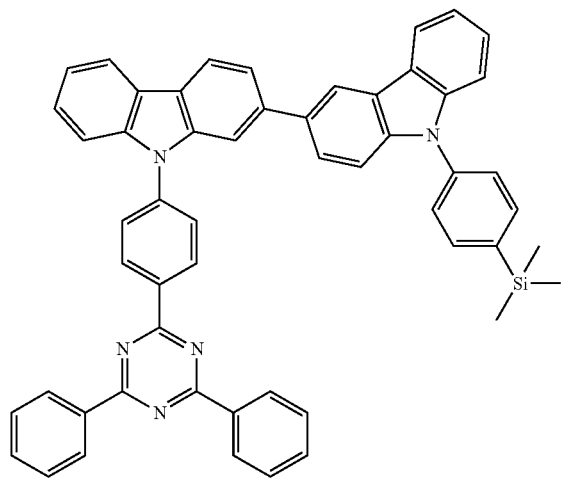
[D-437]
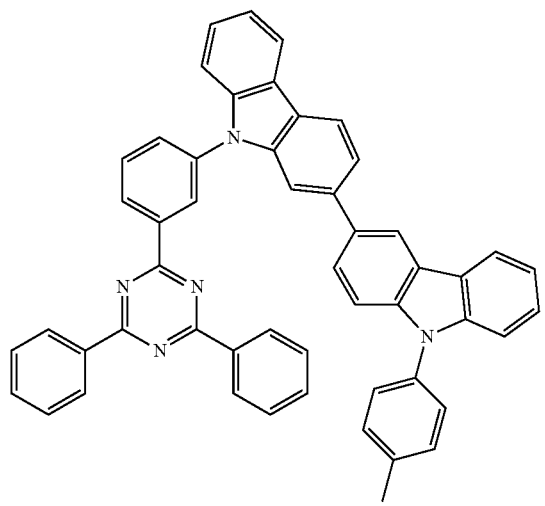
[D-438]
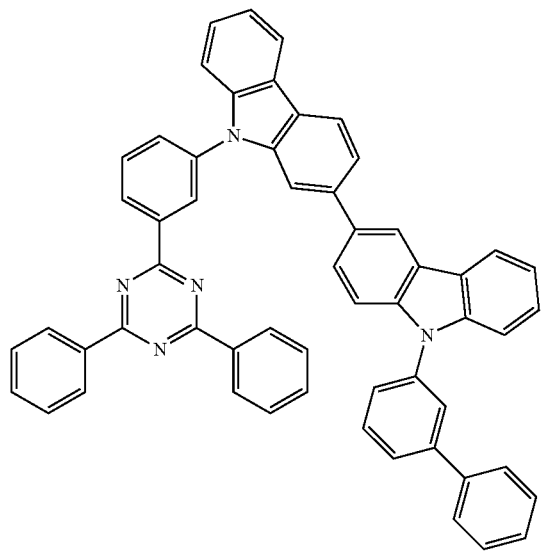

-continued
[D-439]
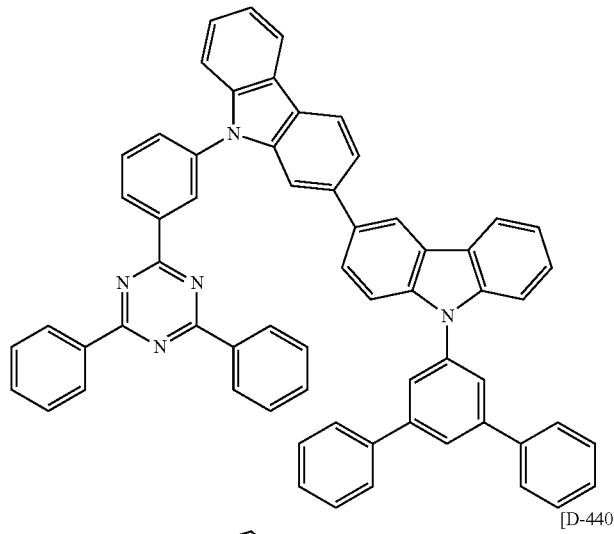
[D-440]
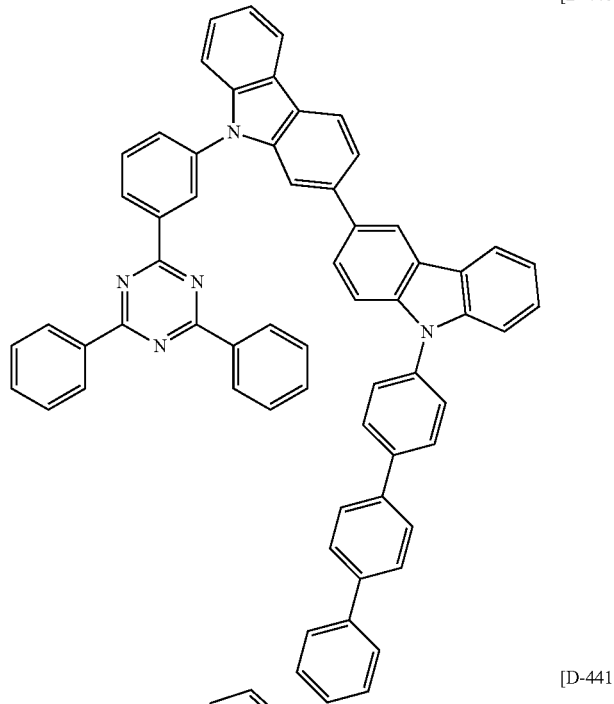
[D-441]
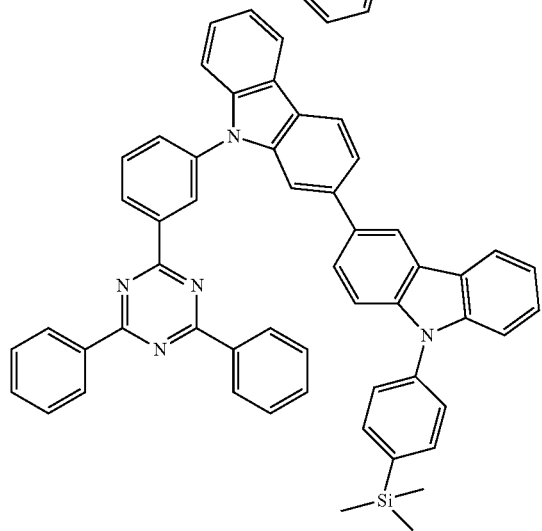

-continued
[D-442]
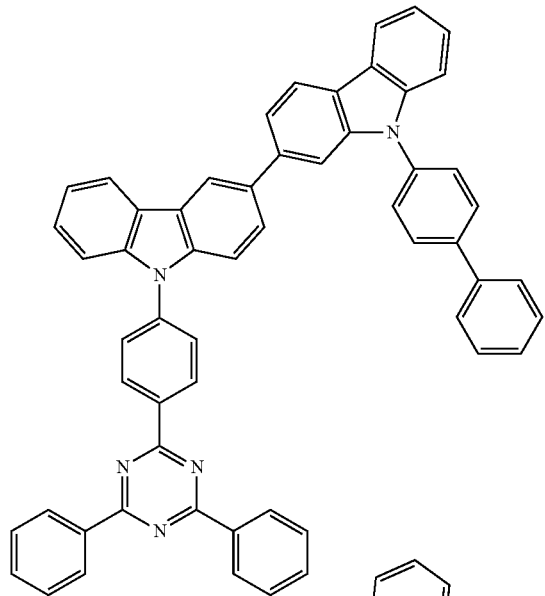
[D-443]
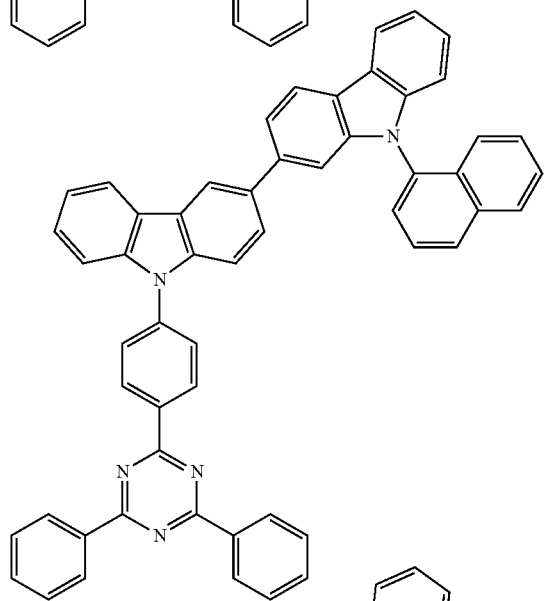
[D-444]
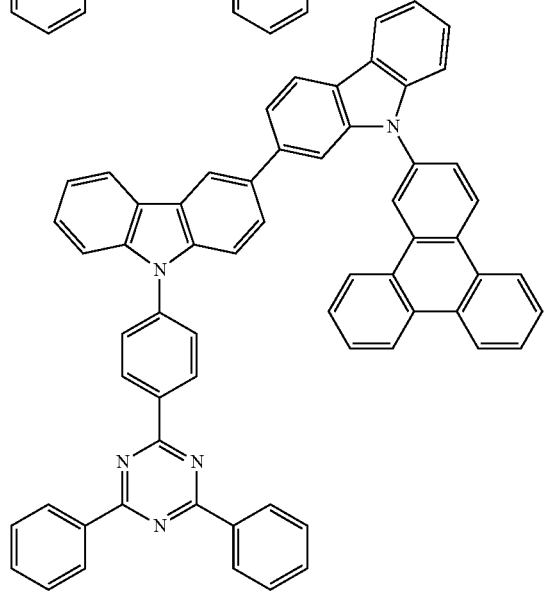

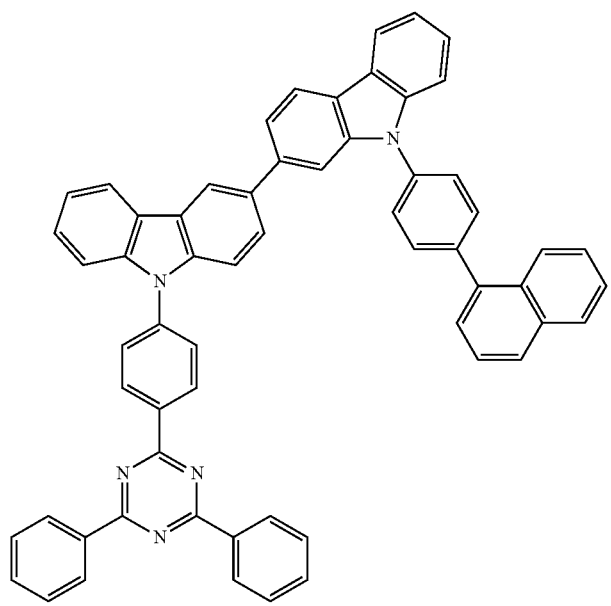
[D-445]
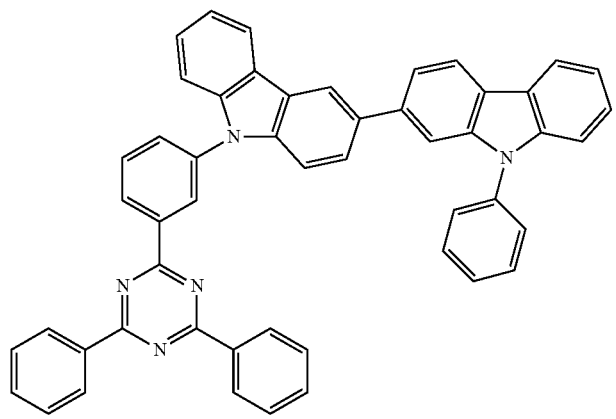
[D-446]
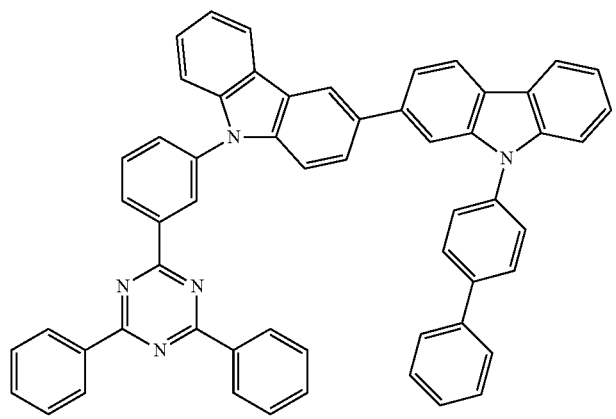
[D-447]

[D-448]
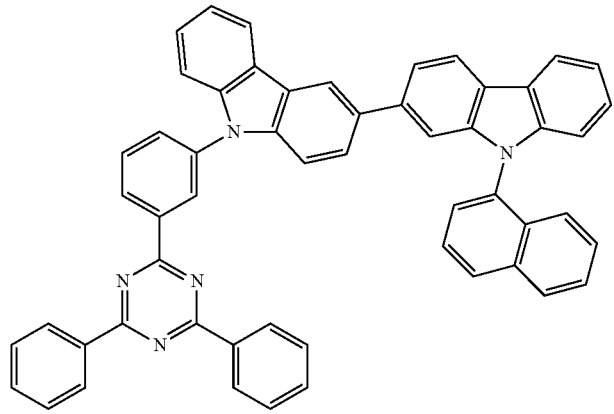
[D-449]
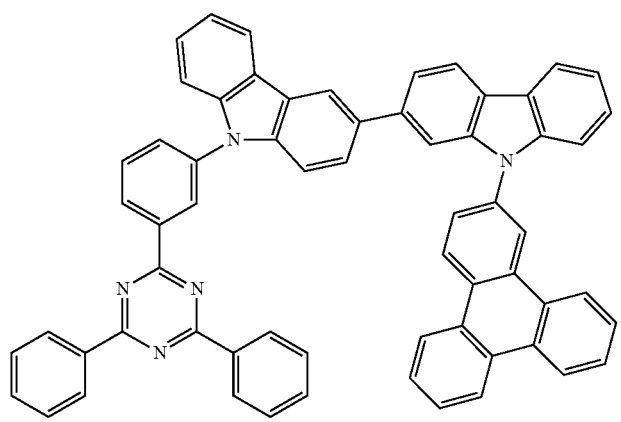
[D-450]
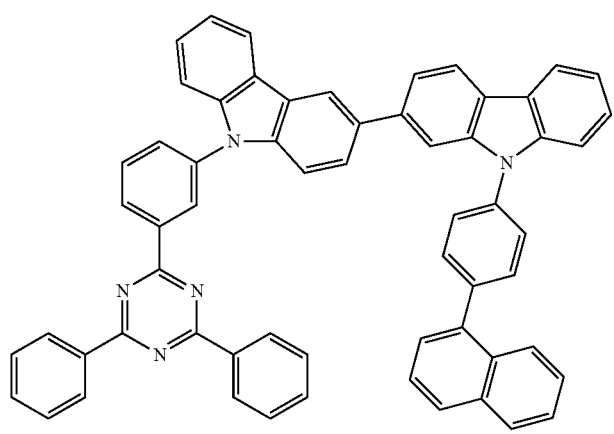

-continued
[D-451]
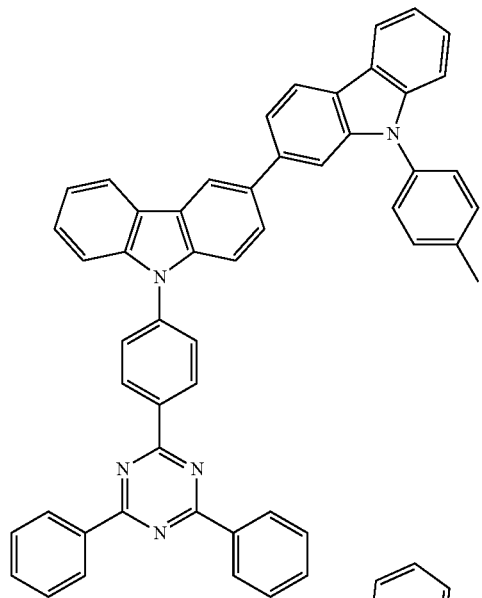
[D-452]
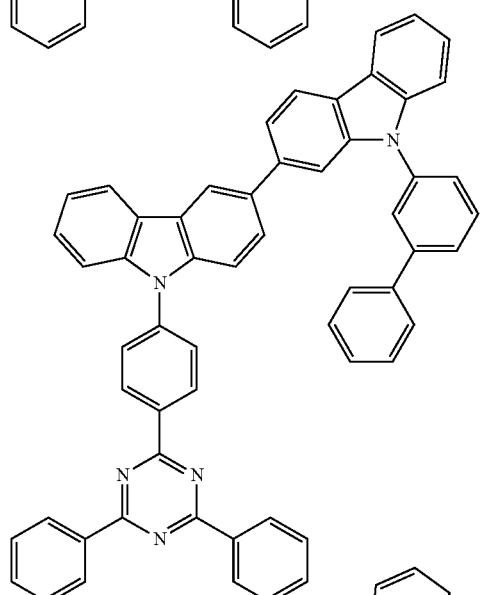
[D-453]
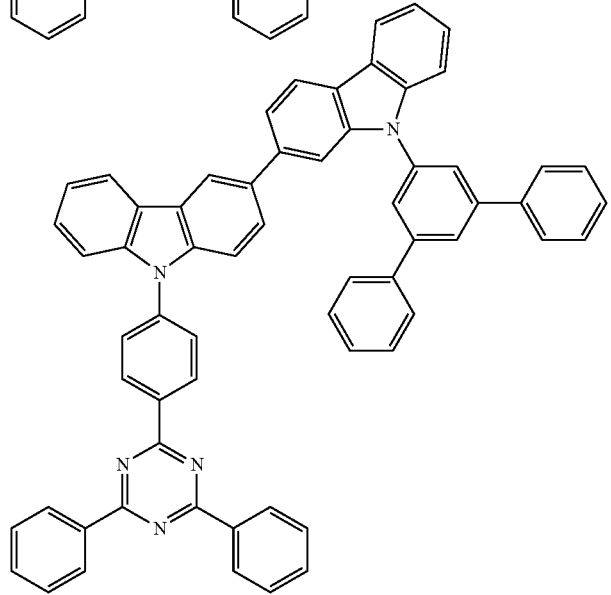

-continued
[D-454]
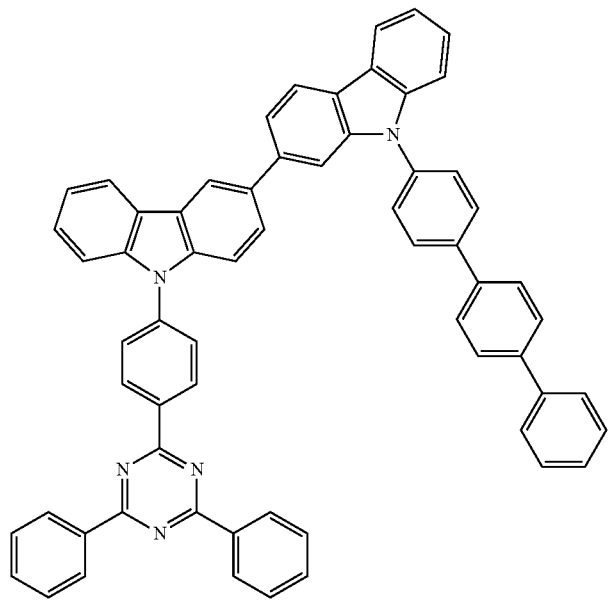
[D-455]
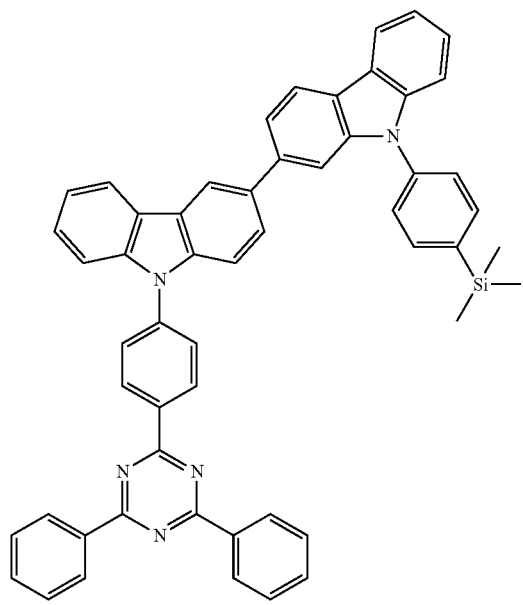
[D-456]
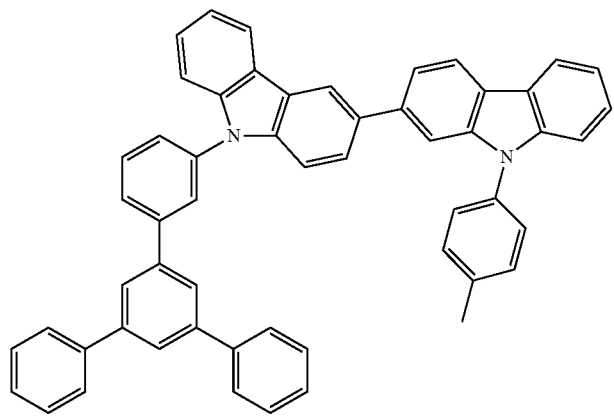

[D-457]
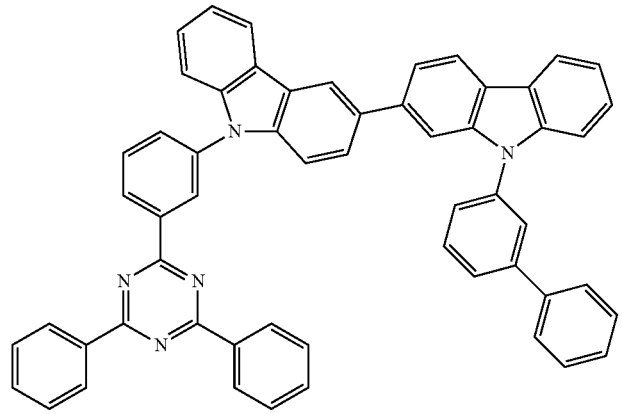
[D-458]
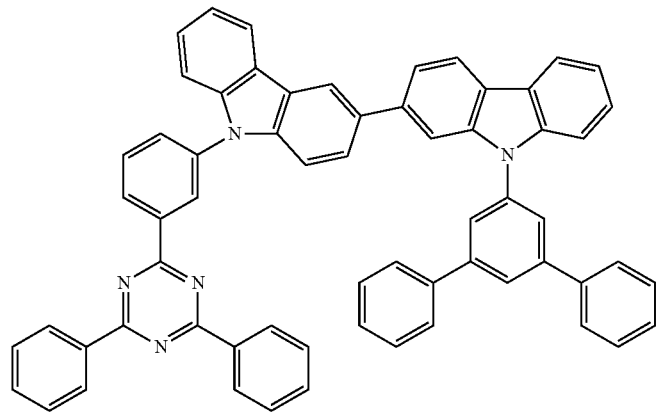
[D-459]
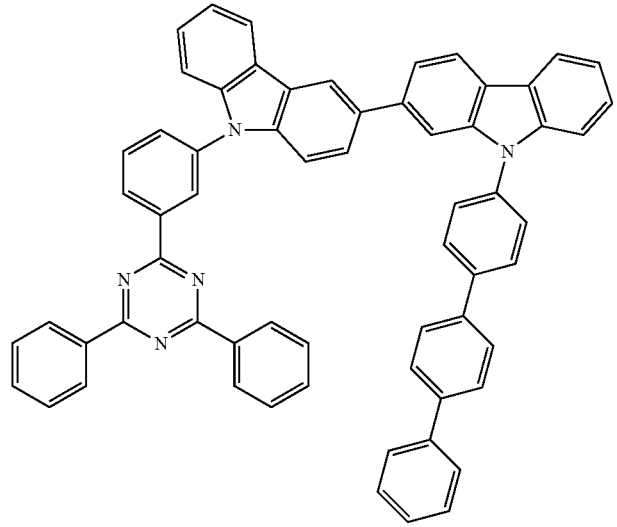

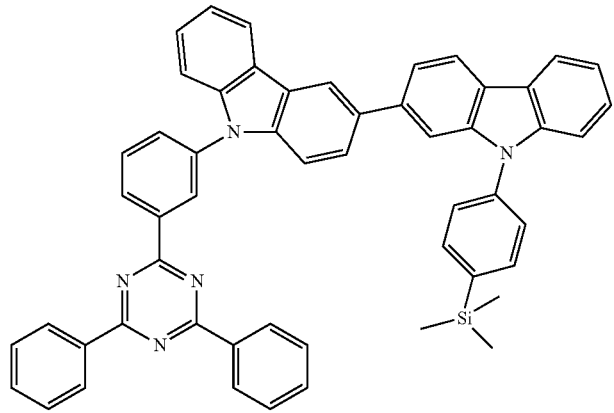
[D-460]
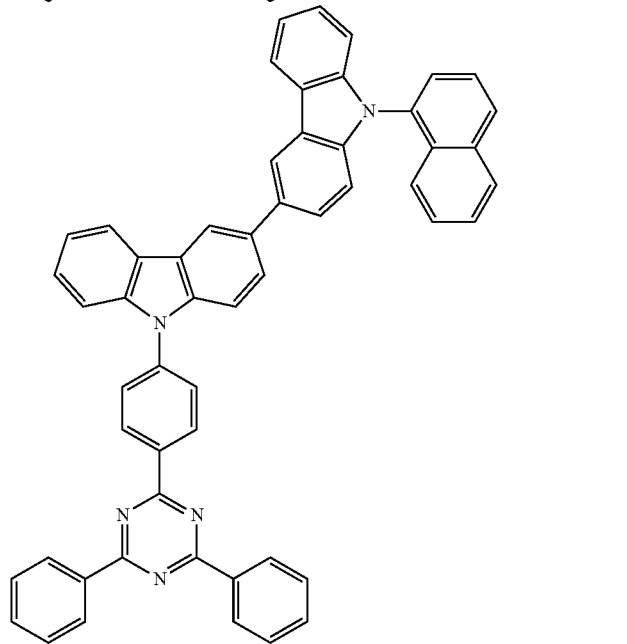
[D-461]
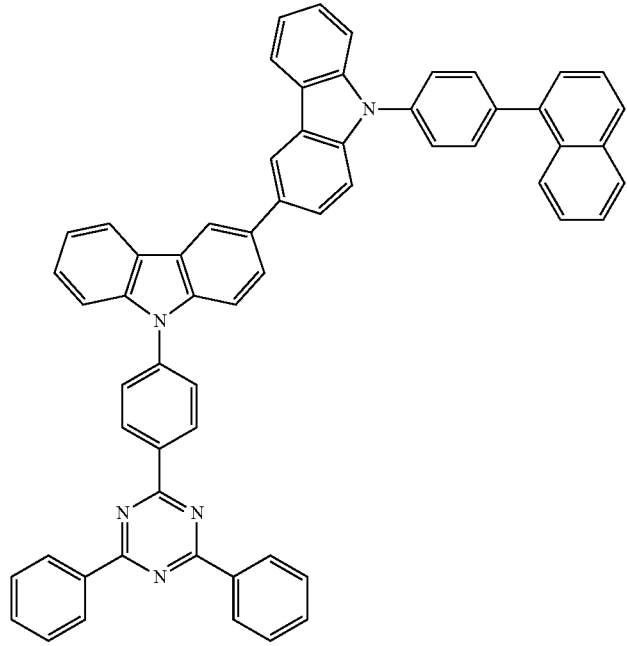
[D-462]

[D-463]
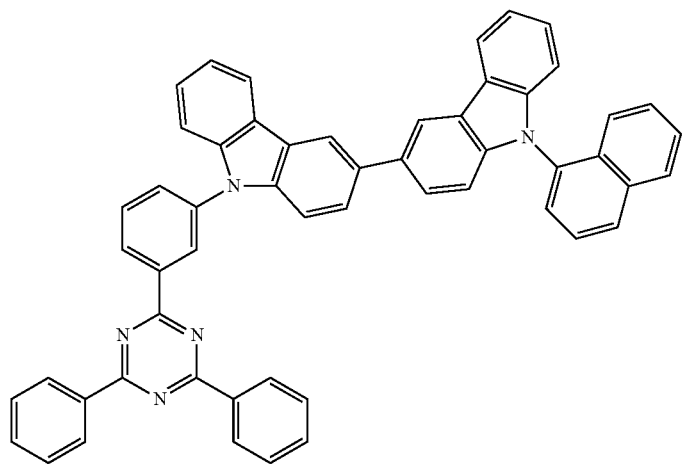
[D-464]
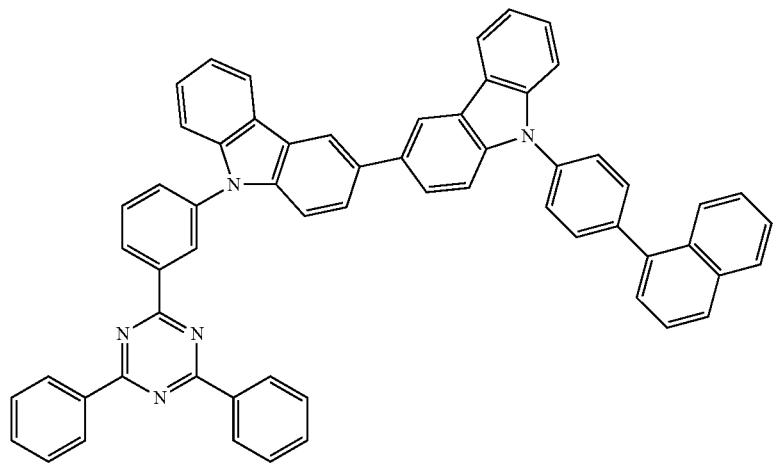
[D-465]
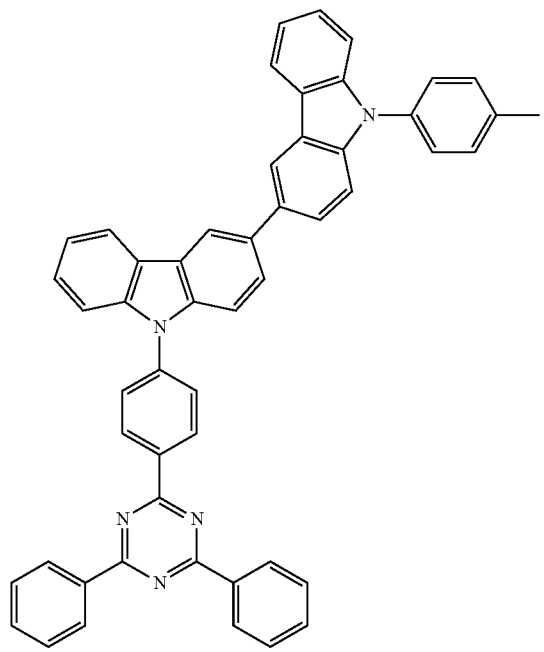

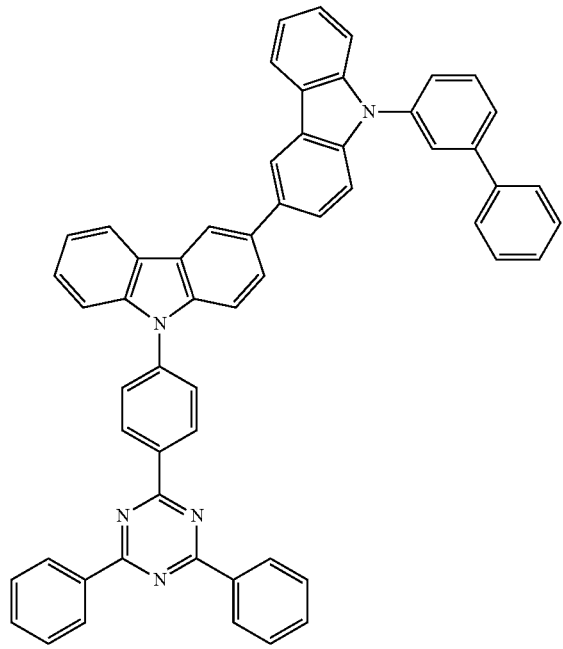
[D-466]
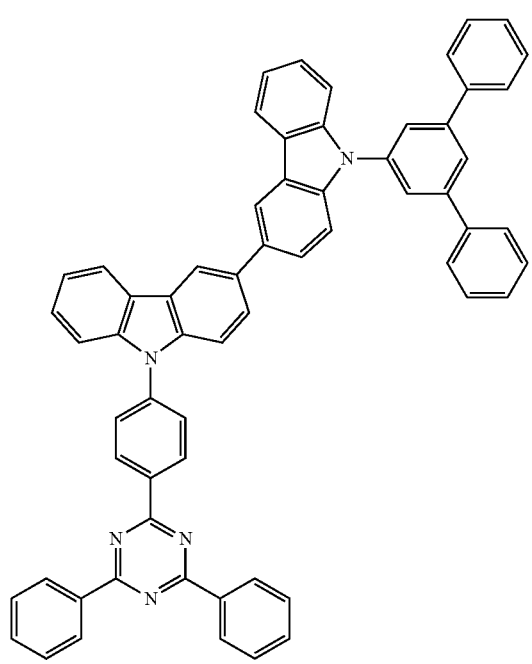
[D-467]

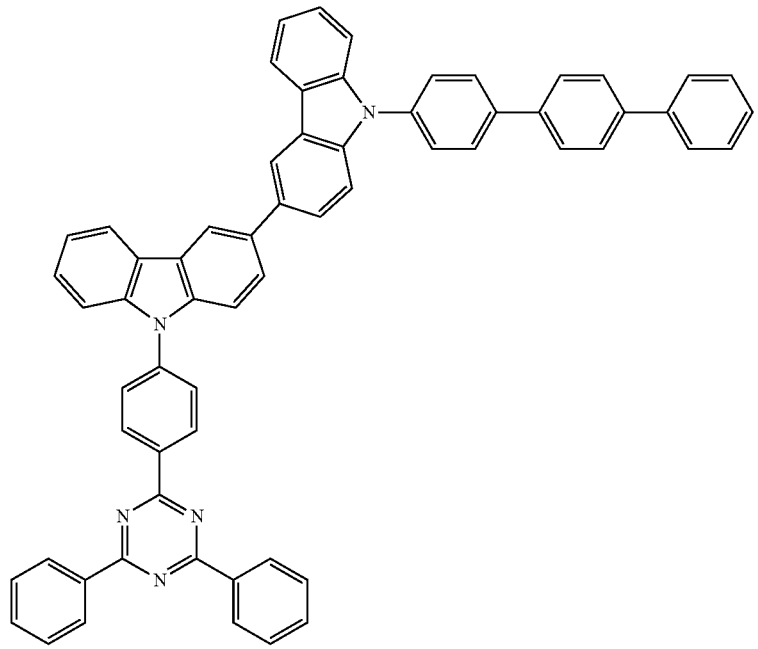
[D-468]
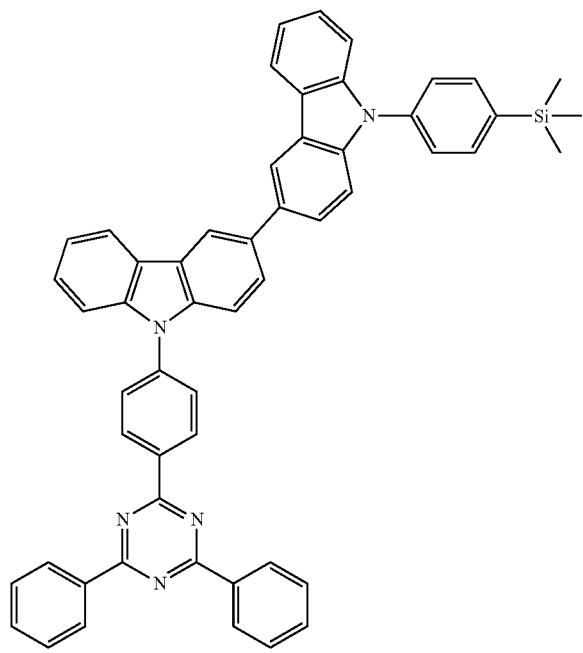
[D-469]

[D-470]
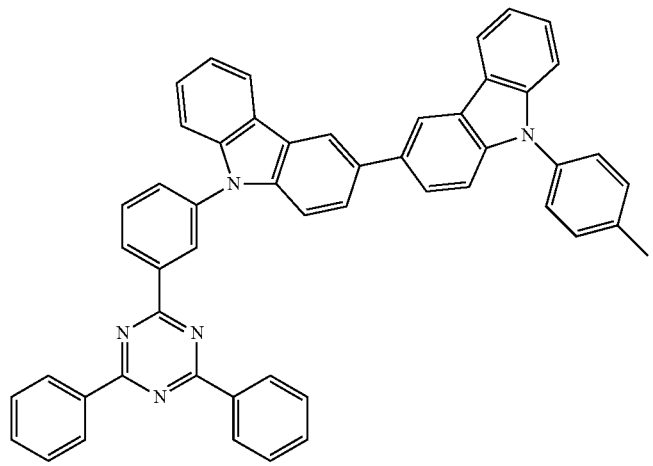
[D-471]
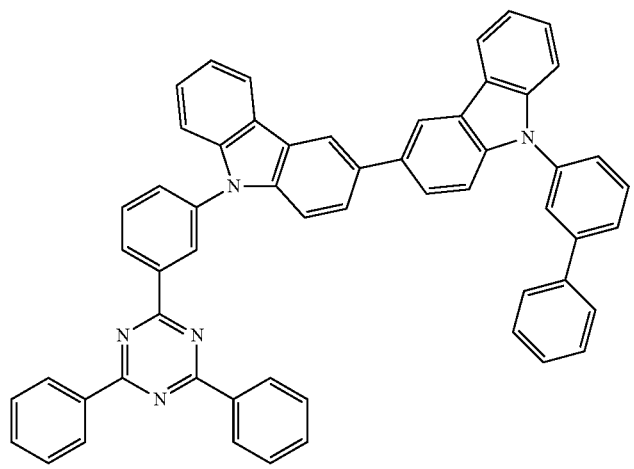
[D-472]
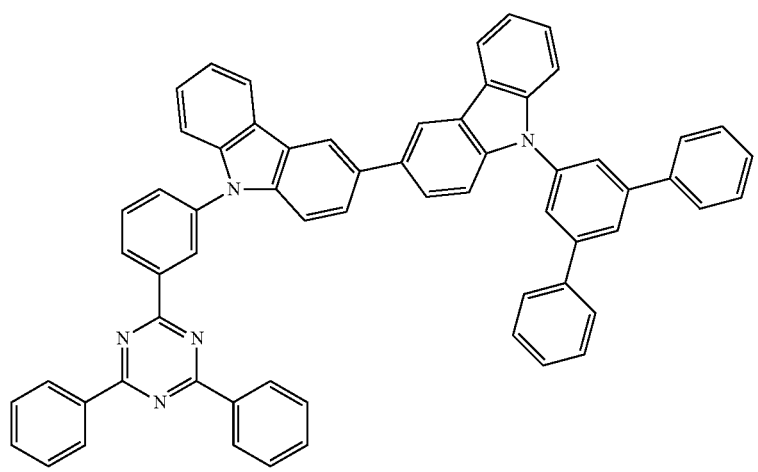

[D-473]
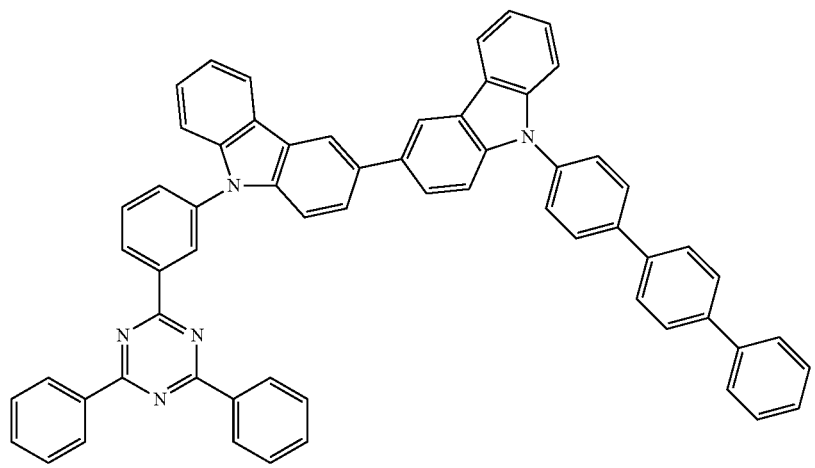
[D-474]
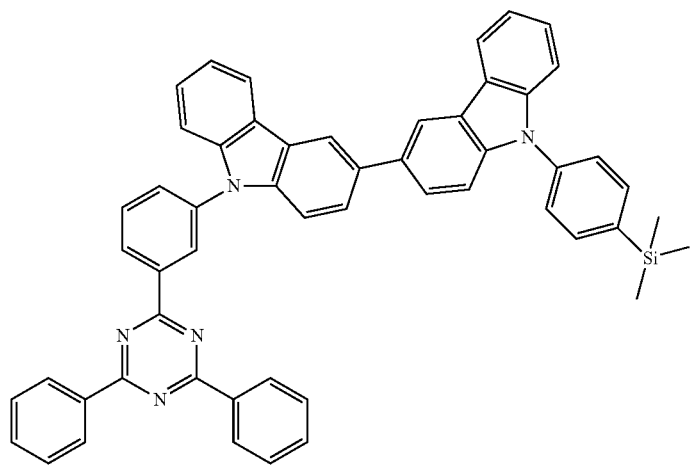
For example, the substituted or unsubstituted C2 to C30 heteroaryl group that has electronic properties may be represented by, e.g., one of the following Chemical Formulae E-1 to E-5.
[Chemical Formula E-1]
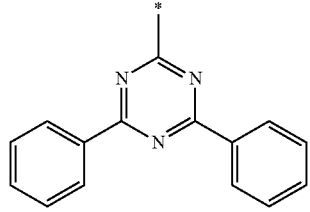
[Chemical Formula E-2]
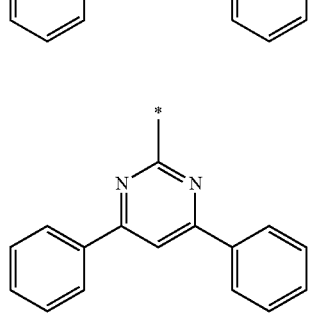
[Chemical Formula E-3]
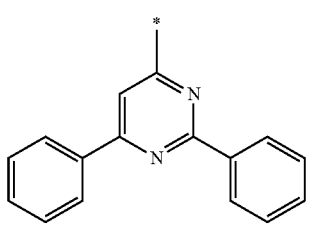
[Chemical Formula E-4]
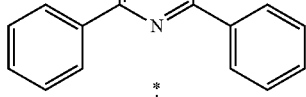
[Chemical Formula E-5]
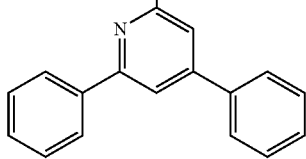

The compound for an organic optoelectronic device may be represented by, e.g., the following Chemical Formulae 3 to 54.
[Chemical Formula 3]
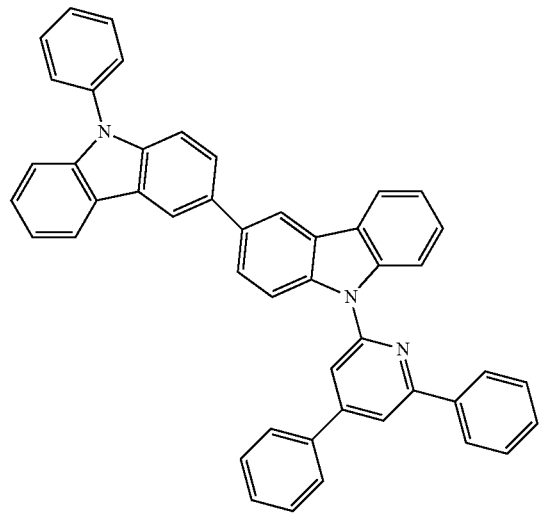
[Chemical Formula 4]
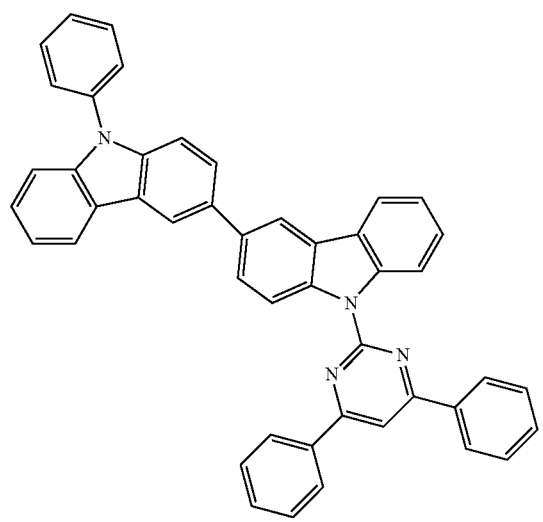
[Chemical Formula 5]
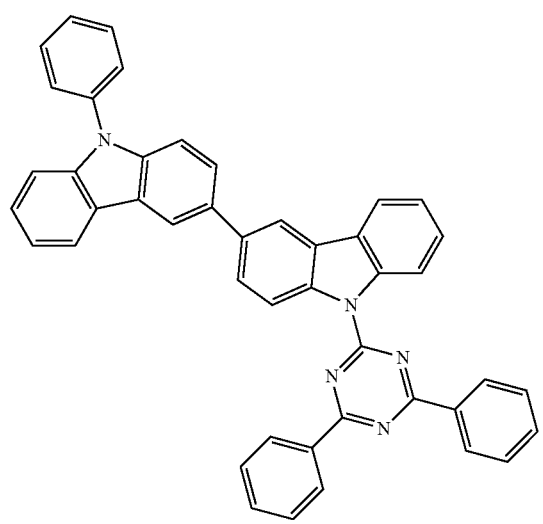
[Chemical Formula 6]
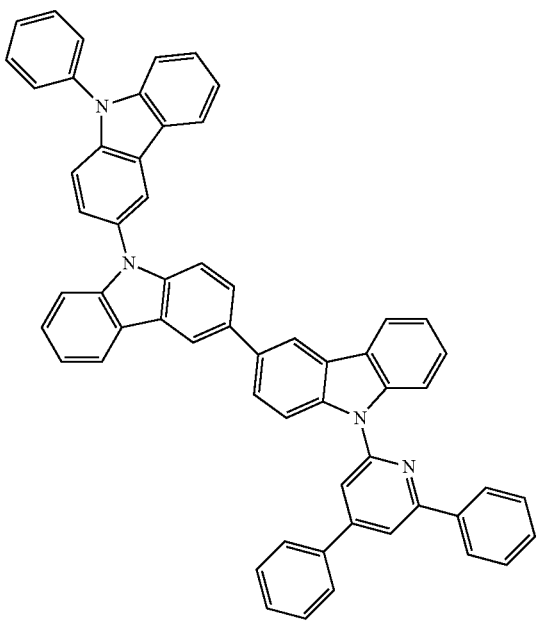
[Chemical Formula 7]
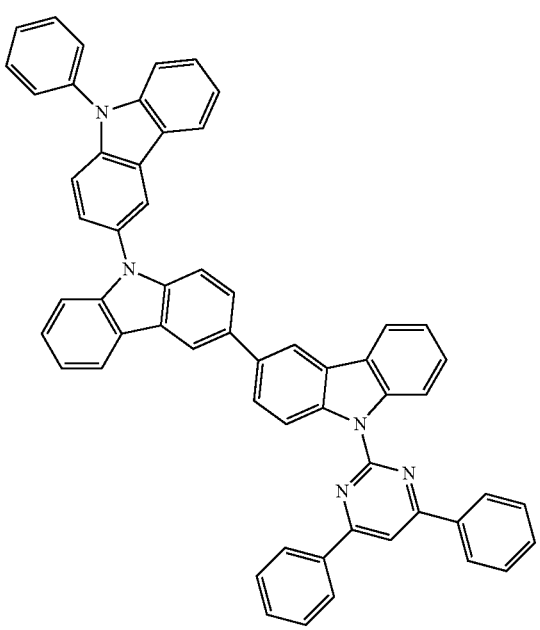

[Chemical Formula 8]
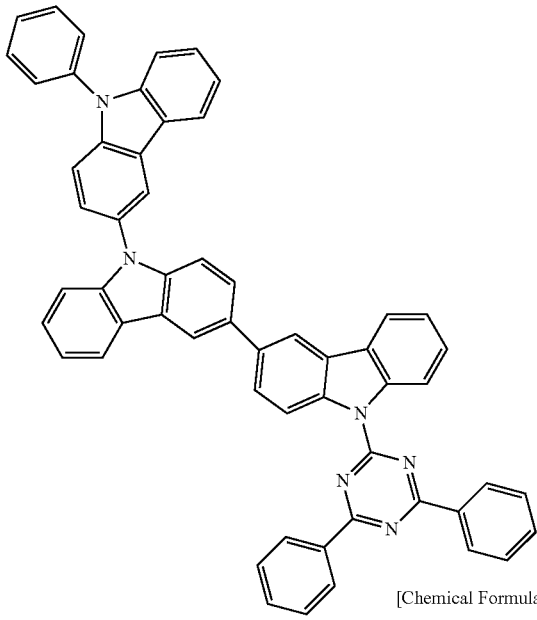
[Chemical Formula 9]
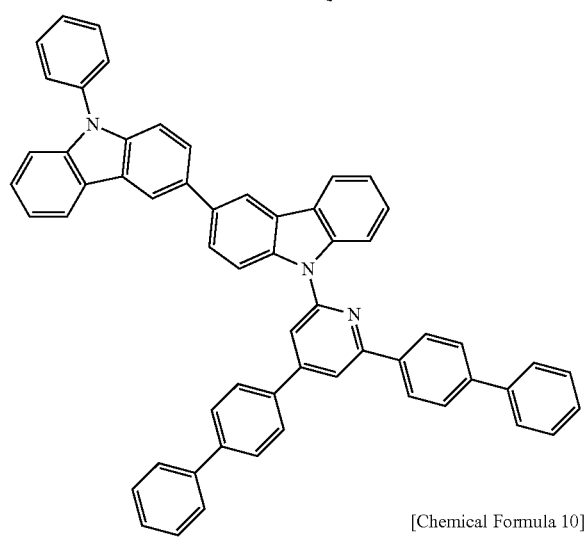
[Chemical Formula 10]
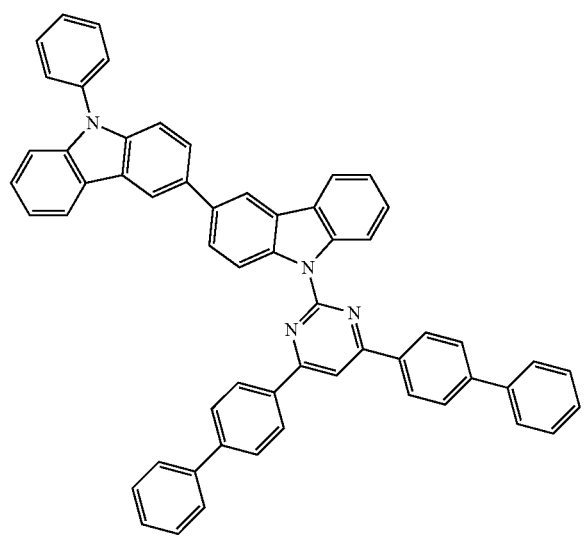
[Chemical Formula 11]
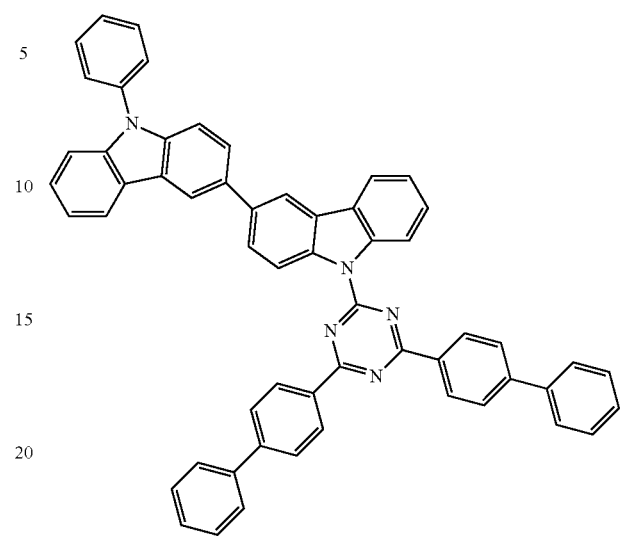
[Chemical Formula 12]
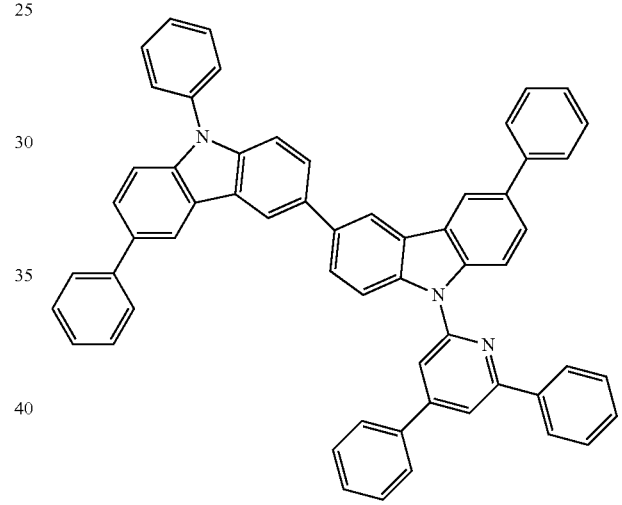
[Chemical Formula 13]
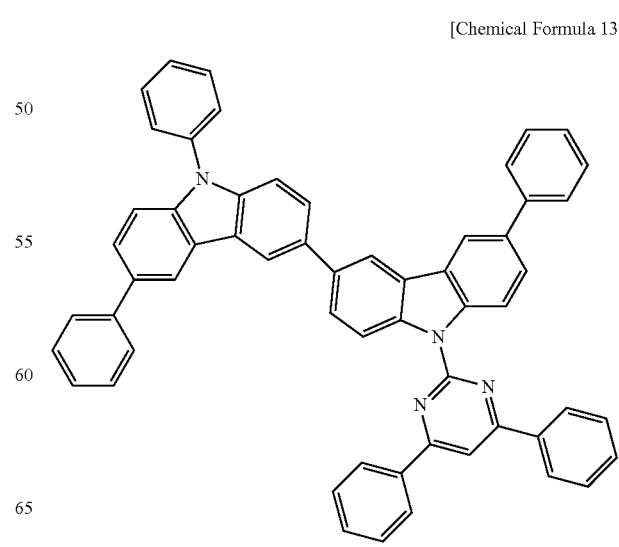

-continued
[Chemical Formula 14]
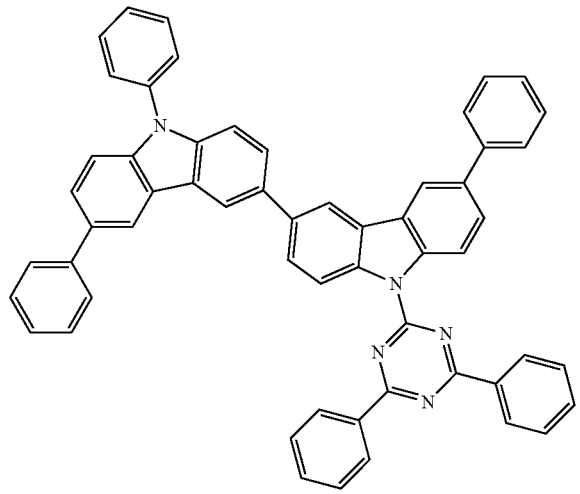
[Chemical Formula 15]
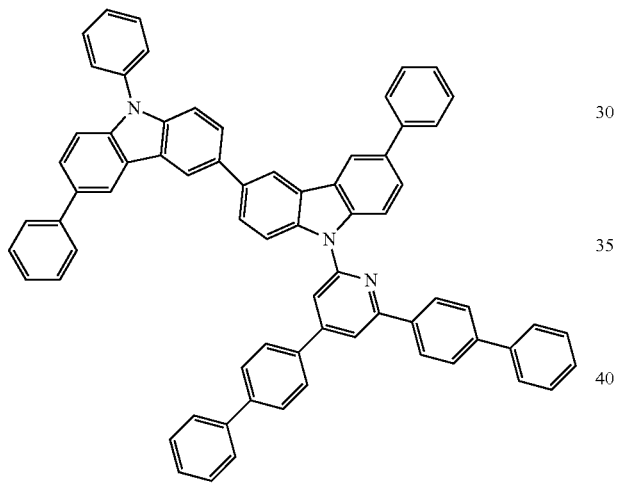
[Chemical Formula 16]
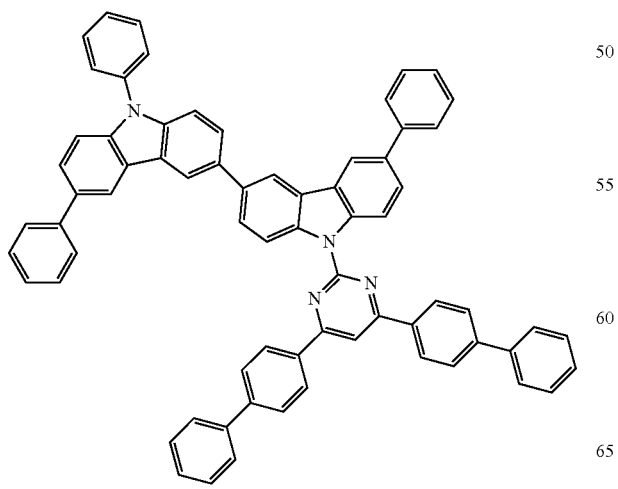
-continued
[Chemical Formula 17]
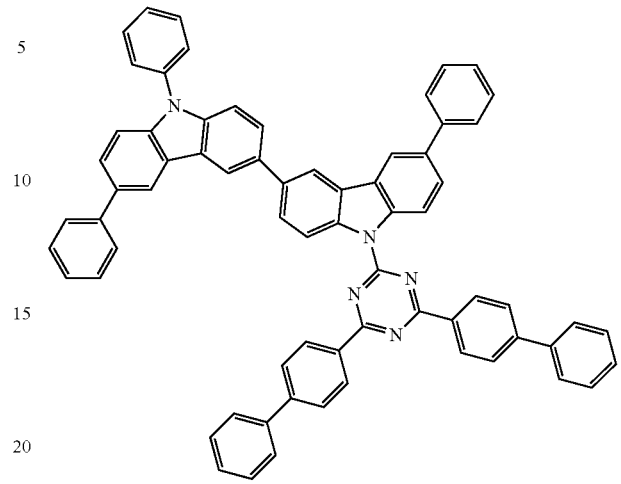
[Chemical Formula 18]
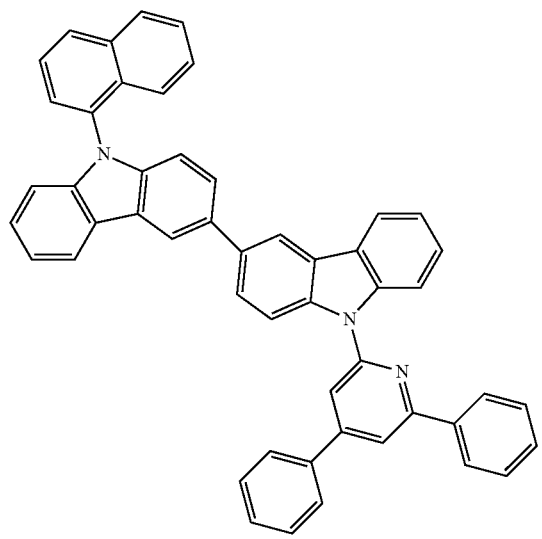
[Chemical Formula 19]
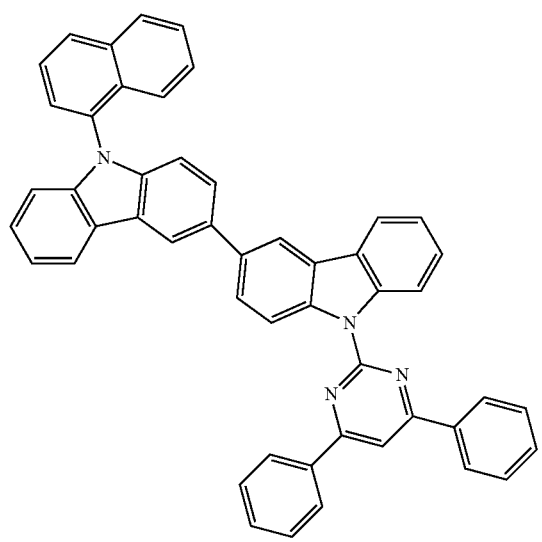

[Chemical Formula 20]
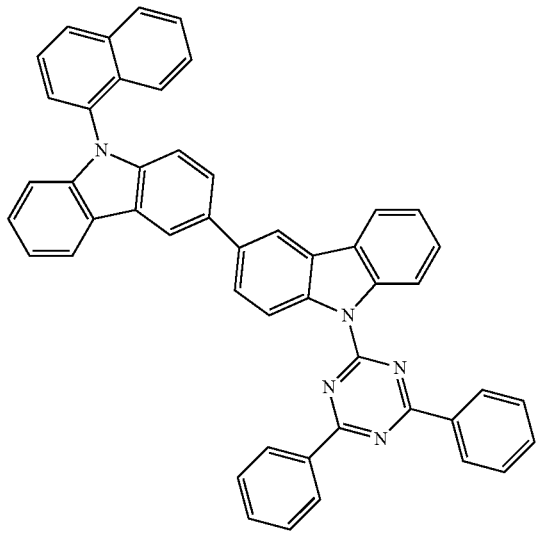
[Chemical Formula 21]
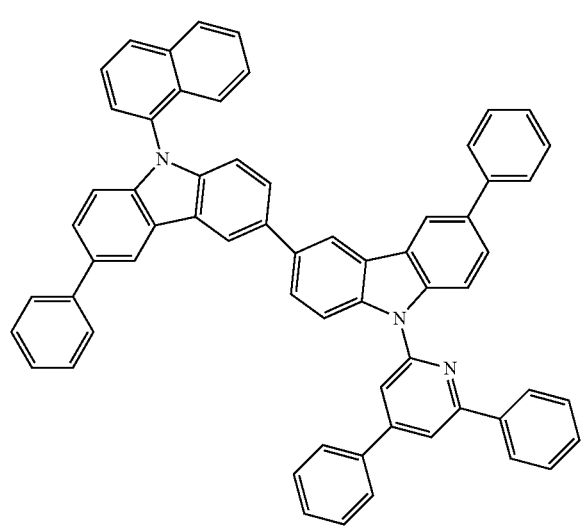
[Chemical Formula 22]
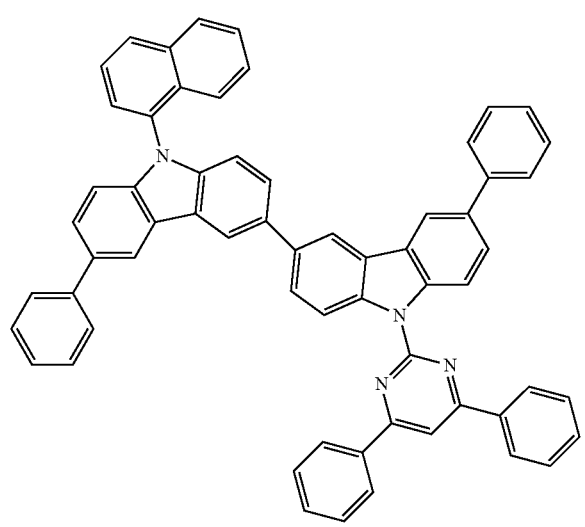
[Chemical Formula 23]
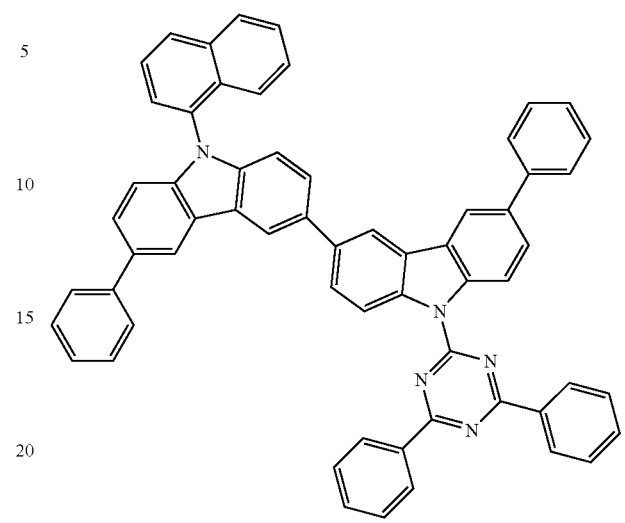
[Chemical Formula 24]
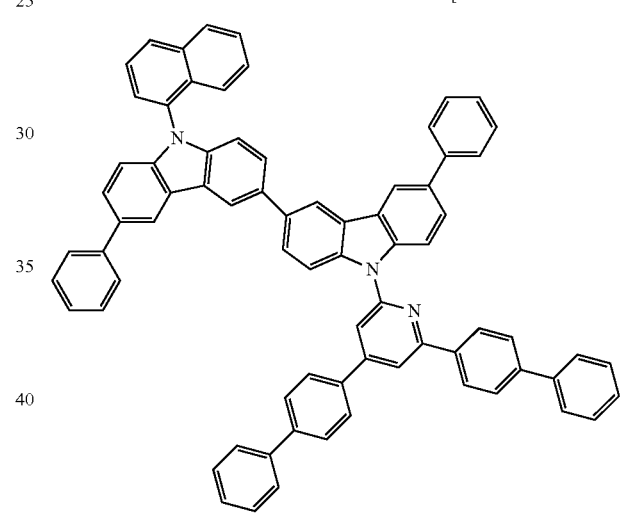
[Chemical Formula 25]
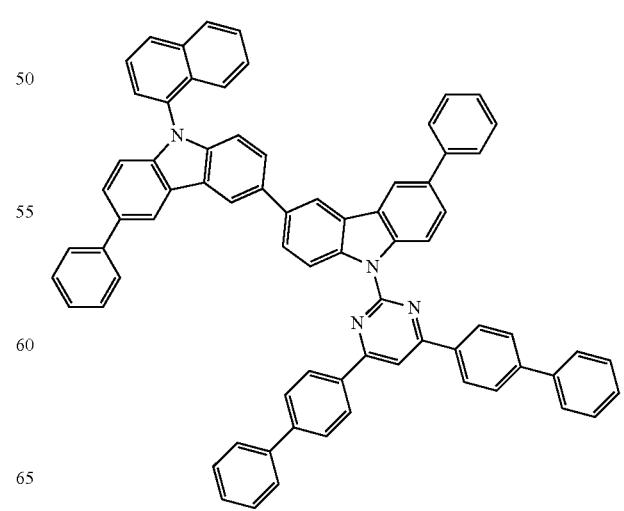

351
-continued
[Chemical Formula 26]
[Chemical Formula 27]
352
-continued
[Chemical Formula 28]
[Chemical Formula 29]
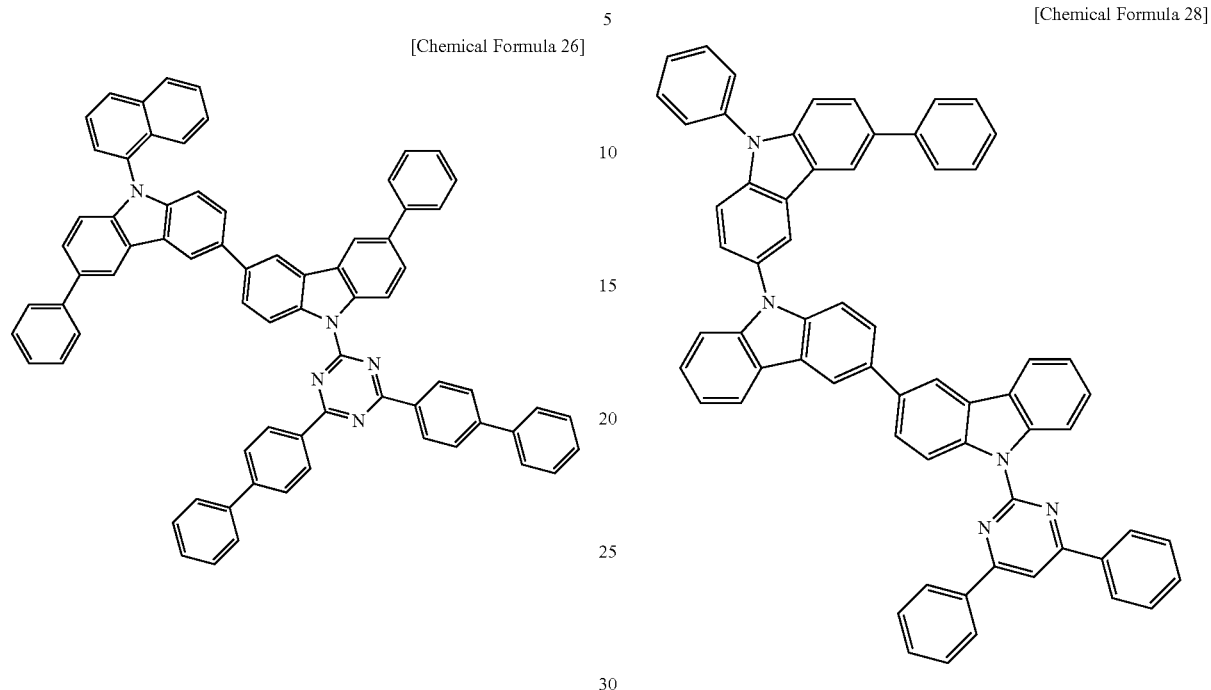
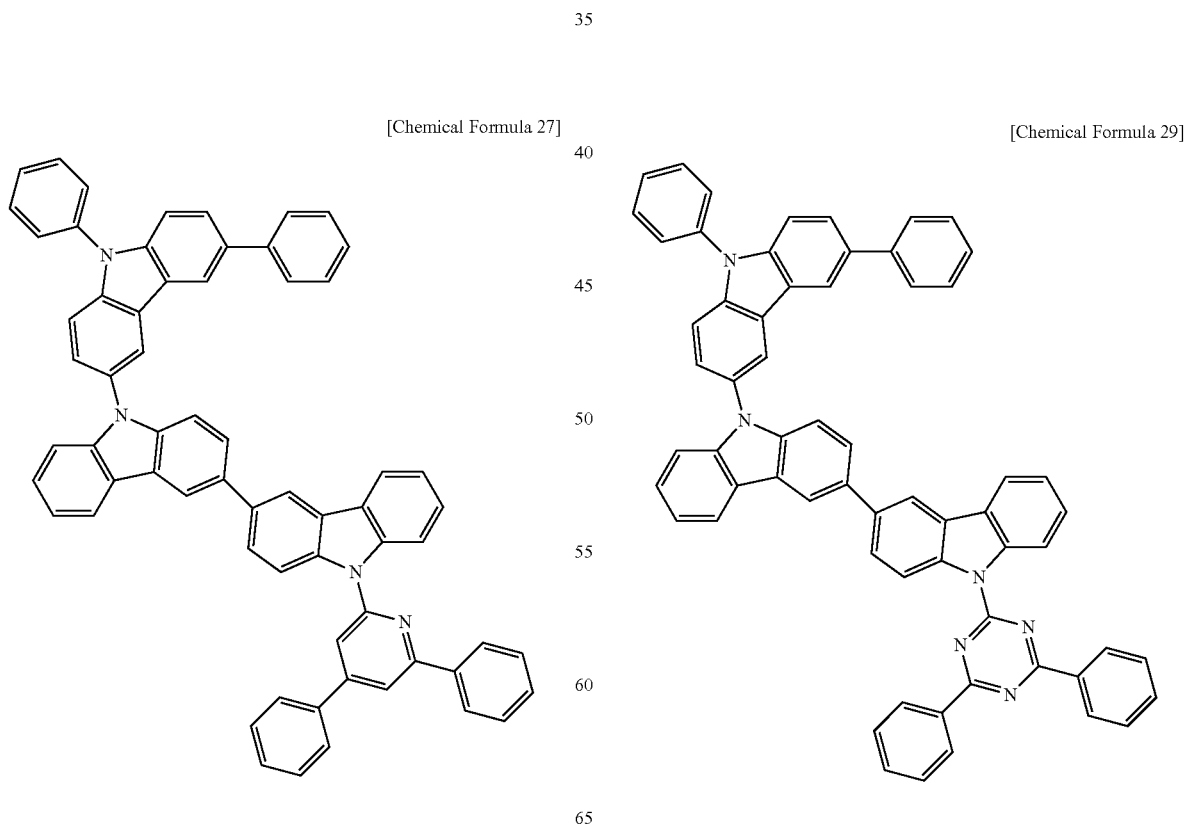

353
-continued
[Chemical Formula 30]
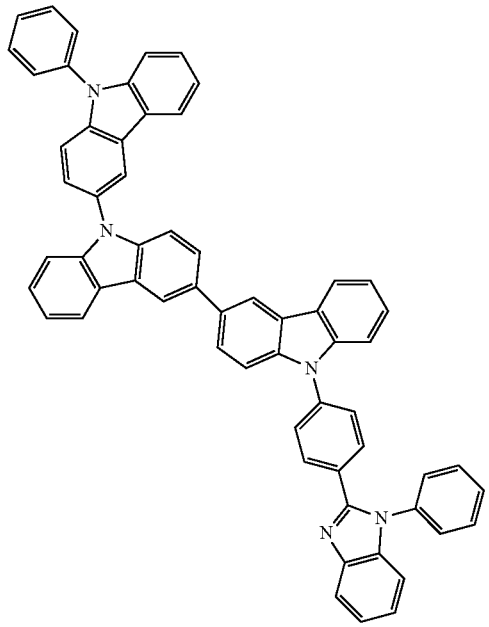
[Chemical Formula 31]
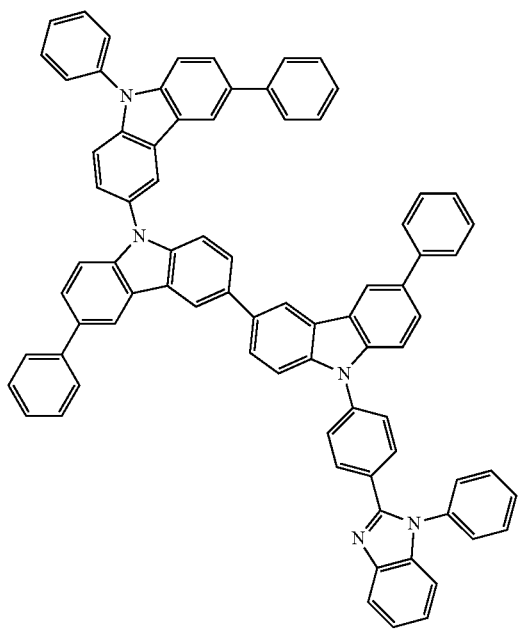
354
-continued
[Chemical Formula 32]
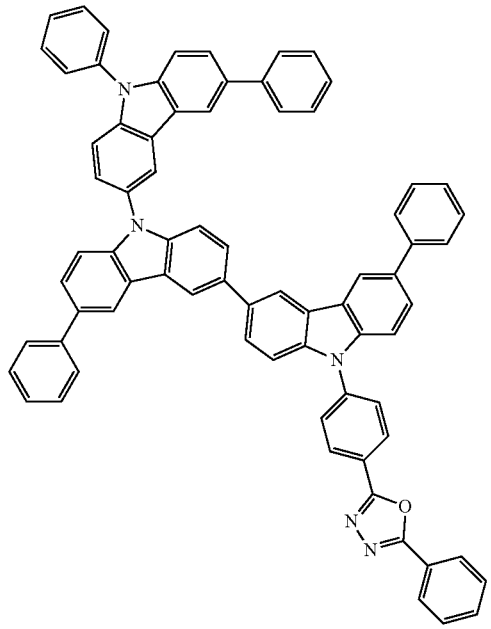
[Chemical Formula 33]
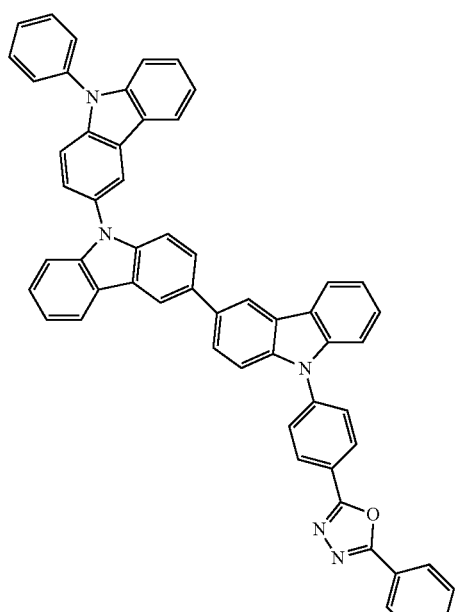

-continued
[Chemical Formula 34]
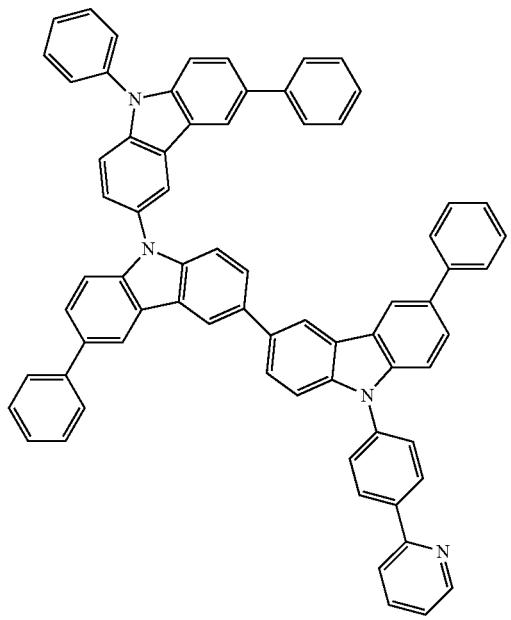
[Chemical Formula 35]
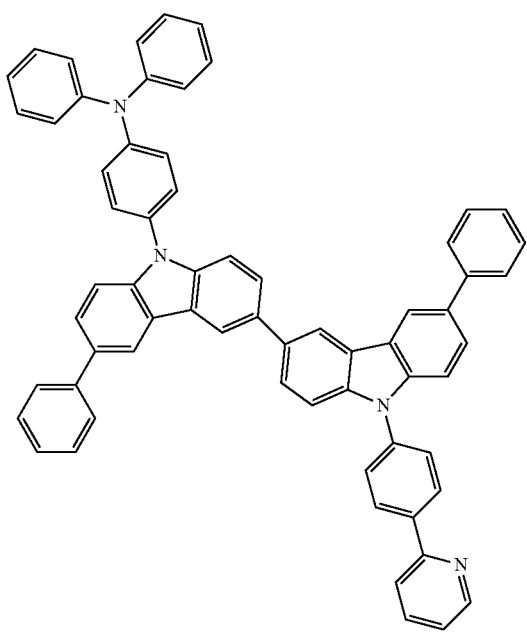
-continued
[Chemical Formula 36]
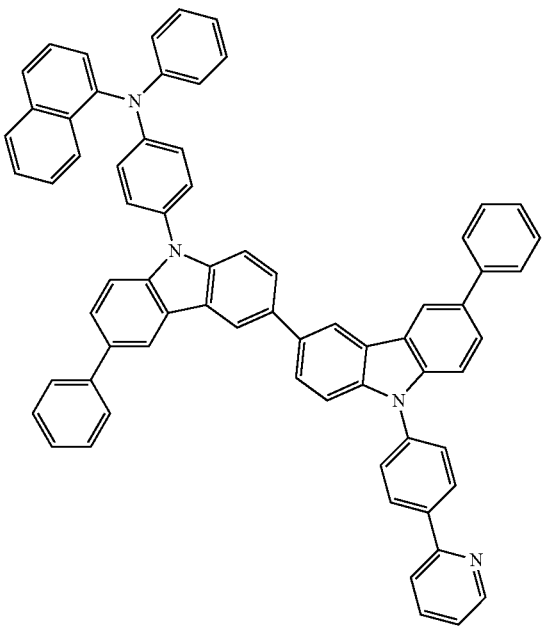
[Chemical Formula 37]
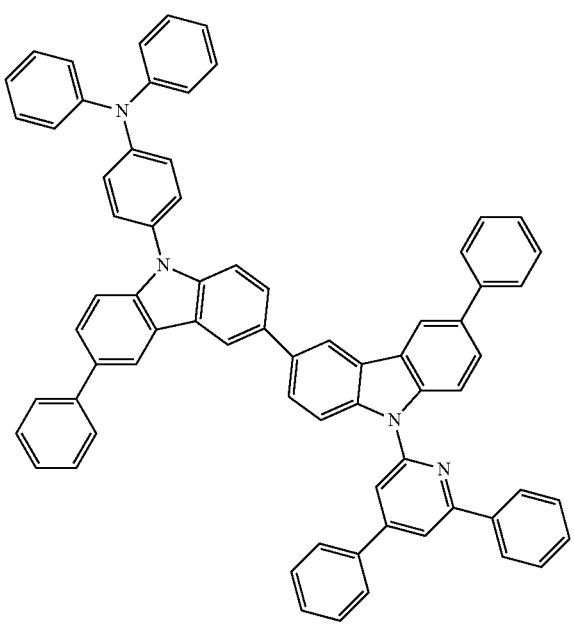

[Chemical Formula 38]
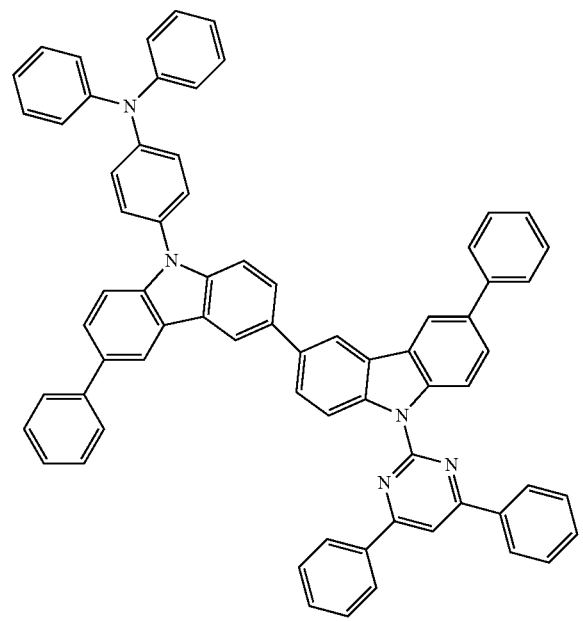
[Chemical Formula 39]
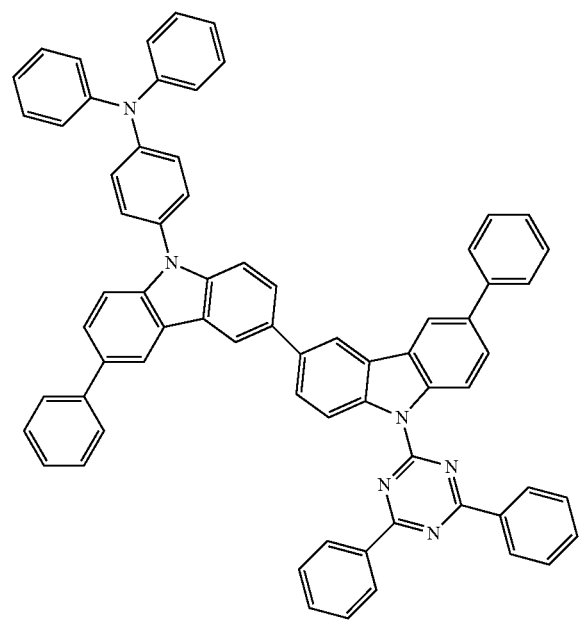
[Chemical Formula 40]
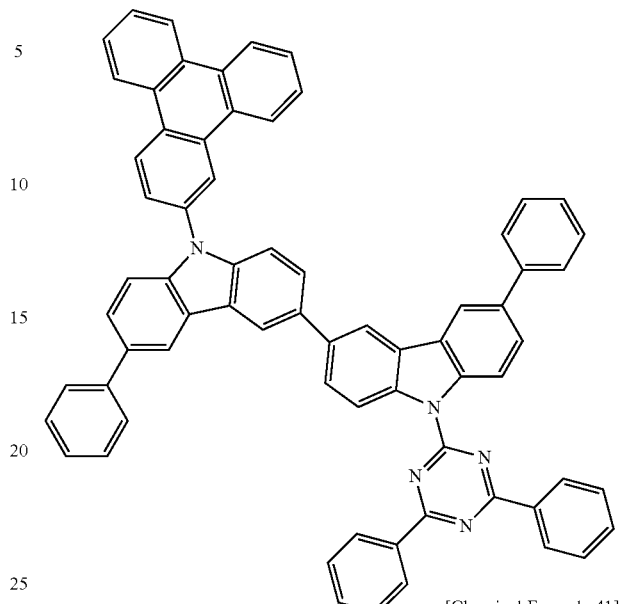
[Chemical Formula 41]
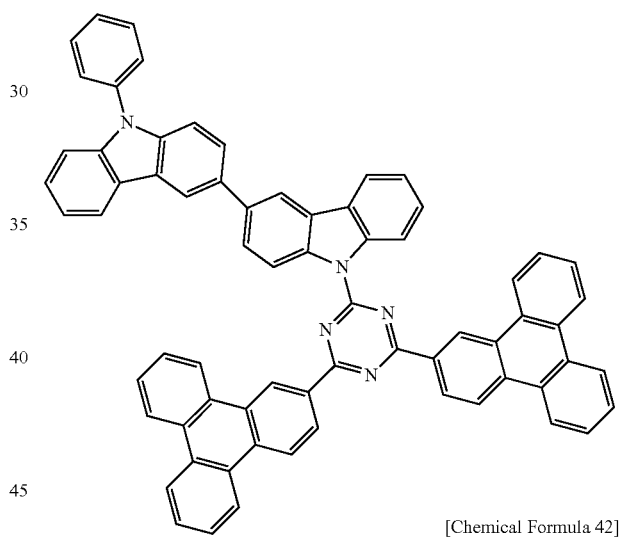
[Chemical Formula 42]
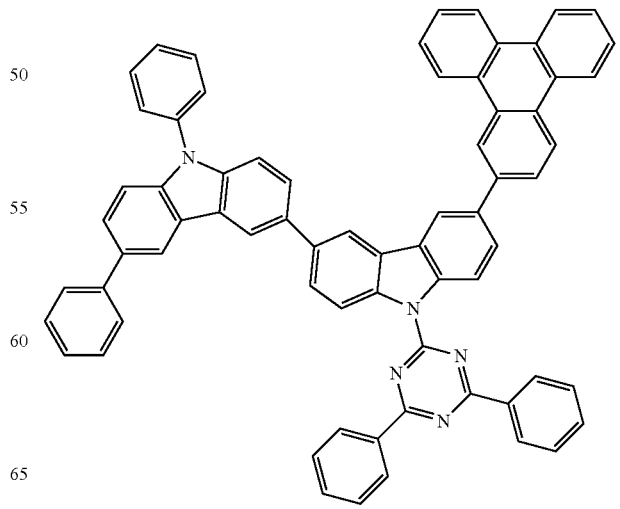

[Chemical Formula 43]
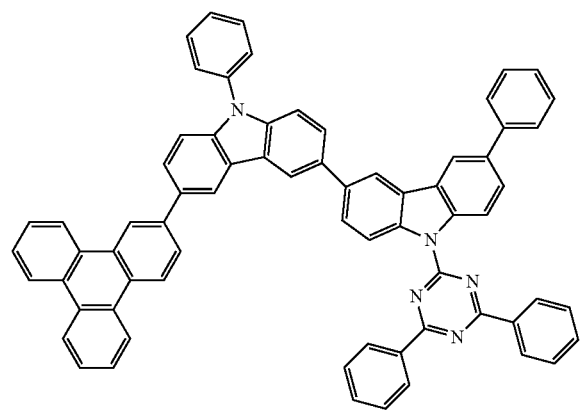
[Chemical Formula 44]
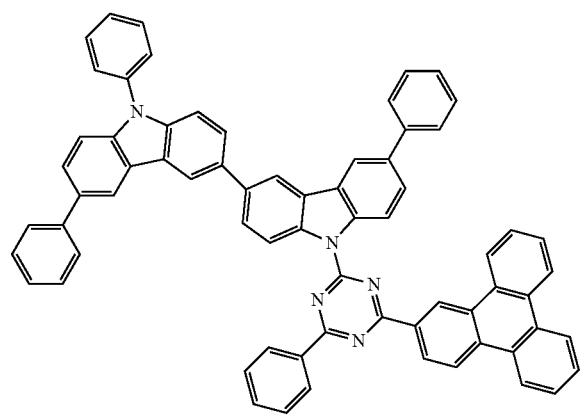
[Chemical Formula 45]
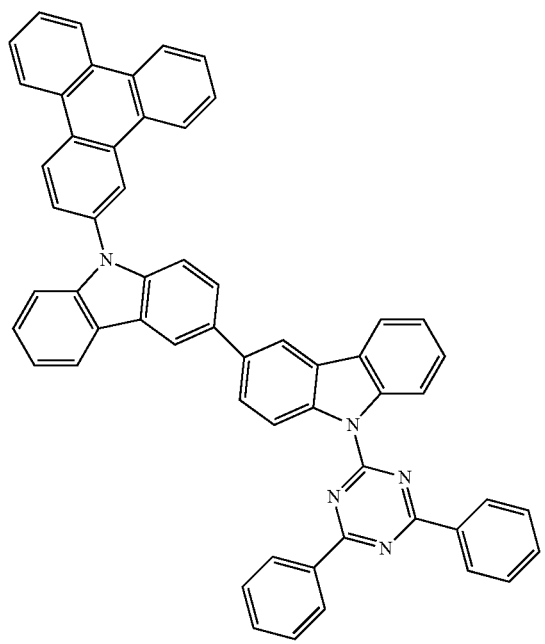
[Chemical Formula 46]
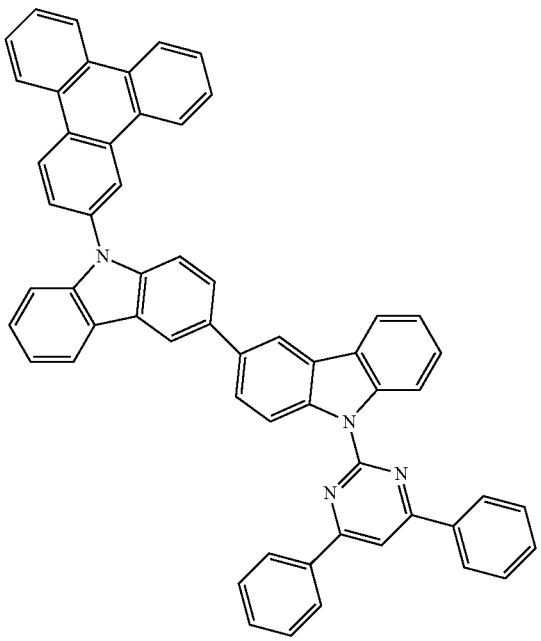
[Chemical Formula 47]
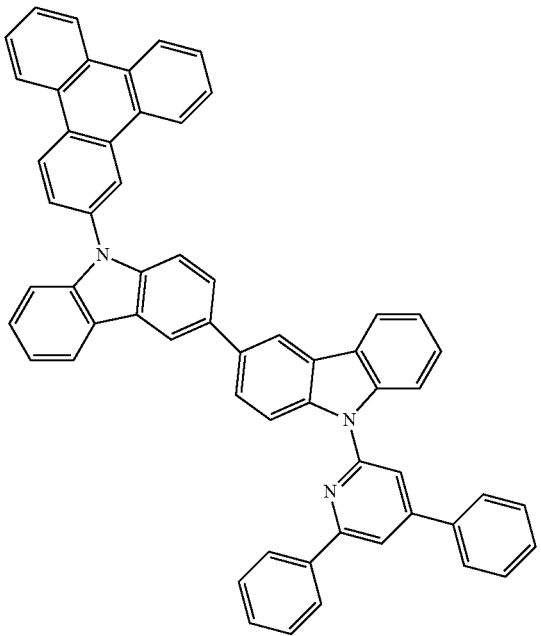

[Chemical Formula 48]
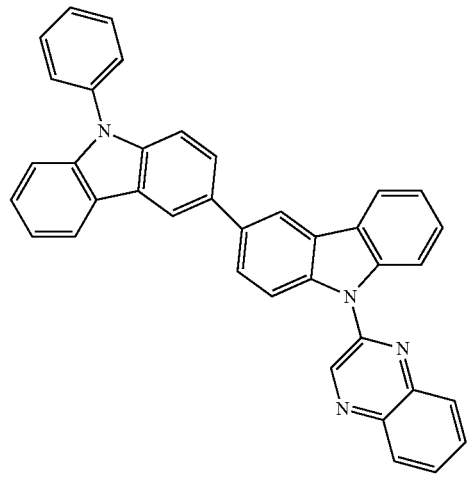
[Chemical Formula 49]
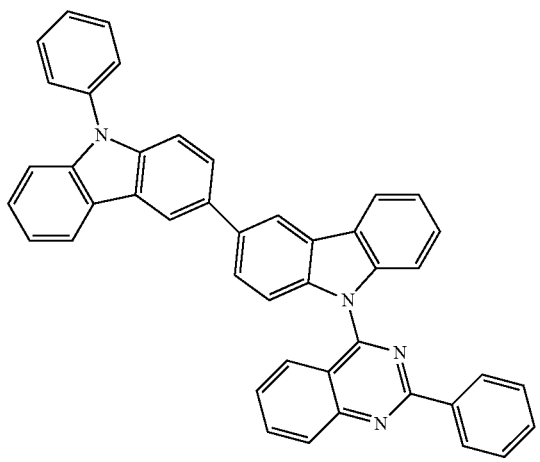
[Chemical Formula 50]
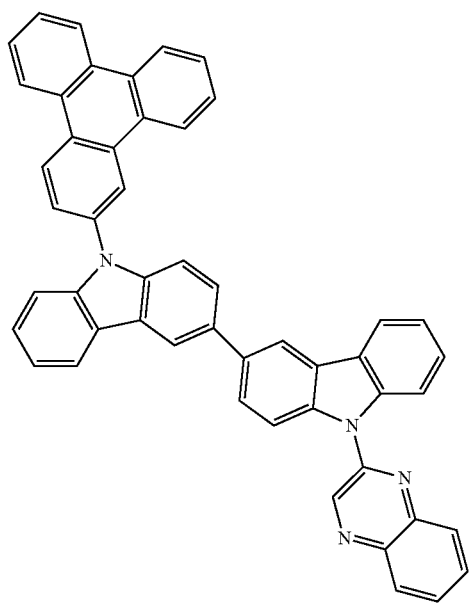
[Chemical Formula 51]
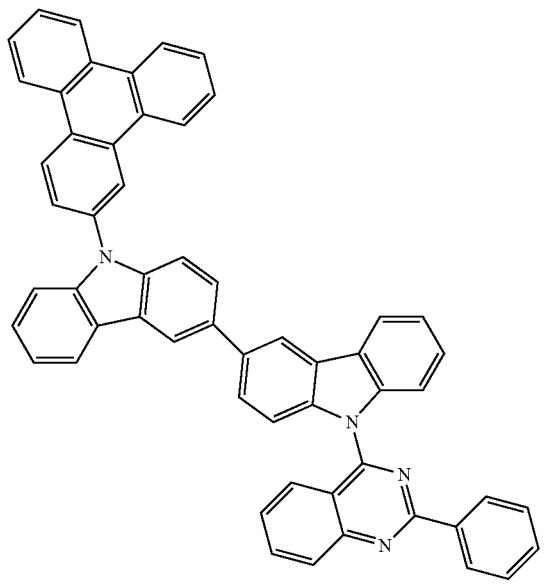
[Chemical Formula 52]
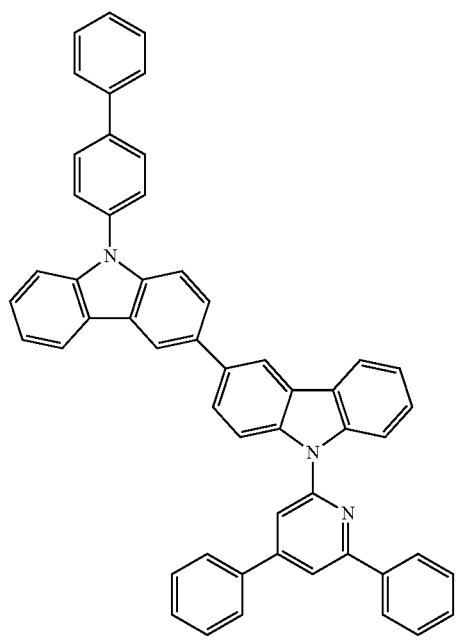

[Chemical Formula 53]
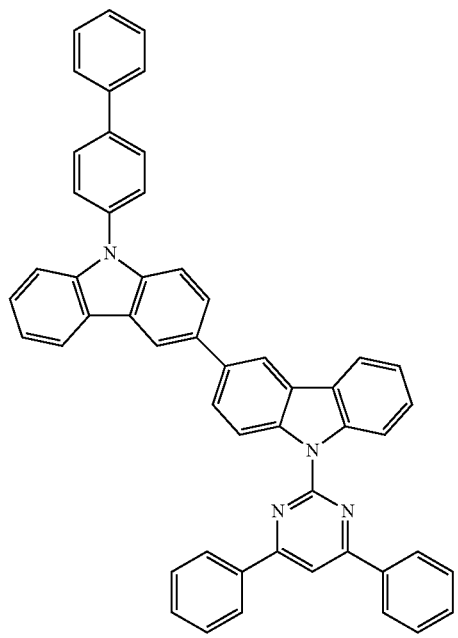
[Chemical Formula 54]
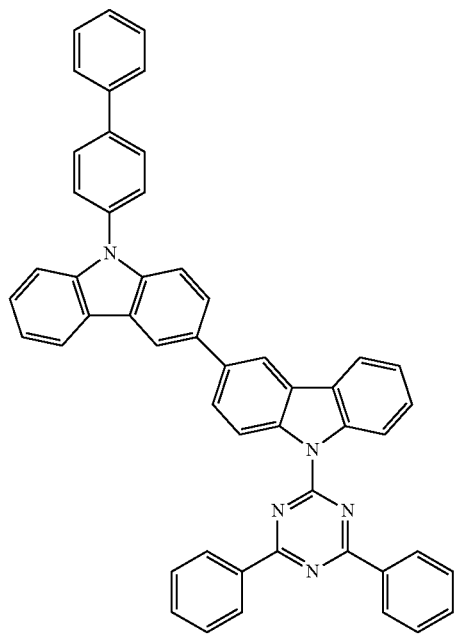
[Chemical Formula A-2]
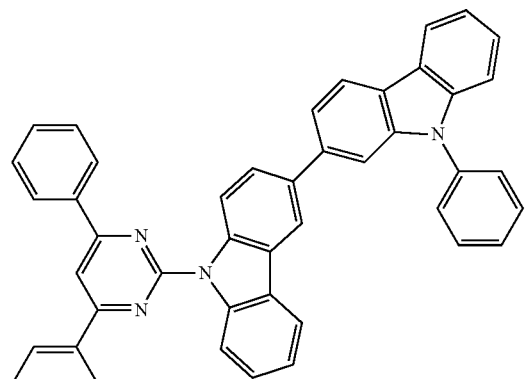
[Chemical Formula A-3]
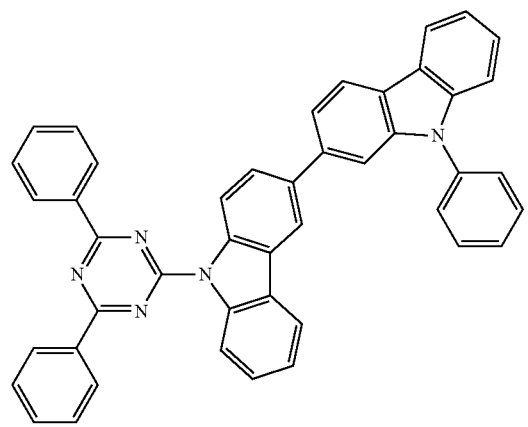
[Chemical Formula A-4]
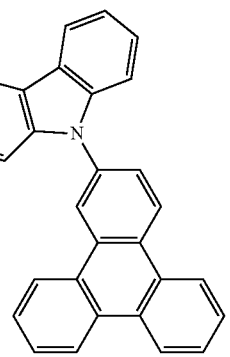
The compound for an organic optoelectronic device may be represented by, e.g., one of the following Chemical Formulae A-2 to A-26:

[Chemical Formula A-5]
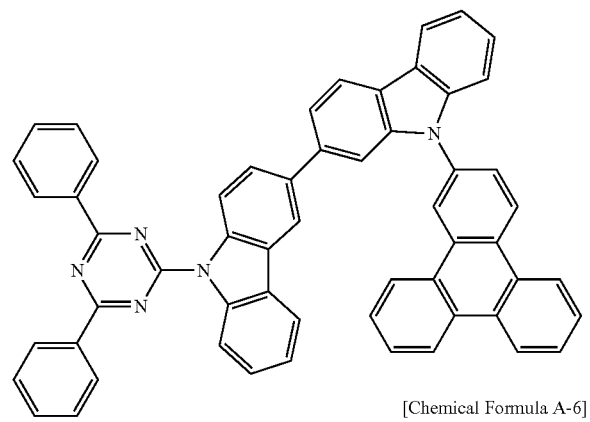
[Chemical Formula A-6]
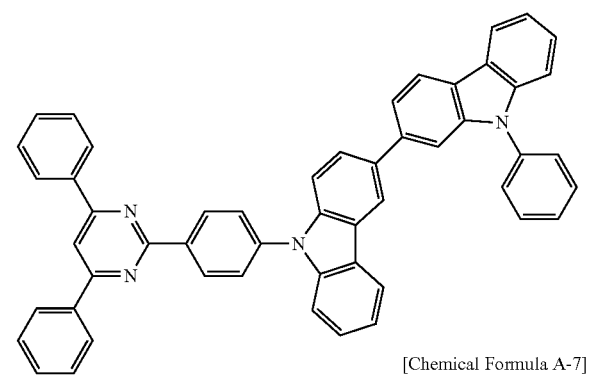
[Chemical Formula A-7]
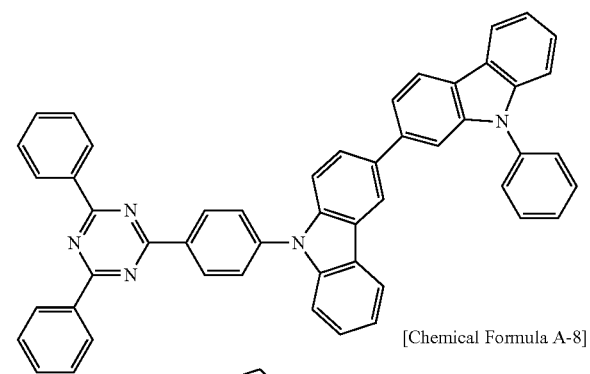
[Chemical Formula A-8]
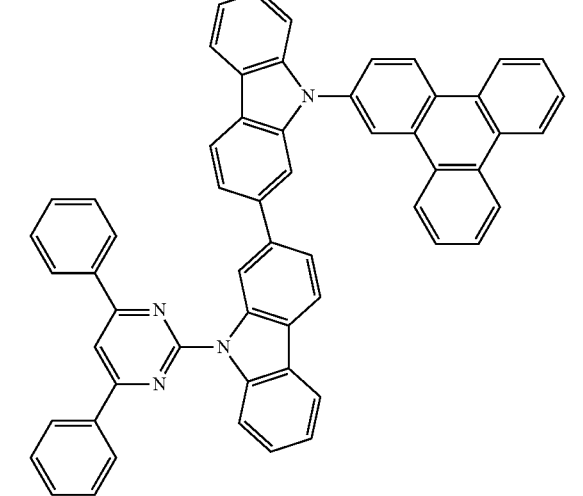
[Chemical Formula A-9]
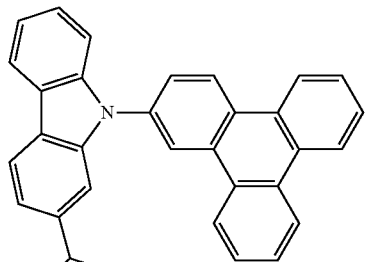
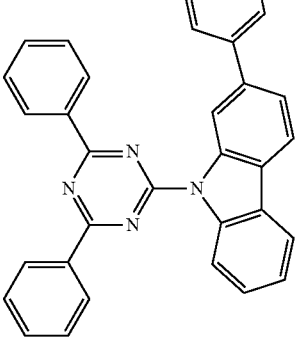
[Chemical Formula A-10]
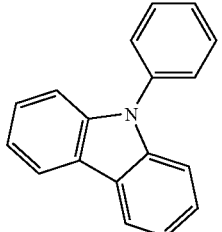
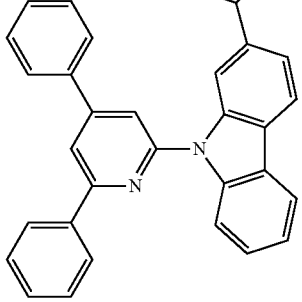
[Chemical Formula A-11]
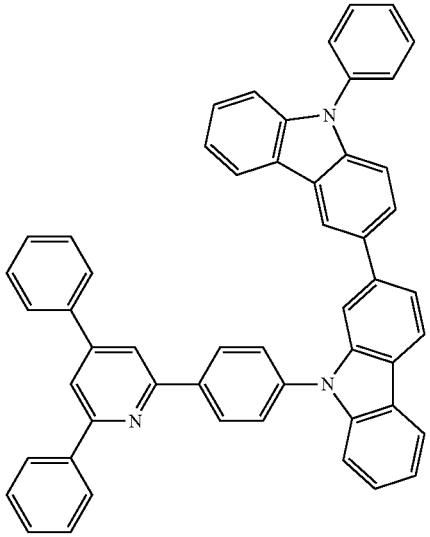

[Chemical Formula A-12]
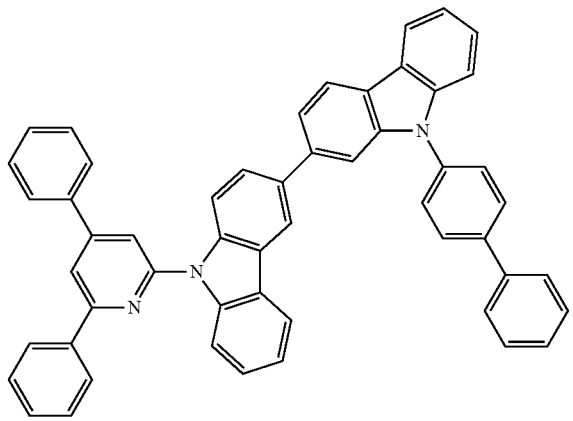
[Chemical Formula A-13]
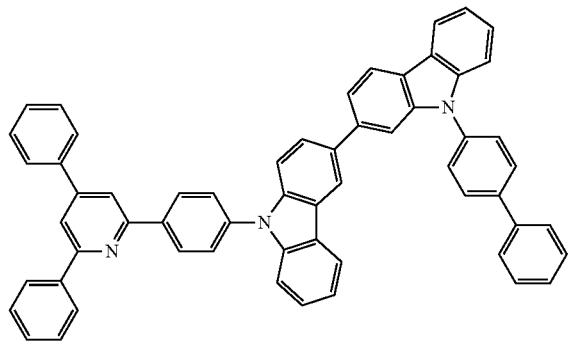
[Chemical Formula A-14]
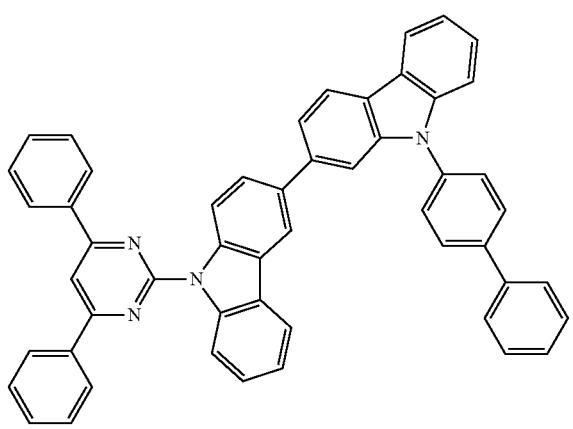
[Chemical Formula A-15]
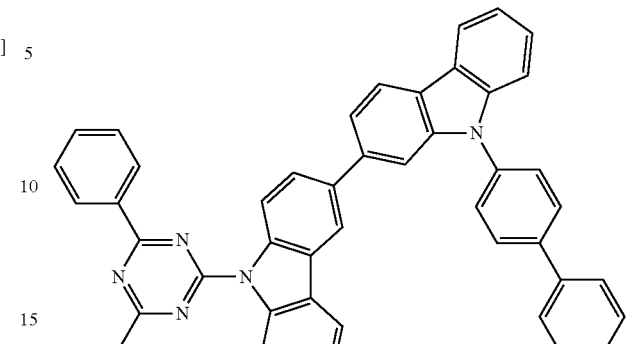
[Chemical Formula A-16]
[Chemical Formula A-17]
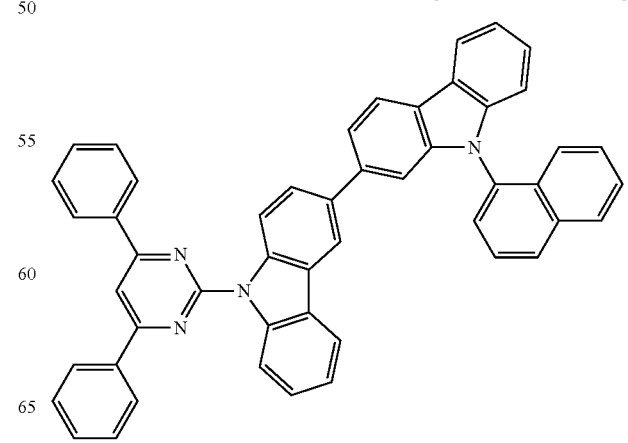

[Chemical Formula A-18]
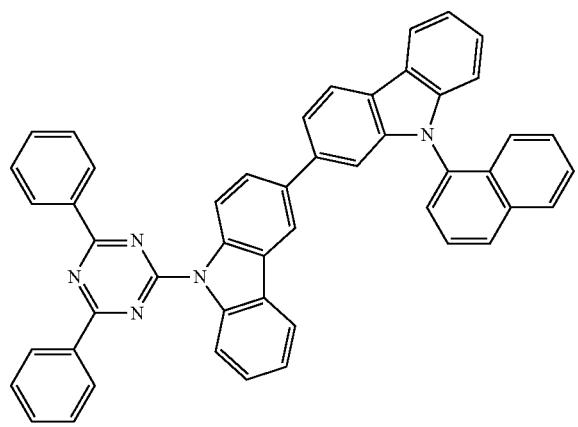
[Chemical Formula A-19]
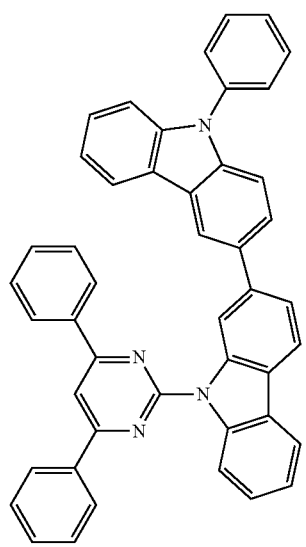
[Chemical Formula A-20]
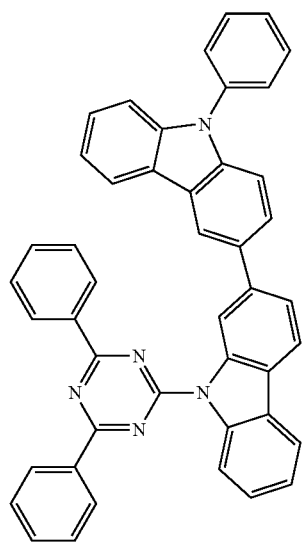
[Chemical Formula A-21]
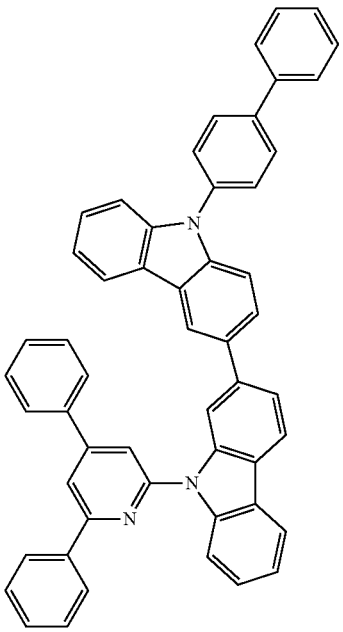
[Chemical Formula A-22]
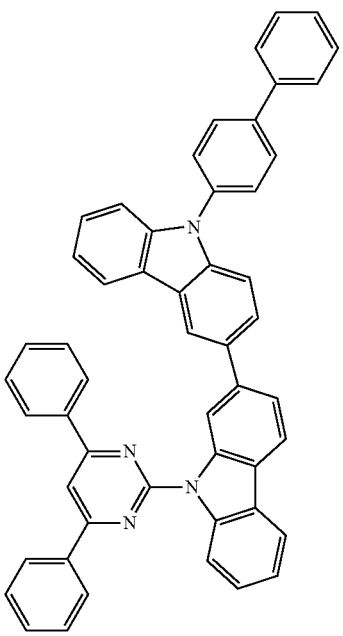

[Chemical Formula A-23]
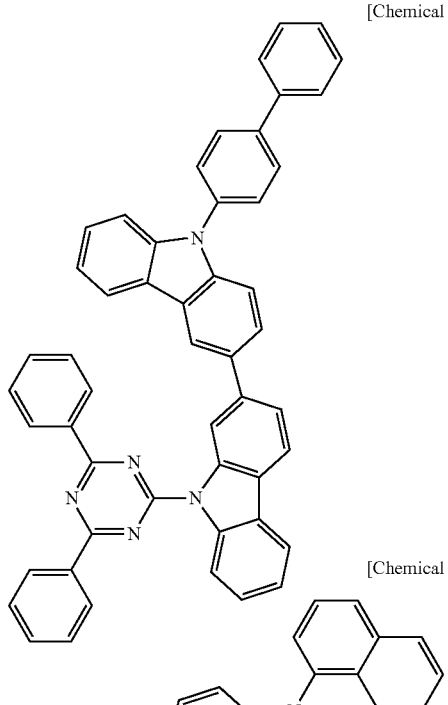
[Chemical Formula A-24]
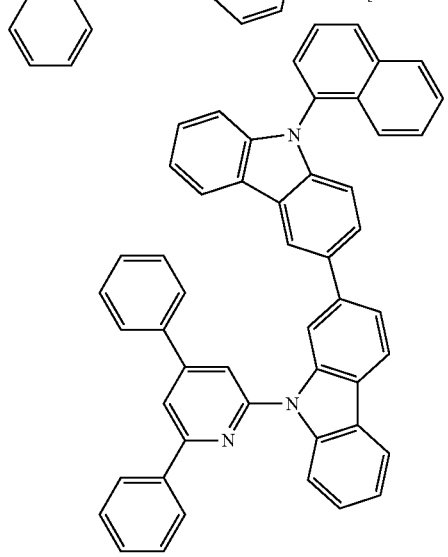
[Chemical Formula A-25]
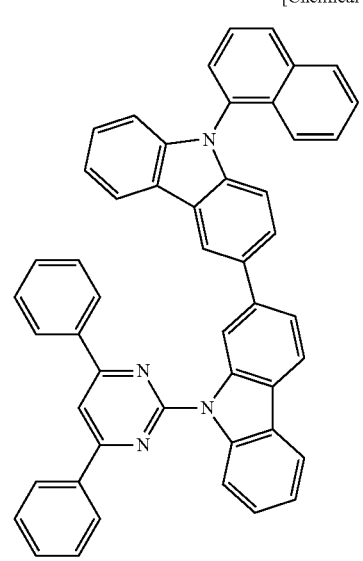
[Chemical Formula A-26]
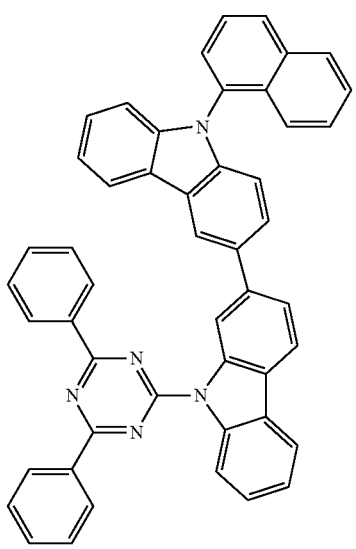
The compound for an organic optoelectronic device may be represented by, e.g., one of the following Chemical Formulae B-3 to B-22:
[Chemical Formula B-3]
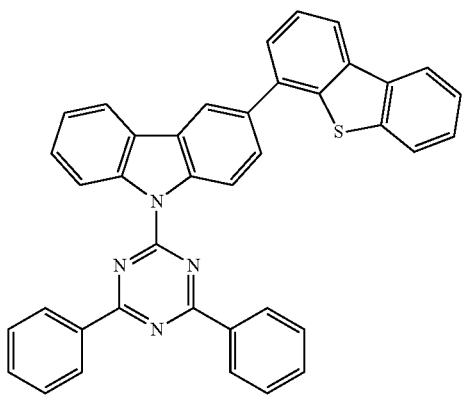
[Chemical Formula B-4]
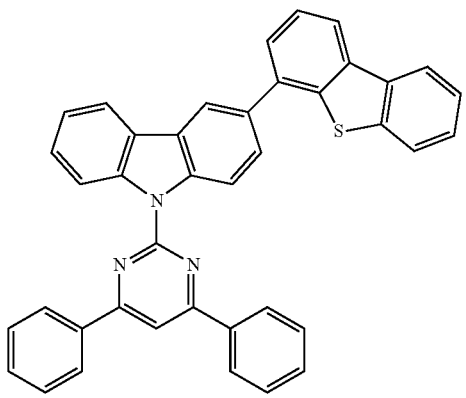

[Chemical Formula B-5]
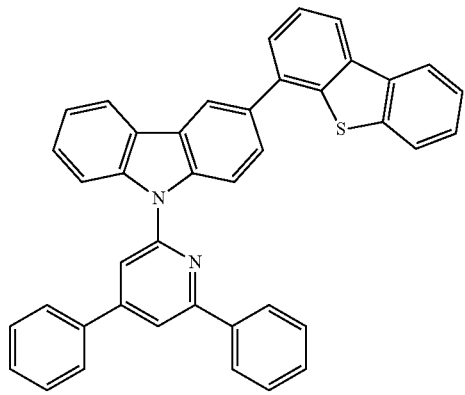
[Chemical Formula B-6]
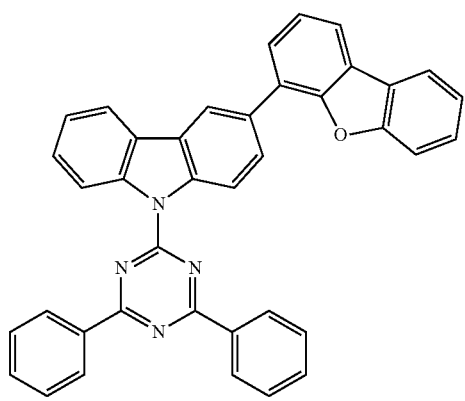
[Chemical Formula B-7]
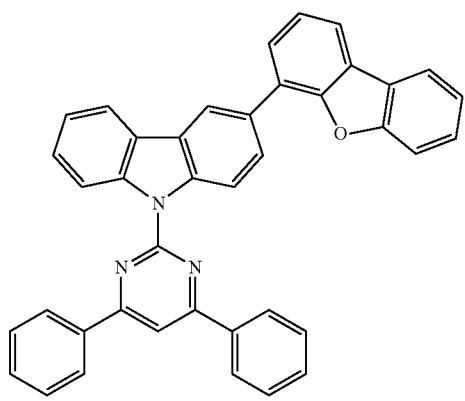
[Chemical Formula B-8]
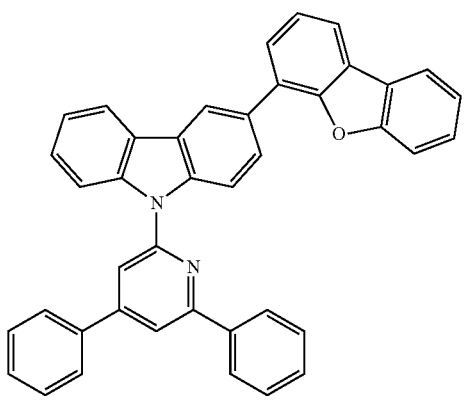
[Chemical Formula B-9]
[Chemical Formula B-10]
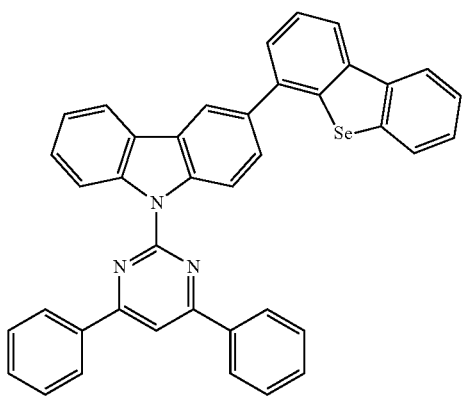

[Chemical Formula B-11]
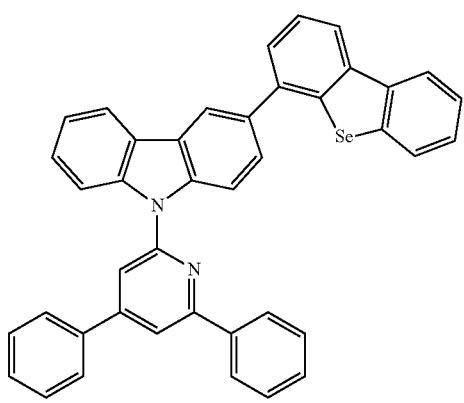
[Chemical Formula B-12]
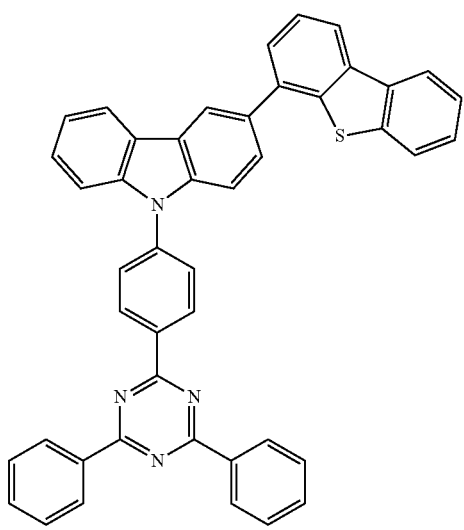
[Chemical Formula B-13]
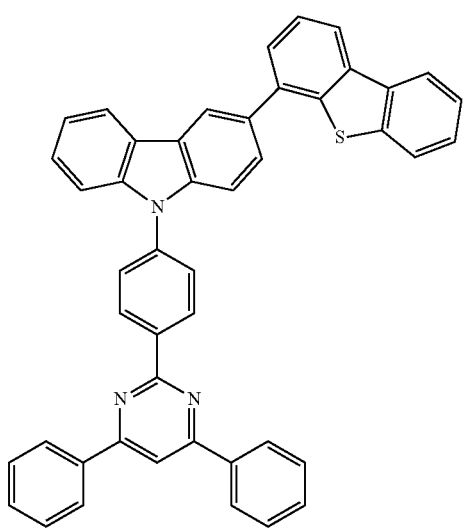
[Chemical Formula B-14]
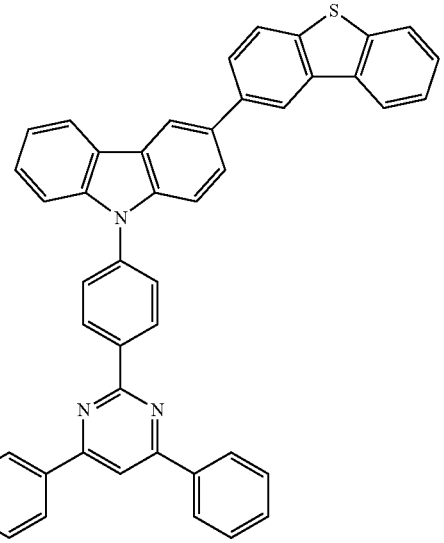
[Chemical Formula B-15]
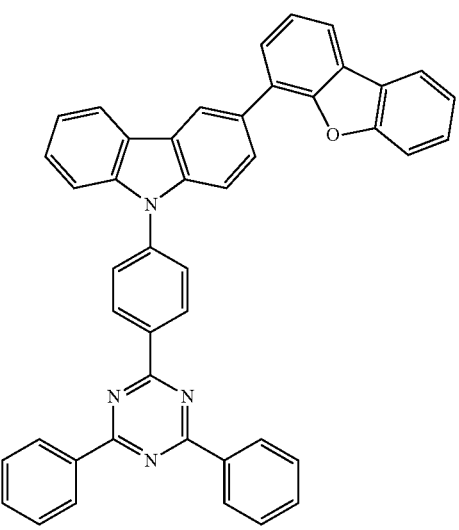
[Chemical Formula B-16]
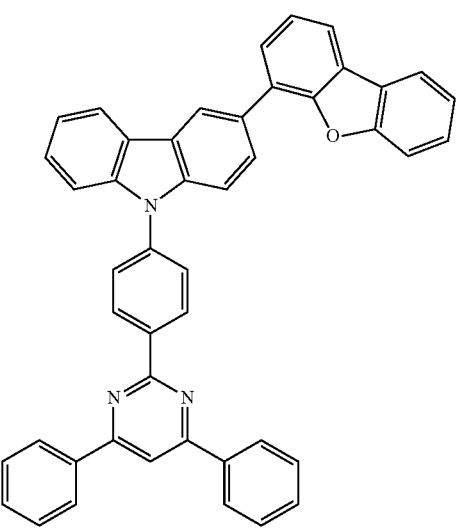

[Chemical Formula B-17]
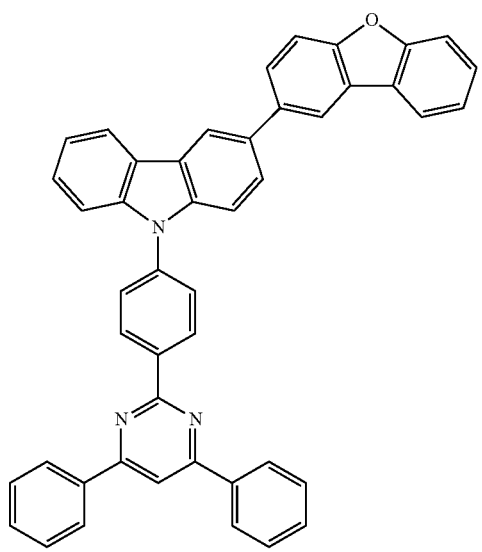
[Chemical Formula B-18]
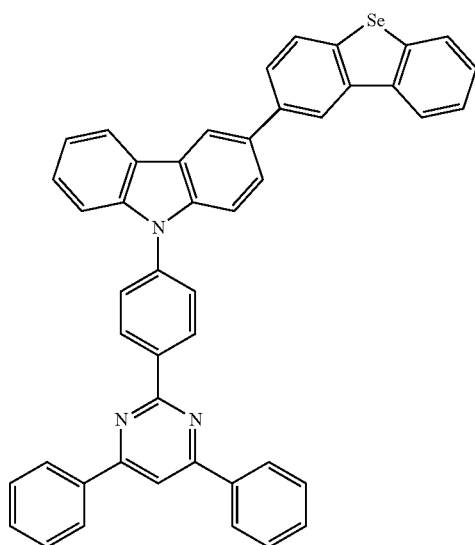
[Chemical Formula B-19]
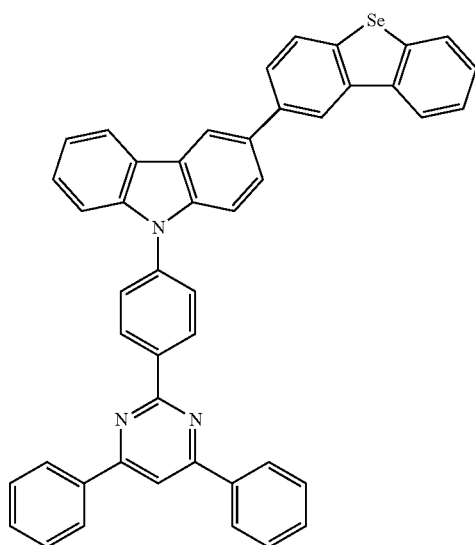
[Chemical Formula B-20]
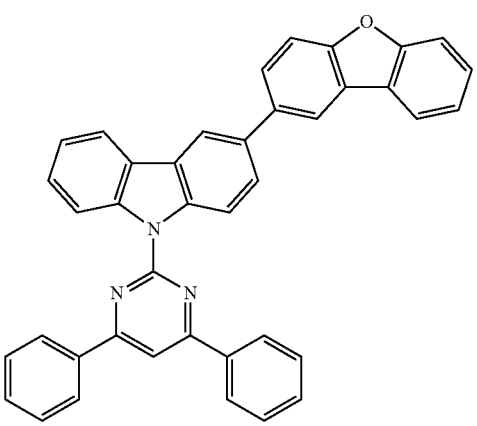
[Chemical Formula B-21]
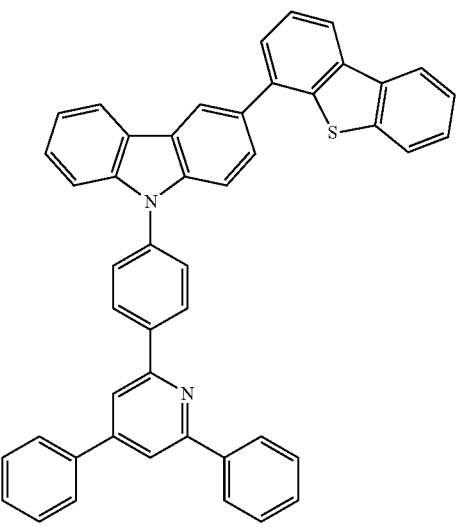
[Chemical Formula B-22]
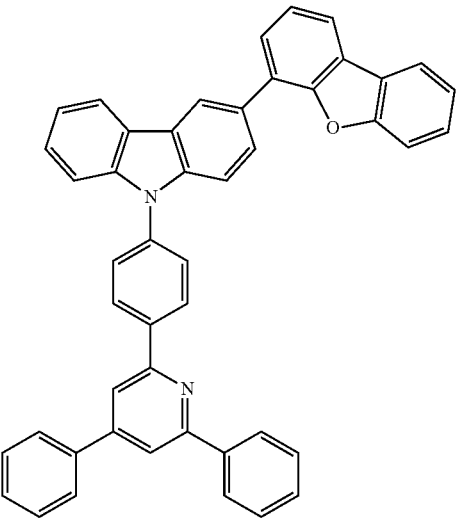
The compound for an organic optoelectronic device may be represented by, e.g., one of the following Chemical Formulae C-1 to C-18:

[Chemical Formula C-1]
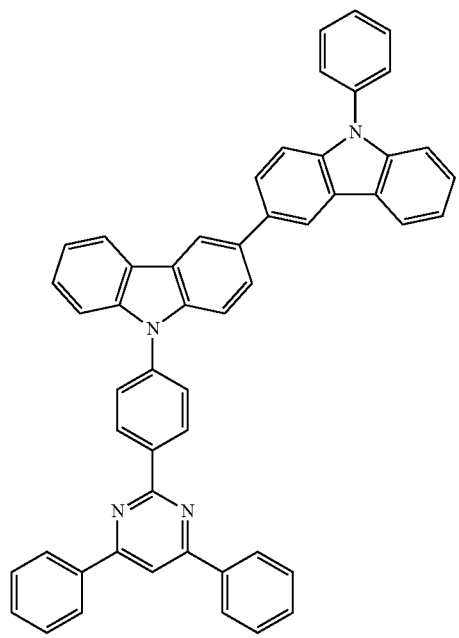
[Chemical Formula C-2]
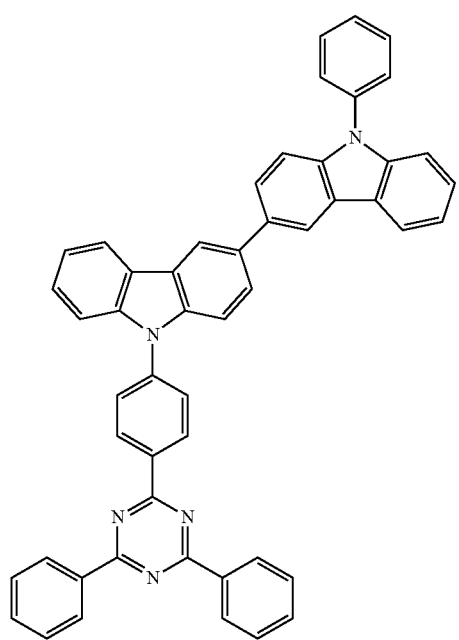
[Chemical Formula C-3]
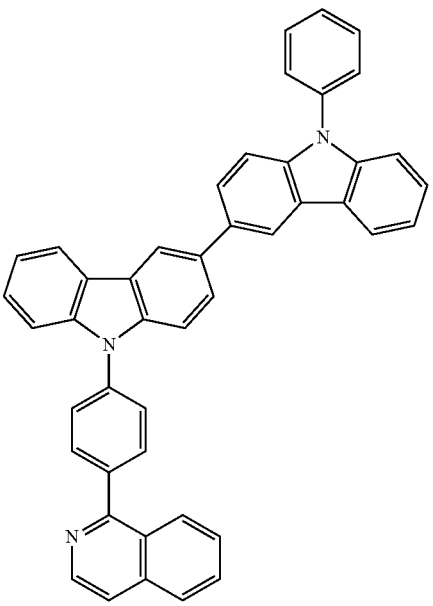
[Chemical Formula C-4]
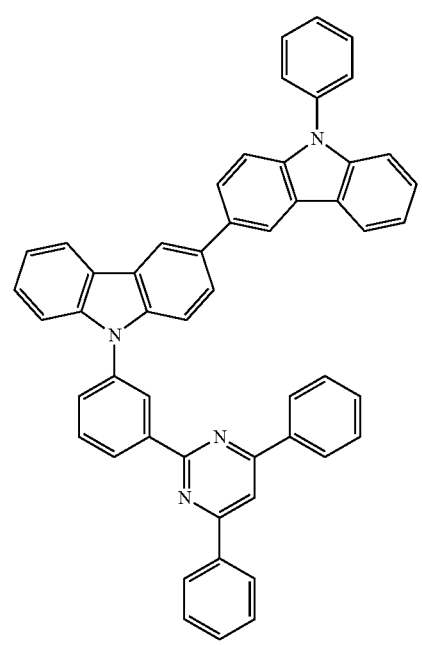

[Chemical Formula C-5]
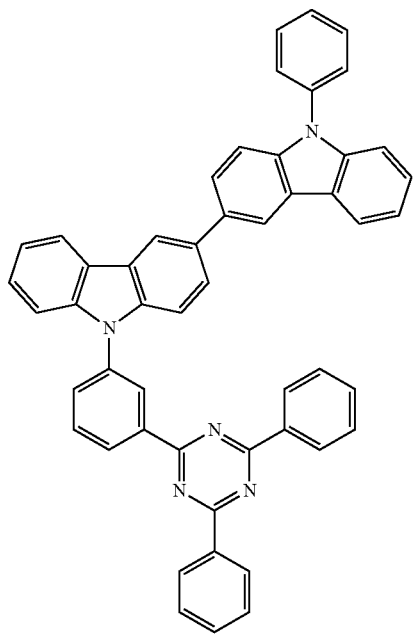
[Chemical Formula C-6]
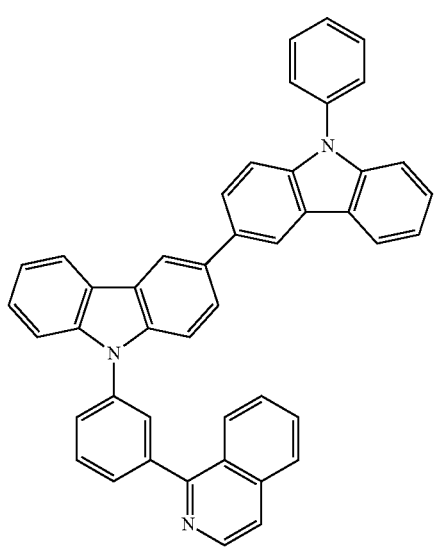
[Chemical Formula C-7]
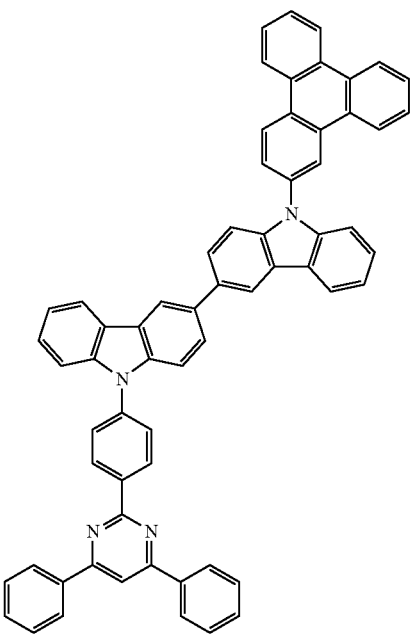
[Chemical Formula C-8]
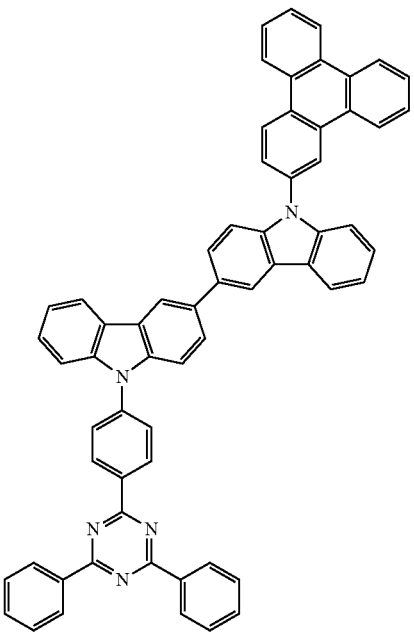

-continued
[Chemical Formula C-9]
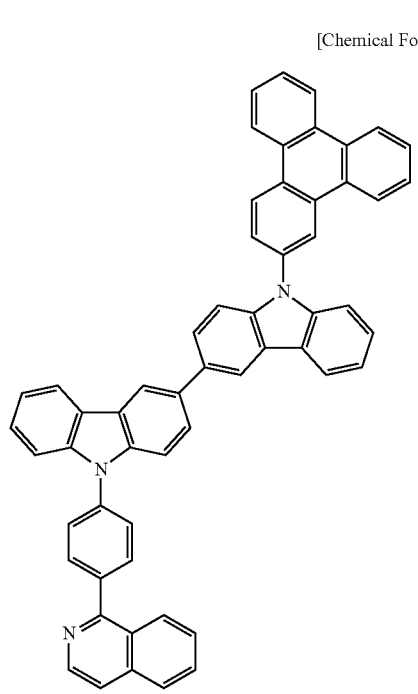
[Chemical Formula C-10]
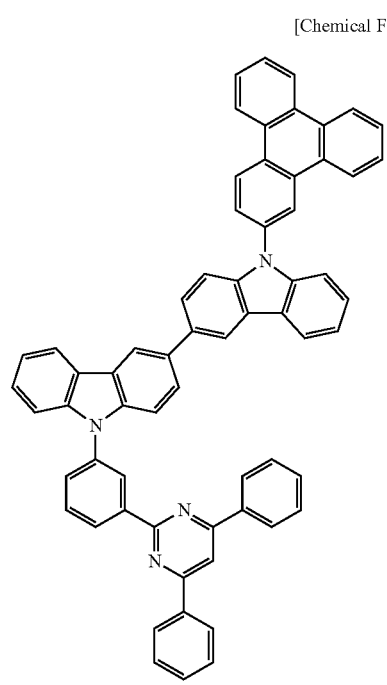
-continued
[Chemical Formula C-11]
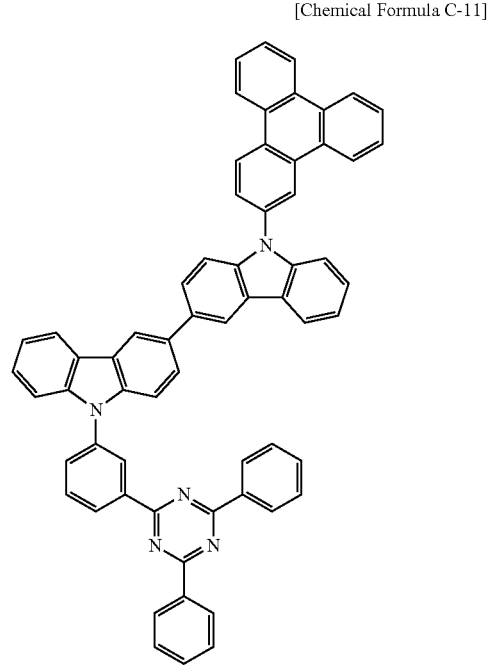
[Chemical Formula C-12]
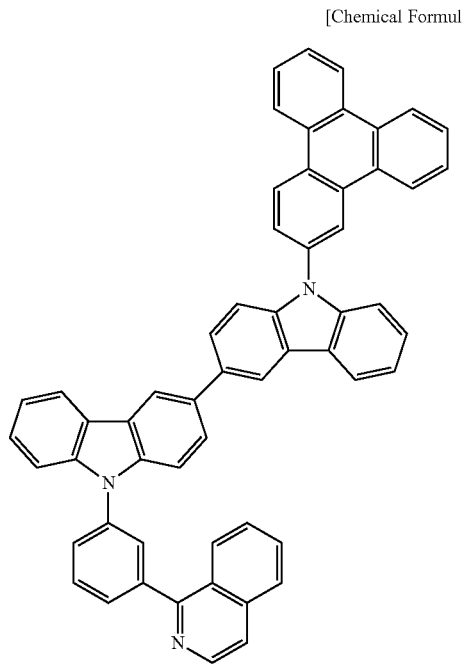

[Chemical Formula C-13]
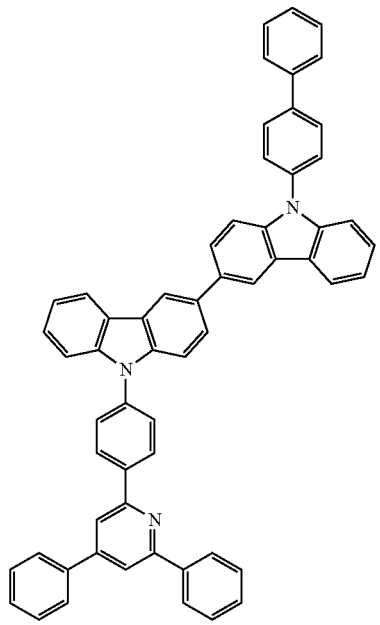
[Chemical Formula C-15]
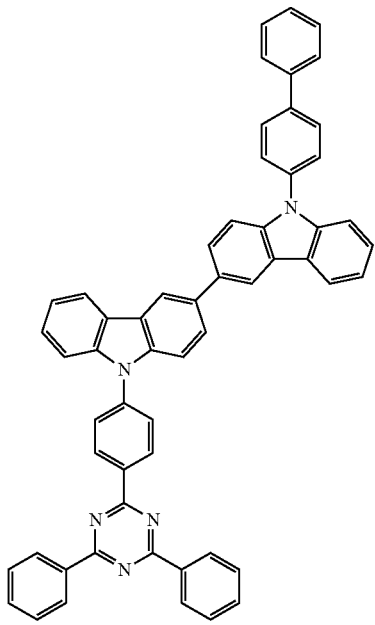
[Chemical Formula C-14]
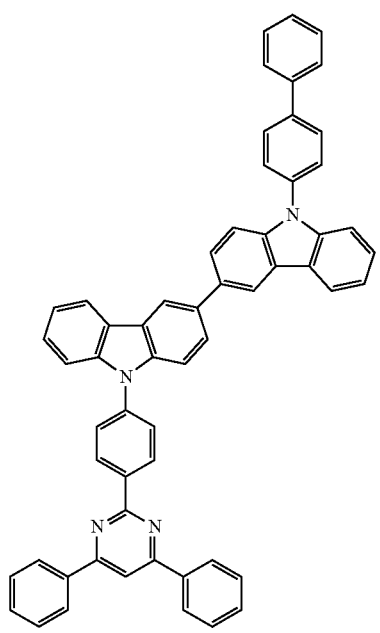
[Chemical Formula C-16]
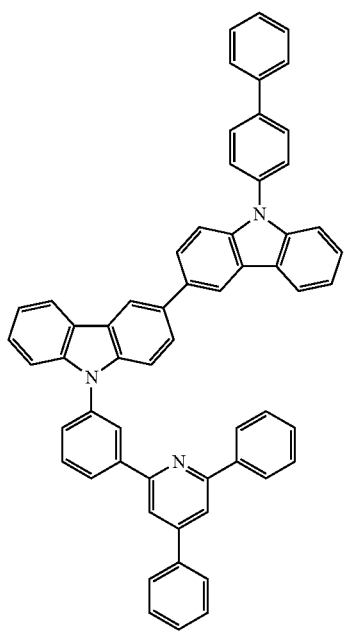

-continued

[Chemical Formula C-17]

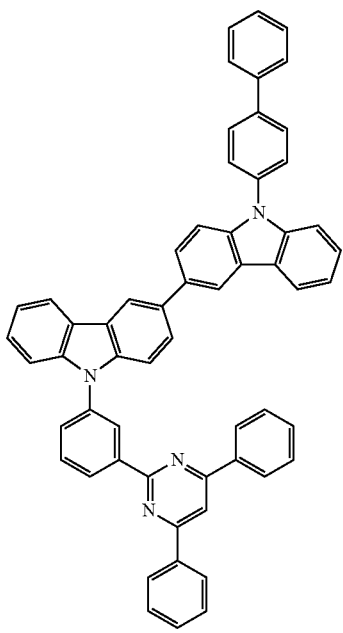

[Chemical Formula C-18]

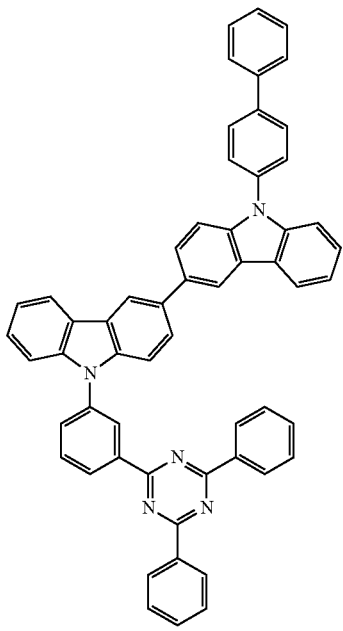

The compound for an organic optoelectronic device including the above compounds may have a glass transition temperature of greater than or equal to 110° C. and a thermal decomposition temperature of greater than or equal to 400° C., indicating improved thermal stability. Thereby, it may be possible to produce an organic optoelectronic device having a high efficiency.

The compound for an organic optoelectronic device including the above compounds may play a role for emitting light or injecting and/or transporting electrons, and also act as a light emitting host with a dopant. The compound for an organic optoelectronic device may be used as, e.g., a phosphorescent or fluorescent host material, a blue light emitting dopant material, or an electron transport material.

The compound for an organic optoelectronic device according to an embodiment may be used for an organic thin layer, and it may improve the life-span characteristic, efficiency characteristic, electrochemical stability, and thermal stability of an organic photoelectric device and decrease the driving voltage.

According to another embodiment, an organic optoelectronic device that includes the compound for an organic optoelectronic device is provided. The organic optoelectronic device may include, e.g., an organic photoelectric device, an organic light emitting diode, an organic solar cell, an organic transistor, an organic photo conductor drum, an organic memory device, or the like. For example, the compound for an organic optoelectronic device according to an embodiment may be included in an electrode or an electrode buffer layer in an organic solar cell to improve quantum efficiency, or it may be used as an electrode material for a gate, a source/drain electrode, or the like in an organic transistor.

Hereinafter, an organic light emitting diode is described.

According to an embodiment, an organic light emitting diode includes an anode, a cathode, and one or more organic thin layers between the anode and the cathode. At least one of the organic thin layers may include the compound for an organic optoelectronic device according to an embodiment.

The organic thin layer including the compound for an organic optoelectronic device may include one or more of an emission layer, a hole transport layer (HTL), a hole injection layer (HIL), an electron transport layer (ETL), an electron injection layer (EIL), or a hole blocking layer. For example, the compound for an organic optoelectronic device according to an embodiment may be included in an electron transport layer (ETL) or an electron injection layer (EIL). When the compound for an organic optoelectronic device is included in the emission layer, the compound for an organic optoelectronic device may be included as, e.g., a phosphorescent or fluorescent host, or as a fluorescent blue dopant material.

FIGS. 1 to 5 illustrate cross-sectional views showing organic light emitting diodes including a compound for an organic optoelectronic device according to an embodiment.

In the examples shown in FIGS. 1 to 5, organic light emitting diodes 100, 200, 300, 400, and 500 according to embodiments include at least one organic thin layer 105 interposed between an anode 120 and a cathode 110.

The anode 120 may include an anode material laving a large work function to help hole injection into an organic thin layer. The anode material may include one or more of, e.g., a metal (such as one or more of nickel, platinum, vanadium, chromium, copper, zinc, and gold, or alloys thereof); a metal oxide (such as one or more of zinc oxide, indium oxide, indium tin oxide (ITO), or indium zinc oxide (IZO)); a bonded metal and oxide (such as one or more of ZnO:Al or SnO$_2$:Sb); a conductive polymer (such as one or more of poly(3-methylthiophene), poly[3,4-(ethylene-1,2-dioxy)thiophene] (PEDT), polypyrrole, or polyaniline); or the like. In an implementation, a transparent electrode including indium tin oxide (ITO) is included as an anode.

The cathode 110 may include a cathode material having a small work function to help electron injection into an organic thin layer. The cathode material may include, e.g., a metal (such as one or more of magnesium, calcium, sodium, potassium, titanium, indium, yttrium, lithium, gadolinium, aluminum, silver, tin, lead, or alloys thereof); a multi-layered material (such as one or more of LiF/Al, Liq/Al, $LiO_2/Al$, LiF/Ca, LiF/Al, or $BaF_2/Ca$), or the like. In an implementation, a metal electrode including aluminum is included as a cathode.

In the example shown in FIG. 1, the organic light emitting diode 100 includes an organic thin layer 105 including only an emission layer 130.

Figure 2:
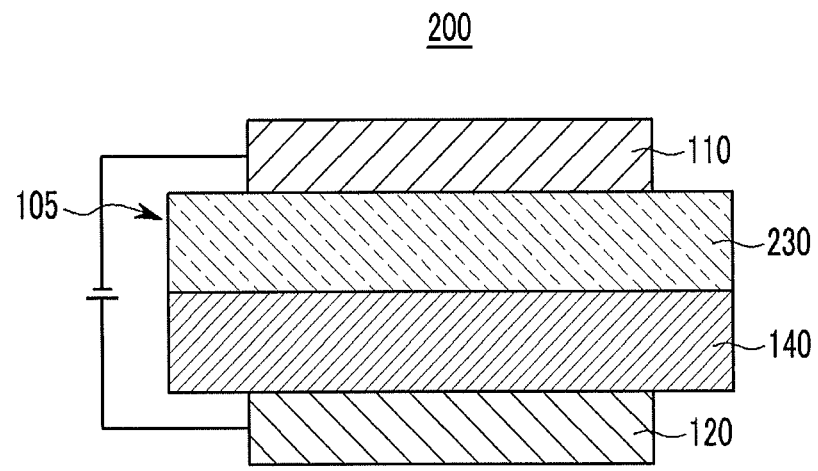

In the example shown in FIG. 2, a double-layered organic light emitting diode 200 includes an organic thin layer 105 including an emission layer 230 including an electron transport layer (ETL), and a hole transport layer (HTL) 140. As shown in FIG. 2, the organic thin layer 105 includes a double layer of the emission layer 230 and hole transport layer (HTL) 140. The emission layer 130 may also function as an electron transport layer (ETL), and the hole transport layer (HTL) 140 layer may have an excellent binding property with a transparent electrode such as ITO or an excellent hole transport capability.

Figure 3:
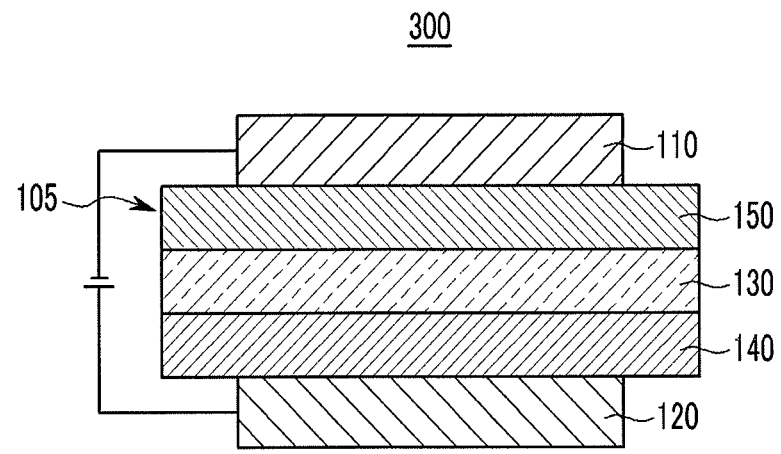

In the example shown in FIG. 3, a three-layered organic light emitting diode 300 includes an organic thin layer 105 including an electron transport layer (ETL) 150, an emission layer 130, and a hole transport layer (HTL) 140. The emission layer 130 is independently installed, and layers having an excellent electron transport capability or an excellent hole transport capability may be separately stacked.

Figure 4:
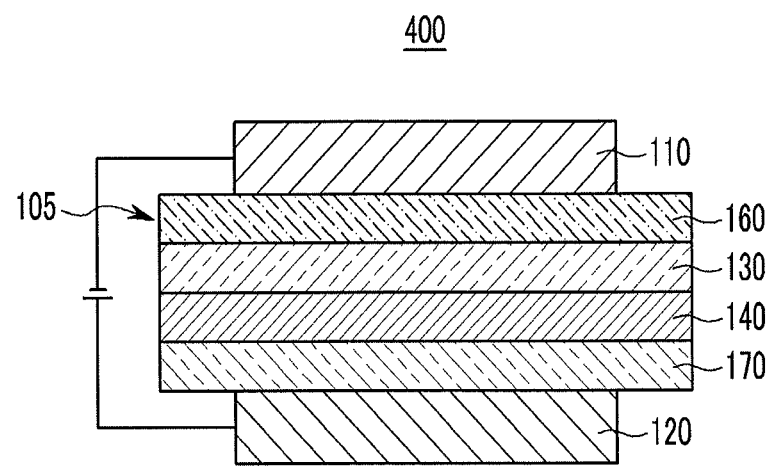

In the example shown in FIG. 4, a four-layered organic light emitting diode 400 includes an organic thin layer 105 including an electron injection layer (EIL) 160, an emission layer 130, a hole transport layer (HTL) 140, and a hole injection layer (HIL) 170 for adherence with the cathode of ITO.

Figure 5:
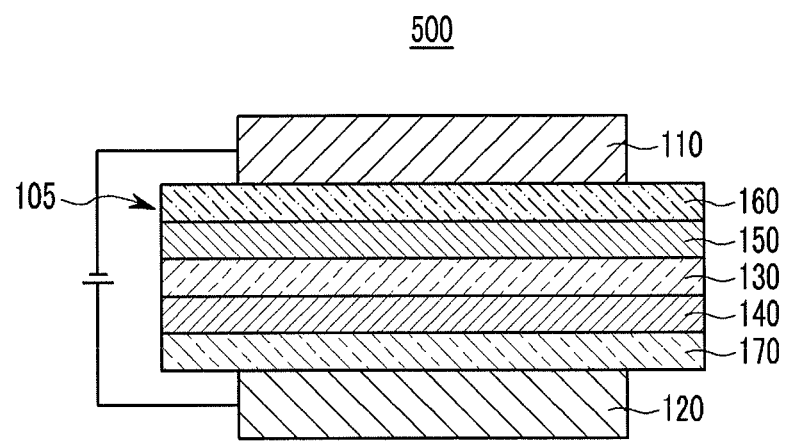

In the example shown in FIG. 5, a five layered organic light emitting diode 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

In FIGS. 1 to 5, the organic thin layer 105 including at least one selected from the group of an electron transport layer (ETL) 150, an electron injection layer (EIL) 160, emission layers 130 and 230, a hole transport layer (HTL) 140, a hole injection layer (HIL) 170, and combinations thereof includes a compound for an organic optoelectronic device according to an embodiment. The compound for an organic optoelectronic device may be used for an electron transport layer (ETL) 150 including the electron transport layer (ETL) 150 or electron injection layer (EIL) 160. When it is used for the electron transport layer (ETL), it may be possible to provide an organic photoelectric device having a simpler structure by eliminating an additional hole blocking layer (not shown).

When the compound for an organic photoelectric device is included in the emission layers 130 and 230, the material for the organic photoelectric device may be included as, e.g., a phosphorescent or fluorescent host or a fluorescent blue dopant.

The organic light emitting diode may be fabricated by, e.g.: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

Another embodiment provides a display device including an organic light emitting diode according to an embodiment.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Preparation of Compound for Organic optoelectronic device

Example 1

Synthesis of Compound Represented by Chemical Formula 4

A compound represented by the above Chemical Formula 4 as a compound for an organic optoelectronic device was synthesized according to the following Reaction Scheme 1.

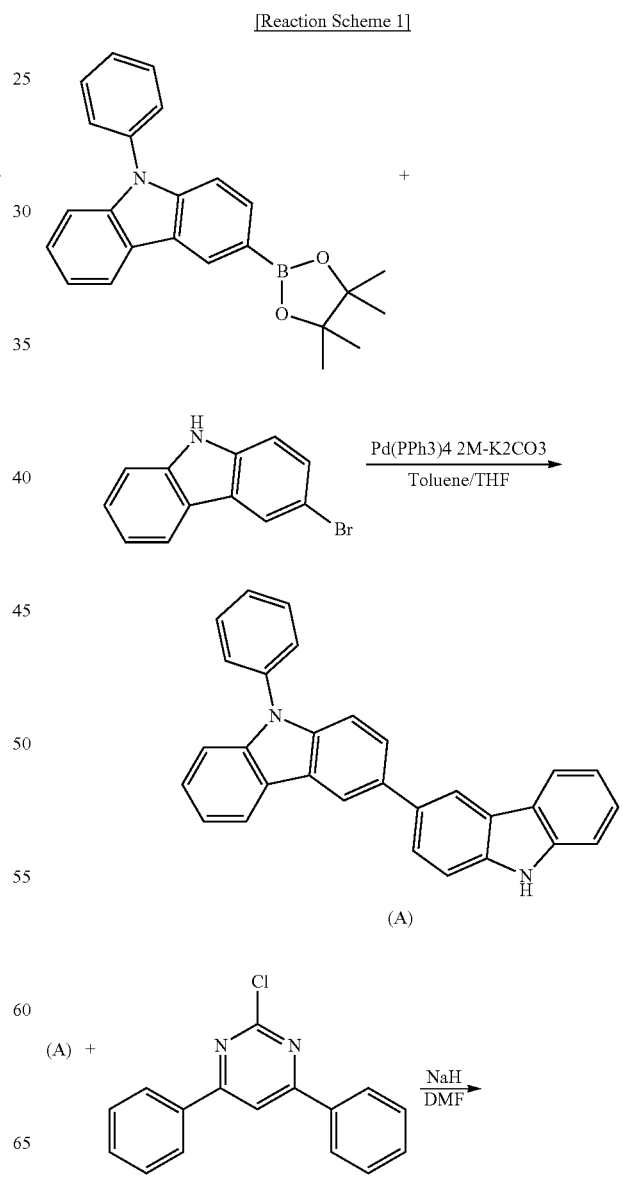

[Reaction Scheme 1]

-continued

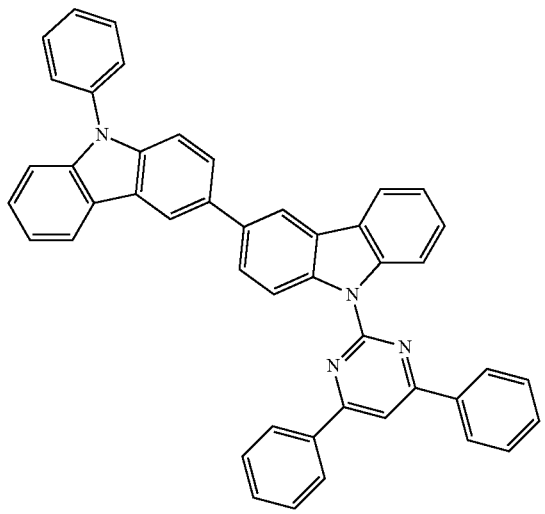

First Step: Synthesis of Compound A 5 g (20 mmol) of a 3-bromo-carbazole compound and 9 g (24 mmol) of N-phenyl-carbazole boronic acid pinacolate were mixed with 100 mL of tetrahydrofuran and a 2M potassium carbonate aqueous solution in a 250 mL round-bottomed flask. The mixture was heated and refluxed for 12 hours under a nitrogen flow. When the reaction was complete, hexane was poured into the reactant. Then, a produced solid was filtered and dissolved in a mixed solution prepared by mixing toluene and tetrahydrofuran in a volume ratio of 50:50, and activated carbon and anhydrous magnesium sulfate were added thereto. The resulting mixture was agitated. The agitated solution was filtered and recrystallized using dichloromethane and hexane, obtaining 7.8 g of a compound A (yield=60%).

Second Step: Synthesis of Compound Represented by Chemical Formula 4

3.5 g (8.55 mmol) of an intermediate product marked as the compound A, 2.74 g (10.26 mmol) of 2-chloro-4,6-diphenyl-pyrimidine, NaH, and dimethylformamide were put in a 100 mL round flask and then, agitated at room temperature under a nitrogen flow. Next, an organic solvent therein was distillated and removed under a reduced pressure and treated through a column chromatography, separating and obtaining a compound represented by Chemical Formula 43.823 g (yield: 70%).

The compound represented by Chemical Formula 4 was subjected to elemental analysis. The result is as follows.

Calcd. $C_{46}H_{30}N_4$: C, 86.49; H, 4.73; N, 8.77. found: C, 86.24; H, 4.89; N, 8.55.

Example 2

Synthesis of Compound Represented by Chemical Formula 5

A compound represented by the above Chemical Formula 5 as a compound for an organic optoelectronic device according to an embodiment was synthesized according to the following Reaction Scheme 2.

[Reaction Scheme 2]

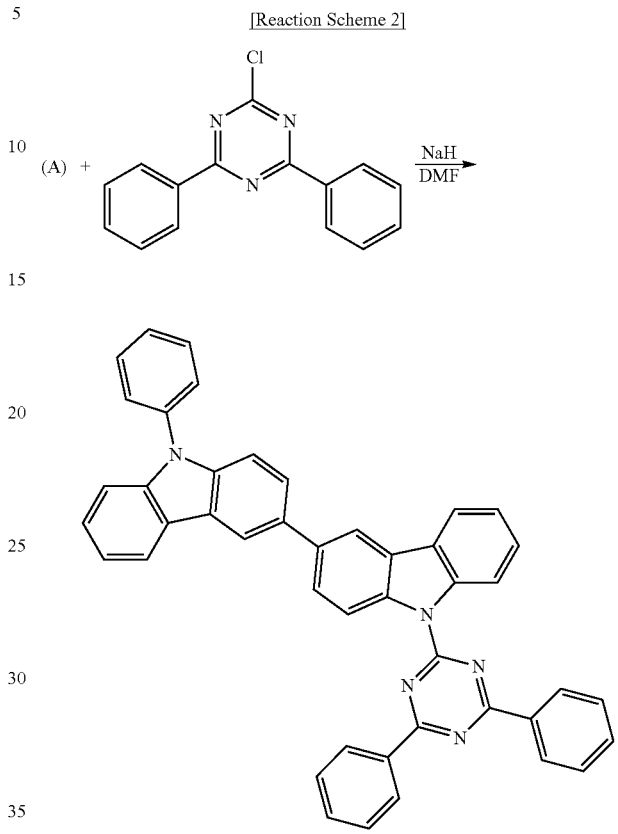

Synthesis of Compound Represented by Chemical Formula 5

3.5 g (8.55 mmol) of an intermediate product marked as the compound A, 2.74 g (10.26 mmol) of 2-chloro-4,6-dibiphenyl-pyrimidine, NaH, and dimethylformamide were put in a 100 mL round flask and then agitated at room temperature under a nitrogen flow. Then, an organic solvent therein was distilled and removed under a reduced pressure and treated through a column chromatography, separating and obtaining 4.1 g (yield: 75%) of a compound 6.

The compound represented by Chemical Formula 5 was subjected to elemental analysis. The result is as follows.

Calcd. $C_{45}H_{29}N_5$: C, 84.48; H, 4.57; N, 10.95. found: C, 84.24; H, 4.65; N, 10.55.

Example 3

Synthesis of Compound Represented by Chemical Formula 14

A compound represented by the above Chemical Formula 14 as a compound for an organic optoelectronic device according to an embodiment was synthesized according to the following Reaction Scheme 3.

[Reaction Scheme 3]

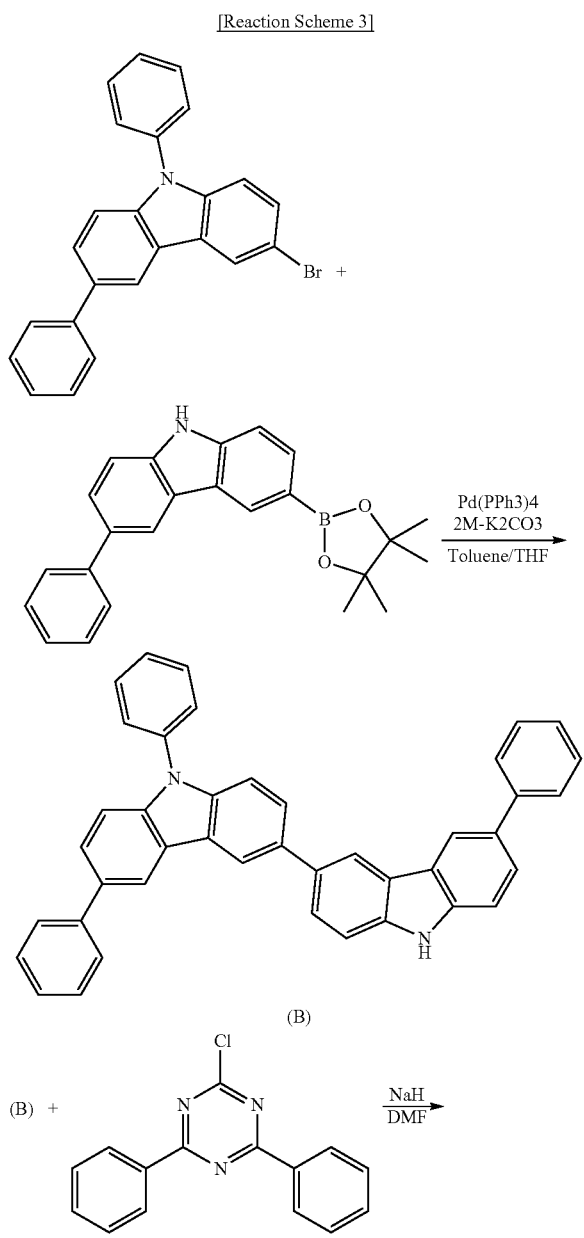

First Step: Synthesis of Compound B 5 g (12.6 mmol) of a 3-bromo-N-phenyl-6-phenylcarbazole compound and 5.56 g (15 mmol) of 3-phenylcarbazole boronic acid pinacolate were mixed with 100 mL of tetrahydrofuran and a 2M potassium carbonate aqueous solution in a 250 mL round-bottomed flask having an agitator and a nitrogen atmosphere and then, heated and refluxed under a nitrogen flow for 12 hours. When the reaction was complete, hexane was poured into the reactant. Then, a solid produced therein was filtered and dissolved in a solution prepared by mixing toluene and tetrahydrofuran in a volume ratio of 50:50, and activated carbon and anhydrous magnesium sulfate were added thereto. The mixture was agitated. The solution was filtered and recrystallized using dichloromethane and hexane, obtaining 6.5 g (yield of 65%) of a compound B.

Second Step: Synthesis of Compound Represented by Chemical Formula 14

6 g (10.5 mmol) of an intermediate product marked as the compound B and 3.44 g (12.84 mmol) of 2-chloro-4,6-diphenyl-triazine were mixed with NaH and dimethylformamide in a 250 mL round flask. The mixture was agitated at room temperature under a nitrogen flow. Next, an organic solvent was distilled and removed under a reduced pressure and treated through a column chromatography, separating and obtaining 3.825 g (yield: 70%) of a compound represented by Chemical Formula 14.

The compound represented by Chemical Formula 14 was subjected to elemental analysis. The result is as follows.

Calcd. $C_{57}H_{37}N_5$: C, 86.45; H, 4.71; N, 8.84. found: C, 86.15; H, 4.57; N, 8.57.

Example 4

Synthesis of Compound Represented by Chemical Formula A-2

A compound represented by the above Chemical Formula A-2 as an example compound for an organic optoelectronic device according to an embodiment was synthesized according to the following Reaction Scheme 4.

[Reaction Scheme 4]

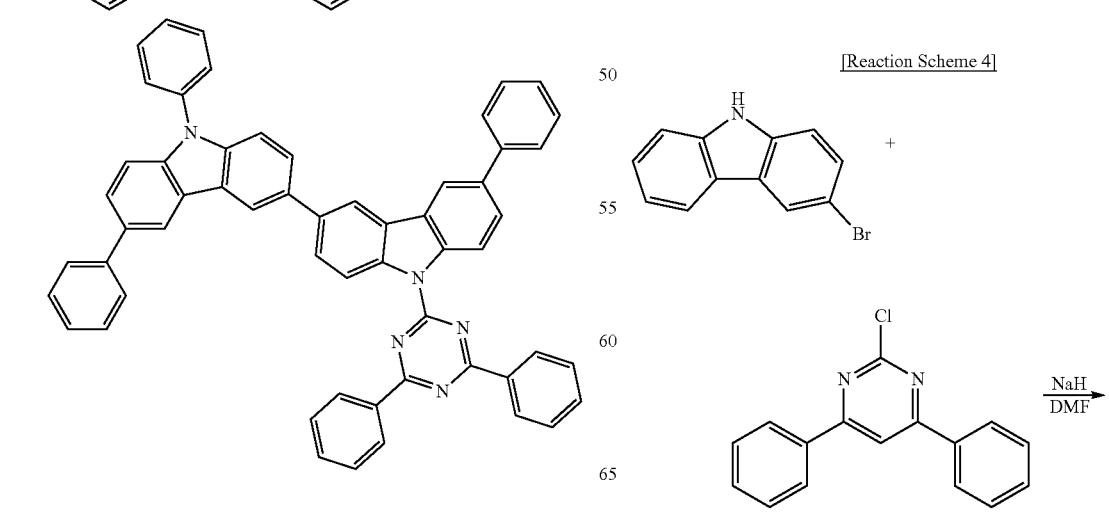

-continued

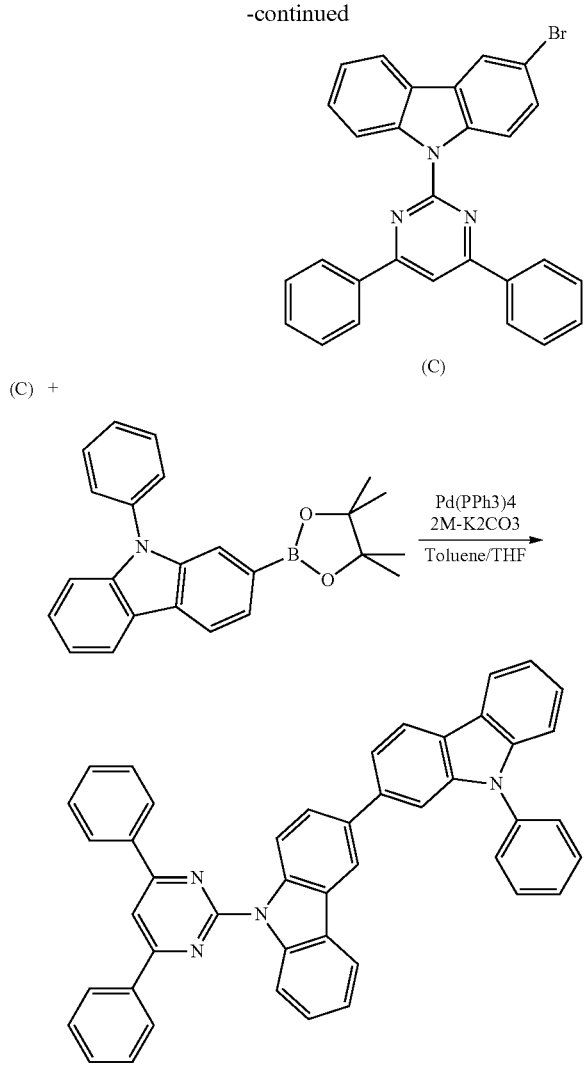

(C) +

First Step: Synthesis of Compound C 28.4 g (115.46 mmol) of 3-bromocarbazole, 36.95 g (138.55 mmol) of 2-chloro-4,6-diphenyl-pyrimidine, and 6.93 g of NaH were mixed with dimethylformamide in a 1,000 mL round flask, and the mixture was agitated at room temperature for 12 hours under a nitrogen flow. The reactant was put in distilled water for crystallization. The crystallized solid was filtered and recrystallized with monochlorobenzene and hexane, obtaining 53 g (yield: 96%) of an intermediate compound C.

Second Step: Synthesis of Compound Represented by Chemical Formula A-2

22.26 g (46.7 mmol) of the compound C and 20.71 g (56.1 mmol) of N-phenyl-carbazole boronic acid pinacolate were mixed with 200 mL of tetrahydrofuran, 200 mL of toluene, and 200 mL of a 2M potassium carbonate aqueous solution in a 1,000 mL round-bottomed flask having an agitator and a nitrogen atmosphere, and the mixture was heated and agitated under a nitrogen flow for 12 hours. When the reaction was complete, hexane was poured into the reactant. Then, a solid produced therein was filtered and dissolved in a solution prepared by mixing toluene and tetrahydrofuran in a volume ratio of 50:50, and activated carbon and anhydrous magnesium sulfate were added thereto. The mixture was agitated. The solution was filtered and recrystallized using chlorobenzene and methanol, obtaining 20 g (yield of 70%) of a compound A-2. The result is as follows.

Calcd. $C_{46}H_{30}N_4$: C, 86.49; H, 4.73; N, 8.77. found: C, 86.44; H, 4.74; N, 8.75.

Example 5

Synthesis of Compound Represented by Chemical Formula A-10

A compound represented by the above Chemical Formula A-10 as an example compound for an organic optoelectronic device according to an embodiment was synthesized according to the following Reaction Scheme 5.

[Reaction Scheme 5]

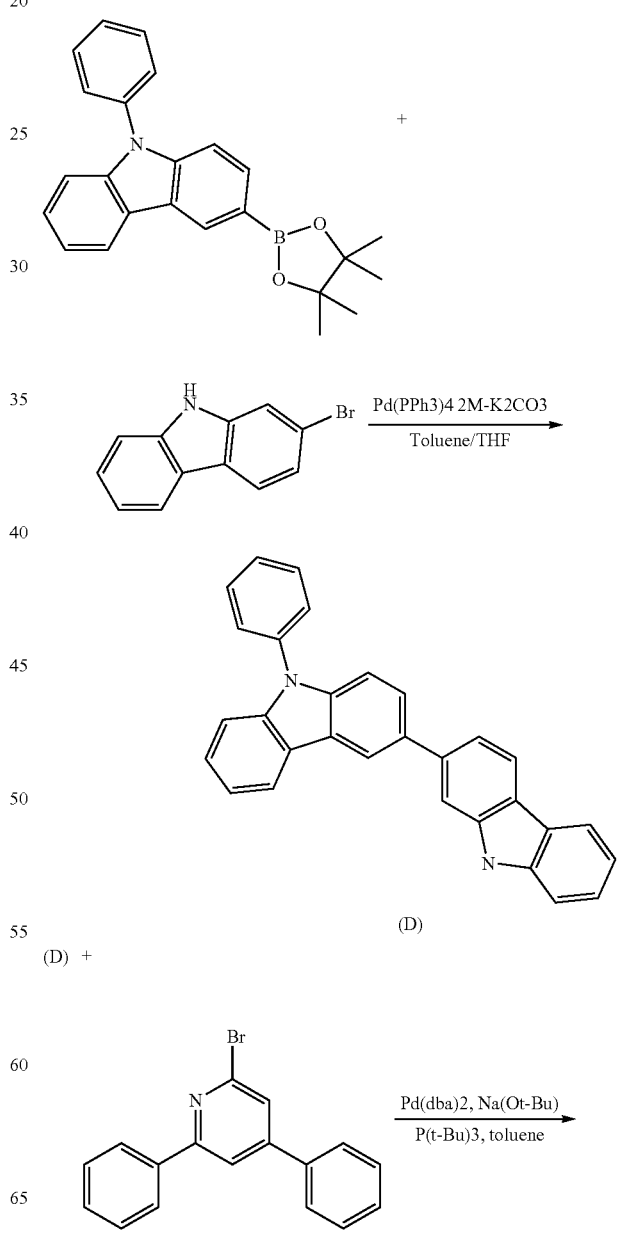

(D) +

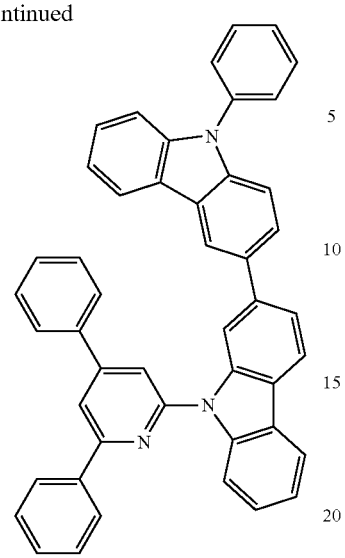

First Step: Synthesis of Compound Represented by Chemical Formula D 17.66 g (71.7 mmol) of a 2-bromo-carbazole compound and 22.08 g (59.8 mmol) of N-phenyl-carbazole boronic acid pinacolate were mixed with 100 mL of tetrahydrofuran and 100 mL of a 2M potassium carbonate aqueous solution, and the mixture was heated and refluxed under a nitrogen flow for 12 hours in a 500 mL round-bottomed flask having an agitator and a nitrogen atmosphere. When the reaction was complete, hexane was poured into the reactant. Then, a solid produced therein was filtered and dissolved in a solution prepared by mixing toluene and tetrahydrofuran in a volume ratio of 50:50, and activated carbon and anhydrous magnesium sulfate were added thereto. The mixture was agitated. The solution was filtered and recrystallized using dichloromethane and hexane, obtaining 19 g (yield of 65%) of a compound D.

Second Step: Synthesis of Compound Represented by Chemical Formula A-10

8.3 g (20.53 mmol) of the compound D, 7.64 g (24.64 mmol) of 2-bromo-4,6-diphenylpyridine, and 3.35 g (34.9 mmol) of sodium tert-butoxide were dissolved in 200 mL of toluene, and 0.47 g (0.51 mmol) of palladium dibenzylideneamine and 0.77 mL (1.54 mmol) of tert-butyl phosphorous were added thereto in a dropwise fashion in a 500 mL round-bottomed flask having an agitator and a nitrogen atmosphere. The reaction solution was heated and agitated under a nitrogen flow for 12 hours at 110° C. When the reaction was complete, methanol was poured into the reactant. Then, a solid produced therein was filtered and dissolved in chlorobenzene, and activated carbon and anhydrous magnesium sulfate were added thereto. The mixture was agitated. The solution was filtered and recrystallized using chlorobenzene and methanol, obtaining 11 g (yield of 84%) of a compound A-10.

Calcd. $C_{47}H_{31}N_3$: C, 88.51; H, 4.90; N, 6.59. found: C, 88.49; H, 4.91; N, 6.61.

Example 6

Synthesis of Compound Represented by Chemical Formula A-12

A compound represented by the above Chemical Formula A-12 as an example compound for an organic optoelectronic device according to an embodiment was synthesized according to the following Reaction Scheme 3.

[Reaction Scheme 6]

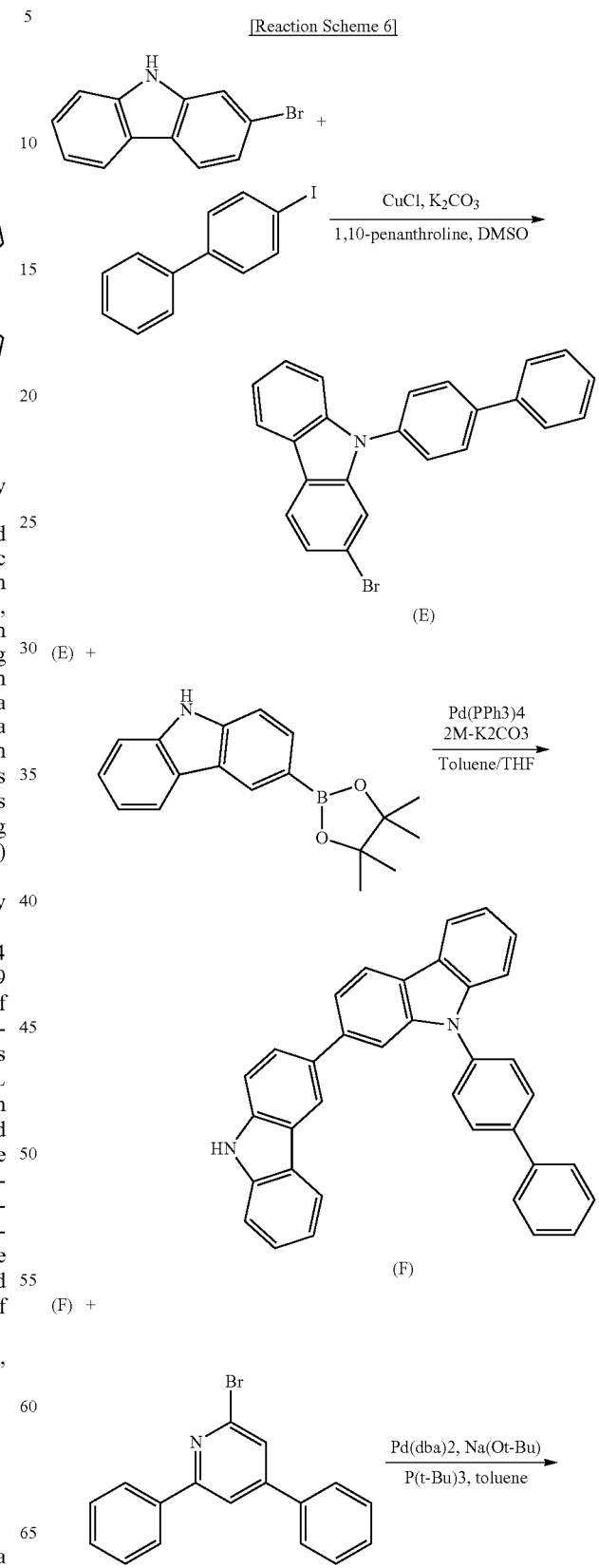

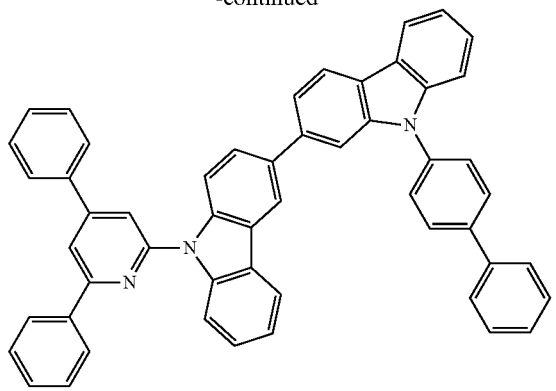

First Step: Synthesis of Compound E 22.22 g (90.3 mmol) of a 2-bromocarbazole compound, 37.94 g (135.5 mmol) of 4-iodobiphenyl and 18.72 g (135.5 mmol) of potassium carbonate were dissolved in 400 mL of dimethylsulfoxide, and 3.26 g (135.47 mmol) of 1,10-phenanthroline and 1.79 g (18.06 mmol) of copper chloride (I) were added therein in a dropwise fashion in a 1,000 mL round-bottomed flask having an agitator and a nitrogen atmosphere. The reaction solution was agitated under a nitrogen flow for 12 hours at 150° C. When the reaction was complete, distilled water was poured into the reactant. Then, a solid produced therein was dissolved in chlorobenzene, and activated carbon and anhydrous magnesium sulfate were added thereto. The mixture was agitated. The solution was filtered and recrystallized using chlorobenzene and methanol, obtaining 25 g (yield=70%) of a compound E.

Second Step: Synthesis of Compound Represented by Chemical Formula F compound 18.2 g (46.7 mmol) of the compound E and 16.4 g (56.1 mmol) of 3-carbazole boronic acid pinacolate were mixed with 200 mL of tetrahydrofuran, 200 mL of toluene, and 200 mL of 2M-potassium carbonate aqueous solution, and the mixture was heated and refluxed under a nitrogen flow for 12 hours in a 1,000 mL round-bottomed flask having an agitator and a nitrogen atmosphere. When the reaction was complete, hexane was poured into the reactant. Then, a solid produced therein was filtered and dissolved in chlorobenzene, and activated carbon and anhydrous magnesium were added thereto. The mixture was agitated. The solution was filtered and recrystallized using chlorobenzene and methanol, obtaining 19.0 g (yield 64%) of a compound F.

Third Step: Synthesis of Compound Represented by Chemical Formula A-12

9.73 g (20.1 mmol) of the compound F, 7.47 g (24.10 mmol) of 2-bromo-4,6-diphenylpyridine, and 3.28 g (34.1 mmol) of sodium tert-butoxide were dissolved in 180 mL of toluene, and 0.46 g (0.5 mmol) of palladium dibenzylideneamine and 0.75 mL (1.51 mmol) of tert-butyl phosphorous were added thereto in a dropwise fashion in a 500 mL round-bottomed flask having an agitator and a nitrogen atmosphere. The reaction solution was heated and agitated under a nitrogen flow for 12 hours at 110° C. When the reaction was complete, methanol was poured into the reactant. Then, a solid produced therein was dissolved in chlorobenzene, and anhydrous magnesium sulfate was added thereto. The mixture was agitated. The solution was filtered and recrystallized using chlorobenzene and methanol, obtaining 9.9 g (yield of 70%) of a compound A-12.

Calcd. $C_{53}H_{35}N_3$: C, 89.17; H, 4.94; N, 5.89. found: C, 89.29; H, 4.96; N, 5.82.

Example 7

Synthesis of Compound Represented by Chemical Formula B-5

A compound represented by the above Chemical Formula B-5 as an example compound for an organic optoelectronic device according to an embodiment was synthesized according to the following Reaction Scheme 7.

[Reaction Scheme 7]

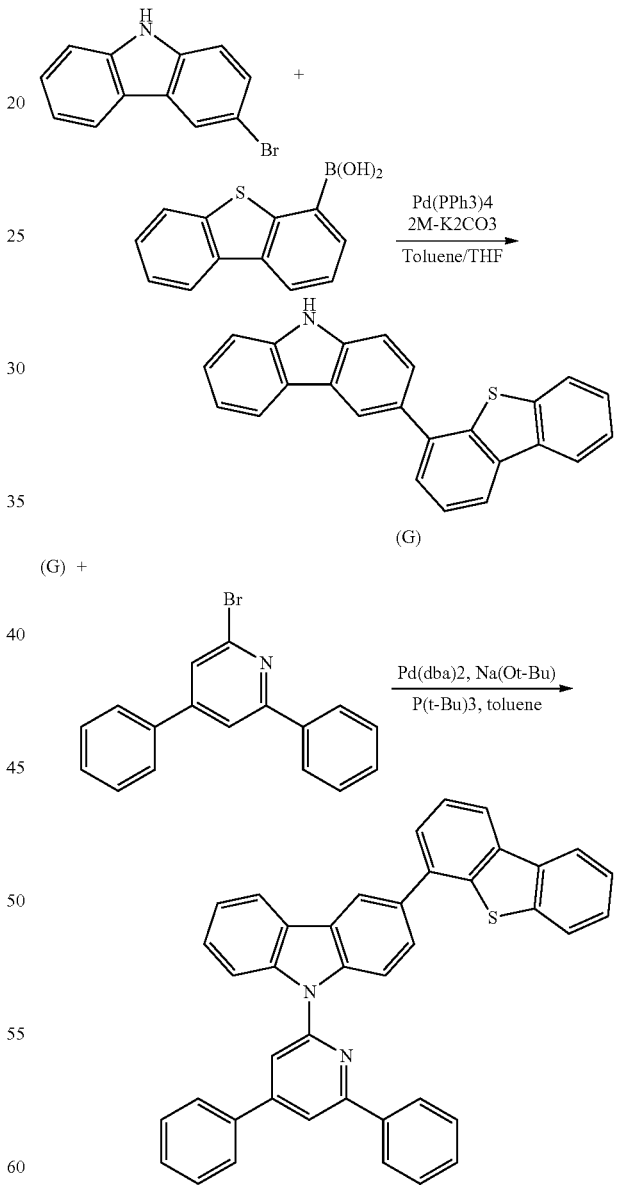

First Step: Synthesis of Compound G 18.53 g (75.3 mmol) of a 3-bromo-carbazole compound, 22.3 g (97.9 mmol) of 4-dibenzothiophene boronic acid, 100 mL of tetrahydrofuran, and 100 mL of a 2M potassium carbonate aqueous solution were mixed in a 500 mL round-bottomed flask and then, heated and refluxed for 12 hours under a nitrogen flow. When the reaction was complete, hexane was poured into the reactant. Then, a solid produced therein was filtered and dissolved in a solution prepared by mixing toluene and tetrahydrofuran in a volume ratio of 50:50, and activated carbon and anhydrous magnesium sulfate were added thereto. The solution was filtered and recrystallized using dichloromethane and hexane, obtaining 15 g (yield of 60%) of a compound D.

Second STEP: Synthesis of Compound Represented by Chemical Formula B-5

10 g (28.80 mmol) of the compound G, 11.6 g (37.4 mmol) of 2-bromo-4,6-diphenylpyridine, and 5.53 g (57.6 mmol) of sodium tert-butoxide were dissolved in 160 mL of toluene, and 1.32 g (1.44 mmol) of palladium dibenzylideneamine and 0.87 mL (4.32 mmol) of tert-butyl phosphorous were added in a dropwise fashion in a 500 mL round-bottomed flask having an agitator and a nitrogen atmosphere. The reaction solution was heated and agitated under a nitrogen flow for 12 hours at 12 at 110° C. When the reaction was complete, methanol was poured into the reactant. Then, a solid produced therein was filtered and dissolved in chlorobenzene, and activated carbon and anhydrous magnesium sulfate were added thereto. The mixture was agitated. The solution was filtered and recrystallized using chlorobenzene and methanol, obtaining 14 g (yield of 85%) of a compound B-5.

Calcd. $C_{41}H_{26}N_2S$: C, 85.09; H, 4.53; N, 4.84; S, 5.54. found: C, 85.11; H, 4.50; N, 4.80; S, 5.50.

Example 8

Synthesis of Compound Represented by Chemical Formula B-8

A compound represented by the above Chemical Formula B-8 as an example compound for an organic optoelectronic according to an embodiment was synthesized according to the following Reaction Scheme 8.

[Reaction Scheme 8]

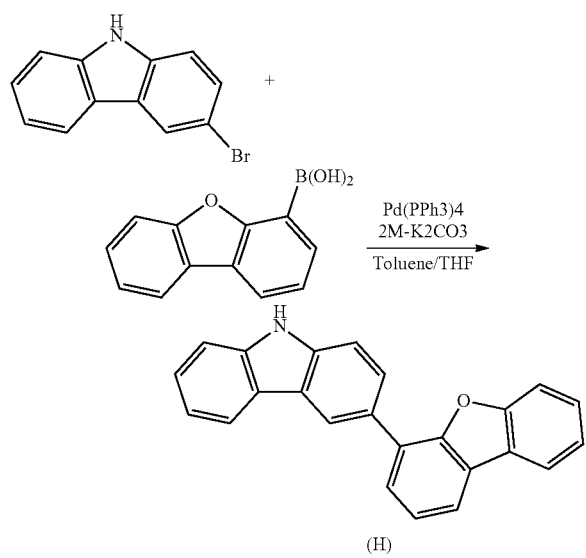

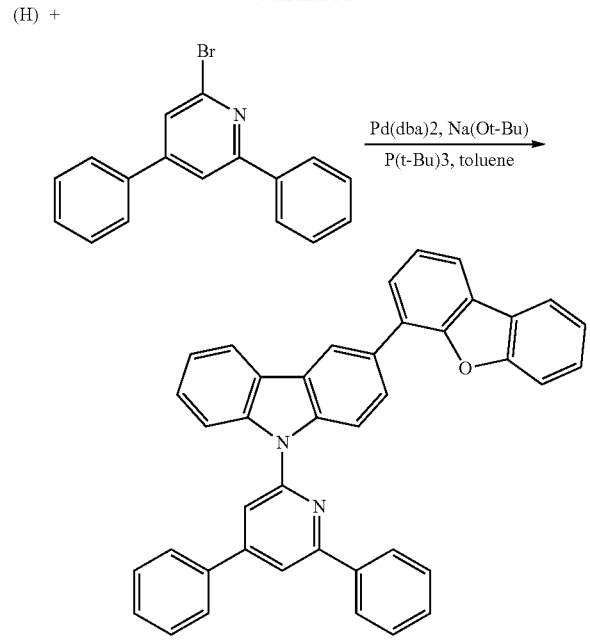

First Step: Synthesis of Compound H 9.84 g (39.99 mmol) of a 3-bromo-carbazole compound, 10.17 g (47.99 mmol) of 4-dibenzofuran boronic acid, 100 mL of tetrahydrofuran, and 100 mL of a 2M potassium carbonate aqueous solution were mixed and then, heated and refluxed under a nitrogen flow for 12 hours in a 500 mL round-bottomed flask having an agitator and a nitrogen atmosphere. When the reaction was complete, hexane was poured into the reactant. Then, a solid produced therein was dissolved in a solution prepared by mixing toluene and tetrahydrofuran in a volume ratio of 50:50, and activated carbon and anhydrous magnesium sulfate were added thereto. The mixture was agitated. The solution was filtered and recrystallized using dichloromethane and hexane, obtaining 11 g (yield of 83%) of a compound H.

Second STEP: Synthesis of Compound Represented by Chemical Formula B-8

10.8 g (32.58 mmol) of the compound H, 11.6 g (37.4 mmol) of 2-bromo-4,6-diphenylpyridine, and 5.53 g (57.6 mmol) of sodium tert-butoxide were dissolved in 160 mL of toluene, and 1.32 g (1.44 mmol) of palladium dibenzylideneamine and 0.87 mL (4.32 mmol) of tert-butyl phosphorous were added thereto in a dropwise fashion in a 500 mL round-bottomed flask having an agitator and a nitrogen atmosphere. The reaction solution was heated and agitated under a nitrogen flow for 12 hours at 110° C. When the reaction was complete, methanol was poured into the reactant. Then, a solid produced therein was filtered and dissolved in chlorobenzene, and activated carbon and anhydrous magnesium sulfate were added thereto. The mixture was agitated. The solution was filtered and recrystallized using chlorobenzene and methanol, obtaining 14 g (yield of 85%) of a compound B-8.

Calcd. $C_{41}H_{26}N_2O$: C, 87.52; H, 4.66; N, 4.98; 0, 2.84. found: C, 87.50; H, 4.68; N, 4.96; O, 2.82.

Example 9

Synthesis of Compound Represented by Chemical Formula B-21

A compound represented by the above Chemical Formula B-21 as an example compound for an organic optoelectronic device according to an embodiment was synthesized according to the Reaction Scheme 9.

[Reaction Scheme 9]

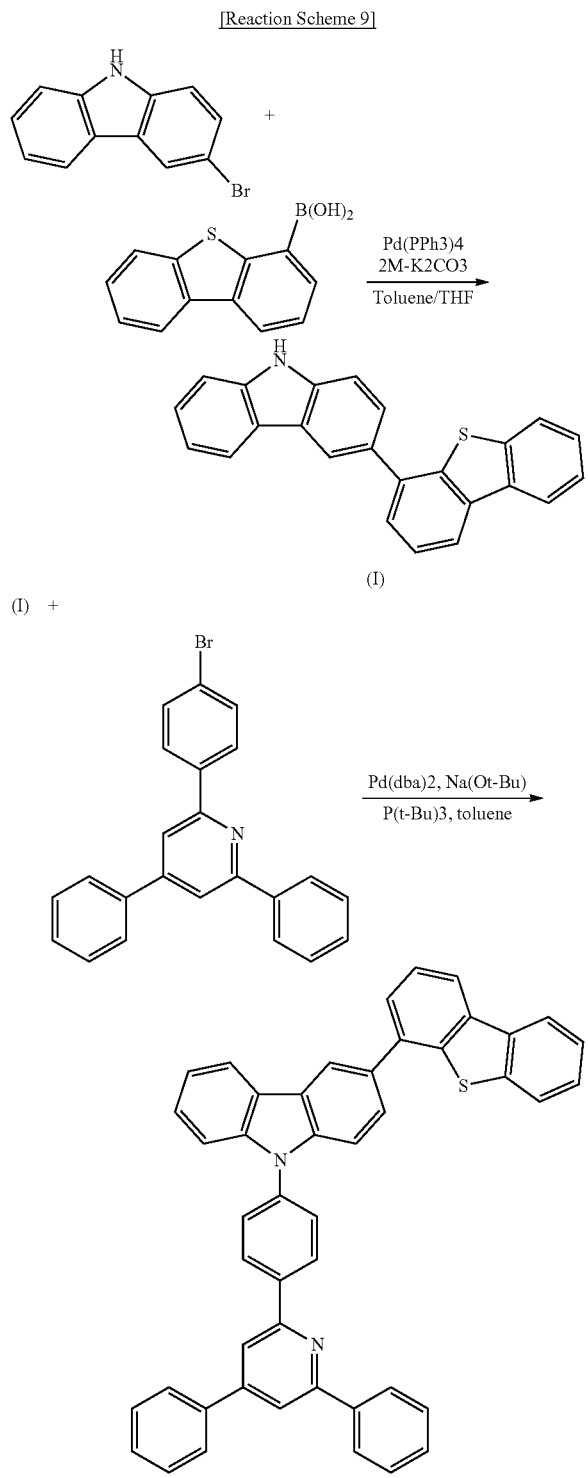

First Step: Synthesis of Compound I 18.53 g (75.3 mmol) of a 3-bromo-carbazole compound, 22.3 g (97.9 mmol) of 4-dibenzothiophene boronic acid, 100 mL of tetrahydrofuran, and 100 mL of a 2M potassium carbonate aqueous solution were mixed and then, heated and refluxed under a nitrogen flow for 12 hours in a 500 mL round-bottomed flask having an agitator and a nitrogen atmosphere. When the reaction was complete, hexane was poured into the reactant. Then, a solid produced therein was dissolved in a solution prepared by mixing toluene and tetrahydrofuran in a volume ratio of 50:50, and activated carbon and anhydrous magnesium sulfate were added thereto. The solution was filtered and recrystallized using dichloromethane and hexane, obtaining 15 g (yield of 60%) of a compound I.

Second STEP: Synthesis of Compound Represented by Chemical Formula B-21

10 g (28.80 mmol) of the compound G, 14.43 g (37.4 mmol) of 2-(4-bromophenyl)-4,6-diphenylpyridine, and 5.53 g (57.6 mmol) of sodium tert-butoxide were dissolved in 160 mL of toluene, and 1.32 g (1.44 mmol) of palladium dibenzylideneamine and 0.87 mL (4.32 mmol) of tert-butyl phosphorous were added thereto in a dropwise fashion in a 500 mL round-bottomed flask having an agitator and a nitrogen atmosphere. The reaction solution was heated and agitated under a nitrogen flow for 12 hours at 110° C. When the reaction was complete, methanol was added to the reactant. Then, a solid produced therein was filtered and dissolved in chlorobenzene, and activated carbon and anhydrous magnesium sulfate were added thereto. The mixture was agitated. The solution was filtered and recrystallized using chlorobenzene and methanol, obtaining 10 g (yield of 60%) of a compound B-21.

Calcd. $C_{47}H_{30}N_2S$: C, 86.21; H, 4.62; N, 4.28; S, 4.90. found: C, 86.20; H, 4.60; N, 4.26; S, 4.88.

Example 10

Synthesis of Compound Represented by Chemical Formula 3

A compound represented by the above Chemical Formula 3 as an example compound for an organic optoelectronic device according to an embodiment was synthesized according to the following Reaction Scheme 10.

[Reaction Scheme 10]

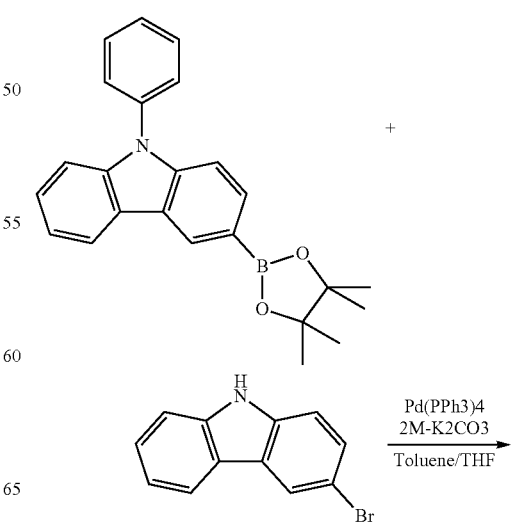

-continued

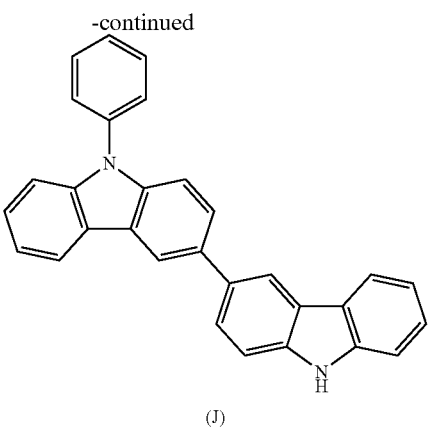

(J) +

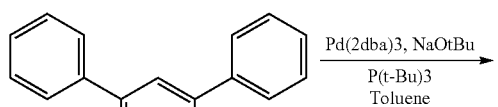

Pd(2dba)3, NaOtBu
P(t-Bu)3
Toluene

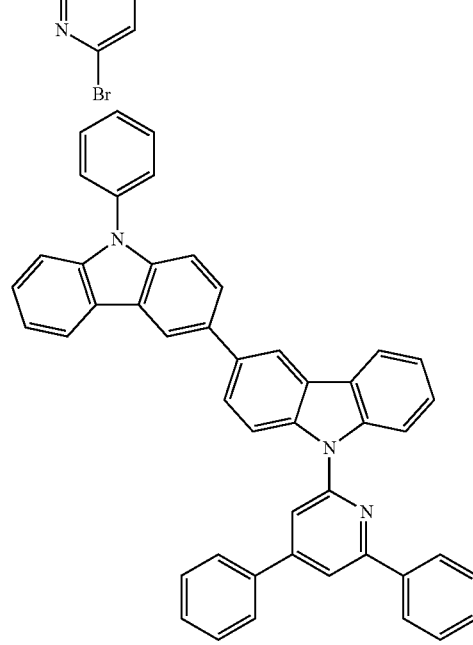

First Step: Synthesis of Compound J 26.96 g (81.4 mmol) of N-phenyl carbazole-3-boronic acid pinacolate, 23.96 g (97.36 mmol) of carbazole-3-boronic acid, 230 mL of tetrahydrofuran, and 100 mL of a 2M potassium carbonate aqueous solution were mixed and then, heated and refluxed under a nitrogen flow for 12 hours in a 500 mL round-bottomed flask having an agitator and a nitrogen atmosphere. When the reaction was complete, methanol was poured into the reactant. Then, a solid produced therein was filtered and dissolved in chlorobenzene, and activated carbon and anhydrous magnesium sulfate were added thereto. The mixture was agitated. The solution was filtered and recrystallized using chlorobenzene and methanol, obtaining 22.6 g (yield of 68%) of a compound J.

Second STEP: Synthesis of Compound Represented by Chemical Formula 3

22.42 g (54.88 mmol) of the compound J, 20.43 g (65.85 mmol) of 2-bromo-4,6-diphenyl pyridine, and 7.92 g (82.32 mmol) of sodium tert-butoxide were dissolved in 400 mL of toluene, and 1.65 g (1.65 mmol) of palladium dibenzylideneamine and 1.78 g (4.39 mmol) of tert-butyl phosphorous were added thereto in a dropwise fashion in a 500 mL round-bottomed flask having an agitator and a nitrogen atmosphere. The reaction solution was agitated under a nitrogen flow for 12 hours at 110° C. When the reaction was complete, methanol was poured into the reactant. Then, a solid produced therein was filtered and dissolved in chlorobenzene, and activated carbon and anhydrous magnesium sulfate were added thereto. The mixture was agitated. When the solution was filtered and recrystallized using chlorobenzene and methanol, obtaining 28.10 g (a yield of 80%) of a compound 3.

Calcd. $C_{47}H_{31}N_3$: C, 88.51; H, 4.90; N, 6.59. found: C, 88.62; H, 4.80; N, 6.47.

Example 11

Synthesis of Compound Represented by Chemical Formula 54

A compound represented by the above Chemical Formula 54 as an example compound for an organic optoelectronic device according to an embodiment was synthesized according to the following Reaction Scheme 11.

[Reaction Scheme 11]

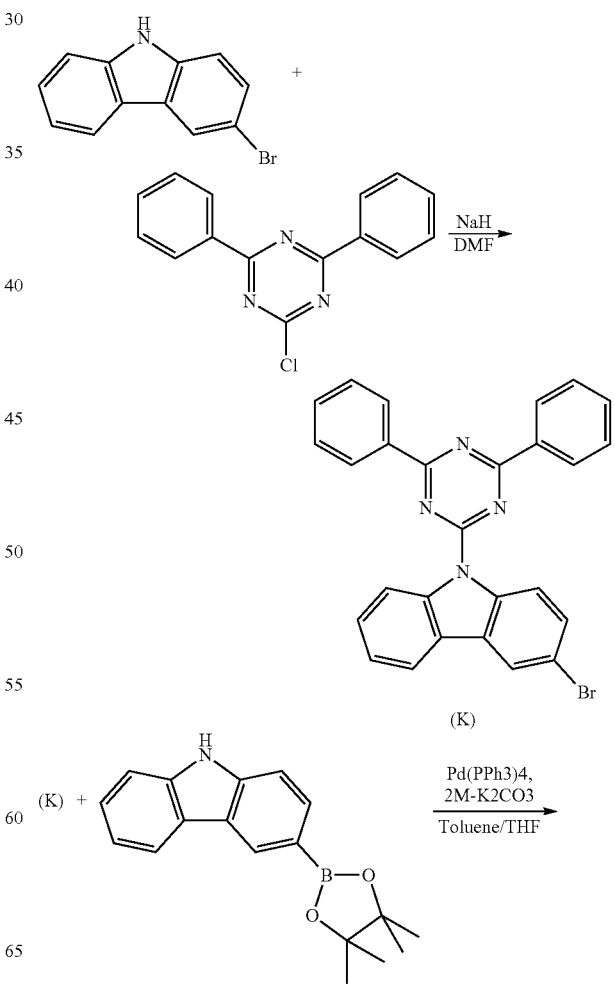

Second Step: Synthesis of Compound L 70.57 g (147.85 mmol) of the compound K and 52.01 g (177.42 mmol) of carbazole-3-boronic acid pinacolate were mixed with 800 mL of a solution prepared by mixing tetrahydrofuran and toluene in a volume ratio of 1:1 and 400 mL of a 2M-potassium carbonate aqueous solution. The mixture was heated and refluxed under a nitrogen flow for 12 hours in a 2 L round-bottomed flask having an agitator and a nitrogen atmosphere. When the reaction was complete, methanol was poured into the reactant. Then, a solid produced therein was filtered and dissolved in chlorobenzene, and activated carbon and anhydrous magnesium sulfate were added thereto. The mixture was agitated. The solution was filtered and recrystallized using chlorobenzene and methanol, obtaining 66 g (yield: 79%) of a compound L.

Third Step: Synthesis of Compound Represented by Chemical Formula 54

10.1 g (17.88 mmol) of the compound L, 5 g (21.46 mmol) of 2-bromobiphenyl, and 3.44 g (35.76 mmol) of sodium tert-butoxide were dissolved in 400 mL of toluene, and 1.03 g (1.79 mmol) of palladium dibenzylideneamine and 2.17 g (5.36 mmol) of tert-butyl phosphorous were added in a dropwise fashion in a 1 L round-bottomed flask having an agitator and a nitrogen atmosphere. The reaction solution was heated and agitated under a nitrogen flow for 12 hours at 110° C. When the reaction was complete, methanol was poured into the reactant. Then, a solid produced therein was filtered and dissolved in chlorobenzene, and activated carbon and anhydrous magnesium sulfate were added thereto. The mixture was agitated. The solution was filtered and recrystallized using chlorobenzene and methanol, obtaining 9.40 g (yield: 73%) of a compound 54.

Calcd. $C_{52}H_{34}N_4$: C, 87.37; H, 4.79; N, 7.84. found: C, 87.47; H, 4.80; N, 7.78.

Example 12

Synthesis of Compound Represented by Chemical Formula C-13

[Reaction Scheme 12]

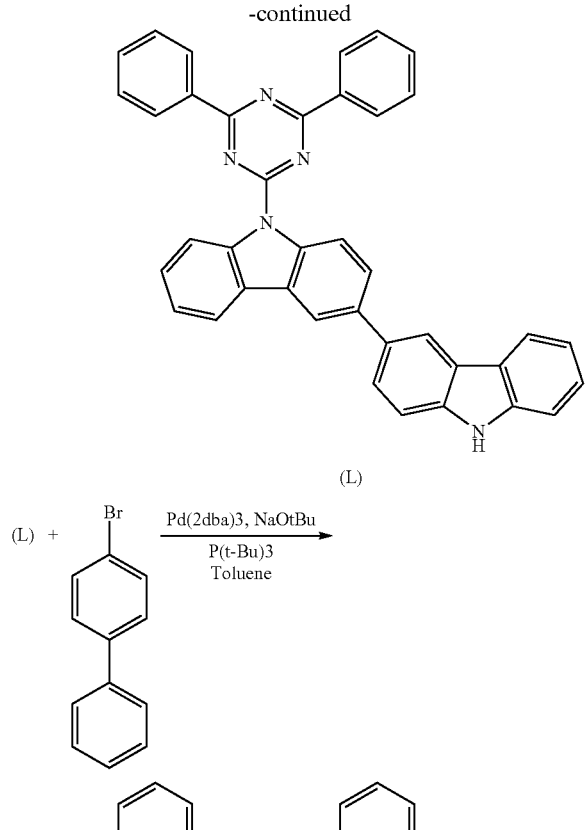

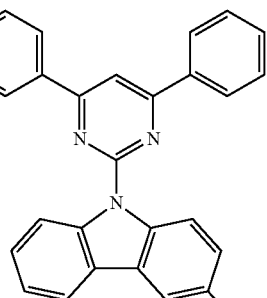

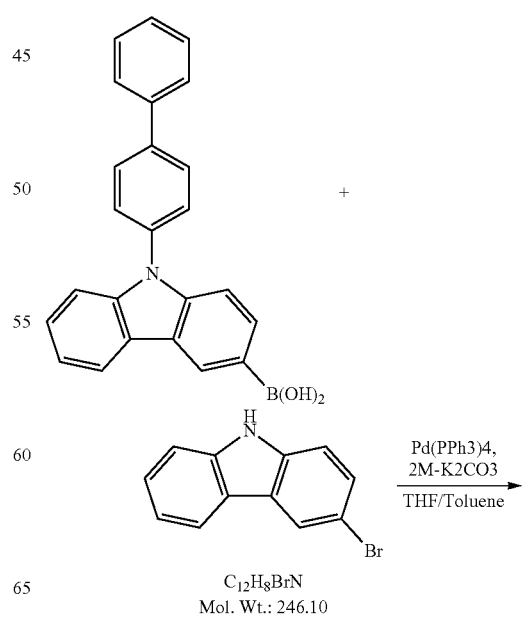

First Step: Synthesis of Compound K 42.97 g (174.57 mmol) of 3-bromocarbazole, 56.1 g (209.5 mmol) of 2-chloro-4,6-diphenyl-triazine, and 10.48 g (261.86 mmol) of NaH were put in dimethylformamide. The mixture was agitated under a nitrogen flow at room temperature for 12 hours in a 1000 mL round flask. The reactant was put in distilled water for crystallization. The crystallized solid was filtered and recrystallized using monochlorobenzene and hexane, obtaining 82 g (yield: 98%) of an intermediate compound K.

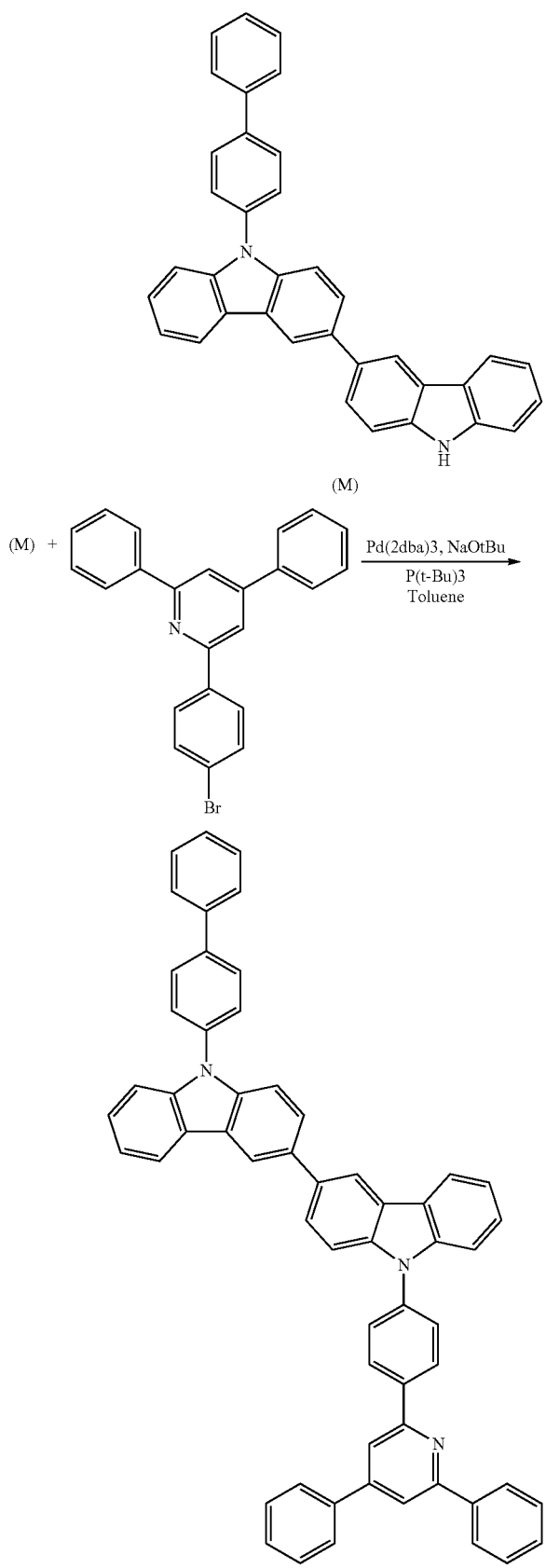

First Step: Synthesis of Compound M 19.3 g (53.06 mmol) of N-biphenyl-3-carbazole boronic acid, 10.9 g (44.22 mmol) of 3-bromo carbazole, 140 mL of a solution prepared by mixing tetrahydrofuran and toluene in a volume ratio of 1:1, and 80 mL of a 2M-potassium carbonate aqueous solution were mixed and then, heated and refluxed under a nitrogen flow for 12 hours in a 500 mL round-bottomed flask having an agitator and a nitrogen atmosphere. When the reaction was complete, methanol was poured into the reactant. Then, a solid produced therein was filtered and dissolved in chlorobenzene, and activated carbon and anhydrous magnesium sulfate were added thereto. The mixture was agitated. The solution was filtered and recrystallized, obtaining 13.7 g (yield: 64%) of a compound M.

Second Step: Synthesis of Compound Represented by Chemical Formula C-13

9.6 g (19.82 mmol) of the compound M, 9.2 g (23.8 mmol) of 2-(4-bromophenyl)-4,6-diphenylpyridine, and 3.2 g (33.7 mmol) of sodium tert-butoxide were dissolved in 160 mL of toluene, and 0.454 g (0.5 mmol) of palladium dibenzylideneamine and 0.6 g (1.49 mmol) of tert-butyl phosphorous were added thereto in a dropwise fashion in a 500 mL round-bottomed flask having an agitator and a nitrogen atmosphere. The reaction solution was heated and agitated under a nitrogen flow for 12 hours at 110° C. When the reaction was complete, methanol was poured into the reactant. Then, a solid produced therein was filtered and dissolved in chlorobenzene, and activated carbon and anhydrous magnesium sulfate were added thereto. The mixture was agitated. The solution was filtered and recrystallized using chlorobenzene and methanol, obtaining 14 g (yield: 89%) of a compound C-13.

Calcd. $C_{59}H_{39}N_3$: C, 89.70; H, 4.98; N, 5.32. found: C, 89.57; H, 4.83; N, 5.65.

Fabrication of Organic Light Emitting Diode

Example 13

An organic light emitting diode was fabricated by using the compound according to Example 1 and $Ir(PPy)_3$ as a dopant. Herein, 1000 Å-thick ITO was used as a positive electrode, while 1000 Å-thick aluminum (Al) was used as a cathode.

A method of manufacturing the organic light emitting diode included cutting an ITO glass substrate having sheet resistance of 15 $\Omega/cm^2$ into a size of 50 mm×50 mm×0.7 mm and ultrasonic wave-cleaning it in acetone, isopropyl alcohol, and pure water for 15 minutes respectively, and then UV-ozone cleaning it for 30 minutes.

On the substrate, a 800 Å-thick hole transport layer (HTL) was formed by depositing N,N'-di(1-naphthyl)-N,N'-diphenylbenzidine (NPB) (70 nm) and 4,4',4''-tri(N-carbazolyl) triphenylamine (TCTA) (10 nm) under conditions of a vacuum degree of 650×10⁻⁷ Pa and a deposition rate of 0.1 to 0.3 nm/s.

Then, a 300 Å-thick emission layer was formed thereon using the compound according to Example 2 under the same vacuum deposition conditions, and $Ir(PPy)_3$ as a phosphorescence dopant was simultaneously deposited. Here, the deposition rate of the phosphorescence dopant was adjusted to include 7 wt % of the phosphorescence dopant based on 100 wt % of the emission layer.

On the emission layer, bis(8-hydroxy-2-methylquinolinolato)-aluminumbiphenoxide (BAlq) was deposit to form a 50 Å-thick hole-blocking layer under the same vacuum deposition conditions.

Next, a 200 Å-thick electron transport layer (ETL) was formed thereon by depositing Alq₃ under the same vacuum deposition conditions.

On the electron transport layer (ETL), LiF and Al were sequentially deposited to form a cathode, fabricating an organic photoelectric device.

The organic photoelectric device had a structure of ITO/NPB (70 nm)/TCTA (10 nm)/EML (the compound of Example 1 (93 wt %)+Ir(PPy)₃ (7 wt %), 30 nm)/Balq (5 nm)/Alq₃ (20 nm)/LiF (1 nm)/Al (100 nm).

Example 14

An organic light emitting diode was fabricated according to the same method as Example 13 except for using the compound according to Example 2 as a host for an emission layer instead of the compound according to Example 1.

Example 15

An organic light emitting diode was fabricated according to the same method as Example 13 except for using the compound according to Example 4 as a host for an emission layer instead of the compound according to Example 1.

Example 16

An organic light emitting diode was fabricated according to the same method as Example 13 except for using the compound according to Example 6 as a host for an emission layer instead of the compound according to Example 1.

Example 17

An organic light emitting diode was fabricated according to the same method as Example 13 except for using the compound according to Example 7 as a host for an emission layer instead of the compound according to Example 1.

Example 18

An organic light emitting diode was fabricated according to the same method as Example 13 except for using the compound according to Example 10 as a host for an emission layer instead of the compound according to Example 1.

Example 19

An organic light emitting diode was fabricated according to the same method as Example 13 except for using the compound according to Example 11 as a host for an emission layer instead of the compound according to Example 1.

Example 20

An organic light emitting diode was fabricated according to the same method as Example 13 except for using the compound according to Example 12 as a host for an emission layer instead of the compound according to Example 1.

Comparative Example 1

An organic light emitting diode was fabricated according to the same method as Example 13 except for using 4,4-N,N-dicarbazolebiphenyl (CBP) as a host for an emission layer instead of the compound according to Example 2.

Comparative Example 2

An organic light emitting diode fabricated using bis[9-(4-methoxyphenyl)carbazol-3-yl] (Jib796-04k) according to Example 6 of Korean Patent Laid Open No. 10-2005-0100673 was compared with a device fabricated using the compound according to an embodiment regarding light emitting characteristics.

Performance Measurement of Organic Light Emitting Diode

Experimental Example

Each organic light emitting diode according to Examples 13 to 20 and Comparative Examples 1 and 2 was measured regarding current density and luminance changes depending on voltage and luminous efficiency. The measurements were specifically performed in the following method. The results are provided in the following Table 1.

(1) Measurement of Current Density Change Depending on Voltage Change

The fabricated organic light emitting diodes were measured for current value flowing in the unit device while increasing the voltage from 0V to 10V using a current-voltage meter (Keithley 2400), and the measured current value was divided by area to provide the result.

(2) Measurement of Luminance Change Depending on Voltage Change

The fabricated organic light emitting diodes were measured for luminance while increasing the voltage from 0V to 10V using a luminance meter (Minolta Cs-1000A).

(3) Measurement of Luminous Efficiency

Current efficiency (cd/A) and electric power efficiency (lm/W) at the same luminance (9000 cd/m²) were calculated by using luminance and current density from the item (1) and (2) and voltage.

TABLE 1

| | | | 9000 cd/m² | |
|---|---|---|---|---|
| | Host material of emission layer | Threshold voltage (V) | Luminous efficiency (cd/A) | life-span (h, T97%) |
| Example 13 | Example 1 | 4.1 | 87.9 | 50 |
| Example 14 | Example 2 | 4.3 | 88.7 | 50 |
| Example 15 | Example 4 | 4.1 | 83.8 | 45 |
| Example 16 | Example 6 | 4.7 | 73.7 | 20 |
| Example 17 | Example 7 | 5.1 | 73.6 | 10 |
| Example 18 | Example 10 | 4.8 | 78.7 | 60 |
| Example 19 | Example 11 | 4.0 | 68.2 | 10 |
| Example 20 | Example 12 | 5.3 | 69.5 | 5 |
| Comparative Example 1 | CBP | 4.8 | 31.4 | <1 |
| Comparative Example 2 | bis[9-(4-methoxyphenyl)carbazol-3-yl] | — | 30 to 35 | — |

Referring to Table 1, a device fabricated using a material according to an embodiment had excellent driving voltage and efficiency compared with one fabricated using CBP, a reference material in terms of luminous efficiency. In addition, life-span was evaluated by measuring time until 3% luminous efficiency decreased. The device fabricated using CBP had a very short life-span of less than one hour, while the device fabricated using the compound of the present invention had a life-span ranging from about 10 hours to about 60 hours.

On the other hand, the device according to Comparative Example 2 had luminous efficiency ranging from 30 to 35 cd/A, which was significantly lower than the ones according to Examples 13 to 20. Compared with the aforementioned two compounds of the Comparative Examples, compound according to embodiments may be well applied to an organic light emitting diode.

By way of summation and review, examples of an organic optoelectronic device may include an organic photoelectric device, an organic light emitting diode, an organic solar cell, an organic photo conductor drum, an organic transistor, or the like, which use one or more of a hole injecting or transport material, an electron injecting or transport material, or a light emitting material.

For example, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. The organic material layer may include a multi-layer including different materials, e.g., one or more of a hole injection layer (HIL), a hole transport layer (HTL), an emission layer, an electron transport layer (ETL), or an electron injection layer (EIL), in order to improve efficiency and stability of an organic photoelectric device.

In an organic light emitting diode, when a voltage is applied between an anode and a cathode, holes from the anode and electrons from the cathode may be injected to an organic material layer and recombine to generate excitons having high energy. The generated excitons may generate light having certain wavelengths while shifting to a ground state.

A phosphorescent light emitting material may be used for a light emitting material of an organic light emitting diode, as may be a fluorescent light emitting material. A phosphorescent material may emits light by transporting the electrons from a ground state to an exited state, non-radiance transiting of a singlet exciton to a triplet exciton through intersystem crossing, and transiting a triplet exciton to a ground state to emit light.

In an organic light emitting diode, an organic material layer may include a light emitting material and a charge transport material, e.g., one or more of a hole injection material, a hole transport material, an electron transport material, an electron injection material, or the like.

The light emitting material may be classified as, e.g., blue, green, or red light emitting materials according to emitted colors, or yellow and orange light emitting materials to emit colors approaching natural colors.

When one material is used as a light emitting material, a maximum light emitting wavelength may be shifted to a long wavelength or color purity may decrease because of interactions between molecules, or device efficiency may decrease because of a light emitting quenching effect. Therefore, a host/dopant system may be included as a light emitting material in order to improve color purity and increase luminous efficiency and stability through energy transfer.

A material constituting an organic material layer, for example a hole injection material, a hole transport material, a light emitting material, an electron transport material, an electron injection material, and a light emitting material such as a host and/or a dopant, should be stable and have good efficiency. Development of an organic material layer forming material for an organic light emitting diode is ongoing. Material development is may also provide benefits for other organic photoelectric devices.

A low molecular organic light emitting diode may be manufactured as a thin film in a vacuum deposition method and may have good efficiency and life-span performance. A polymer organic light emitting diode may be manufactured in an inkjet or spin coating method may have an advantage of low initial cost and being suitable for large-sized substrates.

Both low molecular organic light emitting and polymer organic light emitting diodes may provide a self-light emitting display with high speed response, wide viewing angle, ultra-thin, high image quality, durability, large driving temperature range, etc. They may have good visibility due to self-light emitting characteristic compared with a conventional LCD (liquid crystal display) and have an advantage of decreasing thickness and weight of LCD up to a third, because they may omit a backlight. In addition, since they may have a response speed 1000 times faster than an LCD, they may realize a perfect motion picture without afterimage. They have been developed to have 80 times the efficiency and more than 100 times the life-span since they came out for the first time in the late 1980s. Recently, they have been made larger, e.g., a 40-inch organic light emitting diode panel. It would be beneficial if they were simultaneously to have improved luminous efficiency and life-span in order to be larger. Luminous efficiency may be obtained through smooth combination between holes and electrons in an emission layer. However, an organic material may in general have slower electron mobility than hole mobility. Thus, inefficient combination between holes and electrons could. Increasing electron injection and mobility from a cathode and simultaneously preventing movement of holes is expected to be beneficial.

Improved life-span may be obtained if a material crystallization caused by Joule heating generated during device operating is reduced or be prevented. Accordingly, there has been a strong need for an organic compound having excellent electron injection and mobility, and high electrochemical stability.

As described above, a compound for an organic optoelectronic device may act as light emission and/or electron injection and/or transport material, and may also act as a light emitting host along with a dopant. Thus, an organic light emitting diode having excellent life-span, high luminous efficiency at a low driving voltage, driving voltage, electrochemical stability, and/or thermal stability may be provided. A display device including the organic light emitting diode may also be provided.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

DESCRIPTION OF SYMBOLS

| | |
|---|---|
| 100: organic light emitting diode | 110: cathode |
| 120: anode | 105: organic thin layer |
| 130: emission layer | 140: hole transport layer (HTL) |
| 150: electron transport layer (ETL) | 160: electron injection layer (EIL) |
| 170: hole injection layer (HIL) | 230: emission layer + electron transport layer (ETL) |

What is claimed is:

1. A compound for an organic optoelectronic device, the compound being asymmetrical and represented by the following Chemical Formula 2:

[Chemical Formula 2]

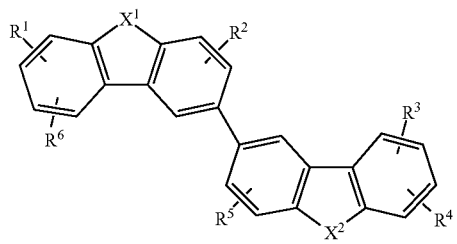

wherein, in Chemical Formula 2, $X^1$ and $X^2$ are each independently selected from the group of —NR'—, —O—, and —S—, wherein R' is selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties, $R^1$ to $R^6$ are each independently selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, the C2 to C30 heteroaryl group having electronic properties, at least one of $R^1$ to $R^6$ or R' is a substituted or unsubstituted C2 to C30 heteroaryl group, the C2 to C30 heteroaryl group having electronic properties, and at least one of $X^1$ and $X^2$ is —NR'— wherein R' includes a substituted or unsubstituted pyridinyl group, a substituted or unsubstituted pyrimidinyl group, or a substituted or unsubstituted triazinyl group.

2. The compound as claimed in claim 1, wherein the compound is represented by the following Chemical Formula B-1:

[Chemical Formula B-1]

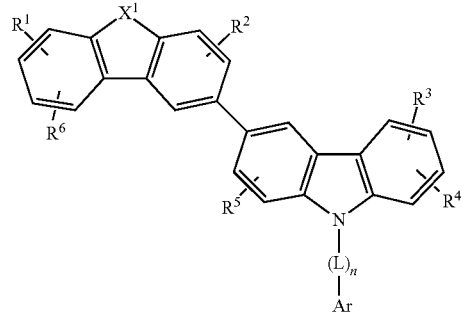

wherein, in Chemical Formulae B-1, $X^1$ is selected from the group of —O— and —S—, $R^1$ to $R^6$ are each independently selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, Ar is represented by one of the following Chemical Formulae E-1 to E-5, L is selected from the group of a single bond, a substituted or unsubstituted C2 to C10 alkenylene group, a substituted or unsubstituted C2 to C10 alkynylene group, a substituted or unsubstituted C6 to C30 arylene group, and a substituted or unsubstituted C2 to C30 heteroarylene group, and n is an integer ranging from 1 to 2,

[Chemical Formula E-1]

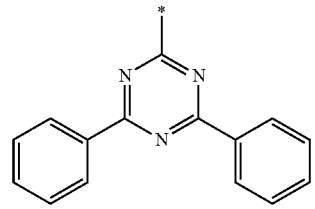

[Chemical Formula E-2]

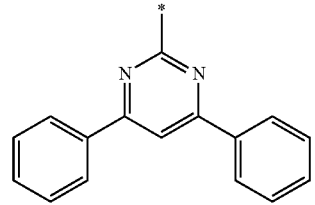

[Chemical Formula E-3]

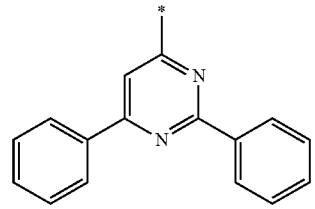

-continued

[Chemical Formula E-4]

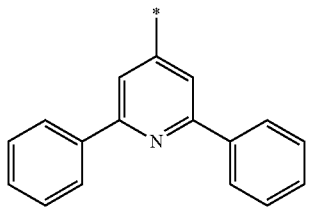

[Chemical Formula E-5]

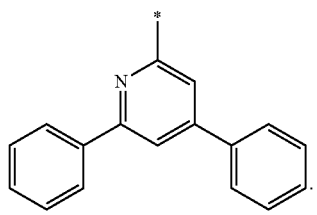

3. An organic light emitting diode, comprising:
an anode; a cathode; and at least one organic thin layer between the anode and the cathode, the at least one organic thin layer including the compound as claimed in claim 1.

4. The organic light emitting diode as claimed in claim 3, wherein the compound is included in an emission layer.

5. The organic light emitting diode as claimed in claim 4, wherein the compound is used as a phosphorescent or fluorescent host material in the emission layer.

6. The organic light emitting diode as claimed in claim 4, wherein the compound is used as a fluorescent blue dopant material in the emission layer.

7. A display device comprising the organic light emitting diode as claimed in claim 3.

8. A compound for an organic optoelectronic device, the compound being asymmetrical and represented by the following Chemical Formula S-2:

[Chemical Formula S-2]

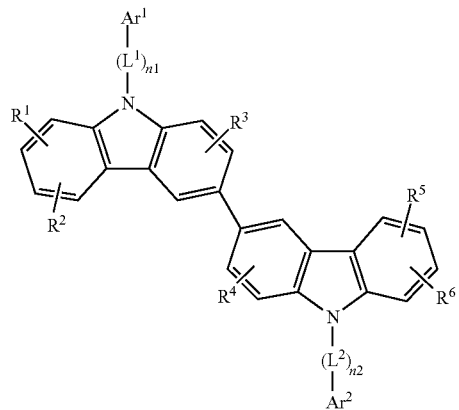

wherein, in Chemical Formula S-2,
$R^1$ to $R^6$ are each independently selected from the group of hydrogen, deuterium, a substituted or unsubstituted C1 to C20 alkyl group, a substituted or unsubstituted C6 to C30 aryl group, and a substituted or unsubstituted C2 to C30 heteroaryl group, $L^1$ and $L^2$ are each independently selected from the group of a single bond, a substituted or unsubstituted C2 to C10 alkenylene group, a substituted or unsubstituted C2 to C10 alkynylene group, a substituted or unsubstituted C6 to C30 arylene group, and substituted or unsubstituted C2 to C30 heteroarylene group, n1 and n2 are each independently an integer ranging from 1 to 2, $Ar^1$ and $Ar^2$ are each independently selected from the group of a substituted or unsubstituted C6 to C30 aryl group and a substituted or unsubstituted C2 to C30 heteroaryl group, the C2 to C30 heteroaryl group having electronic properties, and one of $Ar^1$ and $Ar^2$ is a substituted or unsubstituted pyridinyl group, a substituted or unsubstituted pyrimidinyl group, or a substituted or unsubstituted triazinyl group.

9. The compound as claimed in claim 8, wherein one of $Ar^1$ and $Ar^2$ is represented by one of the following Chemical Formulae E-1 to E-5:

[Chemical Formula E-1]

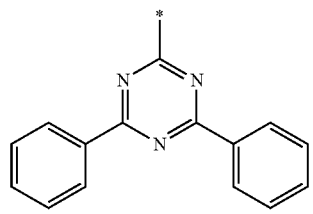

[Chemical Formula E-2]

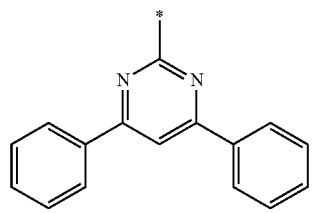

[Chemical Formula E-3]

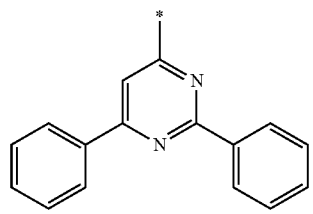

[Chemical Formula E-4]

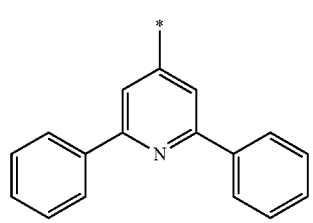

-continued

[Chemical Formula E-5]

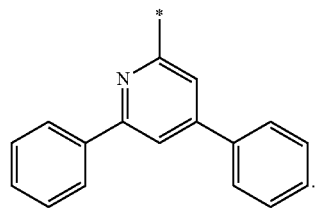

10. An organic light emitting diode, comprising:
an anode; a cathode; and at least one organic thin layer between the anode and the cathode, the at least one organic thin layer including the compound as claimed in claim 8.

11. The organic light emitting diode as claimed in claim 10, wherein the compound is included in an emission layer.

12. The organic light emitting diode as claimed in claim 11, wherein the compound is used as a phosphorescent or fluorescent host material in the emission layer.

13. The organic light emitting diode as claimed in claim 11, wherein the compound is used as a fluorescent blue dopant material in the emission layer.

14. A display device comprising the organic light emitting diode as claimed in claim 10.

* * * * *